(12) United States Patent
Bagasra

(10) Patent No.: US 8,323,891 B2
(45) Date of Patent: Dec. 4, 2012

(54) MIRNA TRIPLEX FORMATIONS FOR THE DOWNREGULATION OF VIRAL REPLICATION

(75) Inventor: Omar Bagasra, Orangeburg, SC (US)

(73) Assignee: Claflin University, Orangeburg, SC (US)

( * ) Notice: Subject to any disclaimer, the term of this patent is extended or adjusted under 35 U.S.C. 154(b) by 396 days.

(21) Appl. No.: 12/512,090

(22) Filed: Jul. 30, 2009

(65) Prior Publication Data

US 2010/0048675 A1 Feb. 25, 2010

Related U.S. Application Data

(60) Provisional application No. 61/137,744, filed on Aug. 1, 2008.

(51) Int. Cl.
*C12Q 1/68* (2006.01)
*C07H 21/04* (2006.01)
*C12N 5/00* (2006.01)
*C12N 15/11* (2006.01)

(52) U.S. Cl. ........ 435/6.1; 435/325; 435/375; 536/23.1; 536/24.5; 514/44 A

(58) Field of Classification Search .................. None
See application file for complete search history.

(56) References Cited

U.S. PATENT DOCUMENTS

| | | | |
|---|---|---|---|
| 5,766,916 A | 6/1998 | Belyaev et al. | |
| 6,153,421 A | 11/2000 | Yanagi et al. | |
| 6,531,123 B1 | 3/2003 | Chang | |
| 6,555,342 B1 | 4/2003 | Kappes et al. | |
| 6,670,462 B2 | 12/2003 | Hope et al. | |
| 6,682,907 B1 | 1/2004 | Charneau et al. | |
| 6,870,043 B2 | 3/2005 | Xiang et al. | |
| 6,933,377 B2 | 8/2005 | Chen | |
| 7,291,723 B2 | 11/2007 | Stapleton et al. | |
| 2003/0175693 A1 | 9/2003 | Wain-Hobson et al. | |
| 2004/0077577 A1 | 4/2004 | Pavlakis | |
| 2004/0152069 A1 | 8/2004 | Wagner et al. | |
| 2007/0087982 A1 | 4/2007 | Nelson et al. | |
| 2007/0099858 A1 | 5/2007 | Jadhav et al. | |
| 2008/0008683 A1 | 1/2008 | Renard et al. | |
| 2008/0038297 A1 | 2/2008 | Gupta | |

OTHER PUBLICATIONS

Jen et al., Stem Cells 2000; 18:307-319.*
Opalinska et al., Nature Reviews, 2002; 1:503-514.*
Braasch, D. A. Biochemistry. Apr. 2002; 41(14): 4503-4510.*
Aagaard et al., Advanced Drug Delivery Reviews, 2007 (59)75-86.*
Paroo et al., TRENDS in Biotechnology, Aug. 2004; 22(8) 390-394.*

* cited by examiner

*Primary Examiner* — Doug Schultz
(74) *Attorney, Agent, or Firm* — McNair Law Firm, P.A.; Seann P. Lahey

(57) ABSTRACT

As discovered herein, using miRNAs having high homology with both HIV-1 and a co-infecting virus such as HHV-6, HHV-7, or GVB-C, one can inhibit viral replication, more particularly HIV-1 replication using such mutually homologous miRNAs that give rise to the creation of stable triplex formations effective in the downregulation and/or inhibition of viral replication.

11 Claims, 5 Drawing Sheets

| TF Sequence no. | Strand | Oligo-nucleotide Sequence & Structure | Details |
|---|---|---|---|
| 1: hsa-let-7i | SS A1 | 5'-Q-GAGGTAGTAATTGTXTCTGT | DS = Double Stranded |
|  | DS B1 | 5'-F-GAGGTAGTAATTAGATCTGT-+<br>3'- CTCCATCATTAATCTAGACA-+<br>H | SS = Single Stranded<br>Q = BHQ-1<br>F = FITC<br>H = SP18 (Linking Molecule) |
| 2: hsa-miR-195 | SS A2 | 5'-Q-GCAGCAXCAGAACAATTTGC |  |
|  | DS B2 | 5'-F-GCAGCAGCAGAACAATTTGC-+<br>3'- CGTCGTCGTCTTGTTAAACG- +<br>H |  |
| 3: hsa-miR-508-3 | SS A3 | 5'-Q-ATTGTAXCCXTTXGGAGTAG |  |
|  | DS B3 | 5'-F-ATTGTAACCATTAGGAGTAG-+<br>3'- TAACATTGGTAATCCTCATC- +<br>H |  |
| 4: hsa-miR-659 | SS A4 | 5'-Q-TTGXTCAGGGAGGGTCTCCA |  |
|  | DS B4 | 5'-F-TTGGGTCAGGGAGGGTCTCCA-+<br>3'- AACCCAGTCCCT--CAGAGGT-+<br>H |  |

Figure 1: The Sequences of HIV-1 duplexes and the third homologous oligonucleotides to study the triplex forming abilities of miRNA in vitro.

SEQUENCE LISTING

<160> NUMBER OF SEQ ID NOS: 1404

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctctcgacgc aggactcggc                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2 ccttcccct ggccttaacc g                                             21

<210> SEQ ID NO 3
<211> LENGTH: 19
<212> TYPE: DNA
<213> ORGANISM: Human immunodeficiency virus

<400> SEQUENCE: 3
accacacaca aggctactt                                               19

<210> SEQ ID NO 4
<211> LENGTH: 19
<212> TYPE: DNA
<213> ORGANISM: Homo sapiens

<400> SEQUENCE: 4
atcacacaca aggcaactt                                               19

<210> SEQ ID NO 5
<211> LENGTH: 20
<212> TYPE: DNA
<213> ORGANISM: Human immunodeficiency virus

```
<400> SEQUENCE: 5
cctattgaga ctgtaccagt                                              20

<210> SEQ ID NO 6
<211> LENGTH: 21
<212> TYPE: DNA
<213> ORGANISM: Homo sapiens

<400> SEQUENCE: 6
cctactgaga ctgatatcag t                                            21

<210> SEQ ID NO 7
<211> LENGTH: 21
<212> TYPE: DNA
<213> ORGANISM: Human immunodeficiency virus

<400> SEQUENCE: 7
ccttggaatg ctagttggag t                                            21

<210> SEQ ID NO 8
<211> LENGTH: 22
<212> TYPE: DNA
<213> ORGANISM: Homo sapiens

<400> SEQUENCE: 8
ccttggaatc ctaggtgtga gt                                           22

<210> SEQ ID NO 9
<211> LENGTH: 20
<212> TYPE: DNA
<213> ORGANISM: Human immunodeficiency virus

<400> SEQUENCE: 9
aagaacctcc attcctttgg                                              20

<210> SEQ ID NO 10
<211> LENGTH: 20
<212> TYPE: DNA
<213> ORGANISM: Homo sapiens

<400> SEQUENCE: 10
aagaacctca gttgcttttg                                              20

<210> SEQ ID NO 11
<211> LENGTH: 23
<212> TYPE: DNA
<213> ORGANISM: Human immunodeficiency virus

<400> SEQUENCE: 11
caaatattac tgggctgcta tta                                          23

<210> SEQ ID NO 12
<211> LENGTH: 23
<212> TYPE: DNA
<213> ORGANISM: Homo sapiens

<400> SEQUENCE: 12
ccaatattac tgtgctgcta tta                                          23

<210> SEQ ID NO 13
<211> LENGTH: 23
<212> TYPE: DNA
<213> ORGANISM: Human immunodeficiency virus
```

```
<400> SEQUENCE: 13
atataataca atagcagtcc tct                                            23

<210> SEQ ID NO 14
<211> LENGTH: 23
<212> TYPE: DNA
<213> ORGANISM: Homo sapiens

<400> SEQUENCE: 14
atattataca gtagcaaccc tct                                            23

<210> SEQ ID NO 15
<211> LENGTH: 19
<212> TYPE: DNA
<213> ORGANISM: Human immunodeficiency virus

<400> SEQUENCE: 15
gctcaatgcc acagccata                                                 19

<210> SEQ ID NO 16
<211> LENGTH: 20
<212> TYPE: DNA
<213> ORGANISM: Homo sapiens

<400> SEQUENCE: 16
gctcaatgca cacacccaca                                                20

<210> SEQ ID NO 17
<211> LENGTH: 19
<212> TYPE: DNA
<213> ORGANISM: Human immunodeficiency virus

<400> SEQUENCE: 17
agaatggagg aaaaagaga                                                 19

<210> SEQ ID NO 18
<211> LENGTH: 20
<212> TYPE: DNA
<213> ORGANISM: Homo sapiens

<400> SEQUENCE: 18
agacgggagg aaagaaggga                                                20

<210> SEQ ID NO 19
<211> LENGTH: 19
<212> TYPE: DNA
<213> ORGANISM: Human immunodeficiency virus

<400> SEQUENCE: 19
gatgtagtaa ttagatctg                                                 19

<210> SEQ ID NO 20
<211> LENGTH: 19
<212> TYPE: DNA
<213> ORGANISM: Homo sapiens

<400> SEQUENCE: 20
gaggtagtaa ttagatctg                                                 19

<210> SEQ ID NO 21
<211> LENGTH: 20
<212> TYPE: DNA
<213> ORGANISM: Human immunodeficiency virus
```

```
<400> SEQUENCE: 21
gcagcagcag aacaatttgc                                              20

<210> SEQ ID NO 22
<211> LENGTH: 20
<212> TYPE: DNA
<213> ORGANISM: Homo sapiens

<400> SEQUENCE: 22
gcagcagcag aacaatttgc                                              20

<210> SEQ ID NO 23
<211> LENGTH: 19
<212> TYPE: DNA
<213> ORGANISM: Human immunodeficiency virus

<400> SEQUENCE: 23
attgaaccat taggagtag                                               19

<210> SEQ ID NO 24
<211> LENGTH: 20
<212> TYPE: DNA
<213> ORGANISM: Homo sapiens

<400> SEQUENCE: 24
attgtaacca ttaggagtag                                              20

<210> SEQ ID NO 25
<211> LENGTH: 19
<212> TYPE: DNA
<213> ORGANISM: Human immunodeficiency virus

<400> SEQUENCE: 25
ttgggtcagg gagtctcca                                               19

<210> SEQ ID NO 26
<211> LENGTH: 21
<212> TYPE: DNA
<213> ORGANISM: Homo sapiens

<400> SEQUENCE: 26
ttgggtcagg gagggtctcc a                                            21

<210> SEQ ID NO 27
<211> LENGTH: 21
<212> TYPE: DNA
<213> ORGANISM: Human herpes virus 6A

<400> SEQUENCE: 27
gtctctttct gctctgcagt c                                            21

<210> SEQ ID NO 28
<211> LENGTH: 20
<212> TYPE: DNA
<213> ORGANISM: Homo sapiens

<400> SEQUENCE: 28
gtgtcttttg ctctgcagtc                                              20

<210> SEQ ID NO 29
<211> LENGTH: 20
<212> TYPE: DNA
<213> ORGANISM: Human herpes virus 6A
```

```
<400> SEQUENCE: 29
gatatgattt gataattagg                                           20

<210> SEQ ID NO 30
<211> LENGTH: 20
<212> TYPE: DNA
<213> ORGANISM: Homo sapiens

<400> SEQUENCE: 30
gatatgtttg atatattagg                                           20

<210> SEQ ID NO 31
<211> LENGTH: 21
<212> TYPE: DNA
<213> ORGANISM: Human herpes virus 6A

<400> SEQUENCE: 31
ttctaaattc tccgcgtctt t                                         21

<210> SEQ ID NO 32
<211> LENGTH: 21
<212> TYPE: DNA
<213> ORGANISM: Homo sapiens

<400> SEQUENCE: 32
ttctaatttc tccacgtctt t                                         21

<210> SEQ ID NO 33
<211> LENGTH: 19
<212> TYPE: DNA
<213> ORGANISM: Human herpes virus 6A

<400> SEQUENCE: 33
aaactctgaa aatcaaaca                                            19

<210> SEQ ID NO 34
<211> LENGTH: 20
<212> TYPE: DNA
<213> ORGANISM: Homo sapiens

<400> SEQUENCE: 34
aaactactga aaatcaaaga                                           20

<210> SEQ ID NO 35
<211> LENGTH: 19
<212> TYPE: DNA
<213> ORGANISM: Human herpes virus 6A

<400> SEQUENCE: 35
aagaagtgga aaaactgta                                            19

<210> SEQ ID NO 36
<211> LENGTH: 19
<212> TYPE: DNA
<213> ORGANISM: Homo sapiens

<400> SEQUENCE: 36
aagatgtgga aaaattgga                                            19

<210> SEQ ID NO 37
<211> LENGTH: 22
<212> TYPE: DNA
<213> ORGANISM: Human herpes virus 6A
```

```
<400> SEQUENCE: 37
tcaaagatgg acaatccttg tt                                        22

<210> SEQ ID NO 38
<211> LENGTH: 21
<212> TYPE: DNA
<213> ORGANISM: Homo sapiens

<400> SEQUENCE: 38
tcatagagga aaatccatgt t                                         21

<210> SEQ ID NO 39
<211> LENGTH: 20
<212> TYPE: DNA
<213> ORGANISM: Human herpes virus 6A

<400> SEQUENCE: 39
tcgtgcactc gatttagagt                                           20

<210> SEQ ID NO 40
<211> LENGTH: 19
<212> TYPE: DNA
<213> ORGANISM: Homo sapiens

<400> SEQUENCE: 40
tcgtgcatcc ctttagagt                                            19

<210> SEQ ID NO 41
<211> LENGTH: 20
<212> TYPE: DNA
<213> ORGANISM: Human herpes virus 6A

<400> SEQUENCE: 41
tctagatgta gaactttctg                                           20

<210> SEQ ID NO 42
<211> LENGTH: 21
<212> TYPE: DNA
<213> ORGANISM: Homo sapiens

<400> SEQUENCE: 42
tctagaggga agcactttct g                                         21

<210> SEQ ID NO 43
<211> LENGTH: 19
<212> TYPE: DNA
<213> ORGANISM: Human herpes virus 6A

<400> SEQUENCE: 43
actctgcaga gtggaatca                                            19

<210> SEQ ID NO 44
<211> LENGTH: 20
<212> TYPE: DNA
<213> ORGANISM: Homo sapiens

<400> SEQUENCE: 44
actcaggaga gtggcaatca                                           20

<210> SEQ ID NO 45
<211> LENGTH: 17
<212> TYPE: DNA
<213> ORGANISM: Human herpes virus 6A
```

```
<400> SEQUENCE: 45
ctgcagagtg gaatcat                                                  17

<210> SEQ ID NO 46
<211> LENGTH: 19
<212> TYPE: DNA
<213> ORGANISM: Homo sapiens

<400> SEQUENCE: 46
ctgcagacgt ggcaatcat                                                19

<210> SEQ ID NO 47
<211> LENGTH: 18
<212> TYPE: DNA
<213> ORGANISM: Human herpes virus 6A

<400> SEQUENCE: 47
gaagaggaga tagcaggg                                                 18

<210> SEQ ID NO 48
<211> LENGTH: 20
<212> TYPE: DNA
<213> ORGANISM: Homo sapiens

<400> SEQUENCE: 48
gtagaggaga tggcgcaggg                                               20

<210> SEQ ID NO 49
<211> LENGTH: 19
<212> TYPE: DNA
<213> ORGANISM: Human herpes virus 6A

<400> SEQUENCE: 49
ctctccaaat ctgatcctg                                                19

<210> SEQ ID NO 50
<211> LENGTH: 18
<212> TYPE: DNA
<213> ORGANISM: Homo sapiens

<400> SEQUENCE: 50
ctctccaaat gtgtcttg                                                 18

<210> SEQ ID NO 51
<211> LENGTH: 19
<212> TYPE: DNA
<213> ORGANISM: Human herpes virus 6A

<400> SEQUENCE: 51
tctagttctg gagtgctga                                                19

<210> SEQ ID NO 52
<211> LENGTH: 19
<212> TYPE: DNA
<213> ORGANISM: Homo sapiens

<400> SEQUENCE: 52
tctaggctgg tactgctga                                                19

<210> SEQ ID NO 53
<211> LENGTH: 18
<212> TYPE: DNA
<213> ORGANISM: Human herpes virus 6A
```

```
<400> SEQUENCE: 53
taatatagtc cgtatctt                                              18

<210> SEQ ID NO 54
<211> LENGTH: 18
<212> TYPE: DNA
<213> ORGANISM: Homo sapiens

<400> SEQUENCE: 54
taatatggtc cacatctt                                              18

<210> SEQ ID NO 55
<211> LENGTH: 18
<212> TYPE: DNA
<213> ORGANISM: Human herpes virus 6A

<400> SEQUENCE: 55
taacggcaag taaatatt                                              18

<210> SEQ ID NO 56
<211> LENGTH: 18
<212> TYPE: DNA
<213> ORGANISM: Homo sapiens

<400> SEQUENCE: 56
tagcagcacg taaatatt                                              18

<210> SEQ ID NO 57
<211> LENGTH: 18
<212> TYPE: DNA
<213> ORGANISM: Human herpes virus 6A

<400> SEQUENCE: 57
agagttacct gatttgtg                                              18

<210> SEQ ID NO 58
<211> LENGTH: 19
<212> TYPE: DNA
<213> ORGANISM: Homo sapiens

<400> SEQUENCE: 58
agagcttagc tgattggtg                                             19

<210> SEQ ID NO 59
<211> LENGTH: 18
<212> TYPE: DNA
<213> ORGANISM: Human herpes virus 6A

<400> SEQUENCE: 59
ttgtgtttgt tttgcagc                                              18

<210> SEQ ID NO 60
<211> LENGTH: 19
<212> TYPE: DNA
<213> ORGANISM: Homo sapiens

<400> SEQUENCE: 60
tcgtgtcttg tgttgcagc                                             19

<210> SEQ ID NO 61
<211> LENGTH: 22
<212> TYPE: DNA
<213> ORGANISM: Human herpes virus 6A
```

-continued

<400> SEQUENCE: 61
agggtggaaa ttgtctaagt cc    22

<210> SEQ ID NO 62
<211> LENGTH: 21
<212> TYPE: DNA
<213> ORGANISM: Homo sapiens

<400> SEQUENCE: 62 aggggggaaag ttctatagtc c    21

<210> SEQ ID NO 63
<211> LENGTH: 21
<212> TYPE: DNA
<213> ORGANISM: Human herpes virus 6A

<400> SEQUENCE: 63
ctctatctcc tgtcgcactc c    21

<210> SEQ ID NO 64
<211> LENGTH: 20
<212> TYPE: DNA
<213> ORGANISM: Homo sapiens

<400> SEQUENCE: 64
ctctttccct gttgcactac    20

<210> SEQ ID NO 65
<211> LENGTH: 20
<212> TYPE: DNA
<213> ORGANISM: Human herpes virus 6A

<400> SEQUENCE: 65
tccagcccca tagtttctgc    20

<210> SEQ ID NO 66
<211> LENGTH: 20
<212> TYPE: DNA
<213> ORGANISM: Homo sapiens

<400> SEQUENCE: 66
tccagcccca cagcctcagc    20

<210> SEQ ID NO 67
<211> LENGTH: 19
<212> TYPE: DNA
<213> ORGANISM: Human herpes virus 6A

<400> SEQUENCE: 67
cttactcctt ccggcacgt    19

<210> SEQ ID NO 68
<211> LENGTH: 19
<212> TYPE: DNA
<213> ORGANISM: Homo sapiens

<400> SEQUENCE: 68
cttactccct caggcacat    19

<210> SEQ ID NO 69
<211> LENGTH: 19
<212> TYPE: DNA
<213> ORGANISM: Human herpes virus 6A -continued

```
<400> SEQUENCE: 69 cccctttgtaa cctatccct                                              19

<210> SEQ ID NO 70
<211> LENGTH: 20
<212> TYPE: DNA
<213> ORGANISM: Homo sapiens

<400> SEQUENCE: 70
ccctttgtca tcctatgcct                                              20

<210> SEQ ID NO 71
<211> LENGTH: 17
<212> TYPE: DNA
<213> ORGANISM: Human herpes virus 6A

<400> SEQUENCE: 71
gattgacaac atttccc                                                 17

<210> SEQ ID NO 72
<211> LENGTH: 18
<212> TYPE: DNA
<213> ORGANISM: Homo sapiens

<400> SEQUENCE: 72
ggttgacata cgtttccc                                                18

<210> SEQ ID NO 73
<211> LENGTH: 18
<212> TYPE: DNA
<213> ORGANISM: Human herpes virus 6A

<400> SEQUENCE: 73
atcacacaaa ggaaattt                                                18

<210> SEQ ID NO 74
<211> LENGTH: 18
<212> TYPE: DNA
<213> ORGANISM: Homo sapiens

<400> SEQUENCE: 74
atcacacaaa ggcaactt                                                18

<210> SEQ ID NO 75
<211> LENGTH: 20
<212> TYPE: DNA
<213> ORGANISM: Human herpes virus 6A

<400> SEQUENCE: 75
gcactgttgg ggtatttggt                                              20

<210> SEQ ID NO 76
<211> LENGTH: 18
<212> TYPE: DNA
<213> ORGANISM: Homo sapiens

<400> SEQUENCE: 76
gcactgtggg tacttgct                                                18

<210> SEQ ID NO 77
<211> LENGTH: 21
<212> TYPE: DNA
<213> ORGANISM: Human herpes virus 6A
```

-continued

```
<400> SEQUENCE: 77
tcagcgagag tgaaaagaga c                                        21

<210> SEQ ID NO 78
<211> LENGTH: 19
<212> TYPE: DNA
<213> ORGANISM: Homo sapiens

<400> SEQUENCE: 78
tcagcggagg aaaagaaac                                           19

<210> SEQ ID NO 79
<211> LENGTH: 20
<212> TYPE: DNA
<213> ORGANISM: Human herpes virus 6A

<400> SEQUENCE: 79
agcttgcaga gggtgctgat                                          20

<210> SEQ ID NO 80
<211> LENGTH: 18
<212> TYPE: DNA
<213> ORGANISM: Homo sapiens

<400> SEQUENCE: 80
agctcagagg gctctgat                                            18

<210> SEQ ID NO 81
<211> LENGTH: 20
<212> TYPE: DNA
<213> ORGANISM: Human herpes virus 6A

<400> SEQUENCE: 81
agtcacgaag atggcatagc                                          20

<210> SEQ ID NO 82
<211> LENGTH: 20
<212> TYPE: DNA
<213> ORGANISM: Homo sapiens

<400> SEQUENCE: 82
aggcaagatg ctggcatagc                                          20

<210> SEQ ID NO 83
<211> LENGTH: 22
<212> TYPE: DNA
<213> ORGANISM: Human herpes virus 6A

<400> SEQUENCE: 83
aaagttgaga gacactctgg ct                                       22

<210> SEQ ID NO 84
<211> LENGTH: 22
<212> TYPE: DNA
<213> ORGANISM: Homo sapiens

<400> SEQUENCE: 84
aaagttctga gacactccga ct                                       22

<210> SEQ ID NO 85
<211> LENGTH: 23
<212> TYPE: DNA
<213> ORGANISM: Human herpes virus 6A
```

```
<400> SEQUENCE: 85
actctgcagc tttttaacaa gtt                                      23

<210> SEQ ID NO 86
<211> LENGTH: 21
<212> TYPE: DNA
<213> ORGANISM: Homo sapiens

<400> SEQUENCE: 86
attctgcatt tttagcaagt t                                        21

<210> SEQ ID NO 87
<211> LENGTH: 19
<212> TYPE: DNA
<213> ORGANISM: Human herpes virus 6A

<400> SEQUENCE: 87
atgtcgtggt ccaataact                                           19

<210> SEQ ID NO 88
<211> LENGTH: 21
<212> TYPE: DNA
<213> ORGANISM: Homo sapiens

<400> SEQUENCE: 88
atgtaacatg gtccactaac t                                        21

<210> SEQ ID NO 89
<211> LENGTH: 19
<212> TYPE: DNA
<213> ORGANISM: Human herpes virus 6A

<400> SEQUENCE: 89
gcctactgtg ctctatctg                                           19

<210> SEQ ID NO 90
<211> LENGTH: 20
<212> TYPE: DNA
<213> ORGANISM: Homo sapiens

<400> SEQUENCE: 90
gcctactgag ctgatatcag                                          20

<210> SEQ ID NO 91
<211> LENGTH: 18
<212> TYPE: DNA
<213> ORGANISM: Human herpes virus 6A

<400> SEQUENCE: 91
ggcagagttt tgttagct                                            18

<210> SEQ ID NO 92
<211> LENGTH: 18
<212> TYPE: DNA
<213> ORGANISM: Homo sapiens

<400> SEQUENCE: 92
ggcagtgtat tgttagct                                            18

<210> SEQ ID NO 93
<211> LENGTH: 23
<212> TYPE: DNA
<213> ORGANISM: Human herpes virus 6A
```

<400> SEQUENCE: 93
tgccctgtgg agactgcatc tgg                                        23

<210> SEQ ID NO 94
<211> LENGTH: 22
<212> TYPE: DNA
<213> ORGANISM: Homo sapiens

<400> SEQUENCE: 94
tgccctgtgg actcagttct gg                                         22

<210> SEQ ID NO 95
<211> LENGTH: 25
<212> TYPE: DNA
<213> ORGANISM: Human herpes virus 6A

<400> SEQUENCE: 95
ccatcataca cgattccctg cctct                                      25

<210> SEQ ID NO 96
<211> LENGTH: 21
<212> TYPE: DNA
<213> ORGANISM: Homo sapiens

<400> SEQUENCE: 96
ccattacact accctgcctc t                                          21

<210> SEQ ID NO 97
<211> LENGTH: 20
<212> TYPE: DNA
<213> ORGANISM: Human herpes virus 6A

<400> SEQUENCE: 97
tgctgacata gcactttcgg                                            20

<210> SEQ ID NO 98
<211> LENGTH: 20
<212> TYPE: DNA
<213> ORGANISM: Homo sapiens

<400> SEQUENCE: 98
tgctgagcta gcacttcccg                                            20

<210> SEQ ID NO 99
<211> LENGTH: 24
<212> TYPE: DNA
<213> ORGANISM: Human herpes virus 6A

<400> SEQUENCE: 99
aggcgagggc tgcagcggga cccc                                       24

<210> SEQ ID NO 100
<211> LENGTH: 22
<212> TYPE: DNA
<213> ORGANISM: Homo sapiens

<400> SEQUENCE: 100
aggcggggcg ccgcgggacc gc                                         22

<210> SEQ ID NO 101
<211> LENGTH: 21
<212> TYPE: DNA
<213> ORGANISM: Human herpes virus 6A

<400> SEQUENCE: 101
tctccatagt tgatgtactc a                                              21

<210> SEQ ID NO 102
<211> LENGTH: 20
<212> TYPE: DNA
<213> ORGANISM: Homo sapiens

<400> SEQUENCE: 102
tttccatagg tgatgagtca                                                20

<210> SEQ ID NO 103
<211> LENGTH: 19
<212> TYPE: DNA
<213> ORGANISM: Human herpes virus 6A

<400> SEQUENCE: 103
tgatgtagaa ggttgttta                                                 19

<210> SEQ ID NO 104
<211> LENGTH: 19
<212> TYPE: DNA
<213> ORGANISM: Homo sapiens

<400> SEQUENCE: 104
tgaggtagga ggttgtata                                                 19

<210> SEQ ID NO 105
<211> LENGTH: 17
<212> TYPE: DNA
<213> ORGANISM: Human herpes virus 6A

<400> SEQUENCE: 105
atacgacgct cctttct                                                   17

<210> SEQ ID NO 106
<211> LENGTH: 20
<212> TYPE: DNA
<213> ORGANISM: Homo sapiens

<400> SEQUENCE: 106
atacgacctg ctgcctttct                                                20

<210> SEQ ID NO 107
<211> LENGTH: 21
<212> TYPE: DNA
<213> ORGANISM: Human herpes virus 6A

<400> SEQUENCE: 107
tggtttacgt ccctcacaac a                                              21

<210> SEQ ID NO 108
<211> LENGTH: 21
<212> TYPE: DNA
<213> ORGANISM: Homo sapiens

<400> SEQUENCE: 108
tggtttaccg tcccacatac a                                              21

<210> SEQ ID NO 109
<211> LENGTH: 21
<212> TYPE: DNA
<213> ORGANISM: Human herpes virus 6A

```
<400> SEQUENCE: 109
atttaccgac aacagccctg c                                              21

<210> SEQ ID NO 110
<211> LENGTH: 21
<212> TYPE: DNA
<213> ORGANISM: Homo sapiens

<400> SEQUENCE: 110
acttacagac aagagccttg c                                              21

<210> SEQ ID NO 111
<211> LENGTH: 21
<212> TYPE: DNA
<213> ORGANISM: Human herpes virus 6A

<400> SEQUENCE: 111
tacagttgtt aataaccagc t                                              21

<210> SEQ ID NO 112
<211> LENGTH: 19
<212> TYPE: DNA
<213> ORGANISM: Homo sapiens

<400> SEQUENCE: 112
tacagttgtt caaccagtt                                                 19

<210> SEQ ID NO 113
<211> LENGTH: 23
<212> TYPE: DNA
<213> ORGANISM: Human herpes virus 6A

<400> SEQUENCE: 113
caatgcaatg atattggtca atg                                            23

<210> SEQ ID NO 114
<211> LENGTH: 22
<212> TYPE: DNA
<213> ORGANISM: Homo sapiens

<400> SEQUENCE: 114
cagtgcaatg atattgtcaa ag                                             22

<210> SEQ ID NO 115
<211> LENGTH: 19
<212> TYPE: DNA
<213> ORGANISM: Human herpes virus 6A

<400> SEQUENCE: 115
aggcagagtt ttgttagct                                                 19

<210> SEQ ID NO 116
<211> LENGTH: 19
<212> TYPE: DNA
<213> ORGANISM: Homo sapiens

<400> SEQUENCE: 116
aggcagtgta ttgttagct                                                 19

<210> SEQ ID NO 117
<211> LENGTH: 18
<212> TYPE: DNA
<213> ORGANISM: Human herpes virus 6A
```

```
<400> SEQUENCE: 117
tgtgaaacac ttccatga                                                    18

<210> SEQ ID NO 118
<211> LENGTH: 18
<212> TYPE: DNA
<213> ORGANISM: Homo sapiens

<400> SEQUENCE: 118
tggggaaccc ttccatga                                                    18

<210> SEQ ID NO 119
<211> LENGTH: 21
<212> TYPE: DNA
<213> ORGANISM: Human herpes virus 6A

<400> SEQUENCE: 119
acggacgcga agcgcgtgca g                                                21

<210> SEQ ID NO 120
<211> LENGTH: 20
<212> TYPE: DNA
<213> ORGANISM: Homo sapiens

<400> SEQUENCE: 120
agggacggga cgcggtgcag                                                  20

<210> SEQ ID NO 121
<211> LENGTH: 22
<212> TYPE: DNA
<213> ORGANISM: Human herpes virus 6A

<400> SEQUENCE: 121
cagaaaccac cgtttcgttt tc                                               22

<210> SEQ ID NO 122
<211> LENGTH: 22
<212> TYPE: DNA
<213> ORGANISM: Homo sapiens

<400> SEQUENCE: 122
caaaaaccac agtttctttt gc                                               22

<210> SEQ ID NO 123
<211> LENGTH: 22
<212> TYPE: DNA
<213> ORGANISM: Human herpes virus 6A

<400> SEQUENCE: 123 gagattttc aaaaatgtgc ag                                                22

<210> SEQ ID NO 124
<211> LENGTH: 22
<212> TYPE: DNA
<213> ORGANISM: Homo sapiens

<400> SEQUENCE: 124
gagcttattc ataaaagtgc ag                                               22

<210> SEQ ID NO 125
<211> LENGTH: 18
<212> TYPE: DNA
<213> ORGANISM: Human herpes virus 6A
```

<400> SEQUENCE: 125
cgccagagcg gtgcactt                                            18

<210> SEQ ID NO 126
<211> LENGTH: 18
<212> TYPE: DNA
<213> ORGANISM: Homo sapiens

<400> SEQUENCE: 126
ctccagaggg atgcactt                                            18

<210> SEQ ID NO 127
<211> LENGTH: 19
<212> TYPE: DNA
<213> ORGANISM: Human herpes virus 6A

<400> SEQUENCE: 127
aataaaactg tggggccac                                           19

<210> SEQ ID NO 128
<211> LENGTH: 19
<212> TYPE: DNA
<213> ORGANISM: Homo sapiens

<400> SEQUENCE: 128
actcaaactg tgggggcac                                           19

<210> SEQ ID NO 129
<211> LENGTH: 19
<212> TYPE: DNA
<213> ORGANISM: Human herpes virus 6A

<400> SEQUENCE: 129
gaggtgcttc gattttagg                                           19

<210> SEQ ID NO 130
<211> LENGTH: 19
<212> TYPE: DNA
<213> ORGANISM: Homo sapiens

<400> SEQUENCE: 130
gaagtgcttc gattttggg                                           19

<210> SEQ ID NO 131
<211> LENGTH: 20
<212> TYPE: DNA
<213> ORGANISM: Human herpes virus 6A

<400> SEQUENCE: 131 cagttttcc acaaaaccct                                           20

<210> SEQ ID NO 132
<211> LENGTH: 20
<212> TYPE: DNA
<213> ORGANISM: Homo sapiens

<400> SEQUENCE: 132
cagttttccc aggaatccct                                          20

<210> SEQ ID NO 133
<211> LENGTH: 20
<212> TYPE: DNA
<213> ORGANISM: Human herpes virus 6A

<400> SEQUENCE: 133
aatccatgaa acttaggttt          20

<210> SEQ ID NO 134
<211> LENGTH: 20
<212> TYPE: DNA
<213> ORGANISM: Homo sapiens

<400> SEQUENCE: 134
aatccttgga acctaggtgt          20

<210> SEQ ID NO 135
<211> LENGTH: 18
<212> TYPE: DNA
<213> ORGANISM: Human herpes virus 6A

<400> SEQUENCE: 135
gaatgttaaa gtatgtat            18

<210> SEQ ID NO 136
<211> LENGTH: 20
<212> TYPE: DNA
<213> ORGANISM: Homo sapiens

<400> SEQUENCE: 136
gaatgtaaag aagtatgtat          20

<210> SEQ ID NO 137
<211> LENGTH: 18
<212> TYPE: DNA
<213> ORGANISM: Human herpes virus 6A

<400> SEQUENCE: 137
tgtgttcgct agctcatt            18

<210> SEQ ID NO 138
<211> LENGTH: 18
<212> TYPE: DNA
<213> ORGANISM: Homo sapiens

<400> SEQUENCE: 138
tgtgttctct agatcagt            18

<210> SEQ ID NO 139
<211> LENGTH: 23
<212> TYPE: DNA
<213> ORGANISM: Human herpes virus 6A

<400> SEQUENCE: 139
tgttgtagaa gattgtataa gtt       23

<210> SEQ ID NO 140
<211> LENGTH: 22
<212> TYPE: DNA
<213> ORGANISM: Homo sapiens

<400> SEQUENCE: 140
tgaggtagta gattgtatag tt        22

<210> SEQ ID NO 141
<211> LENGTH: 20
<212> TYPE: DNA
<213> ORGANISM: Human herpes virus 6A -continued

<400> SEQUENCE: 141
gtgtgcggat gttttctgct                                              20

<210> SEQ ID NO 142
<211> LENGTH: 21
<212> TYPE: DNA
<213> ORGANISM: Homo sapiens

<400> SEQUENCE: 142
gtgtgcggaa atgcttctgc t                                            21

<210> SEQ ID NO 143
<211> LENGTH: 19
<212> TYPE: DNA
<213> ORGANISM: Human herpes virus 6A

<400> SEQUENCE: 143
atttagtgag catgatatt                                               19

<210> SEQ ID NO 144
<211> LENGTH: 19
<212> TYPE: DNA
<213> ORGANISM: Homo sapiens

<400> SEQUENCE: 144
atttagtgtg tgtgatatt                                               19

<210> SEQ ID NO 145
<211> LENGTH: 23
<212> TYPE: DNA
<213> ORGANISM: Human herpes virus 6A

<400> SEQUENCE: 145
aattgtcttc catgttagac tgt                                          23

<210> SEQ ID NO 146
<211> LENGTH: 22
<212> TYPE: DNA
<213> ORGANISM: Homo sapiens

<400> SEQUENCE: 146
aagtgcttcc atgtttgagt gt                                           22

<210> SEQ ID NO 147
<211> LENGTH: 17
<212> TYPE: DNA
<213> ORGANISM: Human herpes virus 6A

<400> SEQUENCE: 147
gggcccgccc tcgtcct                                                 17

<210> SEQ ID NO 148
<211> LENGTH: 18
<212> TYPE: DNA
<213> ORGANISM: Homo sapiens

<400> SEQUENCE: 148
gggccccccc tcaatcct                                                18

<210> SEQ ID NO 149
<211> LENGTH: 18
<212> TYPE: DNA
<213> ORGANISM: Human herpes virus 6A

```
<400> SEQUENCE: 149
tatttttatg taaaagct                                          18

<210> SEQ ID NO 150
<211> LENGTH: 18
<212> TYPE: DNA
<213> ORGANISM: Homo sapiens

<400> SEQUENCE: 150
taattttatg tataagct                                          18

<210> SEQ ID NO 151
<211> LENGTH: 21
<212> TYPE: DNA
<213> ORGANISM: Human herpes virus 6A

<400> SEQUENCE: 151
agaccaagcg gttgtcattt t                                      21

<210> SEQ ID NO 152
<211> LENGTH: 20
<212> TYPE: DNA
<213> ORGANISM: Homo sapiens

<400> SEQUENCE: 152
agaccatggg ttctcattgt                                        20

<210> SEQ ID NO 153
<211> LENGTH: 19
<212> TYPE: DNA
<213> ORGANISM: Human herpes virus 6A

<400> SEQUENCE: 153
atcacttaga cacggccag                                         19

<210> SEQ ID NO 154
<211> LENGTH: 20
<212> TYPE: DNA
<213> ORGANISM: Homo sapiens

<400> SEQUENCE: 154
atcactaacc acacggccag                                        20

<210> SEQ ID NO 155
<211> LENGTH: 20
<212> TYPE: DNA
<213> ORGANISM: Human herpes virus 6A

<400> SEQUENCE: 155
tgatcatctc ccatggttcc                                        20

<210> SEQ ID NO 156
<211> LENGTH: 20
<212> TYPE: DNA
<213> ORGANISM: Homo sapiens

<400> SEQUENCE: 156
tgctcatacc ccatggtttc                                        20

<210> SEQ ID NO 157
<211> LENGTH: 19
<212> TYPE: DNA
<213> ORGANISM: Human herpes virus 6A
```

```
<400> SEQUENCE: 157
acaggagagc gaggtcgca                                                  19

<210> SEQ ID NO 158
<211> LENGTH: 21
<212> TYPE: DNA
<213> ORGANISM: Homo sapiens

<400> SEQUENCE: 158
acagtagagg gaggaatcgc a                                               21

<210> SEQ ID NO 159
<211> LENGTH: 22
<212> TYPE: DNA
<213> ORGANISM: Human herpes virus 6A

<400> SEQUENCE: 159
gcttttattt ccacttatga ga                                              22

<210> SEQ ID NO 160
<211> LENGTH: 19
<212> TYPE: DNA
<213> ORGANISM: Homo sapiens

<400> SEQUENCE: 160
gctttttatt cctatgtga                                                  19

<210> SEQ ID NO 161
<211> LENGTH: 21
<212> TYPE: DNA
<213> ORGANISM: Human herpes virus 6A

<400> SEQUENCE: 161
taaacacatg gtggttctcc t                                               21

<210> SEQ ID NO 162
<211> LENGTH: 23
<212> TYPE: DNA
<213> ORGANISM: Homo sapiens

<400> SEQUENCE: 162
taaatcccat ggtgccttct cct                                             23

<210> SEQ ID NO 163
<211> LENGTH: 21
<212> TYPE: DNA
<213> ORGANISM: Human herpes virus 6A

<400> SEQUENCE: 163
agggcggctg gcttcccttt g                                               21

<210> SEQ ID NO 164
<211> LENGTH: 19
<212> TYPE: DNA
<213> ORGANISM: Homo sapiens

<400> SEQUENCE: 164
aggggctggc tttcctctg                                                  19

<210> SEQ ID NO 165
<211> LENGTH: 20
<212> TYPE: DNA
<213> ORGANISM: Human herpes virus 6A
```

```
<400> SEQUENCE: 165
ctgagacccc taatttgtta                                          20

<210> SEQ ID NO 166
<211> LENGTH: 19
<212> TYPE: DNA
<213> ORGANISM: Homo sapiens

<400> SEQUENCE: 166
ctgagaccct aacttgtga                                           19

<210> SEQ ID NO 167
<211> LENGTH: 21
<212> TYPE: DNA
<213> ORGANISM: Human herpes virus 6A

<400> SEQUENCE: 167
tgacggtctg cacttctgtg c                                        21

<210> SEQ ID NO 168
<211> LENGTH: 22
<212> TYPE: DNA
<213> ORGANISM: Homo sapiens

<400> SEQUENCE: 168
tgcctgtcta cacttgctgt gc                                       22

<210> SEQ ID NO 169
<211> LENGTH: 18
<212> TYPE: DNA
<213> ORGANISM: Human herpes virus 6A

<400> SEQUENCE: 169
gtggtccgcg cgtgtcgc                                            18

<210> SEQ ID NO 170
<211> LENGTH: 20
<212> TYPE: DNA
<213> ORGANISM: Homo sapiens

<400> SEQUENCE: 170
gtggtccgtg gcgcgttcgc                                          20

<210> SEQ ID NO 171
<211> LENGTH: 17
<212> TYPE: DNA
<213> ORGANISM: Human herpes virus 6A

<400> SEQUENCE: 171
ccaccaccgc tgacagt                                             17

<210> SEQ ID NO 172
<211> LENGTH: 20
<212> TYPE: DNA
<213> ORGANISM: Homo sapiens

<400> SEQUENCE: 172
ccaccaccgt gtctgacact                                          20

<210> SEQ ID NO 173
<211> LENGTH: 20
<212> TYPE: DNA
<213> ORGANISM: Human herpes virus 6A
```

-continued

<400> SEQUENCE: 173
agccagagta gtcttgatgt                                              20

<210> SEQ ID NO 174
<211> LENGTH: 19
<212> TYPE: DNA
<213> ORGANISM: Homo sapiens

<400> SEQUENCE: 174
agccaggaag tattgatgt                                               19

<210> SEQ ID NO 175
<211> LENGTH: 21
<212> TYPE: DNA
<213> ORGANISM: Human herpes virus 6A

<400> SEQUENCE: 175
cgtctctacc cccgagtgtt t                                            21

<210> SEQ ID NO 176
<211> LENGTH: 20
<212> TYPE: DNA
<213> ORGANISM: Homo sapiens

<400> SEQUENCE: 176
cgtcttaccc agcagtgttt                                              20

<210> SEQ ID NO 177
<211> LENGTH: 19
<212> TYPE: DNA
<213> ORGANISM: Human herpes virus 6A

<400> SEQUENCE: 177
cagcaacaaa atttcatcc                                               19

<210> SEQ ID NO 178
<211> LENGTH: 19
<212> TYPE: DNA
<213> ORGANISM: Homo sapiens

<400> SEQUENCE: 178
cagtaacaaa gattcatcc                                               19

<210> SEQ ID NO 179
<211> LENGTH: 20
<212> TYPE: DNA
<213> ORGANISM: Human herpes virus 6A

<400> SEQUENCE: 179
ataccagtcg atgtcgctgt                                              20

<210> SEQ ID NO 180
<211> LENGTH: 19
<212> TYPE: DNA
<213> ORGANISM: Homo sapiens

<400> SEQUENCE: 180
acaccagtcg atgggctgt                                               19

<210> SEQ ID NO 181
<211> LENGTH: 21
<212> TYPE: DNA
<213> ORGANISM: Human herpes virus 6A

```
<400> SEQUENCE: 181
tggcaacggg agacagtttt g                                      21

<210> SEQ ID NO 182
<211> LENGTH: 20
<212> TYPE: DNA
<213> ORGANISM: Homo sapiens

<400> SEQUENCE: 182
tagcagcggg aacagttctg                                        20

<210> SEQ ID NO 183
<211> LENGTH: 20
<212> TYPE: DNA
<213> ORGANISM: Human herpes virus 6A

<400> SEQUENCE: 183
agccagagta gtcttgatgt                                        20

<210> SEQ ID NO 184
<211> LENGTH: 19
<212> TYPE: DNA
<213> ORGANISM: Homo sapiens

<400> SEQUENCE: 184
agccaggaag tattgatgt                                         19

<210> SEQ ID NO 185
<211> LENGTH: 20
<212> TYPE: DNA
<213> ORGANISM: Human herpes virus 6A

<400> SEQUENCE: 185
cgtacagtga ttgatactgc                                        20

<210> SEQ ID NO 186
<211> LENGTH: 20
<212> TYPE: DNA
<213> ORGANISM: Homo sapiens

<400> SEQUENCE: 186
cgtaccgtga gtaataatgc                                        20

<210> SEQ ID NO 187
<211> LENGTH: 18
<212> TYPE: DNA
<213> ORGANISM: Human herpes virus 6A

<400> SEQUENCE: 187
ctaataggtt tccattaa                                          18

<210> SEQ ID NO 188
<211> LENGTH: 18
<212> TYPE: DNA
<213> ORGANISM: Homo sapiens

<400> SEQUENCE: 188
ctagtaggtg tccagtaa                                          18

<210> SEQ ID NO 189
<211> LENGTH: 18
<212> TYPE: DNA
<213> ORGANISM: Human herpes virus 6A
```

```
<400> SEQUENCE: 189 ccccttagggt attggggt                                              18

<210> SEQ ID NO 190
<211> LENGTH: 18
<212> TYPE: DNA
<213> ORGANISM: Homo sapiens

<400> SEQUENCE: 190 ccccctagggc attggtgt                                              18

<210> SEQ ID NO 191
<211> LENGTH: 18
<212> TYPE: DNA
<213> ORGANISM: Human herpes virus 6A

<400> SEQUENCE: 191
tcctgctctc agggctcc                                               18

<210> SEQ ID NO 192
<211> LENGTH: 18
<212> TYPE: DNA
<213> ORGANISM: Homo sapiens

<400> SEQUENCE: 192
tccggttctc agggctcc                                               18

<210> SEQ ID NO 193
<211> LENGTH: 20
<212> TYPE: DNA
<213> ORGANISM: Human herpes virus 6A

<400> SEQUENCE: 193
ctgtgcgggg agggcggctg                                             20

<210> SEQ ID NO 194
<211> LENGTH: 21
<212> TYPE: DNA
<213> ORGANISM: Homo sapiens

<400> SEQUENCE: 194
ctgtgcgtgt gacagcggct g                                           21

<210> SEQ ID NO 195
<211> LENGTH: 20
<212> TYPE: DNA
<213> ORGANISM: Human herpes virus 6A

<400> SEQUENCE: 195
aggtggaggt ttctttggag                                             20

<210> SEQ ID NO 196
<211> LENGTH: 18
<212> TYPE: DNA
<213> ORGANISM: Homo sapiens

<400> SEQUENCE: 196
aggtgaggtt cttgggag                                               18

<210> SEQ ID NO 197
<211> LENGTH: 22
<212> TYPE: DNA
<213> ORGANISM: Human herpes virus 6A
```

-continued

```
<400> SEQUENCE: 197
aaattgattc ccttaggtgg gt                                             22

<210> SEQ ID NO 198
<211> LENGTH: 22
<212> TYPE: DNA
<213> ORGANISM: Homo sapiens

<400> SEQUENCE: 198
aaagtgcttc tctttggtgg gt                                             22

<210> SEQ ID NO 199
<211> LENGTH: 21
<212> TYPE: DNA
<213> ORGANISM: Human herpes virus 6A

<400> SEQUENCE: 199
ctcgttcttg ggccacctca g                                              21

<210> SEQ ID NO 200
<211> LENGTH: 20
<212> TYPE: DNA
<213> ORGANISM: Homo sapiens

<400> SEQUENCE: 200
ctcggtctga ggcccctcag                                                20

<210> SEQ ID NO 201
<211> LENGTH: 23
<212> TYPE: DNA
<213> ORGANISM: Human herpes virus 6A

<400> SEQUENCE: 201
tcagaaaacg atttactgtg agc                                            23

<210> SEQ ID NO 202
<211> LENGTH: 22
<212> TYPE: DNA
<213> ORGANISM: Homo sapiens

<400> SEQUENCE: 202
tcagcaaaca tttattgtgt gc                                             22

<210> SEQ ID NO 203
<211> LENGTH: 20
<212> TYPE: DNA
<213> ORGANISM: Human herpes virus 6A

<400> SEQUENCE: 203
tctagatgta gaactttctg                                                20

<210> SEQ ID NO 204
<211> LENGTH: 21
<212> TYPE: DNA
<213> ORGANISM: Homo sapiens

<400> SEQUENCE: 204
tctagaggga agcactttct g                                              21

<210> SEQ ID NO 205
<211> LENGTH: 19
<212> TYPE: DNA
<213> ORGANISM: Human herpes virus 6A
```

```
<400> SEQUENCE: 205
gttgggatcg gtcagtgtt                                              19

<210> SEQ ID NO 206
<211> LENGTH: 21
<212> TYPE: DNA
<213> ORGANISM: Homo sapiens

<400> SEQUENCE: 206
gttgggatcg gttgcaatgc t                                           21

<210> SEQ ID NO 207
<211> LENGTH: 20
<212> TYPE: DNA
<213> ORGANISM: Human herpes virus 6A

<400> SEQUENCE: 207
ctagtctaga ttcatccagt                                             20

<210> SEQ ID NO 208
<211> LENGTH: 20
<212> TYPE: DNA
<213> ORGANISM: Homo sapiens

<400> SEQUENCE: 208
ctagtcctga ctcagccagt                                             20

<210> SEQ ID NO 209
<211> LENGTH: 20
<212> TYPE: DNA
<213> ORGANISM: Human herpes virus 6A

<400> SEQUENCE: 209
aataaccaca tttggttttg                                             20

<210> SEQ ID NO 210
<211> LENGTH: 20
<212> TYPE: DNA
<213> ORGANISM: Homo sapiens

<400> SEQUENCE: 210
aagaacctca gttgcttttg                                             20

<210> SEQ ID NO 211
<211> LENGTH: 19
<212> TYPE: DNA
<213> ORGANISM: Human herpes virus 6A

<400> SEQUENCE: 211
ctccgacatc tttgcatta                                              19

<210> SEQ ID NO 212
<211> LENGTH: 19
<212> TYPE: DNA
<213> ORGANISM: Homo sapiens

<400> SEQUENCE: 212
ctcctacata ttagcatta                                              19

<210> SEQ ID NO 213
<211> LENGTH: 20
<212> TYPE: DNA
<213> ORGANISM: Human herpes virus 6A
```

```
<400> SEQUENCE: 213
aacattttct ggtatcgatg                                              20

<210> SEQ ID NO 214
<211> LENGTH: 20
<212> TYPE: DNA
<213> ORGANISM: Homo sapiens

<400> SEQUENCE: 214
aacactgtct ggtaacgatg                                              20

<210> SEQ ID NO 215
<211> LENGTH: 18
<212> TYPE: DNA
<213> ORGANISM: Human herpes virus 6A

<400> SEQUENCE: 215
acagacgatt ttagagga                                                18

<210> SEQ ID NO 216
<211> LENGTH: 20
<212> TYPE: DNA
<213> ORGANISM: Homo sapiens

<400> SEQUENCE: 216
acagattcga ttctagggga                                              20

<210> SEQ ID NO 217
<211> LENGTH: 18
<212> TYPE: DNA
<213> ORGANISM: Human herpes virus 6A

<400> SEQUENCE: 217
ggaattgggg cagaaggc                                                18

<210> SEQ ID NO 218
<211> LENGTH: 19
<212> TYPE: DNA
<213> ORGANISM: Homo sapiens

<400> SEQUENCE: 218
ggacttaggg tcagaaggc                                               19

<210> SEQ ID NO 219
<211> LENGTH: 19
<212> TYPE: DNA
<213> ORGANISM: Human herpes virus 6A

<400> SEQUENCE: 219
tacagtactc gatagctga                                               19

<210> SEQ ID NO 220
<211> LENGTH: 20
<212> TYPE: DNA
<213> ORGANISM: Homo sapiens

<400> SEQUENCE: 220
tacagtactg tgataactga                                              20

<210> SEQ ID NO 221
<211> LENGTH: 19
<212> TYPE: DNA
<213> ORGANISM: Human herpes virus 6A
```

```
<400> SEQUENCE: 221
tttaatatgg cggcagttg                                            19

<210> SEQ ID NO 222
<211> LENGTH: 19
<212> TYPE: DNA
<213> ORGANISM: Homo sapiens

<400> SEQUENCE: 222
tttaacatgg aggcacttg                                            19

<210> SEQ ID NO 223
<211> LENGTH: 20
<212> TYPE: DNA
<213> ORGANISM: Human herpes virus 6A

<400> SEQUENCE: 223
atgaagataa ttatggaaat                                           20

<210> SEQ ID NO 224
<211> LENGTH: 20
<212> TYPE: DNA
<213> ORGANISM: Homo sapiens

<400> SEQUENCE: 224
atggagatag atatagaaat                                           20

<210> SEQ ID NO 225
<211> LENGTH: 19
<212> TYPE: DNA
<213> ORGANISM: Human herpes virus 6A

<400> SEQUENCE: 225
tgatgtagaa ggttgttta                                            19

<210> SEQ ID NO 226
<211> LENGTH: 19
<212> TYPE: DNA
<213> ORGANISM: Homo sapiens

<400> SEQUENCE: 226
tgaggtagta ggttgtata                                            19

<210> SEQ ID NO 227
<211> LENGTH: 21
<212> TYPE: DNA
<213> ORGANISM: Human herpes virus 6A

<400> SEQUENCE: 227
gatggtcttc tttttagagg c                                         21

<210> SEQ ID NO 228
<211> LENGTH: 22
<212> TYPE: DNA
<213> ORGANISM: Homo sapiens

<400> SEQUENCE: 228
gaaagtgctt cctttagag gc                                         22

<210> SEQ ID NO 229
<211> LENGTH: 19
<212> TYPE: DNA
<213> ORGANISM: Human herpes virus 6A
```

<210> SEQ ID NO 229
<211> LENGTH: 19
<212> TYPE: DNA
<213> ORGANISM: Homo sapiens

<400> SEQUENCE: 229
ttcttcagta gagacttta                                                  19

<210> SEQ ID NO 230
<211> LENGTH: 20
<212> TYPE: DNA
<213> ORGANISM: Homo sapiens

<400> SEQUENCE: 230
ttcttcagtg gcaagcttta                                                 20

<210> SEQ ID NO 231
<211> LENGTH: 20
<212> TYPE: DNA
<213> ORGANISM: Human herpes virus 6A

<400> SEQUENCE: 231
tgaattcctg gacatggtga                                                 20

<210> SEQ ID NO 232
<211> LENGTH: 19
<212> TYPE: DNA
<213> ORGANISM: Homo sapiens

<400> SEQUENCE: 232
tgggttcctg gcatgctga                                                  19

<210> SEQ ID NO 233
<211> LENGTH: 21
<212> TYPE: DNA
<213> ORGANISM: Human herpes virus 6A

<400> SEQUENCE: 233
tggatgtgct cctcagttgt c                                               21

<210> SEQ ID NO 234
<211> LENGTH: 19
<212> TYPE: DNA
<213> ORGANISM: Homo sapiens

<400> SEQUENCE: 234
tggatggctc ctccatgtc                                                  19

<210> SEQ ID NO 235
<211> LENGTH: 18
<212> TYPE: DNA
<213> ORGANISM: Human herpes virus 6A

<400> SEQUENCE: 235
gctgacgtat tttctgga                                                   18

<210> SEQ ID NO 236
<211> LENGTH: 18
<212> TYPE: DNA
<213> ORGANISM: Homo sapiens

<400> SEQUENCE: 236
gctgacatat ttactaga                                                   18

<210> SEQ ID NO 237
<211> LENGTH: 19
<212> TYPE: DNA
<213> ORGANISM: Human herpes virus 6A

<400> SEQUENCE: 237
ccactgacct ttaactgta                                               19

<210> SEQ ID NO 238
<211> LENGTH: 19
<212> TYPE: DNA
<213> ORGANISM: Homo sapiens

<400> SEQUENCE: 238
ccactgaccg ttgactgta                                               19

<210> SEQ ID NO 239
<211> LENGTH: 18
<212> TYPE: DNA
<213> ORGANISM: Human herpes virus 6A

<400> SEQUENCE: 239
aaaacgtacc actactga                                                18

<210> SEQ ID NO 240
<211> LENGTH: 19
<212> TYPE: DNA
<213> ORGANISM: Homo sapiens

<400> SEQUENCE: 240
aaaccgttac cattactga                                               19

<210> SEQ ID NO 241
<211> LENGTH: 21
<212> TYPE: DNA
<213> ORGANISM: Human herpes virus 6A

<400> SEQUENCE: 241
aacatacttc ctgtccgtga g                                            21

<210> SEQ ID NO 242
<211> LENGTH: 21
<212> TYPE: DNA
<213> ORGANISM: Homo sapiens

<400> SEQUENCE: 242
aacattcaac ctgtcggtga g                                            21

<210> SEQ ID NO 243
<211> LENGTH: 20
<212> TYPE: DNA
<213> ORGANISM: Human herpes virus 6A

<400> SEQUENCE: 243
cgagcagtca cagtttcagt                                              20

<210> SEQ ID NO 244
<211> LENGTH: 20
<212> TYPE: DNA
<213> ORGANISM: Homo sapiens

<400> SEQUENCE: 244
cgaggagctc acagtctagt                                              20

<210> SEQ ID NO 245
<211> LENGTH: 23
<212> TYPE: DNA
<213> ORGANISM: Human herpes virus 6A

<400> SEQUENCE: 245
ggagagaaca gagctggtcc tga                                            23

<210> SEQ ID NO 246
<211> LENGTH: 21
<212> TYPE: DNA
<213> ORGANISM: Homo sapiens

<400> SEQUENCE: 246
ggagagaaag gcagttcctg a                                              21

<210> SEQ ID NO 247
<211> LENGTH: 20
<212> TYPE: DNA
<213> ORGANISM: Human herpes virus 6A

<400> SEQUENCE: 247
tctagatgta gaactttctg                                                20

<210> SEQ ID NO 248
<211> LENGTH: 21
<212> TYPE: DNA
<213> ORGANISM: Homo sapiens

<400> SEQUENCE: 248
tctagaggga agcactttct g                                              21

<210> SEQ ID NO 249
<211> LENGTH: 21
<212> TYPE: DNA
<213> ORGANISM: Human herpes virus 6A

<400> SEQUENCE: 249
accggcataa aatttagttt t                                              21

<210> SEQ ID NO 250
<211> LENGTH: 22
<212> TYPE: DNA
<213> ORGANISM: Homo sapiens

<400> SEQUENCE: 250
acctggcata caatgtagat tt                                             22

<210> SEQ ID NO 251
<211> LENGTH: 21
<212> TYPE: DNA
<213> ORGANISM: Human herpes virus 6A

<400> SEQUENCE: 251
tcctcttcct cctcctcccc g                                              21

<210> SEQ ID NO 252
<211> LENGTH: 21
<212> TYPE: DNA
<213> ORGANISM: Homo sapiens

<400> SEQUENCE: 252
tcctcttctc cctcctccca g                                              21

<210> SEQ ID NO 253
<211> LENGTH: 20
<212> TYPE: DNA
<213> ORGANISM: Human herpes virus 6A

```
<400> SEQUENCE: 253
tgggtgatgg atgtgcactt                                              20

<210> SEQ ID NO 254
<211> LENGTH: 20
<212> TYPE: DNA
<213> ORGANISM: Homo sapiens

<400> SEQUENCE: 254
tgggaggtgg atgtttactt                                              20

<210> SEQ ID NO 255
<211> LENGTH: 19
<212> TYPE: DNA
<213> ORGANISM: Human herpes virus 6A

<400> SEQUENCE: 255
atgagttcat tgaatatca                                               19

<210> SEQ ID NO 256
<211> LENGTH: 20
<212> TYPE: DNA
<213> ORGANISM: Homo sapiens

<400> SEQUENCE: 256
atgagctcat tgtaatatga                                              20

<210> SEQ ID NO 257
<211> LENGTH: 21
<212> TYPE: DNA
<213> ORGANISM: Human herpes virus 6A

<400> SEQUENCE: 257
ttcatatcca tatattttt t                                             21

<210> SEQ ID NO 258
<211> LENGTH: 21
<212> TYPE: DNA
<213> ORGANISM: Homo sapiens

<400> SEQUENCE: 258
ttcctatgca tatacttctt t                                            21

<210> SEQ ID NO 259
<211> LENGTH: 21
<212> TYPE: DNA
<213> ORGANISM: Human herpes virus 6A

<400> SEQUENCE: 259
ctcctcctcc tcttcctcct c                                            21

<210> SEQ ID NO 260
<211> LENGTH: 19
<212> TYPE: DNA
<213> ORGANISM: Homo sapiens

<400> SEQUENCE: 260
ccccacctcc tctctcctc                                               19

<210> SEQ ID NO 261
<211> LENGTH: 20
<212> TYPE: DNA
<213> ORGANISM: Human herpes virus 6A
```

-continued

```
<400> SEQUENCE: 261
acagtagtca ccggattggt                                              20

<210> SEQ ID NO 262
<211> LENGTH: 20
<212> TYPE: DNA
<213> ORGANISM: Homo sapiens

<400> SEQUENCE: 262
acagtagtct gcacattggt                                              20

<210> SEQ ID NO 263
<211> LENGTH: 20
<212> TYPE: DNA
<213> ORGANISM: Human herpes virus 6A

<400> SEQUENCE: 263
gacctaggcc cgtacctcag                                              20

<210> SEQ ID NO 264
<211> LENGTH: 19
<212> TYPE: DNA
<213> ORGANISM: Homo sapiens

<400> SEQUENCE: 264
gacctggccc agacctcag                                               19

<210> SEQ ID NO 265
<211> LENGTH: 18
<212> TYPE: DNA
<213> ORGANISM: Human herpes virus 6A

<400> SEQUENCE: 265
aacacgaaac tgcttgcg                                                18

<210> SEQ ID NO 266
<211> LENGTH: 18
<212> TYPE: DNA
<213> ORGANISM: Homo sapiens

<400> SEQUENCE: 266
aacaagaaac tgcctgag                                                18

<210> SEQ ID NO 267
<211> LENGTH: 19
<212> TYPE: DNA
<213> ORGANISM: Human herpes virus 6A

<400> SEQUENCE: 267
agtttatcag aatgatatt                                               19

<210> SEQ ID NO 268
<211> LENGTH: 19
<212> TYPE: DNA
<213> ORGANISM: Homo sapiens

<400> SEQUENCE: 268
agcttatcag actgatgtt                                               19

<210> SEQ ID NO 269
<211> LENGTH: 21
<212> TYPE: DNA
<213> ORGANISM: Human herpes virus 6A
```

```
<400> SEQUENCE: 269
ctgctcctgc tctcagggct c                                              21

<210> SEQ ID NO 270
<211> LENGTH: 21
<212> TYPE: DNA
<213> ORGANISM: Homo sapiens

<400> SEQUENCE: 270
ctgactccta gtccagggct c                                              21

<210> SEQ ID NO 271
<211> LENGTH: 21
<212> TYPE: DNA
<213> ORGANISM: Human herpes virus 6A

<400> SEQUENCE: 271
gtagactagt ttgattatgt t                                              21

<210> SEQ ID NO 272
<211> LENGTH: 19
<212> TYPE: DNA
<213> ORGANISM: Homo sapiens

<400> SEQUENCE: 272
gaagactagt gattttgtt                                                 19

<210> SEQ ID NO 273
<211> LENGTH: 20
<212> TYPE: DNA
<213> ORGANISM: Human herpes virus 6A

<400> SEQUENCE: 273
gcttccatct gttttagcag                                                20

<210> SEQ ID NO 274
<211> LENGTH: 18
<212> TYPE: DNA
<213> ORGANISM: Homo sapiens

<400> SEQUENCE: 274
gcttccatgt tttagtag                                                  18

<210> SEQ ID NO 275
<211> LENGTH: 20
<212> TYPE: DNA
<213> ORGANISM: Human herpes virus 6A

<400> SEQUENCE: 275
cgccgcgtct tgccaagtgg                                                20

<210> SEQ ID NO 276
<211> LENGTH: 20
<212> TYPE: DNA
<213> ORGANISM: Homo sapiens

<400> SEQUENCE: 276
cgcctgttct tgccaggtgg                                                20

<210> SEQ ID NO 277
<211> LENGTH: 20
<212> TYPE: DNA
<213> ORGANISM: Human herpes virus 6A
```

-continued

<400> SEQUENCE: 277
acagtagtca ccggattggt                                             20

<210> SEQ ID NO 278
<211> LENGTH: 20
<212> TYPE: DNA
<213> ORGANISM: Homo sapiens

<400> SEQUENCE: 278
acagtagtct gcacattggt                                             20

<210> SEQ ID NO 279
<211> LENGTH: 22
<212> TYPE: DNA
<213> ORGANISM: Human herpes virus 6A

<400> SEQUENCE: 279
gaagttattt tcgtggttga tt                                          22

<210> SEQ ID NO 280
<211> LENGTH: 20
<212> TYPE: DNA
<213> ORGANISM: Homo sapiens

<400> SEQUENCE: 280
gaagttgttc gtggtggatt                                             20

<210> SEQ ID NO 281
<211> LENGTH: 19
<212> TYPE: DNA
<213> ORGANISM: Human herpes virus 6A

<400> SEQUENCE: 281
gagtttcgtg atgtcttgc                                              19

<210> SEQ ID NO 282
<211> LENGTH: 19
<212> TYPE: DNA
<213> ORGANISM: Homo sapiens

<400> SEQUENCE: 282
gagtcttgtg atgtcttgc                                              19

<210> SEQ ID NO 283
<211> LENGTH: 18
<212> TYPE: DNA
<213> ORGANISM: Human herpes virus 6A

<400> SEQUENCE: 283
gatataatat ggttcctg                                               18

<210> SEQ ID NO 284
<211> LENGTH: 19
<212> TYPE: DNA
<213> ORGANISM: Homo sapiens

<400> SEQUENCE: 284
gataaaatat tggtacctg                                              19

<210> SEQ ID NO 285
<211> LENGTH: 18
<212> TYPE: DNA
<213> ORGANISM: Human herpes virus 6A

```
<400> SEQUENCE: 285
gtcgtgcacg gcactcct                                                   18

<210> SEQ ID NO 286
<211> LENGTH: 18
<212> TYPE: DNA
<213> ORGANISM: Homo sapiens

<400> SEQUENCE: 286
gtcatacacg gctctcct                                                   18

<210> SEQ ID NO 287
<211> LENGTH: 22
<212> TYPE: DNA
<213> ORGANISM: Human herpes virus 6A

<400> SEQUENCE: 287
acgggttaga gattttggaa gc                                              22

<210> SEQ ID NO 288
<211> LENGTH: 21
<212> TYPE: DNA
<213> ORGANISM: Homo sapiens

<400> SEQUENCE: 288
acgggttagg ctcttgggag c                                               21

<210> SEQ ID NO 289
<211> LENGTH: 19
<212> TYPE: DNA
<213> ORGANISM: Human herpes virus 6A

<400> SEQUENCE: 289
cagccatcgg cagatccac                                                  19

<210> SEQ ID NO 290
<211> LENGTH: 20
<212> TYPE: DNA
<213> ORGANISM: Homo sapiens

<400> SEQUENCE: 290
cagtccatgg gcatatacac                                                 20

<210> SEQ ID NO 291
<211> LENGTH: 18
<212> TYPE: DNA
<213> ORGANISM: Human herpes virus 6A

<400> SEQUENCE: 291
atacgcgccg actctctc                                                   18

<210> SEQ ID NO 292
<211> LENGTH: 20
<212> TYPE: DNA
<213> ORGANISM: Homo sapiens

<400> SEQUENCE: 292
atacaagggc agactctctc                                                 20

<210> SEQ ID NO 293
<211> LENGTH: 23
<212> TYPE: DNA
<213> ORGANISM: Human herpes virus 6A
```

```
<400> SEQUENCE: 293
aggtagtgcg tcctggtgtt ggg                                    23

<210> SEQ ID NO 294
<211> LENGTH: 21
<212> TYPE: DNA
<213> ORGANISM: Homo sapiens

<400> SEQUENCE: 294
aggtagtttc ctgttgttgg g                                      21

<210> SEQ ID NO 295
<211> LENGTH: 21
<212> TYPE: DNA
<213> ORGANISM: Human herpes virus 6A

<400> SEQUENCE: 295
gtagcattcg acagggctgt c                                      21

<210> SEQ ID NO 296
<211> LENGTH: 21
<212> TYPE: DNA
<213> ORGANISM: Homo sapiens

<400> SEQUENCE: 296
gcagcattgt acagggctat c                                      21

<210> SEQ ID NO 297
<211> LENGTH: 22
<212> TYPE: DNA
<213> ORGANISM: Human herpes virus 6A

<400> SEQUENCE: 297
agaattgtag gcttccatct gt                                     22

<210> SEQ ID NO 298
<211> LENGTH: 22
<212> TYPE: DNA
<213> ORGANISM: Homo sapiens

<400> SEQUENCE: 298
agaattgtgg ctggacatct gt                                     22

<210> SEQ ID NO 299
<211> LENGTH: 21
<212> TYPE: DNA
<213> ORGANISM: Human herpes virus 6A

<400> SEQUENCE: 299
gtggtttctt ttggagcagt t                                      21

<210> SEQ ID NO 300
<211> LENGTH: 20
<212> TYPE: DNA
<213> ORGANISM: Homo sapiens

<400> SEQUENCE: 300
gtgccttctt ttggagcgtt                                        20

<210> SEQ ID NO 301
<211> LENGTH: 21
<212> TYPE: DNA
<213> ORGANISM: Human herpes virus 6A
```

-continued

```
<400> SEQUENCE: 301
caatacaacc taccctcttt c                                          21

<210> SEQ ID NO 302
<211> LENGTH: 21
<212> TYPE: DNA
<213> ORGANISM: Homo sapiens

<400> SEQUENCE: 302
ctatacaatc tactgtcttt c                                          21

<210> SEQ ID NO 303
<211> LENGTH: 19
<212> TYPE: DNA
<213> ORGANISM: Human herpes virus 6A

<400> SEQUENCE: 303
attttaacat tgaagtttt                                             19

<210> SEQ ID NO 304
<211> LENGTH: 21
<212> TYPE: DNA
<213> ORGANISM: Homo sapiens

<400> SEQUENCE: 304
actttaacat ggaagtgctt t                                          21

<210> SEQ ID NO 305
<211> LENGTH: 20
<212> TYPE: DNA
<213> ORGANISM: Human herpes virus 6A

<400> SEQUENCE: 305
ataataactg gataatcttt                                            20

<210> SEQ ID NO 306
<211> LENGTH: 20
<212> TYPE: DNA
<213> ORGANISM: Homo sapiens

<400> SEQUENCE: 306
ataatacatg gttgatcttt                                            20

<210> SEQ ID NO 307
<211> LENGTH: 18
<212> TYPE: DNA
<213> ORGANISM: Human herpes virus 6A

<400> SEQUENCE: 307
agtcttatgt gctgccga                                              18

<210> SEQ ID NO 308
<211> LENGTH: 20
<212> TYPE: DNA
<213> ORGANISM: Homo sapiens

<400> SEQUENCE: 308
agtattaact gtgctgctga                                            20

<210> SEQ ID NO 309
<211> LENGTH: 24
<212> TYPE: DNA
<213> ORGANISM: Human herpes virus 6A
```

-continued

<210> SEQ ID NO 310
<211> LENGTH: 21
<212> TYPE: DNA
<213> ORGANISM: Homo sapiens

<400> SEQUENCE: 310
aagtgctgcg acatttgagc g                                             21

<210> SEQ ID NO 311
<211> LENGTH: 19
<212> TYPE: DNA
<213> ORGANISM: Human herpes virus 6A

<400> SEQUENCE: 311
ataatgatgg ctccggtgt                                                19

<210> SEQ ID NO 312
<211> LENGTH: 22
<212> TYPE: DNA
<213> ORGANISM: Homo sapiens

<400> SEQUENCE: 312
atcatgatgg gctcctcggt gt                                            22

<210> SEQ ID NO 313
<211> LENGTH: 21
<212> TYPE: DNA
<213> ORGANISM: Human herpes virus 6A

<400> SEQUENCE: 313
taaacacatg gtggttctcc t                                             21

<210> SEQ ID NO 314
<211> LENGTH: 20
<212> TYPE: DNA
<213> ORGANISM: Homo sapiens

<400> SEQUENCE: 314
tcaacacttg ctggtttcct                                               20

<210> SEQ ID NO 315
<211> LENGTH: 18
<212> TYPE: DNA
<213> ORGANISM: Human herpes virus 6A

<400> SEQUENCE: 315
ctgcacactg ttgtttt                                                  18

<210> SEQ ID NO 316
<211> LENGTH: 18
<212> TYPE: DNA
<213> ORGANISM: Homo sapiens

<400> SEQUENCE: 316
cagcacactg tggtttgt                                                 18

<210> SEQ ID NO 317
<211> LENGTH: 20
<212> TYPE: DNA
<213> ORGANISM: Human herpes virus 6A

```
<400> SEQUENCE: 317
gcgtcccaac ttgttttctg                                           20

<210> SEQ ID NO 318
<211> LENGTH: 21
<212> TYPE: DNA
<213> ORGANISM: Homo sapiens

<400> SEQUENCE: 318
gcgacccata cttggtttca g                                         21

<210> SEQ ID NO 319
<211> LENGTH: 17
<212> TYPE: DNA
<213> ORGANISM: Human herpes virus 6A

<400> SEQUENCE: 319
acacgggcga gcggcgg                                              17

<210> SEQ ID NO 320
<211> LENGTH: 19
<212> TYPE: DNA
<213> ORGANISM: Homo sapiens

<400> SEQUENCE: 320
acacgggcga cagctgcgg                                            19

<210> SEQ ID NO 321
<211> LENGTH: 19
<212> TYPE: DNA
<213> ORGANISM: Human herpes virus 6A

<400> SEQUENCE: 321
cgacgggatt tagtgagca                                            19

<210> SEQ ID NO 322
<211> LENGTH: 20
<212> TYPE: DNA
<213> ORGANISM: Homo sapiens

<400> SEQUENCE: 322
caacgggtat ttattgagca                                           20

<210> SEQ ID NO 323
<211> LENGTH: 23
<212> TYPE: DNA
<213> ORGANISM: Human herpes virus 6A

<400> SEQUENCE: 323
tccgtctcag tgtcacttat ata                                       23

<210> SEQ ID NO 324
<211> LENGTH: 20
<212> TYPE: DNA
<213> ORGANISM: Homo sapiens

<400> SEQUENCE: 324
tccgtctcag ttactttata                                           20

<210> SEQ ID NO 325
<211> LENGTH: 20
<212> TYPE: DNA
<213> ORGANISM: Human herpes virus 6A
```

```
<400> SEQUENCE: 325
ggtggcaccg aatccggaat                                               20

<210> SEQ ID NO 326
<211> LENGTH: 21
<212> TYPE: DNA
<213> ORGANISM: Homo sapiens

<400> SEQUENCE: 326
ggtgggcaca gaatctggac t                                             21

<210> SEQ ID NO 327
<211> LENGTH: 19
<212> TYPE: DNA
<213> ORGANISM: Human herpes virus 6A

<400> SEQUENCE: 327
agtttatcag aatgatatt                                                19

<210> SEQ ID NO 328
<211> LENGTH: 19
<212> TYPE: DNA
<213> ORGANISM: Homo sapiens

<400> SEQUENCE: 328
agcttatcag actgatgtt                                                19

<210> SEQ ID NO 329
<211> LENGTH: 19
<212> TYPE: DNA
<213> ORGANISM: Human herpes virus 6A

<400> SEQUENCE: 329
gagtttcgtg atgtcttgc                                                19

<210> SEQ ID NO 330
<211> LENGTH: 19
<212> TYPE: DNA
<213> ORGANISM: Homo sapiens

<400> SEQUENCE: 330
gagtcttgtg atgtcttgc                                                19

<210> SEQ ID NO 331
<211> LENGTH: 18
<212> TYPE: DNA
<213> ORGANISM: Human herpes virus 6A

<400> SEQUENCE: 331
gatataatat ggttcctg                                                 18

<210> SEQ ID NO 332
<211> LENGTH: 19
<212> TYPE: DNA
<213> ORGANISM: Homo sapiens

<400> SEQUENCE: 332
gataaaatat tggtacctg                                                19

<210> SEQ ID NO 333
<211> LENGTH: 21
<212> TYPE: DNA
<213> ORGANISM: Human herpes virus 6A
```

```
<400> SEQUENCE: 333
gtagcattcg acagggctgt c                                              21

<210> SEQ ID NO 334
<211> LENGTH: 21
<212> TYPE: DNA
<213> ORGANISM: Homo sapiens

<400> SEQUENCE: 334
gcagcattgt acagggctat c                                              21

<210> SEQ ID NO 335
<211> LENGTH: 20
<212> TYPE: DNA
<213> ORGANISM: Human herpes virus 6A

<400> SEQUENCE: 335
cgccgcgtct tgccaagtgg                                                20

<210> SEQ ID NO 336
<211> LENGTH: 20
<212> TYPE: DNA
<213> ORGANISM: Homo sapiens

<400> SEQUENCE: 336
cgcctgttct tgccaggtgg                                                20

<210> SEQ ID NO 337
<211> LENGTH: 20
<212> TYPE: DNA
<213> ORGANISM: Human herpes virus 6A

<400> SEQUENCE: 337
acagtagtca ccggattggt                                                20

<210> SEQ ID NO 338
<211> LENGTH: 20
<212> TYPE: DNA
<213> ORGANISM: Homo sapiens

<400> SEQUENCE: 338
acagtagtct gcacattggt                                                20

<210> SEQ ID NO 339
<211> LENGTH: 22
<212> TYPE: DNA
<213> ORGANISM: Human herpes virus 6A

<400> SEQUENCE: 339
acgggttaga gattttggaa gc                                             22

<210> SEQ ID NO 340
<211> LENGTH: 21
<212> TYPE: DNA
<213> ORGANISM: Homo sapiens

<400> SEQUENCE: 340
acgggttagg ctcttgggag c                                              21

<210> SEQ ID NO 341
<211> LENGTH: 18
<212> TYPE: DNA
<213> ORGANISM: Human herpes virus 6A
```

```
<400> SEQUENCE: 341
atacgcgccg actctctc                                                    18

<210> SEQ ID NO 342
<211> LENGTH: 20
<212> TYPE: DNA
<213> ORGANISM: Homo sapiens

<400> SEQUENCE: 342
atacaagggc agactctctc                                                  20

<210> SEQ ID NO 343
<211> LENGTH: 21
<212> TYPE: DNA
<213> ORGANISM: Human herpes virus 6A

<400> SEQUENCE: 343
caatacaacc taccctcttt c                                                21

<210> SEQ ID NO 344
<211> LENGTH: 21
<212> TYPE: DNA
<213> ORGANISM: Homo sapiens

<400> SEQUENCE: 344
ctatacaatc tactgtcttt c                                                21

<210> SEQ ID NO 345
<211> LENGTH: 18
<212> TYPE: DNA
<213> ORGANISM: Human herpes virus 6A

<400> SEQUENCE: 345
gtcgtgcacg gcactcct                                                    18

<210> SEQ ID NO 346
<211> LENGTH: 18
<212> TYPE: DNA
<213> ORGANISM: Homo sapiens

<400> SEQUENCE: 346
gtcatacacg gctctcct                                                    18

<210> SEQ ID NO 347
<211> LENGTH: 21
<212> TYPE: DNA
<213> ORGANISM: Human herpes virus 6A

<400> SEQUENCE: 347
gtggtttctt ttggagcagt t                                                21

<210> SEQ ID NO 348
<211> LENGTH: 20
<212> TYPE: DNA
<213> ORGANISM: Homo sapiens

<400> SEQUENCE: 348
gtgccttctt ttggagcgtt                                                  20

<210> SEQ ID NO 349
<211> LENGTH: 22
<212> TYPE: DNA
<213> ORGANISM: Human herpes virus 6A
```

```
<400> SEQUENCE: 349
agaattgtag gcttccatct gt                                              22

<210> SEQ ID NO 350
<211> LENGTH: 22
<212> TYPE: DNA
<213> ORGANISM: Homo sapiens

<400> SEQUENCE: 350
agaattgtgg ctggacatct gt                                              22

<210> SEQ ID NO 351
<211> LENGTH: 19
<212> TYPE: DNA
<213> ORGANISM: Human herpes virus 6A

<400> SEQUENCE: 351
cagccatcgg cagatccac                                                  19

<210> SEQ ID NO 352
<211> LENGTH: 20
<212> TYPE: DNA
<213> ORGANISM: Homo sapiens

<400> SEQUENCE: 352
cagtccatgg gcatatacac                                                 20

<210> SEQ ID NO 353
<211> LENGTH: 23
<212> TYPE: DNA
<213> ORGANISM: Human herpes virus 6A

<400> SEQUENCE: 353
aggtagtgcg tcctggtgtt ggg                                             23

<210> SEQ ID NO 354
<211> LENGTH: 21
<212> TYPE: DNA
<213> ORGANISM: Homo sapiens

<400> SEQUENCE: 354
aggtagtttc ctgttgttgg g                                               21

<210> SEQ ID NO 355
<211> LENGTH: 18
<212> TYPE: DNA
<213> ORGANISM: Human herpes virus 6A

<400> SEQUENCE: 355
ctgcacactg ttgttttt                                                   18

<210> SEQ ID NO 356
<211> LENGTH: 18
<212> TYPE: DNA
<213> ORGANISM: Homo sapiens

<400> SEQUENCE: 356
cagcacactg tggtttgt                                                   18

<210> SEQ ID NO 357
<211> LENGTH: 24
<212> TYPE: DNA
<213> ORGANISM: Human herpes virus 6A
```

-continued

<400> SEQUENCE: 357
aagtgctgcg acattttag agtg                                    24

<210> SEQ ID NO 358
<211> LENGTH: 21
<212> TYPE: DNA
<213> ORGANISM: Homo sapiens

<400> SEQUENCE: 358
aagtgctgcg acatttgagc g                                      21

<210> SEQ ID NO 359
<211> LENGTH: 20
<212> TYPE: DNA
<213> ORGANISM: Human herpes virus 6A

<400> SEQUENCE: 359
gcgtcccaac ttgttttctg                                        20

<210> SEQ ID NO 360
<211> LENGTH: 21
<212> TYPE: DNA
<213> ORGANISM: Homo sapiens

<400> SEQUENCE: 360
gcgacccata cttggtttca g                                      21

<210> SEQ ID NO 361
<211> LENGTH: 19
<212> TYPE: DNA
<213> ORGANISM: Human herpes virus 6A

<400> SEQUENCE: 361
attttaacat tgaagtttt                                         19

<210> SEQ ID NO 362
<211> LENGTH: 21
<212> TYPE: DNA
<213> ORGANISM: Homo sapiens

<400> SEQUENCE: 362
actttaacat ggaagtgctt t                                      21

<210> SEQ ID NO 363
<211> LENGTH: 21
<212> TYPE: DNA
<213> ORGANISM: Human herpes virus 6A

<400> SEQUENCE: 363
taaacacatg gtggttctcc t                                      21

<210> SEQ ID NO 364
<211> LENGTH: 20
<212> TYPE: DNA
<213> ORGANISM: Homo sapiens

<400> SEQUENCE: 364
tcaacacttg ctggtttcct                                        20

<210> SEQ ID NO 365
<211> LENGTH: 20
<212> TYPE: DNA
<213> ORGANISM: Human herpes virus 6A

```
<400> SEQUENCE: 365
ataataactg gataatcttt                                            20

<210> SEQ ID NO 366
<211> LENGTH: 20
<212> TYPE: DNA
<213> ORGANISM: Homo sapiens

<400> SEQUENCE: 366
ataatacatg gttgatcttt                                            20

<210> SEQ ID NO 367
<211> LENGTH: 18
<212> TYPE: DNA
<213> ORGANISM: Human herpes virus 6A

<400> SEQUENCE: 367
agtcttatgt gctgccga                                              18

<210> SEQ ID NO 368
<211> LENGTH: 20
<212> TYPE: DNA
<213> ORGANISM: Homo sapiens

<400> SEQUENCE: 368
agtattaact gtgctgctga                                            20

<210> SEQ ID NO 369
<211> LENGTH: 19
<212> TYPE: DNA
<213> ORGANISM: Human herpes virus 6A

<400> SEQUENCE: 369
ataatgatgg ctccggtgt                                             19

<210> SEQ ID NO 370
<211> LENGTH: 22
<212> TYPE: DNA
<213> ORGANISM: Homo sapiens

<400> SEQUENCE: 370
atcatgatgg gctcctcggt gt                                         22

<210> SEQ ID NO 371
<211> LENGTH: 20
<212> TYPE: DNA
<213> ORGANISM: Human herpes virus 6A

<400> SEQUENCE: 371
ggtggcaccg aatccggaat                                            20

<210> SEQ ID NO 372
<211> LENGTH: 21
<212> TYPE: DNA
<213> ORGANISM: Homo sapiens

<400> SEQUENCE: 372
ggtgggcaca gaatctggac t                                          21

<210> SEQ ID NO 373
<211> LENGTH: 17
<212> TYPE: DNA
<213> ORGANISM: Human herpes virus 6A
```

```
<400> SEQUENCE: 373
acacgggcga gcggcgg                                                      17

<210> SEQ ID NO 374
<211> LENGTH: 19
<212> TYPE: DNA
<213> ORGANISM: Homo sapiens

<400> SEQUENCE: 374
acacgggcga cagctgcgg                                                    19

<210> SEQ ID NO 375
<211> LENGTH: 19
<212> TYPE: DNA
<213> ORGANISM: Human herpes virus 6A

<400> SEQUENCE: 375
cgacgggatt tagtgagca                                                    19

<210> SEQ ID NO 376
<211> LENGTH: 20
<212> TYPE: DNA
<213> ORGANISM: Homo sapiens

<400> SEQUENCE: 376
caacgggtat ttattgagca                                                   20

<210> SEQ ID NO 377
<211> LENGTH: 23
<212> TYPE: DNA
<213> ORGANISM: Human herpes virus 6A

<400> SEQUENCE: 377
tccgtctcag tgtcacttat ata                                               23

<210> SEQ ID NO 378
<211> LENGTH: 20
<212> TYPE: DNA
<213> ORGANISM: Homo sapiens

<400> SEQUENCE: 378
tccgtctcag ttactttata                                                   20

<210> SEQ ID NO 379
<211> LENGTH: 21
<212> TYPE: DNA
<213> ORGANISM: Human herpes virus 6B

<400> SEQUENCE: 379
gtctctttct gctctgcagt c                                                 21

<210> SEQ ID NO 380
<211> LENGTH: 20
<212> TYPE: DNA
<213> ORGANISM: Homo sapiens

<400> SEQUENCE: 380
gtgtcttttg ctctgcagtc                                                   20

<210> SEQ ID NO 381
<211> LENGTH: 20
<212> TYPE: DNA
<213> ORGANISM: Human herpes virus 6B
```

-continued

```
<400> SEQUENCE: 381
gatatgattt gataattagg                                               20

<210> SEQ ID NO 382
<211> LENGTH: 20
<212> TYPE: DNA
<213> ORGANISM: Homo sapiens

<400> SEQUENCE: 382
gatatgtttg atatattagg                                               20

<210> SEQ ID NO 383
<211> LENGTH: 21
<212> TYPE: DNA
<213> ORGANISM: Human herpes virus 6B

<400> SEQUENCE: 383
ttctaaattc tccgcgtctt t                                             21

<210> SEQ ID NO 384
<211> LENGTH: 21
<212> TYPE: DNA
<213> ORGANISM: Homo sapiens

<400> SEQUENCE: 384
ttctaatttc tccacgtctt t                                             21

<210> SEQ ID NO 385
<211> LENGTH: 19
<212> TYPE: DNA
<213> ORGANISM: Human herpes virus 6B

<400> SEQUENCE: 385
aaactctgaa aatcaaaca                                                19

<210> SEQ ID NO 386
<211> LENGTH: 20
<212> TYPE: DNA
<213> ORGANISM: Homo sapiens

<400> SEQUENCE: 386
aaactactga aaatcaaaga                                               20

<210> SEQ ID NO 387
<211> LENGTH: 19
<212> TYPE: DNA
<213> ORGANISM: Human herpes virus 6B

<400> SEQUENCE: 387
aagaagtgga aaaactgta                                                19

<210> SEQ ID NO 388
<211> LENGTH: 19
<212> TYPE: DNA
<213> ORGANISM: Homo sapiens

<400> SEQUENCE: 388
aagatgtgga aaaattgga                                                19

<210> SEQ ID NO 389
<211> LENGTH: 22
<212> TYPE: DNA
<213> ORGANISM: Human herpes virus 6B
```

-continued

<400> SEQUENCE: 389
tcaaagatgg acaatccttg tt                                           22

<210> SEQ ID NO 390
<211> LENGTH: 21
<212> TYPE: DNA
<213> ORGANISM: Homo sapiens

<400> SEQUENCE: 390
tcatagagga aaatccatgt t                                            21

<210> SEQ ID NO 391
<211> LENGTH: 20
<212> TYPE: DNA
<213> ORGANISM: Human herpes virus 6B

<400> SEQUENCE: 391
tcgtgcactc gatttagagt                                              20

<210> SEQ ID NO 392
<211> LENGTH: 19
<212> TYPE: DNA
<213> ORGANISM: Homo sapiens

<400> SEQUENCE: 392
tcgtgcatcc ctttagagt                                               19

<210> SEQ ID NO 393
<211> LENGTH: 20
<212> TYPE: DNA
<213> ORGANISM: Human herpes virus 6B

<400> SEQUENCE: 393
tctagatgta gaactttctg                                              20

<210> SEQ ID NO 394
<211> LENGTH: 21
<212> TYPE: DNA
<213> ORGANISM: Homo sapiens

<400> SEQUENCE: 394
tctagaggga agcactttct g                                            21

<210> SEQ ID NO 395
<211> LENGTH: 19
<212> TYPE: DNA
<213> ORGANISM: Human herpes virus 6B

<400> SEQUENCE: 395
actctgcaga gtggaatca                                               19

<210> SEQ ID NO 396
<211> LENGTH: 20
<212> TYPE: DNA
<213> ORGANISM: Homo sapiens

<400> SEQUENCE: 396
actcaggaga gtggcaatca                                              20

<210> SEQ ID NO 397
<211> LENGTH: 17
<212> TYPE: DNA
<213> ORGANISM: Human herpes virus 6B

```
<400> SEQUENCE: 397
ctgcagagtg gaatcat                                                  17

<210> SEQ ID NO 398
<211> LENGTH: 19
<212> TYPE: DNA
<213> ORGANISM: Homo sapiens

<400> SEQUENCE: 398
ctgcagacgt ggcaatcat                                                19

<210> SEQ ID NO 399
<211> LENGTH: 18
<212> TYPE: DNA
<213> ORGANISM: Human herpes virus 6B

<400> SEQUENCE: 399
gaagaggaga tagcaggg                                                 18

<210> SEQ ID NO 400
<211> LENGTH: 20
<212> TYPE: DNA
<213> ORGANISM: Homo sapiens

<400> SEQUENCE: 400
gtagaggaga tggcgcaggg                                               20

<210> SEQ ID NO 401
<211> LENGTH: 19
<212> TYPE: DNA
<213> ORGANISM: Human herpes virus 6B

<400> SEQUENCE: 401
ctctccaaat ctgatcctg                                                19

<210> SEQ ID NO 402
<211> LENGTH: 18
<212> TYPE: DNA
<213> ORGANISM: Homo sapiens

<400> SEQUENCE: 402
ctctccaaat gtgtcttg                                                 18

<210> SEQ ID NO 403
<211> LENGTH: 19
<212> TYPE: DNA
<213> ORGANISM: Human herpes virus 6B

<400> SEQUENCE: 403
tctagttctg gagtgctga                                                19

<210> SEQ ID NO 404
<211> LENGTH: 19
<212> TYPE: DNA
<213> ORGANISM: Homo sapiens

<400> SEQUENCE: 404
tctaggctgg tactgctga                                                19

<210> SEQ ID NO 405
<211> LENGTH: 18
<212> TYPE: DNA
<213> ORGANISM: Human herpes virus 6B
```

```
<400> SEQUENCE: 405
taatatagtc cgtatctt                                                 18

<210> SEQ ID NO 406
<211> LENGTH: 18
<212> TYPE: DNA
<213> ORGANISM: Homo sapiens

<400> SEQUENCE: 406
taatatggtc cacatctt                                                 18

<210> SEQ ID NO 407
<211> LENGTH: 18
<212> TYPE: DNA
<213> ORGANISM: Human herpes virus 6B

<400> SEQUENCE: 407
taacggcaag taaatatt                                                 18

<210> SEQ ID NO 408
<211> LENGTH: 18
<212> TYPE: DNA
<213> ORGANISM: Homo sapiens

<400> SEQUENCE: 408
tagcagcacg taaatatt                                                 18

<210> SEQ ID NO 409
<211> LENGTH: 18
<212> TYPE: DNA
<213> ORGANISM: Human herpes virus 6B

<400> SEQUENCE: 409
agagttacct gatttgtg                                                 18

<210> SEQ ID NO 410
<211> LENGTH: 19
<212> TYPE: DNA
<213> ORGANISM: Homo sapiens

<400> SEQUENCE: 410
agagcttagc tgattggtg                                                19

<210> SEQ ID NO 411
<211> LENGTH: 18
<212> TYPE: DNA
<213> ORGANISM: Human herpes virus 6B

<400> SEQUENCE: 411
ttgtgtttgt tttgcagc                                                 18

<210> SEQ ID NO 412
<211> LENGTH: 19
<212> TYPE: DNA
<213> ORGANISM: Homo sapiens

<400> SEQUENCE: 412
tcgtgtcttg tgttgcagc                                                19

<210> SEQ ID NO 413
<211> LENGTH: 22
<212> TYPE: DNA
<213> ORGANISM: Human herpes virus 6B
```

<400> SEQUENCE: 413
agggtggaaa ttgtctaagt cc					22

<210> SEQ ID NO 414
<211> LENGTH: 21
<212> TYPE: DNA
<213> ORGANISM: Homo sapiens

<400> SEQUENCE: 414 aggggggaaag ttctatagtc c					21

<210> SEQ ID NO 415
<211> LENGTH: 21
<212> TYPE: DNA
<213> ORGANISM: Human herpes virus 6B

<400> SEQUENCE: 415
ctctatctcc tgtcgcactc c					21

<210> SEQ ID NO 416
<211> LENGTH: 20
<212> TYPE: DNA
<213> ORGANISM: Homo sapiens

<400> SEQUENCE: 416
ctctttccct gttgcactac					20

<210> SEQ ID NO 417
<211> LENGTH: 20
<212> TYPE: DNA
<213> ORGANISM: Human herpes virus 6B

<400> SEQUENCE: 417
tccagcccca tagtttctgc					20

<210> SEQ ID NO 418
<211> LENGTH: 20
<212> TYPE: DNA
<213> ORGANISM: Homo sapiens

<400> SEQUENCE: 418
tccagcccca cagcctcagc					20

<210> SEQ ID NO 419
<211> LENGTH: 19
<212> TYPE: DNA
<213> ORGANISM: Human herpes virus 6B

<400> SEQUENCE: 419
cttactcctt ccggcacgt					19

<210> SEQ ID NO 420
<211> LENGTH: 19
<212> TYPE: DNA
<213> ORGANISM: Homo sapiens

<400> SEQUENCE: 420
cttactccct caggcacat					19

<210> SEQ ID NO 421
<211> LENGTH: 19
<212> TYPE: DNA
<213> ORGANISM: Human herpes virus 6B

```
<400> SEQUENCE: 421 cccctttgtaa cctatccct                                        19

<210> SEQ ID NO 422
<211> LENGTH: 20
<212> TYPE: DNA
<213> ORGANISM: Homo sapiens

<400> SEQUENCE: 422 cccctttgtca tcctatgcct                                       20

<210> SEQ ID NO 423
<211> LENGTH: 17
<212> TYPE: DNA
<213> ORGANISM: Human herpes virus 6B

<400> SEQUENCE: 423
gattgacaac atttccc                                           17

<210> SEQ ID NO 424
<211> LENGTH: 18
<212> TYPE: DNA
<213> ORGANISM: Homo sapiens

<400> SEQUENCE: 424
ggttgacata cgtttccc                                          18

<210> SEQ ID NO 425
<211> LENGTH: 18
<212> TYPE: DNA
<213> ORGANISM: Human herpes virus 6B

<400> SEQUENCE: 425
atcacacaaa ggaaattt                                          18

<210> SEQ ID NO 426
<211> LENGTH: 18
<212> TYPE: DNA
<213> ORGANISM: Homo sapiens

<400> SEQUENCE: 426
atcacacaaa ggcaactt                                          18

<210> SEQ ID NO 427
<211> LENGTH: 20
<212> TYPE: DNA
<213> ORGANISM: Human herpes virus 6B

<400> SEQUENCE: 427
gcactgttgg ggtatttggt                                        20

<210> SEQ ID NO 428
<211> LENGTH: 18
<212> TYPE: DNA
<213> ORGANISM: Homo sapiens

<400> SEQUENCE: 428
gcactgtggg tacttgct                                          18

<210> SEQ ID NO 429
<211> LENGTH: 21
<212> TYPE: DNA
<213> ORGANISM: Human herpes virus 6B
```

<210> SEQ ID NO 429 tcagcgagag tgaaaagaga c    21

<210> SEQ ID NO 430
<211> LENGTH: 19
<212> TYPE: DNA
<213> ORGANISM: Homo sapiens

<400> SEQUENCE: 430
tcagcggagg aaaagaaac    19

<210> SEQ ID NO 431
<211> LENGTH: 20
<212> TYPE: DNA
<213> ORGANISM: Human herpes virus 6B

<400> SEQUENCE: 431
agcttgcaga gggtgctgat    20

<210> SEQ ID NO 432
<211> LENGTH: 18
<212> TYPE: DNA
<213> ORGANISM: Homo sapiens

<400> SEQUENCE: 432
agctcagagg gctctgat    18

<210> SEQ ID NO 433
<211> LENGTH: 20
<212> TYPE: DNA
<213> ORGANISM: Human herpes virus 6B

<400> SEQUENCE: 433
agtcacgaag atggcatagc    20

<210> SEQ ID NO 434
<211> LENGTH: 20
<212> TYPE: DNA
<213> ORGANISM: Homo sapiens

<400> SEQUENCE: 434
aggcaagatg ctggcatagc    20

<210> SEQ ID NO 435
<211> LENGTH: 22
<212> TYPE: DNA
<213> ORGANISM: Human herpes virus 6B

<400> SEQUENCE: 435
aaagttgaga gacactctgg ct    22

<210> SEQ ID NO 436
<211> LENGTH: 22
<212> TYPE: DNA
<213> ORGANISM: Homo sapiens

<400> SEQUENCE: 436
aaagttctga gacactccga ct    22

<210> SEQ ID NO 437
<211> LENGTH: 23
<212> TYPE: DNA
<213> ORGANISM: Human herpes virus 6B

<400> SEQUENCE: 437
actctgcagc tttttaacaa gtt                                          23

<210> SEQ ID NO 438
<211> LENGTH: 21
<212> TYPE: DNA
<213> ORGANISM: Homo sapiens

<400> SEQUENCE: 438
attctgcatt tttagcaagt t                                            21

<210> SEQ ID NO 439
<211> LENGTH: 19
<212> TYPE: DNA
<213> ORGANISM: Human herpes virus 6B

<400> SEQUENCE: 439
atgtcgtggt ccaataact                                               19

<210> SEQ ID NO 440
<211> LENGTH: 21
<212> TYPE: DNA
<213> ORGANISM: Homo sapiens

<400> SEQUENCE: 440
atgtaacatg gtccactaac t                                            21

<210> SEQ ID NO 441
<211> LENGTH: 19
<212> TYPE: DNA
<213> ORGANISM: Human herpes virus 6B

<400> SEQUENCE: 441
gcctactgtg ctctatctg                                               19

<210> SEQ ID NO 442
<211> LENGTH: 20
<212> TYPE: DNA
<213> ORGANISM: Homo sapiens

<400> SEQUENCE: 442
gcctactgag ctgatatcag                                              20

<210> SEQ ID NO 443
<211> LENGTH: 18
<212> TYPE: DNA
<213> ORGANISM: Human herpes virus 6B

<400> SEQUENCE: 443
ggcagagttt tgttagct                                                18

<210> SEQ ID NO 444
<211> LENGTH: 18
<212> TYPE: DNA
<213> ORGANISM: Homo sapiens

<400> SEQUENCE: 444
ggcagtgtat tgttagct                                                18

<210> SEQ ID NO 445
<211> LENGTH: 23
<212> TYPE: DNA
<213> ORGANISM: Human herpes virus 6B

```
<400> SEQUENCE: 445
tgccctgtgg agactgcatc tgg                                            23

<210> SEQ ID NO 446
<211> LENGTH: 22
<212> TYPE: DNA
<213> ORGANISM: Homo sapiens

<400> SEQUENCE: 446
tgccctgtgg actcagttct gg                                             22

<210> SEQ ID NO 447
<211> LENGTH: 25
<212> TYPE: DNA
<213> ORGANISM: Human herpes virus 6B

<400> SEQUENCE: 447
ccatcataca cgattccctg cctct                                          25

<210> SEQ ID NO 448
<211> LENGTH: 21
<212> TYPE: DNA
<213> ORGANISM: Homo sapiens

<400> SEQUENCE: 448
ccattacact accctgcctc t                                              21

<210> SEQ ID NO 449
<211> LENGTH: 20
<212> TYPE: DNA
<213> ORGANISM: Human herpes virus 6B

<400> SEQUENCE: 449
tgctgacata gcactttcgg                                                20

<210> SEQ ID NO 450
<211> LENGTH: 20
<212> TYPE: DNA
<213> ORGANISM: Homo sapiens

<400> SEQUENCE: 450
tgctgagcta gcacttcccg                                                20

<210> SEQ ID NO 451
<211> LENGTH: 24
<212> TYPE: DNA
<213> ORGANISM: Human herpes virus 6B

<400> SEQUENCE: 451
aggcgagggc tgcagcggga cccc                                           24

<210> SEQ ID NO 452
<211> LENGTH: 22
<212> TYPE: DNA
<213> ORGANISM: Homo sapiens

<400> SEQUENCE: 452
aggcggggcg ccgcgggacc gc                                             22

<210> SEQ ID NO 453
<211> LENGTH: 21
<212> TYPE: DNA
<213> ORGANISM: Human herpes virus 6B
```

```
<400> SEQUENCE: 453
tctccatagt tgatgtactc a                                        21

<210> SEQ ID NO 454
<211> LENGTH: 20
<212> TYPE: DNA
<213> ORGANISM: Homo sapiens

<400> SEQUENCE: 454
tttccatagg tgatgagtca                                          20

<210> SEQ ID NO 455
<211> LENGTH: 19
<212> TYPE: DNA
<213> ORGANISM: Human herpes virus 6B

<400> SEQUENCE: 455
tgatgtagaa ggttgttta                                           19

<210> SEQ ID NO 456
<211> LENGTH: 19
<212> TYPE: DNA
<213> ORGANISM: Homo sapiens

<400> SEQUENCE: 456
tgaggtagga ggttgtata                                           19

<210> SEQ ID NO 457
<211> LENGTH: 17
<212> TYPE: DNA
<213> ORGANISM: Human herpes virus 6B

<400> SEQUENCE: 457
atacgacgct cctttct                                             17

<210> SEQ ID NO 458
<211> LENGTH: 20
<212> TYPE: DNA
<213> ORGANISM: Homo sapiens

<400> SEQUENCE: 458
atacgacctg ctgcctttct                                          20

<210> SEQ ID NO 459
<211> LENGTH: 21
<212> TYPE: DNA
<213> ORGANISM: Human herpes virus 6B

<400> SEQUENCE: 459
tggtttacgt ccctcacaac a                                        21

<210> SEQ ID NO 460
<211> LENGTH: 21
<212> TYPE: DNA
<213> ORGANISM: Homo sapiens

<400> SEQUENCE: 460
tggtttaccg tcccacatac a                                        21

<210> SEQ ID NO 461
<211> LENGTH: 21
<212> TYPE: DNA
<213> ORGANISM: Human herpes virus 6B
```

```
<400> SEQUENCE: 461
atttaccgac aacagccctg c                                              21

<210> SEQ ID NO 462
<211> LENGTH: 21
<212> TYPE: DNA
<213> ORGANISM: Homo sapiens

<400> SEQUENCE: 462
acttacagac aagagccttg c                                              21

<210> SEQ ID NO 463
<211> LENGTH: 21
<212> TYPE: DNA
<213> ORGANISM: Human herpes virus 6B

<400> SEQUENCE: 463
tacagttgtt aataaccagc t                                              21

<210> SEQ ID NO 464
<211> LENGTH: 19
<212> TYPE: DNA
<213> ORGANISM: Homo sapiens

<400> SEQUENCE: 464
tacagttgtt caaccagtt                                                 19

<210> SEQ ID NO 465
<211> LENGTH: 23
<212> TYPE: DNA
<213> ORGANISM: Human herpes virus 6B

<400> SEQUENCE: 465
caatgcaatg atattggtca atg                                            23

<210> SEQ ID NO 466
<211> LENGTH: 22
<212> TYPE: DNA
<213> ORGANISM: Homo sapiens

<400> SEQUENCE: 466
cagtgcaatg atattgtcaa ag                                             22

<210> SEQ ID NO 467
<211> LENGTH: 19
<212> TYPE: DNA
<213> ORGANISM: Human herpes virus 6B

<400> SEQUENCE: 467
aggcagagtt ttgttagct                                                 19

<210> SEQ ID NO 468
<211> LENGTH: 19
<212> TYPE: DNA
<213> ORGANISM: Homo sapiens

<400> SEQUENCE: 468
aggcagtgta ttgttagct                                                 19

<210> SEQ ID NO 469
<211> LENGTH: 18
<212> TYPE: DNA
<213> ORGANISM: Human herpes virus 6B
```

<400> SEQUENCE: 469
tgtgaaacac ttccatga                                                                      18

<210> SEQ ID NO 470
<211> LENGTH: 18
<212> TYPE: DNA
<213> ORGANISM: Homo sapiens

<400> SEQUENCE: 470
tggggaaccc ttccatga                                                                      18

<210> SEQ ID NO 471
<211> LENGTH: 21
<212> TYPE: DNA
<213> ORGANISM: Human herpes virus 6B

<400> SEQUENCE: 471
acggacgcga agcgcgtgca g                                                                  21

<210> SEQ ID NO 472
<211> LENGTH: 20
<212> TYPE: DNA
<213> ORGANISM: Homo sapiens

<400> SEQUENCE: 472
agggacggga cgcggtgcag                                                                    20

<210> SEQ ID NO 473
<211> LENGTH: 22
<212> TYPE: DNA
<213> ORGANISM: Human herpes virus 6B

<400> SEQUENCE: 473
cagaaaccac cgtttcgttt tc                                                                 22

<210> SEQ ID NO 474
<211> LENGTH: 22
<212> TYPE: DNA
<213> ORGANISM: Homo sapiens

<400> SEQUENCE: 474
caaaaaccac agtttctttt gc                                                                 22

<210> SEQ ID NO 475
<211> LENGTH: 22
<212> TYPE: DNA
<213> ORGANISM: Human herpes virus 6B

<400> SEQUENCE: 475 gagattttc aaaaatgtgc ag                                                                  22

<210> SEQ ID NO 476
<211> LENGTH: 22
<212> TYPE: DNA
<213> ORGANISM: Homo sapiens

<400> SEQUENCE: 476
gagcttattc ataaaagtgc ag                                                                 22

<210> SEQ ID NO 477
<211> LENGTH: 18
<212> TYPE: DNA
<213> ORGANISM: Human herpes virus 6B

```
<400> SEQUENCE: 477
cgccagagcg gtgcactt                                                  18

<210> SEQ ID NO 478
<211> LENGTH: 18
<212> TYPE: DNA
<213> ORGANISM: Homo sapiens

<400> SEQUENCE: 478
ctccagaggg atgcactt                                                  18

<210> SEQ ID NO 479
<211> LENGTH: 19
<212> TYPE: DNA
<213> ORGANISM: Human herpes virus 6B

<400> SEQUENCE: 479
aataaaactg tggggccac                                                 19

<210> SEQ ID NO 480
<211> LENGTH: 19
<212> TYPE: DNA
<213> ORGANISM: Homo sapiens

<400> SEQUENCE: 480
actcaaactg tgggggcac                                                 19

<210> SEQ ID NO 481
<211> LENGTH: 19
<212> TYPE: DNA
<213> ORGANISM: Human herpes virus 6B

<400> SEQUENCE: 481
gaggtgcttc gattttagg                                                 19

<210> SEQ ID NO 482
<211> LENGTH: 19
<212> TYPE: DNA
<213> ORGANISM: Homo sapiens

<400> SEQUENCE: 482
gaagtgcttc gattttggg                                                 19

<210> SEQ ID NO 483
<211> LENGTH: 20
<212> TYPE: DNA
<213> ORGANISM: Human herpes virus 6B

<400> SEQUENCE: 483
cagtttttcc acaaaaccct                                                20

<210> SEQ ID NO 484
<211> LENGTH: 20
<212> TYPE: DNA
<213> ORGANISM: Homo sapiens

<400> SEQUENCE: 484
cagttttccc aggaatccct                                                20

<210> SEQ ID NO 485
<211> LENGTH: 20
<212> TYPE: DNA
<213> ORGANISM: Human herpes virus 6B
```

```
<400> SEQUENCE: 485
aatccatgaa acttaggttt                                              20

<210> SEQ ID NO 486
<211> LENGTH: 20
<212> TYPE: DNA
<213> ORGANISM: Homo sapiens

<400> SEQUENCE: 486
aatccttgga acctaggtgt                                              20

<210> SEQ ID NO 487
<211> LENGTH: 18
<212> TYPE: DNA
<213> ORGANISM: Human herpes virus 6B

<400> SEQUENCE: 487
gaatgttaaa gtatgtat                                                18

<210> SEQ ID NO 488
<211> LENGTH: 20
<212> TYPE: DNA
<213> ORGANISM: Homo sapiens

<400> SEQUENCE: 488
gaatgtaaag aagtatgtat                                              20

<210> SEQ ID NO 489
<211> LENGTH: 18
<212> TYPE: DNA
<213> ORGANISM: Human herpes virus 6B

<400> SEQUENCE: 489
tgtgttcgct agctcatt                                                18

<210> SEQ ID NO 490
<211> LENGTH: 18
<212> TYPE: DNA
<213> ORGANISM: Homo sapiens

<400> SEQUENCE: 490
tgtgttctct agatcagt                                                18

<210> SEQ ID NO 491
<211> LENGTH: 23
<212> TYPE: DNA
<213> ORGANISM: Human herpes virus 6B

<400> SEQUENCE: 491
tgttgtagaa gattgtataa gtt                                          23

<210> SEQ ID NO 492
<211> LENGTH: 22
<212> TYPE: DNA
<213> ORGANISM: Homo sapiens

<400> SEQUENCE: 492
tgaggtagta gattgtatag tt                                           22

<210> SEQ ID NO 493
<211> LENGTH: 20
<212> TYPE: DNA
<213> ORGANISM: Human herpes virus 6B
```

```
<400> SEQUENCE: 493
gtgtgcggat gttttctgct                                            20

<210> SEQ ID NO 494
<211> LENGTH: 21
<212> TYPE: DNA
<213> ORGANISM: Homo sapiens

<400> SEQUENCE: 494
gtgtgcggaa atgcttctgc t                                          21

<210> SEQ ID NO 495
<211> LENGTH: 19
<212> TYPE: DNA
<213> ORGANISM: Human herpes virus 6B

<400> SEQUENCE: 495
atttagtgag catgatatt                                             19

<210> SEQ ID NO 496
<211> LENGTH: 19
<212> TYPE: DNA
<213> ORGANISM: Homo sapiens

<400> SEQUENCE: 496
atttagtgtg tgtgatatt                                             19

<210> SEQ ID NO 497
<211> LENGTH: 23
<212> TYPE: DNA
<213> ORGANISM: Human herpes virus 6B

<400> SEQUENCE: 497
aattgtcttc catgttagac tgt                                        23

<210> SEQ ID NO 498
<211> LENGTH: 22
<212> TYPE: DNA
<213> ORGANISM: Homo sapiens

<400> SEQUENCE: 498
aagtgcttcc atgtttgagt gt                                         22

<210> SEQ ID NO 499
<211> LENGTH: 17
<212> TYPE: DNA
<213> ORGANISM: Human herpes virus 6B

<400> SEQUENCE: 499
gggcccgccc tcgtcct                                               17

<210> SEQ ID NO 500
<211> LENGTH: 18
<212> TYPE: DNA
<213> ORGANISM: Homo sapiens

<400> SEQUENCE: 500
gggccccccc tcaatcct                                              18

<210> SEQ ID NO 501
<211> LENGTH: 18
<212> TYPE: DNA
<213> ORGANISM: Human herpes virus 6B
```

```
<400> SEQUENCE: 501
tatttttatg taaaagct                                                 18

<210> SEQ ID NO 502
<211> LENGTH: 18
<212> TYPE: DNA
<213> ORGANISM: Homo sapiens

<400> SEQUENCE: 502
taattttatg tataagct                                                 18

<210> SEQ ID NO 503
<211> LENGTH: 21
<212> TYPE: DNA
<213> ORGANISM: Human herpes virus 6B

<400> SEQUENCE: 503
agaccaagcg gttgtcattt t                                             21

<210> SEQ ID NO 504
<211> LENGTH: 20
<212> TYPE: DNA
<213> ORGANISM: Homo sapiens

<400> SEQUENCE: 504
agaccatggg ttctcattgt                                               20

<210> SEQ ID NO 505
<211> LENGTH: 19
<212> TYPE: DNA
<213> ORGANISM: Human herpes virus 6B

<400> SEQUENCE: 505
atcacttaga cacggccag                                                19

<210> SEQ ID NO 506
<211> LENGTH: 20
<212> TYPE: DNA
<213> ORGANISM: Homo sapiens

<400> SEQUENCE: 506
atcactaacc acacggccag                                               20

<210> SEQ ID NO 507
<211> LENGTH: 20
<212> TYPE: DNA
<213> ORGANISM: Human herpes virus 6B

<400> SEQUENCE: 507
tgatcatctc ccatggttcc                                               20

<210> SEQ ID NO 508
<211> LENGTH: 20
<212> TYPE: DNA
<213> ORGANISM: Homo sapiens

<400> SEQUENCE: 508
tgctcatacc ccatggtttc                                               20

<210> SEQ ID NO 509
<211> LENGTH: 19
<212> TYPE: DNA
<213> ORGANISM: Human herpes virus 6B
```

```
<400> SEQUENCE: 509
acaggagagc gaggtcgca                                                      19

<210> SEQ ID NO 510
<211> LENGTH: 21
<212> TYPE: DNA
<213> ORGANISM: Homo sapiens

<400> SEQUENCE: 510
acagtagagg gaggaatcgc a                                                   21

<210> SEQ ID NO 511
<211> LENGTH: 22
<212> TYPE: DNA
<213> ORGANISM: Human herpes virus 6B

<400> SEQUENCE: 511
gctttttatt ccacttatga ga                                                  22

<210> SEQ ID NO 512
<211> LENGTH: 19
<212> TYPE: DNA
<213> ORGANISM: Homo sapiens

<400> SEQUENCE: 512 gcttttttatt cctatgtga                                                     19

<210> SEQ ID NO 513
<211> LENGTH: 21
<212> TYPE: DNA
<213> ORGANISM: Human herpes virus 6B

<400> SEQUENCE: 513
taaacacatg gtggttctcc t                                                   21

<210> SEQ ID NO 514
<211> LENGTH: 23
<212> TYPE: DNA
<213> ORGANISM: Homo sapiens

<400> SEQUENCE: 514
taaatcccat ggtgccttct cct                                                 23

<210> SEQ ID NO 515
<211> LENGTH: 21
<212> TYPE: DNA
<213> ORGANISM: Human herpes virus 6B

<400> SEQUENCE: 515
agggcggctg gcttcccttt g                                                   21

<210> SEQ ID NO 516
<211> LENGTH: 19
<212> TYPE: DNA
<213> ORGANISM: Homo sapiens

<400> SEQUENCE: 516
aggggctggc tttcctctg                                                      19

<210> SEQ ID NO 517
<211> LENGTH: 20
<212> TYPE: DNA
<213> ORGANISM: Human herpes virus 6B
```

```
<400> SEQUENCE: 517
ctgagacccc taatttgtta                                              20

<210> SEQ ID NO 518
<211> LENGTH: 19
<212> TYPE: DNA
<213> ORGANISM: Homo sapiens

<400> SEQUENCE: 518
ctgagaccct aacttgtga                                               19

<210> SEQ ID NO 519
<211> LENGTH: 21
<212> TYPE: DNA
<213> ORGANISM: Human herpes virus 6B

<400> SEQUENCE: 519
tgacggtctg cacttctgtg c                                            21

<210> SEQ ID NO 520
<211> LENGTH: 22
<212> TYPE: DNA
<213> ORGANISM: Homo sapiens

<400> SEQUENCE: 520
tgcctgtcta cacttgctgt gc                                           22

<210> SEQ ID NO 521
<211> LENGTH: 18
<212> TYPE: DNA
<213> ORGANISM: Human herpes virus 6B

<400> SEQUENCE: 521
gtggtccgcg cgtgtcgc                                                18

<210> SEQ ID NO 522
<211> LENGTH: 20
<212> TYPE: DNA
<213> ORGANISM: Homo sapiens

<400> SEQUENCE: 522
gtggtccgtg gcgcgttcgc                                              20

<210> SEQ ID NO 523
<211> LENGTH: 17
<212> TYPE: DNA
<213> ORGANISM: Human herpes virus 6B

<400> SEQUENCE: 523
ccaccaccgc tgacagt                                                 17

<210> SEQ ID NO 524
<211> LENGTH: 20
<212> TYPE: DNA
<213> ORGANISM: Homo sapiens

<400> SEQUENCE: 524
ccaccaccgt gtctgacact                                              20

<210> SEQ ID NO 525
<211> LENGTH: 20
<212> TYPE: DNA
<213> ORGANISM: Human herpes virus 6B
```

<400> SEQUENCE: 525
agccagagta gtcttgatgt                     20

<210> SEQ ID NO 526
<211> LENGTH: 19
<212> TYPE: DNA
<213> ORGANISM: Homo sapiens

<400> SEQUENCE: 526
agccaggaag tattgatgt                      19

<210> SEQ ID NO 527
<211> LENGTH: 21
<212> TYPE: DNA
<213> ORGANISM: Human herpes virus 6B

<400> SEQUENCE: 527
cgtctctacc cccgagtgtt t                   21

<210> SEQ ID NO 528
<211> LENGTH: 20
<212> TYPE: DNA
<213> ORGANISM: Homo sapiens

<400> SEQUENCE: 528
cgtcttaccc agcagtgttt                     20

<210> SEQ ID NO 529
<211> LENGTH: 19
<212> TYPE: DNA
<213> ORGANISM: Human herpes virus 6B

<400> SEQUENCE: 529
cagcaacaaa atttcatcc                      19

<210> SEQ ID NO 530
<211> LENGTH: 19
<212> TYPE: DNA
<213> ORGANISM: Homo sapiens

<400> SEQUENCE: 530
cagtaacaaa gattcatcc                      19

<210> SEQ ID NO 531
<211> LENGTH: 20
<212> TYPE: DNA
<213> ORGANISM: Human herpes virus 6B

<400> SEQUENCE: 531
ataccagtcg atgtcgctgt                     20

<210> SEQ ID NO 532
<211> LENGTH: 19
<212> TYPE: DNA
<213> ORGANISM: Homo sapiens

<400> SEQUENCE: 532
acaccagtcg atgggctgt                      19

<210> SEQ ID NO 533
<211> LENGTH: 21
<212> TYPE: DNA
<213> ORGANISM: Human herpes virus 6B

```
<400> SEQUENCE: 533
tggcaacggg agacagtttt g                                         21

<210> SEQ ID NO 534
<211> LENGTH: 20
<212> TYPE: DNA
<213> ORGANISM: Homo sapiens

<400> SEQUENCE: 534
tagcagcggg aacagttctg                                           20

<210> SEQ ID NO 535
<211> LENGTH: 20
<212> TYPE: DNA
<213> ORGANISM: Human herpes virus 6B

<400> SEQUENCE: 535
agccagagta gtcttgatgt                                           20

<210> SEQ ID NO 536
<211> LENGTH: 19
<212> TYPE: DNA
<213> ORGANISM: Homo sapiens

<400> SEQUENCE: 536
agccaggaag tattgatgt                                            19

<210> SEQ ID NO 537
<211> LENGTH: 20
<212> TYPE: DNA
<213> ORGANISM: Human herpes virus 6B

<400> SEQUENCE: 537
cgtacagtga ttgatactgc                                           20

<210> SEQ ID NO 538
<211> LENGTH: 20
<212> TYPE: DNA
<213> ORGANISM: Homo sapiens

<400> SEQUENCE: 538
cgtaccgtga gtaataatgc                                           20

<210> SEQ ID NO 539
<211> LENGTH: 18
<212> TYPE: DNA
<213> ORGANISM: Human herpes virus 6B

<400> SEQUENCE: 539
ctaataggtt tccattaa                                             18

<210> SEQ ID NO 540
<211> LENGTH: 18
<212> TYPE: DNA
<213> ORGANISM: Homo sapiens

<400> SEQUENCE: 540
ctagtaggtg tccagtaa                                             18

<210> SEQ ID NO 541
<211> LENGTH: 18
<212> TYPE: DNA
<213> ORGANISM: Human herpes virus 6B
```

-continued

```
<400> SEQUENCE: 541
cccttagggt attggggt                                                18

<210> SEQ ID NO 542
<211> LENGTH: 18
<212> TYPE: DNA
<213> ORGANISM: Homo sapiens

<400> SEQUENCE: 542
ccactagggc attggtgt                                                18

<210> SEQ ID NO 543
<211> LENGTH: 18
<212> TYPE: DNA
<213> ORGANISM: Human herpes virus 6B

<400> SEQUENCE: 543
tcctgctctc agggctcc                                                18

<210> SEQ ID NO 544
<211> LENGTH: 18
<212> TYPE: DNA
<213> ORGANISM: Homo sapiens

<400> SEQUENCE: 544
tccggttctc agggctcc                                                18

<210> SEQ ID NO 545
<211> LENGTH: 20
<212> TYPE: DNA
<213> ORGANISM: Human herpes virus 6B

<400> SEQUENCE: 545
ctgtgcgggg agggcggctg                                              20

<210> SEQ ID NO 546
<211> LENGTH: 21
<212> TYPE: DNA
<213> ORGANISM: Homo sapiens

<400> SEQUENCE: 546
ctgtgcgtgt gacagcggct g                                            21

<210> SEQ ID NO 547
<211> LENGTH: 20
<212> TYPE: DNA
<213> ORGANISM: Human herpes virus 6B

<400> SEQUENCE: 547
aggtggaggt ttctttggag                                              20

<210> SEQ ID NO 548
<211> LENGTH: 18
<212> TYPE: DNA
<213> ORGANISM: Homo sapiens

<400> SEQUENCE: 548
aggtgaggtt cttgggag                                                18

<210> SEQ ID NO 549
<211> LENGTH: 22
<212> TYPE: DNA
<213> ORGANISM: Human herpes virus 6B
```

```
<400> SEQUENCE: 549
aaattgattc ccttaggtgg gt                                              22

<210> SEQ ID NO 550
<211> LENGTH: 22
<212> TYPE: DNA
<213> ORGANISM: Homo sapiens

<400> SEQUENCE: 550
aaagtgcttc tctttggtgg gt                                              22

<210> SEQ ID NO 551
<211> LENGTH: 21
<212> TYPE: DNA
<213> ORGANISM: Human herpes virus 6B

<400> SEQUENCE: 551
ctcgttcttg ggccacctca g                                               21

<210> SEQ ID NO 552
<211> LENGTH: 20
<212> TYPE: DNA
<213> ORGANISM: Homo sapiens

<400> SEQUENCE: 552
ctcggtctga ggcccctcag                                                 20

<210> SEQ ID NO 553
<211> LENGTH: 23
<212> TYPE: DNA
<213> ORGANISM: Human herpes virus 6B

<400> SEQUENCE: 553
tcagaaaacg atttactgtg agc                                             23

<210> SEQ ID NO 554
<211> LENGTH: 22
<212> TYPE: DNA
<213> ORGANISM: Homo sapiens

<400> SEQUENCE: 554
tcagcaaaca tttattgtgt gc                                              22

<210> SEQ ID NO 555
<211> LENGTH: 20
<212> TYPE: DNA
<213> ORGANISM: Human herpes virus 6B

<400> SEQUENCE: 555
tctagatgta gaactttctg                                                 20

<210> SEQ ID NO 556
<211> LENGTH: 21
<212> TYPE: DNA
<213> ORGANISM: Homo sapiens

<400> SEQUENCE: 556
tctagaggga agcactttct g                                               21

<210> SEQ ID NO 557
<211> LENGTH: 19
<212> TYPE: DNA
<213> ORGANISM: Human herpes virus 6B
```

```
<400> SEQUENCE: 557
gttgggatcg gtcagtgtt                                          19

<210> SEQ ID NO 558
<211> LENGTH: 21
<212> TYPE: DNA
<213> ORGANISM: Homo sapiens

<400> SEQUENCE: 558
gttgggatcg gttgcaatgc t                                       21

<210> SEQ ID NO 559
<211> LENGTH: 20
<212> TYPE: DNA
<213> ORGANISM: Human herpes virus 6B

<400> SEQUENCE: 559
ctagtctaga ttcatccagt                                         20

<210> SEQ ID NO 560
<211> LENGTH: 20
<212> TYPE: DNA
<213> ORGANISM: Homo sapiens

<400> SEQUENCE: 560
ctagtcctga ctcagccagt                                         20

<210> SEQ ID NO 561
<211> LENGTH: 20
<212> TYPE: DNA
<213> ORGANISM: Human herpes virus 6B

<400> SEQUENCE: 561
aataaccaca tttggttttg                                         20

<210> SEQ ID NO 562
<211> LENGTH: 20
<212> TYPE: DNA
<213> ORGANISM: Homo sapiens

<400> SEQUENCE: 562
aagaacctca gttgcttttg                                         20

<210> SEQ ID NO 563
<211> LENGTH: 19
<212> TYPE: DNA
<213> ORGANISM: Human herpes virus 6B

<400> SEQUENCE: 563
ctccgacatc tttgcatta                                          19

<210> SEQ ID NO 564
<211> LENGTH: 19
<212> TYPE: DNA
<213> ORGANISM: Homo sapiens

<400> SEQUENCE: 564
ctcctacata ttagcatta                                          19

<210> SEQ ID NO 565
<211> LENGTH: 20
<212> TYPE: DNA
<213> ORGANISM: Human herpes virus 6B
```

```
<400> SEQUENCE: 565
aacattttct ggtatcgatg                                          20

<210> SEQ ID NO 566
<211> LENGTH: 20
<212> TYPE: DNA
<213> ORGANISM: Homo sapiens

<400> SEQUENCE: 566
aacactgtct ggtaacgatg                                          20

<210> SEQ ID NO 567
<211> LENGTH: 18
<212> TYPE: DNA
<213> ORGANISM: Human herpes virus 6B

<400> SEQUENCE: 567
acagacgatt ttagagga                                            18

<210> SEQ ID NO 568
<211> LENGTH: 20
<212> TYPE: DNA
<213> ORGANISM: Homo sapiens

<400> SEQUENCE: 568
acagattcga ttctagggga                                          20

<210> SEQ ID NO 569
<211> LENGTH: 18
<212> TYPE: DNA
<213> ORGANISM: Human herpes virus 6B

<400> SEQUENCE: 569
ggaattgggg cagaaggc                                            18

<210> SEQ ID NO 570
<211> LENGTH: 19
<212> TYPE: DNA
<213> ORGANISM: Homo sapiens

<400> SEQUENCE: 570
ggacttaggg tcagaaggc                                           19

<210> SEQ ID NO 571
<211> LENGTH: 19
<212> TYPE: DNA
<213> ORGANISM: Human herpes virus 6B

<400> SEQUENCE: 571
tacagtactc gatagctga                                           19

<210> SEQ ID NO 572
<211> LENGTH: 20
<212> TYPE: DNA
<213> ORGANISM: Homo sapiens

<400> SEQUENCE: 572
tacagtactg tgataactga                                          20

<210> SEQ ID NO 573
<211> LENGTH: 19
<212> TYPE: DNA
<213> ORGANISM: Human herpes virus 6B
```

-continued

```
<400> SEQUENCE: 573
tttaatatgg cggcagttg                                                  19

<210> SEQ ID NO 574
<211> LENGTH: 19
<212> TYPE: DNA
<213> ORGANISM: Homo sapiens

<400> SEQUENCE: 574
tttaacatgg aggcacttg                                                  19

<210> SEQ ID NO 575
<211> LENGTH: 20
<212> TYPE: DNA
<213> ORGANISM: Human herpes virus 6B

<400> SEQUENCE: 575
atgaagataa ttatggaaat                                                 20

<210> SEQ ID NO 576
<211> LENGTH: 20
<212> TYPE: DNA
<213> ORGANISM: Homo sapiens

<400> SEQUENCE: 576
atggagatag atatagaaat                                                 20

<210> SEQ ID NO 577
<211> LENGTH: 19
<212> TYPE: DNA
<213> ORGANISM: Human herpes virus 6B

<400> SEQUENCE: 577
tgatgtagaa ggttgttta                                                  19

<210> SEQ ID NO 578
<211> LENGTH: 19
<212> TYPE: DNA
<213> ORGANISM: Homo sapiens

<400> SEQUENCE: 578
tgaggtagta ggttgtata                                                  19

<210> SEQ ID NO 579
<211> LENGTH: 21
<212> TYPE: DNA
<213> ORGANISM: Human herpes virus 6B

<400> SEQUENCE: 579
gatggtcttc tttttagagg c                                               21

<210> SEQ ID NO 580
<211> LENGTH: 22
<212> TYPE: DNA
<213> ORGANISM: Homo sapiens

<400> SEQUENCE: 580
gaaagtgctt cctttagag gc                                               22

<210> SEQ ID NO 581
<211> LENGTH: 19
<212> TYPE: DNA
<213> ORGANISM: Human herpes virus 6B
```

<400> SEQUENCE: 581
ttcttcagta gagacttta                              19

<210> SEQ ID NO 582
<211> LENGTH: 20
<212> TYPE: DNA
<213> ORGANISM: Homo sapiens

<400> SEQUENCE: 582
ttcttcagtg gcaagcttta                             20

<210> SEQ ID NO 583
<211> LENGTH: 20
<212> TYPE: DNA
<213> ORGANISM: Human herpes virus 6B

<400> SEQUENCE: 583
tgaattcctg gacatggtga                             20

<210> SEQ ID NO 584
<211> LENGTH: 19
<212> TYPE: DNA
<213> ORGANISM: Homo sapiens

<400> SEQUENCE: 584
tgggttcctg gcatgctga                              19

<210> SEQ ID NO 585
<211> LENGTH: 21
<212> TYPE: DNA
<213> ORGANISM: Human herpes virus 6B

<400> SEQUENCE: 585
tggatgtgct cctcagttgt c                           21

<210> SEQ ID NO 586
<211> LENGTH: 19
<212> TYPE: DNA
<213> ORGANISM: Homo sapiens

<400> SEQUENCE: 586
tggatggctc ctccatgtc                              19

<210> SEQ ID NO 587
<211> LENGTH: 18
<212> TYPE: DNA
<213> ORGANISM: Human herpes virus 6B

<400> SEQUENCE: 587
gctgacgtat tttctgga                               18

<210> SEQ ID NO 588
<211> LENGTH: 18
<212> TYPE: DNA
<213> ORGANISM: Homo sapiens

<400> SEQUENCE: 588
gctgacatat ttactaga                               18

<210> SEQ ID NO 589
<211> LENGTH: 19
<212> TYPE: DNA
<213> ORGANISM: Human herpes virus 6B

```
<400> SEQUENCE: 589
ccactgacct ttaactgta                                                   19

<210> SEQ ID NO 590
<211> LENGTH: 19
<212> TYPE: DNA
<213> ORGANISM: Homo sapiens

<400> SEQUENCE: 590
ccactgaccg ttgactgta                                                   19

<210> SEQ ID NO 591
<211> LENGTH: 18
<212> TYPE: DNA
<213> ORGANISM: Human herpes virus 6B

<400> SEQUENCE: 591
aaaacgtacc actactga                                                    18

<210> SEQ ID NO 592
<211> LENGTH: 19
<212> TYPE: DNA
<213> ORGANISM: Homo sapiens

<400> SEQUENCE: 592
aaaccgttac cattactga                                                   19

<210> SEQ ID NO 593
<211> LENGTH: 21
<212> TYPE: DNA
<213> ORGANISM: Human herpes virus 6B

<400> SEQUENCE: 593
aacatacttc ctgtccgtga g                                                21

<210> SEQ ID NO 594
<211> LENGTH: 21
<212> TYPE: DNA
<213> ORGANISM: Homo sapiens

<400> SEQUENCE: 594
aacattcaac ctgtcggtga g                                                21

<210> SEQ ID NO 595
<211> LENGTH: 20
<212> TYPE: DNA
<213> ORGANISM: Human herpes virus 6B

<400> SEQUENCE: 595
cgagcagtca cagtttcagt                                                  20

<210> SEQ ID NO 596
<211> LENGTH: 20
<212> TYPE: DNA
<213> ORGANISM: Homo sapiens

<400> SEQUENCE: 596
cgaggagctc acagtctagt                                                  20

<210> SEQ ID NO 597
<211> LENGTH: 23
<212> TYPE: DNA
<213> ORGANISM: Human herpes virus 6B
```

```
<400> SEQUENCE: 597
ggagagaaca gagctggtcc tga                                              23

<210> SEQ ID NO 598
<211> LENGTH: 21
<212> TYPE: DNA
<213> ORGANISM: Homo sapiens

<400> SEQUENCE: 598
ggagagaaag gcagttcctg a                                                21

<210> SEQ ID NO 599
<211> LENGTH: 20
<212> TYPE: DNA
<213> ORGANISM: Human herpes virus 6B

<400> SEQUENCE: 599
tctagatgta gaactttctg                                                  20

<210> SEQ ID NO 600
<211> LENGTH: 21
<212> TYPE: DNA
<213> ORGANISM: Homo sapiens

<400> SEQUENCE: 600
tctagaggga agcactttct g                                                21

<210> SEQ ID NO 601
<211> LENGTH: 21
<212> TYPE: DNA
<213> ORGANISM: Human herpes virus 6B

<400> SEQUENCE: 601
accggcataa aatttagttt t                                                21

<210> SEQ ID NO 602
<211> LENGTH: 22
<212> TYPE: DNA
<213> ORGANISM: Homo sapiens

<400> SEQUENCE: 602
acctggcata caatgtagat tt                                               22

<210> SEQ ID NO 603
<211> LENGTH: 21
<212> TYPE: DNA
<213> ORGANISM: Human herpes virus 6B

<400> SEQUENCE: 603
tcctcttcct cctcctcccc g                                                21

<210> SEQ ID NO 604
<211> LENGTH: 21
<212> TYPE: DNA
<213> ORGANISM: Homo sapiens

<400> SEQUENCE: 604
tcctcttctc cctcctccca g                                                21

<210> SEQ ID NO 605
<211> LENGTH: 20
<212> TYPE: DNA
<213> ORGANISM: Human herpes virus 6B
```

```
<400> SEQUENCE: 605
tgggtgatgg atgtgcactt                                            20

<210> SEQ ID NO 606
<211> LENGTH: 20
<212> TYPE: DNA
<213> ORGANISM: Homo sapiens

<400> SEQUENCE: 606
tgggaggtgg atgtttactt                                            20

<210> SEQ ID NO 607
<211> LENGTH: 19
<212> TYPE: DNA
<213> ORGANISM: Human herpes virus 6B

<400> SEQUENCE: 607
atgagttcat tgaatatca                                             19

<210> SEQ ID NO 608
<211> LENGTH: 20
<212> TYPE: DNA
<213> ORGANISM: Homo sapiens

<400> SEQUENCE: 608
atgagctcat tgtaatatga                                            20

<210> SEQ ID NO 609
<211> LENGTH: 21
<212> TYPE: DNA
<213> ORGANISM: Human herpes virus 6B

<400> SEQUENCE: 609
ttcatatcca tatatttttt t                                          21

<210> SEQ ID NO 610
<211> LENGTH: 21
<212> TYPE: DNA
<213> ORGANISM: Homo sapiens

<400> SEQUENCE: 610
ttcctatgca tatacttctt t                                          21

<210> SEQ ID NO 611
<211> LENGTH: 21
<212> TYPE: DNA
<213> ORGANISM: Human herpes virus 6B

<400> SEQUENCE: 611
ctcctcctcc tcttcctcct c                                          21

<210> SEQ ID NO 612
<211> LENGTH: 19
<212> TYPE: DNA
<213> ORGANISM: Homo sapiens

<400> SEQUENCE: 612
ccccacctcc tctctcctc                                             19

<210> SEQ ID NO 613
<211> LENGTH: 20
<212> TYPE: DNA
<213> ORGANISM: Human herpes virus 6B
```

-continued

```
<400> SEQUENCE: 613
acagtagtca ccggattggt                                          20

<210> SEQ ID NO 614
<211> LENGTH: 20
<212> TYPE: DNA
<213> ORGANISM: Homo sapiens

<400> SEQUENCE: 614
acagtagtct gcacattggt                                          20

<210> SEQ ID NO 615
<211> LENGTH: 20
<212> TYPE: DNA
<213> ORGANISM: Human herpes virus 6B

<400> SEQUENCE: 615
gacctaggcc cgtacctcag                                          20

<210> SEQ ID NO 616
<211> LENGTH: 19
<212> TYPE: DNA
<213> ORGANISM: Homo sapiens

<400> SEQUENCE: 616
gacctggccc agacctcag                                           19

<210> SEQ ID NO 617
<211> LENGTH: 18
<212> TYPE: DNA
<213> ORGANISM: Human herpes virus 6B

<400> SEQUENCE: 617
aacacgaaac tgcttgcg                                            18

<210> SEQ ID NO 618
<211> LENGTH: 18
<212> TYPE: DNA
<213> ORGANISM: Homo sapiens

<400> SEQUENCE: 618
aacaagaaac tgcctgag                                            18

<210> SEQ ID NO 619
<211> LENGTH: 19
<212> TYPE: DNA
<213> ORGANISM: Human herpes virus 6B

<400> SEQUENCE: 619
agtttatcag aatgatatt                                           19

<210> SEQ ID NO 620
<211> LENGTH: 19
<212> TYPE: DNA
<213> ORGANISM: Homo sapiens

<400> SEQUENCE: 620
agcttatcag actgatgtt                                           19

<210> SEQ ID NO 621
<211> LENGTH: 21
<212> TYPE: DNA
<213> ORGANISM: Human herpes virus 6B
```

<400> SEQUENCE: 621
ctgctcctgc tctcagggct c                                            21

<210> SEQ ID NO 622
<211> LENGTH: 21
<212> TYPE: DNA
<213> ORGANISM: Homo sapiens

<400> SEQUENCE: 622
ctgactccta gtccagggct c                                            21

<210> SEQ ID NO 623
<211> LENGTH: 21
<212> TYPE: DNA
<213> ORGANISM: Human herpes virus 6B

<400> SEQUENCE: 623
gtagactagt ttgattatgt t                                            21

<210> SEQ ID NO 624
<211> LENGTH: 19
<212> TYPE: DNA
<213> ORGANISM: Homo sapiens

<400> SEQUENCE: 624
gaagactagt gattttgtt                                               19

<210> SEQ ID NO 625
<211> LENGTH: 20
<212> TYPE: DNA
<213> ORGANISM: Human herpes virus 6B

<400> SEQUENCE: 625
gcttccatct gttttagcag                                              20

<210> SEQ ID NO 626
<211> LENGTH: 18
<212> TYPE: DNA
<213> ORGANISM: Homo sapiens

<400> SEQUENCE: 626
gcttccatgt tttagtag                                                18

<210> SEQ ID NO 627
<211> LENGTH: 20
<212> TYPE: DNA
<213> ORGANISM: Human herpes virus 6B

<400> SEQUENCE: 627
cgccgcgtct tgccaagtgg                                              20

<210> SEQ ID NO 628
<211> LENGTH: 20
<212> TYPE: DNA
<213> ORGANISM: Homo sapiens

<400> SEQUENCE: 628
cgcctgttct tgccaggtgg                                              20

<210> SEQ ID NO 629
<211> LENGTH: 20
<212> TYPE: DNA
<213> ORGANISM: Human herpes virus 6B

<400> SEQUENCE: 629
acagtagtca ccggattggt                                        20

<210> SEQ ID NO 630
<211> LENGTH: 20
<212> TYPE: DNA
<213> ORGANISM: Homo sapiens

<400> SEQUENCE: 630
acagtagtct gcacattggt                                        20

<210> SEQ ID NO 631
<211> LENGTH: 22
<212> TYPE: DNA
<213> ORGANISM: Human herpes virus 6B

<400> SEQUENCE: 631
gaagttattt tcgtggttga tt                                     22

<210> SEQ ID NO 632
<211> LENGTH: 20
<212> TYPE: DNA
<213> ORGANISM: Homo sapiens

<400> SEQUENCE: 632
gaagttgttc gtggtggatt                                        20

<210> SEQ ID NO 633
<211> LENGTH: 19
<212> TYPE: DNA
<213> ORGANISM: Human herpes virus 6B

<400> SEQUENCE: 633
gagtttcgtg atgtcttgc                                         19

<210> SEQ ID NO 634
<211> LENGTH: 19
<212> TYPE: DNA
<213> ORGANISM: Homo sapiens

<400> SEQUENCE: 634
gagtcttgtg atgtcttgc                                         19

<210> SEQ ID NO 635
<211> LENGTH: 18
<212> TYPE: DNA
<213> ORGANISM: Human herpes virus 6B

<400> SEQUENCE: 635
gatataatat ggttcctg                                          18

<210> SEQ ID NO 636
<211> LENGTH: 19
<212> TYPE: DNA
<213> ORGANISM: Homo sapiens

<400> SEQUENCE: 636
gataaaatat tggtacctg                                         19

<210> SEQ ID NO 637
<211> LENGTH: 18
<212> TYPE: DNA
<213> ORGANISM: Human herpes virus 6B

```
<400> SEQUENCE: 637
gtcgtgcacg gcactcct                                              18

<210> SEQ ID NO 638
<211> LENGTH: 18
<212> TYPE: DNA
<213> ORGANISM: Homo sapiens

<400> SEQUENCE: 638
gtcatacacg gctctcct                                              18

<210> SEQ ID NO 639
<211> LENGTH: 22
<212> TYPE: DNA
<213> ORGANISM: Human herpes virus 6B

<400> SEQUENCE: 639
acgggttaga gattttggaa gc                                         22

<210> SEQ ID NO 640
<211> LENGTH: 21
<212> TYPE: DNA
<213> ORGANISM: Homo sapiens

<400> SEQUENCE: 640
acgggttagg ctcttgggag c                                          21

<210> SEQ ID NO 641
<211> LENGTH: 19
<212> TYPE: DNA
<213> ORGANISM: Human herpes virus 6B

<400> SEQUENCE: 641
cagccatcgg cagatccac                                             19

<210> SEQ ID NO 642
<211> LENGTH: 20
<212> TYPE: DNA
<213> ORGANISM: Homo sapiens

<400> SEQUENCE: 642
cagtccatgg gcatatacac                                            20

<210> SEQ ID NO 643
<211> LENGTH: 18
<212> TYPE: DNA
<213> ORGANISM: Human herpes virus 6B

<400> SEQUENCE: 643
atacgcgccg actctctc                                              18

<210> SEQ ID NO 644
<211> LENGTH: 20
<212> TYPE: DNA
<213> ORGANISM: Homo sapiens

<400> SEQUENCE: 644
atacaagggc agactctctc                                            20

<210> SEQ ID NO 645
<211> LENGTH: 23
<212> TYPE: DNA
<213> ORGANISM: Human herpes virus 6B
```

```
<400> SEQUENCE: 645
aggtagtgcg tcctggtgtt ggg                                            23

<210> SEQ ID NO 646
<211> LENGTH: 21
<212> TYPE: DNA
<213> ORGANISM: Homo sapiens

<400> SEQUENCE: 646
aggtagtttc ctgttgttgg g                                              21

<210> SEQ ID NO 647
<211> LENGTH: 21
<212> TYPE: DNA
<213> ORGANISM: Human herpes virus 6B

<400> SEQUENCE: 647
gtagcattcg acagggctgt c                                              21

<210> SEQ ID NO 648
<211> LENGTH: 21
<212> TYPE: DNA
<213> ORGANISM: Homo sapiens

<400> SEQUENCE: 648
gcagcattgt acagggctat c                                              21

<210> SEQ ID NO 649
<211> LENGTH: 22
<212> TYPE: DNA
<213> ORGANISM: Human herpes virus 6B

<400> SEQUENCE: 649
agaattgtag gcttccatct gt                                             22

<210> SEQ ID NO 650
<211> LENGTH: 22
<212> TYPE: DNA
<213> ORGANISM: Homo sapiens

<400> SEQUENCE: 650
agaattgtgg ctggacatct gt                                             22

<210> SEQ ID NO 651
<211> LENGTH: 21
<212> TYPE: DNA
<213> ORGANISM: Human herpes virus 6B

<400> SEQUENCE: 651
gtggtttctt ttggagcagt t                                              21

<210> SEQ ID NO 652
<211> LENGTH: 20
<212> TYPE: DNA
<213> ORGANISM: Homo sapiens

<400> SEQUENCE: 652
gtgccttctt ttggagcgtt                                                20

<210> SEQ ID NO 653
<211> LENGTH: 21
<212> TYPE: DNA
<213> ORGANISM: Human herpes virus 6B
```

<400> SEQUENCE: 653
caatacaacc taccctcttt c                                    21

<210> SEQ ID NO 654
<211> LENGTH: 21
<212> TYPE: DNA
<213> ORGANISM: Homo sapiens

<400> SEQUENCE: 654
ctatacaatc tactgtcttt c                                    21

<210> SEQ ID NO 655
<211> LENGTH: 19
<212> TYPE: DNA
<213> ORGANISM: Human herpes virus 6B

<400> SEQUENCE: 655
attttaacat tgaagtttt                                       19

<210> SEQ ID NO 656
<211> LENGTH: 21
<212> TYPE: DNA
<213> ORGANISM: Homo sapiens

<400> SEQUENCE: 656
actttaacat ggaagtgctt t                                    21

<210> SEQ ID NO 657
<211> LENGTH: 20
<212> TYPE: DNA
<213> ORGANISM: Human herpes virus 6B

<400> SEQUENCE: 657
ataataactg gataatcttt                                      20

<210> SEQ ID NO 658
<211> LENGTH: 20
<212> TYPE: DNA
<213> ORGANISM: Homo sapiens

<400> SEQUENCE: 658
ataatacatg gttgatcttt                                      20

<210> SEQ ID NO 659
<211> LENGTH: 18
<212> TYPE: DNA
<213> ORGANISM: Human herpes virus 6B

<400> SEQUENCE: 659
agtcttatgt gctgccga                                        18

<210> SEQ ID NO 660
<211> LENGTH: 20
<212> TYPE: DNA
<213> ORGANISM: Homo sapiens

<400> SEQUENCE: 660
agtattaact gtgctgctga                                      20

<210> SEQ ID NO 661
<211> LENGTH: 24
<212> TYPE: DNA
<213> ORGANISM: Human herpes virus 6B

```
<400> SEQUENCE: 661
aagtgctgcg acatttttag agtg                                          24

<210> SEQ ID NO 662
<211> LENGTH: 21
<212> TYPE: DNA
<213> ORGANISM: Homo sapiens

<400> SEQUENCE: 662
aagtgctgcg acatttgagc g                                             21

<210> SEQ ID NO 663
<211> LENGTH: 19
<212> TYPE: DNA
<213> ORGANISM: Human herpes virus 6B

<400> SEQUENCE: 663
ataatgatgg ctccggtgt                                                19

<210> SEQ ID NO 664
<211> LENGTH: 22
<212> TYPE: DNA
<213> ORGANISM: Homo sapiens

<400> SEQUENCE: 664
atcatgatgg gctcctcggt gt                                            22

<210> SEQ ID NO 665
<211> LENGTH: 21
<212> TYPE: DNA
<213> ORGANISM: Human herpes virus 6B

<400> SEQUENCE: 665
taaacacatg gtggttctcc t                                             21

<210> SEQ ID NO 666
<211> LENGTH: 20
<212> TYPE: DNA
<213> ORGANISM: Homo sapiens

<400> SEQUENCE: 666
tcaacacttg ctggtttcct                                               20

<210> SEQ ID NO 667
<211> LENGTH: 18
<212> TYPE: DNA
<213> ORGANISM: Human herpes virus 6B

<400> SEQUENCE: 667
ctgcacactg ttgttttt                                                 18

<210> SEQ ID NO 668
<211> LENGTH: 18
<212> TYPE: DNA
<213> ORGANISM: Homo sapiens

<400> SEQUENCE: 668
cagcacactg tggtttgt                                                 18

<210> SEQ ID NO 669
<211> LENGTH: 20
<212> TYPE: DNA
<213> ORGANISM: Human herpes virus 6B
```

```
<400> SEQUENCE: 669
gcgtcccaac ttgttttctg                                            20

<210> SEQ ID NO 670
<211> LENGTH: 21
<212> TYPE: DNA
<213> ORGANISM: Homo sapiens

<400> SEQUENCE: 670
gcgacccata cttggtttca g                                          21

<210> SEQ ID NO 671
<211> LENGTH: 17
<212> TYPE: DNA
<213> ORGANISM: Human herpes virus 6B

<400> SEQUENCE: 671
acacgggcga gcggcgg                                               17

<210> SEQ ID NO 672
<211> LENGTH: 19
<212> TYPE: DNA
<213> ORGANISM: Homo sapiens

<400> SEQUENCE: 672
acacgggcga cagctgcgg                                             19

<210> SEQ ID NO 673
<211> LENGTH: 19
<212> TYPE: DNA
<213> ORGANISM: Human herpes virus 6B

<400> SEQUENCE: 673
cgacgggatt tagtgagca                                             19

<210> SEQ ID NO 674
<211> LENGTH: 20
<212> TYPE: DNA
<213> ORGANISM: Homo sapiens

<400> SEQUENCE: 674
caacgggtat ttattgagca                                            20

<210> SEQ ID NO 675
<211> LENGTH: 23
<212> TYPE: DNA
<213> ORGANISM: Human herpes virus 6B

<400> SEQUENCE: 675
tccgtctcag tgtcacttat ata                                        23

<210> SEQ ID NO 676
<211> LENGTH: 20
<212> TYPE: DNA
<213> ORGANISM: Homo sapiens

<400> SEQUENCE: 676
tccgtctcag ttactttata                                            20

<210> SEQ ID NO 677
<211> LENGTH: 20
<212> TYPE: DNA
<213> ORGANISM: Human herpes virus 6B
```

```
<400> SEQUENCE: 677
ggtggcaccg aatccggaat                                               20

<210> SEQ ID NO 678
<211> LENGTH: 21
<212> TYPE: DNA
<213> ORGANISM: Homo sapiens

<400> SEQUENCE: 678
ggtgggcaca gaatctggac t                                             21

<210> SEQ ID NO 679
<211> LENGTH: 19
<212> TYPE: DNA
<213> ORGANISM: Human herpes virus 6B

<400> SEQUENCE: 679
agtttatcag aatgatatt                                                19

<210> SEQ ID NO 680
<211> LENGTH: 19
<212> TYPE: DNA
<213> ORGANISM: Homo sapiens

<400> SEQUENCE: 680
agcttatcag actgatgtt                                                19

<210> SEQ ID NO 681
<211> LENGTH: 19
<212> TYPE: DNA
<213> ORGANISM: Human herpes virus 6B

<400> SEQUENCE: 681
gagtttcgtg atgtcttgc                                                19

<210> SEQ ID NO 682
<211> LENGTH: 19
<212> TYPE: DNA
<213> ORGANISM: Homo sapiens

<400> SEQUENCE: 682
gagtcttgtg atgtcttgc                                                19

<210> SEQ ID NO 683
<211> LENGTH: 18
<212> TYPE: DNA
<213> ORGANISM: Human herpes virus 6B

<400> SEQUENCE: 683
gatataatat ggttcctg                                                 18

<210> SEQ ID NO 684
<211> LENGTH: 19
<212> TYPE: DNA
<213> ORGANISM: Homo sapiens

<400> SEQUENCE: 684
gataaaatat tggtacctg                                                19

<210> SEQ ID NO 685
<211> LENGTH: 21
<212> TYPE: DNA
<213> ORGANISM: Human herpes virus 6B
```

```
<400> SEQUENCE: 685
gtagcattcg acagggctgt c                                              21

<210> SEQ ID NO 686
<211> LENGTH: 21
<212> TYPE: DNA
<213> ORGANISM: Homo sapiens

<400> SEQUENCE: 686
gcagcattgt acagggctat c                                              21

<210> SEQ ID NO 687
<211> LENGTH: 20
<212> TYPE: DNA
<213> ORGANISM: Human herpes virus 6B

<400> SEQUENCE: 687
cgccgcgtct tgccaagtgg                                                20

<210> SEQ ID NO 688
<211> LENGTH: 20
<212> TYPE: DNA
<213> ORGANISM: Homo sapiens

<400> SEQUENCE: 688
cgcctgttct tgccaggtgg                                                20

<210> SEQ ID NO 689
<211> LENGTH: 20
<212> TYPE: DNA
<213> ORGANISM: Human herpes virus 6B

<400> SEQUENCE: 689
acagtagtca ccggattggt                                                20

<210> SEQ ID NO 690
<211> LENGTH: 20
<212> TYPE: DNA
<213> ORGANISM: Homo sapiens

<400> SEQUENCE: 690
acagtagtct gcacattggt                                                20

<210> SEQ ID NO 691
<211> LENGTH: 22
<212> TYPE: DNA
<213> ORGANISM: Human herpes virus 6B

<400> SEQUENCE: 691
acgggttaga gattttggaa gc                                             22

<210> SEQ ID NO 692
<211> LENGTH: 21
<212> TYPE: DNA
<213> ORGANISM: Homo sapiens

<400> SEQUENCE: 692
acgggttagg ctcttgggag c                                              21

<210> SEQ ID NO 693
<211> LENGTH: 18
<212> TYPE: DNA
<213> ORGANISM: Human herpes virus 6B
```

```
<400> SEQUENCE: 693
atacgcgccg actctctc                                                18

<210> SEQ ID NO 694
<211> LENGTH: 20
<212> TYPE: DNA
<213> ORGANISM: Homo sapiens

<400> SEQUENCE: 694
atacaagggc agactctctc                                              20

<210> SEQ ID NO 695
<211> LENGTH: 21
<212> TYPE: DNA
<213> ORGANISM: Human herpes virus 6B

<400> SEQUENCE: 695
caatacaacc taccctcttt c                                            21

<210> SEQ ID NO 696
<211> LENGTH: 21
<212> TYPE: DNA
<213> ORGANISM: Homo sapiens

<400> SEQUENCE: 696
ctatacaatc tactgtcttt c                                            21

<210> SEQ ID NO 697
<211> LENGTH: 18
<212> TYPE: DNA
<213> ORGANISM: Human herpes virus 6B

<400> SEQUENCE: 697
gtcgtgcacg gcactcct                                                18

<210> SEQ ID NO 698
<211> LENGTH: 18
<212> TYPE: DNA
<213> ORGANISM: Homo sapiens

<400> SEQUENCE: 698
gtcatacacg gctctcct                                                18

<210> SEQ ID NO 699
<211> LENGTH: 21
<212> TYPE: DNA
<213> ORGANISM: Human herpes virus 6B

<400> SEQUENCE: 699
gtggtttctt ttggagcagt t                                            21

<210> SEQ ID NO 700
<211> LENGTH: 20
<212> TYPE: DNA
<213> ORGANISM: Homo sapiens

<400> SEQUENCE: 700
gtgccttctt ttggagcgtt                                              20

<210> SEQ ID NO 701
<211> LENGTH: 22
<212> TYPE: DNA
<213> ORGANISM: Human herpes virus 6B
```

```
<400> SEQUENCE: 701
agaattgtag gcttccatct gt                                              22

<210> SEQ ID NO 702
<211> LENGTH: 22
<212> TYPE: DNA
<213> ORGANISM: Homo sapiens

<400> SEQUENCE: 702
agaattgtgg ctggacatct gt                                              22

<210> SEQ ID NO 703
<211> LENGTH: 19
<212> TYPE: DNA
<213> ORGANISM: Human herpes virus 6B

<400> SEQUENCE: 703
cagccatcgg cagatccac                                                  19

<210> SEQ ID NO 704
<211> LENGTH: 20
<212> TYPE: DNA
<213> ORGANISM: Homo sapiens

<400> SEQUENCE: 704
cagtccatgg gcatatacac                                                 20

<210> SEQ ID NO 705
<211> LENGTH: 23
<212> TYPE: DNA
<213> ORGANISM: Human herpes virus 6B

<400> SEQUENCE: 705
aggtagtgcg tcctggtgtt ggg                                             23

<210> SEQ ID NO 706
<211> LENGTH: 21
<212> TYPE: DNA
<213> ORGANISM: Homo sapiens

<400> SEQUENCE: 706
aggtagtttc ctgttgttgg g                                               21

<210> SEQ ID NO 707
<211> LENGTH: 18
<212> TYPE: DNA
<213> ORGANISM: Human herpes virus 6B

<400> SEQUENCE: 707
ctgcacactg ttgttttt                                                   18

<210> SEQ ID NO 708
<211> LENGTH: 18
<212> TYPE: DNA
<213> ORGANISM: Homo sapiens

<400> SEQUENCE: 708
cagcacactg tggtttgt                                                   18

<210> SEQ ID NO 709
<211> LENGTH: 24
<212> TYPE: DNA
<213> ORGANISM: Human herpes virus 6B
```

-continued

```
<400> SEQUENCE: 709
aagtgctgcg acatttttag agtg                                          24

<210> SEQ ID NO 710
<211> LENGTH: 21
<212> TYPE: DNA
<213> ORGANISM: Homo sapiens

<400> SEQUENCE: 710
aagtgctgcg acatttgagc g                                             21

<210> SEQ ID NO 711
<211> LENGTH: 20
<212> TYPE: DNA
<213> ORGANISM: Human herpes virus 6B

<400> SEQUENCE: 711
gcgtcccaac ttgttttctg                                               20

<210> SEQ ID NO 712
<211> LENGTH: 21
<212> TYPE: DNA
<213> ORGANISM: Homo sapiens

<400> SEQUENCE: 712
gcgacccata cttggtttca g                                             21

<210> SEQ ID NO 713
<211> LENGTH: 19
<212> TYPE: DNA
<213> ORGANISM: Human herpes virus 6B

<400> SEQUENCE: 713
attttaacat tgaagtttt                                                19

<210> SEQ ID NO 714
<211> LENGTH: 21
<212> TYPE: DNA
<213> ORGANISM: Homo sapiens

<400> SEQUENCE: 714
actttaacat ggaagtgctt t                                             21

<210> SEQ ID NO 715
<211> LENGTH: 21
<212> TYPE: DNA
<213> ORGANISM: Human herpes virus 6B

<400> SEQUENCE: 715
taaacacatg gtggttctcc t                                             21

<210> SEQ ID NO 716
<211> LENGTH: 20
<212> TYPE: DNA
<213> ORGANISM: Homo sapiens

<400> SEQUENCE: 716
tcaacacttg ctggtttcct                                               20

<210> SEQ ID NO 717
<211> LENGTH: 20
<212> TYPE: DNA
<213> ORGANISM: Human herpes virus 6B
```

```
<400> SEQUENCE: 717
ataataactg gataatcttt                                              20

<210> SEQ ID NO 718
<211> LENGTH: 20
<212> TYPE: DNA
<213> ORGANISM: Homo sapiens

<400> SEQUENCE: 718
ataatacatg gttgatcttt                                              20

<210> SEQ ID NO 719
<211> LENGTH: 18
<212> TYPE: DNA
<213> ORGANISM: Human herpes virus 6B

<400> SEQUENCE: 719
agtcttatgt gctgccga                                                18

<210> SEQ ID NO 720
<211> LENGTH: 20
<212> TYPE: DNA
<213> ORGANISM: Homo sapiens

<400> SEQUENCE: 720
agtattaact gtgctgctga                                              20

<210> SEQ ID NO 721
<211> LENGTH: 19
<212> TYPE: DNA
<213> ORGANISM: Human herpes virus 6B

<400> SEQUENCE: 721
ataatgatgg ctccggtgt                                               19

<210> SEQ ID NO 722
<211> LENGTH: 22
<212> TYPE: DNA
<213> ORGANISM: Homo sapiens

<400> SEQUENCE: 722
atcatgatgg gctcctcggt gt                                           22

<210> SEQ ID NO 723
<211> LENGTH: 20
<212> TYPE: DNA
<213> ORGANISM: Human herpes virus 6B

<400> SEQUENCE: 723
ggtggcaccg aatccggaat                                              20

<210> SEQ ID NO 724
<211> LENGTH: 21
<212> TYPE: DNA
<213> ORGANISM: Homo sapiens

<400> SEQUENCE: 724
ggtgggcaca gaatctggac t                                            21

<210> SEQ ID NO 725
<211> LENGTH: 17
<212> TYPE: DNA
<213> ORGANISM: Human herpes virus 6B
```

```
<400> SEQUENCE: 725
acacgggcga gcggcgg                                                      17

<210> SEQ ID NO 726
<211> LENGTH: 19
<212> TYPE: DNA
<213> ORGANISM: Homo sapiens

<400> SEQUENCE: 726
acacgggcga cagctgcgg                                                    19

<210> SEQ ID NO 727
<211> LENGTH: 19
<212> TYPE: DNA
<213> ORGANISM: Human herpes virus 6B

<400> SEQUENCE: 727
cgacgggatt tagtgagca                                                    19

<210> SEQ ID NO 728
<211> LENGTH: 20
<212> TYPE: DNA
<213> ORGANISM: Homo sapiens

<400> SEQUENCE: 728
caacgggtat ttattgagca                                                   20

<210> SEQ ID NO 729
<211> LENGTH: 23
<212> TYPE: DNA
<213> ORGANISM: Human herpes virus 6B

<400> SEQUENCE: 729
tccgtctcag tgtcacttat ata                                               23

<210> SEQ ID NO 730
<211> LENGTH: 20
<212> TYPE: DNA
<213> ORGANISM: Homo sapiens

<400> SEQUENCE: 730
tccgtctcag ttactttata                                                   20

<210> SEQ ID NO 731
<211> LENGTH: 23
<212> TYPE: DNA
<213> ORGANISM: Human herpes virus 7

<400> SEQUENCE: 731
aaatgtggaa aataggtaa atc                                                23

<210> SEQ ID NO 732
<211> LENGTH: 21
<212> TYPE: DNA
<213> ORGANISM: Homo sapiens

<400> SEQUENCE: 732
agatgtggaa aaattggaat c                                                 21

<210> SEQ ID NO 733
<211> LENGTH: 18
<212> TYPE: DNA
<213> ORGANISM: Human herpes virus 7
```

```
<400> SEQUENCE: 733
ccagatggaa gcacgttc                                              18

<210> SEQ ID NO 734
<211> LENGTH: 18
<212> TYPE: DNA
<213> ORGANISM: Homo sapiens

<400> SEQUENCE: 734
ctagagggaa gcactttc                                              18

<210> SEQ ID NO 735
<211> LENGTH: 18
<212> TYPE: DNA
<213> ORGANISM: Human herpes virus 7

<400> SEQUENCE: 735
aagtttgagg atgtgcca                                              18

<210> SEQ ID NO 736
<211> LENGTH: 18
<212> TYPE: DNA
<213> ORGANISM: Homo sapiens

<400> SEQUENCE: 736
atgtttgagc atgtgcta                                              18

<210> SEQ ID NO 737
<211> LENGTH: 19
<212> TYPE: DNA
<213> ORGANISM: Human herpes virus 7

<400> SEQUENCE: 737
agcatcacga tatattggc                                             19

<210> SEQ ID NO 738
<211> LENGTH: 20
<212> TYPE: DNA
<213> ORGANISM: Homo sapiens

<400> SEQUENCE: 738
agcagcacgt aaatattggc                                            20

<210> SEQ ID NO 739
<211> LENGTH: 21
<212> TYPE: DNA
<213> ORGANISM: Human herpes virus 7

<400> SEQUENCE: 739
tatagactga tacgctttct g                                          21

<210> SEQ ID NO 740
<211> LENGTH: 21
<212> TYPE: DNA
<213> ORGANISM: Homo sapiens

<400> SEQUENCE: 740
tctagaggga agcgctttct g                                          21

<210> SEQ ID NO 741
<211> LENGTH: 22
<212> TYPE: DNA
<213> ORGANISM: Human herpes virus 7
```

```
<400> SEQUENCE: 741
tgtgccaaat tcgataagtg aa                                         22

<210> SEQ ID NO 742
<211> LENGTH: 21
<212> TYPE: DNA
<213> ORGANISM: Homo sapiens

<400> SEQUENCE: 742
tgtgacagat tgataactga a                                          21

<210> SEQ ID NO 743
<211> LENGTH: 21
<212> TYPE: DNA
<213> ORGANISM: Human herpes virus 7

<400> SEQUENCE: 743
tatagactga tacgctttct g                                          21

<210> SEQ ID NO 744
<211> LENGTH: 21
<212> TYPE: DNA
<213> ORGANISM: Homo sapiens

<400> SEQUENCE: 744
tctagaggga agcgctttct g                                          21

<210> SEQ ID NO 745
<211> LENGTH: 21
<212> TYPE: DNA
<213> ORGANISM: Human herpes virus 7

<400> SEQUENCE: 745
aagatccagt aatgaagaac t                                          21

<210> SEQ ID NO 746
<211> LENGTH: 20
<212> TYPE: DNA
<213> ORGANISM: Homo sapiens

<400> SEQUENCE: 746
aagctgccag ttgaagaact                                            20

<210> SEQ ID NO 747
<211> LENGTH: 25
<212> TYPE: DNA
<213> ORGANISM: Human herpes virus 7

<400> SEQUENCE: 747
ttgtacattt tatggctttt tcatt                                      25

<210> SEQ ID NO 748
<211> LENGTH: 22
<212> TYPE: DNA
<213> ORGANISM: Homo sapiens

<400> SEQUENCE: 748
ttgtacatgg taggctttca tt                                         22

<210> SEQ ID NO 749
<211> LENGTH: 21
<212> TYPE: DNA
<213> ORGANISM: Human herpes virus 7
```

```
<400> SEQUENCE: 749
agctaggggt gttgtaaaca g                                              21

<210> SEQ ID NO 750
<211> LENGTH: 19
<212> TYPE: DNA
<213> ORGANISM: Homo sapiens

<400> SEQUENCE: 750
agctggtgtt gtgaatcag                                                 19

<210> SEQ ID NO 751
<211> LENGTH: 20
<212> TYPE: DNA
<213> ORGANISM: Human herpes virus 7

<400> SEQUENCE: 751
tgggctgtgg ctgttgtgtg                                                20

<210> SEQ ID NO 752
<211> LENGTH: 20
<212> TYPE: DNA
<213> ORGANISM: Homo sapiens

<400> SEQUENCE: 752
tgggcggggg caggtgtgtg                                                20

<210> SEQ ID NO 753
<211> LENGTH: 20
<212> TYPE: DNA
<213> ORGANISM: Human herpes virus 7

<400> SEQUENCE: 753
aaagtaactg tagtattttc                                                20

<210> SEQ ID NO 754
<211> LENGTH: 20
<212> TYPE: DNA
<213> ORGANISM: Homo sapiens

<400> SEQUENCE: 754
aaagtagctg taccatttgc                                                20

<210> SEQ ID NO 755
<211> LENGTH: 20
<212> TYPE: DNA
<213> ORGANISM: Human herpes virus 7

<400> SEQUENCE: 755
tgactatgaa tttgacagtc                                                20

<210> SEQ ID NO 756
<211> LENGTH: 20
<212> TYPE: DNA
<213> ORGANISM: Homo sapiens

<400> SEQUENCE: 756
tgacctatga attgacagcc                                                20

<210> SEQ ID NO 757
<211> LENGTH: 20
<212> TYPE: DNA
<213> ORGANISM: Human herpes virus 7
```

```
<400> SEQUENCE: 757
agagattaca tcctgctaag                                               20

<210> SEQ ID NO 758
<211> LENGTH: 20
<212> TYPE: DNA
<213> ORGANISM: Homo sapiens

<400> SEQUENCE: 758
atataataca acctgctaag                                               20

<210> SEQ ID NO 759
<211> LENGTH: 19
<212> TYPE: DNA
<213> ORGANISM: Human herpes virus 7

<400> SEQUENCE: 759
tctcacagtg ctgaaagct                                                19

<210> SEQ ID NO 760
<211> LENGTH: 18
<212> TYPE: DNA
<213> ORGANISM: Homo sapiens

<400> SEQUENCE: 760
tatcacagtg ctgatgct                                                 18

<210> SEQ ID NO 761
<211> LENGTH: 20
<212> TYPE: DNA
<213> ORGANISM: Human herpes virus 7

<400> SEQUENCE: 761
aatcaagcga ggttgtagac                                               20

<210> SEQ ID NO 762
<211> LENGTH: 19
<212> TYPE: DNA
<213> ORGANISM: Homo sapiens

<400> SEQUENCE: 762
aatcaagcgt gggtgagac                                                19

<210> SEQ ID NO 763
<211> LENGTH: 19
<212> TYPE: DNA
<213> ORGANISM: Human herpes virus 7

<400> SEQUENCE: 763
gtcaatcctt ttagagatt                                                19

<210> SEQ ID NO 764
<211> LENGTH: 19
<212> TYPE: DNA
<213> ORGANISM: Homo sapiens

<400> SEQUENCE: 764
gtgcatcctt ttagaggtt                                                19

<210> SEQ ID NO 765
<211> LENGTH: 18
<212> TYPE: DNA
<213> ORGANISM: Human herpes virus 7
```

<400> SEQUENCE: 765
aacacttaat acaggagt                                               18

<210> SEQ ID NO 766
<211> LENGTH: 19
<212> TYPE: DNA
<213> ORGANISM: Homo sapiens

<400> SEQUENCE: 766
aacggcttca tacaggagt                                              19

<210> SEQ ID NO 767
<211> LENGTH: 18
<212> TYPE: DNA
<213> ORGANISM: Human herpes virus 7

<400> SEQUENCE: 767
gcactagcat atatttgc                                               18

<210> SEQ ID NO 768
<211> LENGTH: 18
<212> TYPE: DNA
<213> ORGANISM: Homo sapiens

<400> SEQUENCE: 768
gcactagcac atttttgc                                               18

<210> SEQ ID NO 769
<211> LENGTH: 20
<212> TYPE: DNA
<213> ORGANISM: Human herpes virus 7

<400> SEQUENCE: 769
tcacaaaccc aaggctcaca                                             20

<210> SEQ ID NO 770
<211> LENGTH: 20
<212> TYPE: DNA
<213> ORGANISM: Homo sapiens

<400> SEQUENCE: 770
tcccacaccc aaggcttgca                                             20

<210> SEQ ID NO 771
<211> LENGTH: 22
<212> TYPE: DNA
<213> ORGANISM: Human herpes virus 7

<400> SEQUENCE: 771
atcacttata ggaaactttt tt                                          22

<210> SEQ ID NO 772
<211> LENGTH: 22
<212> TYPE: DNA
<213> ORGANISM: Homo sapiens

<400> SEQUENCE: 772
atcacacaaa ggcaactttt gt                                          22

<210> SEQ ID NO 773
<211> LENGTH: 20
<212> TYPE: DNA
<213> ORGANISM: Human herpes virus 7

<400> SEQUENCE: 773
cgcactgttg gactgtcctg                                          20

<210> SEQ ID NO 774
<211> LENGTH: 20
<212> TYPE: DNA
<213> ORGANISM: Homo sapiens

<400> SEQUENCE: 774
cgcactgtgg gtacttgctg                                          20

<210> SEQ ID NO 775
<211> LENGTH: 22
<212> TYPE: DNA
<213> ORGANISM: Human herpes virus 7

<400> SEQUENCE: 775
aaaaatattt gtgattttcg cc                                       22

<210> SEQ ID NO 776
<211> LENGTH: 22
<212> TYPE: DNA
<213> ORGANISM: Homo sapiens

<400> SEQUENCE: 776
aaaagtaatt gtggttttgg cc                                       22

<210> SEQ ID NO 777
<211> LENGTH: 26
<212> TYPE: DNA
<213> ORGANISM: Human herpes virus 7

<400> SEQUENCE: 777
ccaatattac ttttgatatg gattta                                   26

<210> SEQ ID NO 778
<211> LENGTH: 22
<212> TYPE: DNA
<213> ORGANISM: Homo sapiens

<400> SEQUENCE: 778
ccaatattac tgtgctgctt ta                                       22

<210> SEQ ID NO 779
<211> LENGTH: 15
<212> TYPE: DNA
<213> ORGANISM: Human herpes virus 7

<400> SEQUENCE: 779
agccagggac ggagc                                               15

<210> SEQ ID NO 780
<211> LENGTH: 18
<212> TYPE: DNA
<213> ORGANISM: Homo sapiens

<400> SEQUENCE: 780
agccagttgg acaggagc                                            18

<210> SEQ ID NO 781
<211> LENGTH: 18
<212> TYPE: DNA
<213> ORGANISM: Human herpes virus 7

```
<400> SEQUENCE: 781
tgttcgttcc acgcttga                                                 18

<210> SEQ ID NO 782
<211> LENGTH: 20
<212> TYPE: DNA
<213> ORGANISM: Homo sapiens

<400> SEQUENCE: 782
tgttcgttcg gctcgcgtga                                               20

<210> SEQ ID NO 783
<211> LENGTH: 20
<212> TYPE: DNA
<213> ORGANISM: Human herpes virus 7

<400> SEQUENCE: 783
aagttctaca cattcccact                                               20

<210> SEQ ID NO 784
<211> LENGTH: 21
<212> TYPE: DNA
<213> ORGANISM: Homo sapiens

<400> SEQUENCE: 784
aagttctgag acactccgac t                                             21

<210> SEQ ID NO 785
<211> LENGTH: 19
<212> TYPE: DNA
<213> ORGANISM: Human herpes virus 7

<400> SEQUENCE: 785
agatgaagaa atgttagct                                                19

<210> SEQ ID NO 786
<211> LENGTH: 18
<212> TYPE: DNA
<213> ORGANISM: Homo sapiens

<400> SEQUENCE: 786
agatgaagca ctgtagct                                                 18

<210> SEQ ID NO 787
<211> LENGTH: 18
<212> TYPE: DNA
<213> ORGANISM: Human herpes virus 7

<400> SEQUENCE: 787
attaagtaga acaatact                                                 18

<210> SEQ ID NO 788
<211> LENGTH: 20
<212> TYPE: DNA
<213> ORGANISM: Homo sapiens

<400> SEQUENCE: 788
ataaagtaga aagcactact                                               20

<210> SEQ ID NO 789
<211> LENGTH: 22
<212> TYPE: DNA
<213> ORGANISM: Human herpes virus 7
```

```
<400> SEQUENCE: 789
cacaccaggt gtatgacaca tt                                            22

<210> SEQ ID NO 790
<211> LENGTH: 20
<212> TYPE: DNA
<213> ORGANISM: Homo sapiens

<400> SEQUENCE: 790
cacaccgtat ctgacacttt                                               20

<210> SEQ ID NO 791
<211> LENGTH: 14
<212> TYPE: DNA
<213> ORGANISM: Human herpes virus 7

<400> SEQUENCE: 791
tactgaatat cagt                                                     14

<210> SEQ ID NO 792
<211> LENGTH: 18
<212> TYPE: DNA
<213> ORGANISM: Homo sapiens

<400> SEQUENCE: 792
tactgagctg atatcagt                                                 18

<210> SEQ ID NO 793
<211> LENGTH: 15
<212> TYPE: DNA
<213> ORGANISM: Human herpes virus 7

<400> SEQUENCE: 793
ttttgcacct ttagt                                                    15

<210> SEQ ID NO 794
<211> LENGTH: 18
<212> TYPE: DNA
<213> ORGANISM: Homo sapiens

<400> SEQUENCE: 794
ttttgcacct tttggagt                                                 18

<210> SEQ ID NO 795
<211> LENGTH: 22
<212> TYPE: DNA
<213> ORGANISM: Human herpes virus 7

<400> SEQUENCE: 795
ctgattgcat atttggttta ga                                            22

<210> SEQ ID NO 796
<211> LENGTH: 23
<212> TYPE: DNA
<213> ORGANISM: Homo sapiens

<400> SEQUENCE: 796
ctggtttcat atggtggttt aga                                           23

<210> SEQ ID NO 797
<211> LENGTH: 21
<212> TYPE: DNA
<213> ORGANISM: Human herpes virus 7
```

```
<400> SEQUENCE: 797
atatgtttga actatatcag g                                         21

<210> SEQ ID NO 798
<211> LENGTH: 19
<212> TYPE: DNA
<213> ORGANISM: Homo sapiens

<400> SEQUENCE: 798
atatgtttga tatattagg                                            19

<210> SEQ ID NO 799
<211> LENGTH: 20
<212> TYPE: DNA
<213> ORGANISM: Human herpes virus 7

<400> SEQUENCE: 799
gcaaatcctt gtcaaaaatg                                           20

<210> SEQ ID NO 800
<211> LENGTH: 19
<212> TYPE: DNA
<213> ORGANISM: Homo sapiens

<400> SEQUENCE: 800
gcaaatccat gcaaaactg                                            19

<210> SEQ ID NO 801
<211> LENGTH: 22
<212> TYPE: DNA
<213> ORGANISM: Human herpes virus 7

<400> SEQUENCE: 801
ctgaactcgt tacgcgtcct cc                                        22

<210> SEQ ID NO 802
<211> LENGTH: 19
<212> TYPE: DNA
<213> ORGANISM: Homo sapiens

<400> SEQUENCE: 802
ctgactgttg ccgtcctcc                                            19

<210> SEQ ID NO 803
<211> LENGTH: 25
<212> TYPE: DNA
<213> ORGANISM: Human herpes virus 7

<400> SEQUENCE: 803
cacagcatcc aattttccgg gtaga                                     25

<210> SEQ ID NO 804
<211> LENGTH: 22
<212> TYPE: DNA
<213> ORGANISM: Homo sapiens

<400> SEQUENCE: 804
cactggctcc tttctgggta ga                                        22

<210> SEQ ID NO 805
<211> LENGTH: 21
<212> TYPE: DNA
<213> ORGANISM: Human herpes virus 7
```

```
<400> SEQUENCE: 805
gtcctgtgga ctaaagtcct g                                             21

<210> SEQ ID NO 806
<211> LENGTH: 20
<212> TYPE: DNA
<213> ORGANISM: Homo sapiens

<400> SEQUENCE: 806
gccctgtgga ctcagttctg                                               20

<210> SEQ ID NO 807
<211> LENGTH: 18
<212> TYPE: DNA
<213> ORGANISM: Human herpes virus 7

<400> SEQUENCE: 807
acactctgtt acttttgc                                                 18

<210> SEQ ID NO 808
<211> LENGTH: 21
<212> TYPE: DNA
<213> ORGANISM: Homo sapiens

<400> SEQUENCE: 808
acacactgca attactttg c                                              21

<210> SEQ ID NO 809
<211> LENGTH: 18
<212> TYPE: DNA
<213> ORGANISM: Human herpes virus 7

<400> SEQUENCE: 809
ttttgcataa ttgttaca                                                 18

<210> SEQ ID NO 810
<211> LENGTH: 20
<212> TYPE: DNA
<213> ORGANISM: Homo sapiens

<400> SEQUENCE: 810
ttttgcatag ttgcactaca                                               20

<210> SEQ ID NO 811
<211> LENGTH: 19
<212> TYPE: DNA
<213> ORGANISM: Human herpes virus 7

<400> SEQUENCE: 811
tgcctgttaa aagtgaacc                                                19

<210> SEQ ID NO 812
<211> LENGTH: 18
<212> TYPE: DNA
<213> ORGANISM: Homo sapiens

<400> SEQUENCE: 812
tgcccttaaa ggtgaacc                                                 18

<210> SEQ ID NO 813
<211> LENGTH: 21
<212> TYPE: DNA
<213> ORGANISM: Human herpes virus 7
```

<400> SEQUENCE: 813
acacacatac acacacacac a                                      21

<210> SEQ ID NO 814
<211> LENGTH: 21
<212> TYPE: DNA
<213> ORGANISM: Homo sapiens

<400> SEQUENCE: 814
acgctcatgc acacacccac a                                      21

<210> SEQ ID NO 815
<211> LENGTH: 21
<212> TYPE: DNA
<213> ORGANISM: Human herpes virus 7

<400> SEQUENCE: 815
tctcggtgaa cagttctctt t                                      21

<210> SEQ ID NO 816
<211> LENGTH: 21
<212> TYPE: DNA
<213> ORGANISM: Homo sapiens

<400> SEQUENCE: 816
tcacagtgaa ccggtctctt t                                      21

<210> SEQ ID NO 817
<211> LENGTH: 20
<212> TYPE: DNA
<213> ORGANISM: Human herpes virus 7

<400> SEQUENCE: 817
ttacccgatt aactttttat                                        20

<210> SEQ ID NO 818
<211> LENGTH: 20
<212> TYPE: DNA
<213> ORGANISM: Homo sapiens

<400> SEQUENCE: 818
ttacccgagc aactttgcat                                        20

<210> SEQ ID NO 819
<211> LENGTH: 21
<212> TYPE: DNA
<213> ORGANISM: Human herpes virus 7

<400> SEQUENCE: 819
tttgttgact ttggacacat c                                      21

<210> SEQ ID NO 820
<211> LENGTH: 21
<212> TYPE: DNA
<213> ORGANISM: Homo sapiens

<400> SEQUENCE: 820
tatgtgcctt tggactacat c                                      21

<210> SEQ ID NO 821
<211> LENGTH: 20
<212> TYPE: DNA
<213> ORGANISM: Human herpes virus 7

<400> SEQUENCE: 821
ccttgcagaa gctgttcgtt                                              20

<210> SEQ ID NO 822
<211> LENGTH: 20
<212> TYPE: DNA
<213> ORGANISM: Homo sapiens

<400> SEQUENCE: 822
ccttgcaggg gctgttgggt                                              20

<210> SEQ ID NO 823
<211> LENGTH: 18
<212> TYPE: DNA
<213> ORGANISM: Human herpes virus 7

<400> SEQUENCE: 823
cagcattgta cagcggta                                                18

<210> SEQ ID NO 824
<211> LENGTH: 18
<212> TYPE: DNA
<213> ORGANISM: Homo sapiens

<400> SEQUENCE: 824
cagcattgta cagggcta                                                18

<210> SEQ ID NO 825
<211> LENGTH: 19
<212> TYPE: DNA
<213> ORGANISM: Human herpes virus 7

<400> SEQUENCE: 825
ccatttcatt atcagagtt                                               19

<210> SEQ ID NO 826
<211> LENGTH: 18
<212> TYPE: DNA
<213> ORGANISM: Homo sapiens

<400> SEQUENCE: 826
ccattgcata tcggagtt                                                18

<210> SEQ ID NO 827
<211> LENGTH: 20
<212> TYPE: DNA
<213> ORGANISM: Human herpes virus 7

<400> SEQUENCE: 827
tcaatcacta cagactttgt                                              20

<210> SEQ ID NO 828
<211> LENGTH: 22
<212> TYPE: DNA
<213> ORGANISM: Homo sapiens

<400> SEQUENCE: 828
tcagtgcact acagaacttt gt                                           22

<210> SEQ ID NO 829
<211> LENGTH: 26
<212> TYPE: DNA
<213> ORGANISM: Human herpes virus 7

```
<400> SEQUENCE: 829
atgcatattg tgtattttat aggtcc                                          26

<210> SEQ ID NO 830
<211> LENGTH: 21
<212> TYPE: DNA
<213> ORGANISM: Homo sapiens

<400> SEQUENCE: 830
atgcattgta ttttaggtc c                                                21

<210> SEQ ID NO 831
<211> LENGTH: 19
<212> TYPE: DNA
<213> ORGANISM: Human herpes virus 7

<400> SEQUENCE: 831
ttacattgtt caaagttac                                                  19

<210> SEQ ID NO 832
<211> LENGTH: 22
<212> TYPE: DNA
<213> ORGANISM: Homo sapiens

<400> SEQUENCE: 832
ttacagttgt tcaaccagtt ac                                              22

<210> SEQ ID NO 833
<211> LENGTH: 18
<212> TYPE: DNA
<213> ORGANISM: Human herpes virus 7

<400> SEQUENCE: 833
aaacatcctc caccccgc                                                   18

<210> SEQ ID NO 834
<211> LENGTH: 18
<212> TYPE: DNA
<213> ORGANISM: Homo sapiens

<400> SEQUENCE: 834
aaacatccta cactcagc                                                   18

<210> SEQ ID NO 835
<211> LENGTH: 21
<212> TYPE: DNA
<213> ORGANISM: Human herpes virus 7

<400> SEQUENCE: 835
tgagacgagc atctagcttg t                                               21

<210> SEQ ID NO 836
<211> LENGTH: 21
<212> TYPE: DNA
<213> ORGANISM: Homo sapiens

<400> SEQUENCE: 836
taagacgagc aaaaagcttg t                                               21

<210> SEQ ID NO 837
<211> LENGTH: 22
<212> TYPE: DNA
<213> ORGANISM: Human herpes virus 7
```

```
<400> SEQUENCE: 837
taaggccagc ctaaaaatac tt                                              22

<210> SEQ ID NO 838
<211> LENGTH: 20
<212> TYPE: DNA
<213> ORGANISM: Homo sapiens

<400> SEQUENCE: 838
taatgcccct aaaaatcctt                                                 20

<210> SEQ ID NO 839
<211> LENGTH: 19
<212> TYPE: DNA
<213> ORGANISM: Human herpes virus 7

<400> SEQUENCE: 839
atgctgtgat attgttagc                                                  19

<210> SEQ ID NO 840
<211> LENGTH: 18
<212> TYPE: DNA
<213> ORGANISM: Homo sapiens

<400> SEQUENCE: 840
aggcagtgta ttgttagc                                                   18

<210> SEQ ID NO 841
<211> LENGTH: 25
<212> TYPE: DNA
<213> ORGANISM: Human herpes virus 7

<400> SEQUENCE: 841
aagtgtgttc caagtttttc agtgg                                           25

<210> SEQ ID NO 842
<211> LENGTH: 22
<212> TYPE: DNA
<213> ORGANISM: Homo sapiens

<400> SEQUENCE: 842
aagtgcttcc atgtttcagt gg                                              22

<210> SEQ ID NO 843
<211> LENGTH: 22
<212> TYPE: DNA
<213> ORGANISM: Human herpes virus 7

<400> SEQUENCE: 843
aaagttctga aaaatcatag at                                              22

<210> SEQ ID NO 844
<211> LENGTH: 21
<212> TYPE: DNA
<213> ORGANISM: Homo sapiens

<400> SEQUENCE: 844
aaactactga aaatcaaaga t                                               21

<210> SEQ ID NO 845
<211> LENGTH: 18
<212> TYPE: DNA
<213> ORGANISM: Human herpes virus 7
```

```
<400> SEQUENCE: 845
ccagatggaa gcacgttc                                                   18

<210> SEQ ID NO 846
<211> LENGTH: 18
<212> TYPE: DNA
<213> ORGANISM: Homo sapiens

<400> SEQUENCE: 846
ccagagggaa gtactttc                                                   18

<210> SEQ ID NO 847
<211> LENGTH: 19
<212> TYPE: DNA
<213> ORGANISM: Human herpes virus 7

<400> SEQUENCE: 847
atcaacagcc atctaattg                                                  19

<210> SEQ ID NO 848
<211> LENGTH: 18
<212> TYPE: DNA
<213> ORGANISM: Homo sapiens

<400> SEQUENCE: 848
atcaacagac attaattg                                                   18

<210> SEQ ID NO 849
<211> LENGTH: 21
<212> TYPE: DNA
<213> ORGANISM: Human herpes virus 7

<400> SEQUENCE: 849
aagacatgga aacagcacct c                                               21

<210> SEQ ID NO 850
<211> LENGTH: 23
<212> TYPE: DNA
<213> ORGANISM: Homo sapiens

<400> SEQUENCE: 850
aagacatagg atagagtcac ctc                                             23

<210> SEQ ID NO 851
<211> LENGTH: 22
<212> TYPE: DNA
<213> ORGANISM: Human herpes virus 7

<400> SEQUENCE: 851
tctgaaattt ccatttttc ag                                               22

<210> SEQ ID NO 852
<211> LENGTH: 20
<212> TYPE: DNA
<213> ORGANISM: Homo sapiens

<400> SEQUENCE: 852
tctgaaattc agttcttcag                                                 20

<210> SEQ ID NO 853
<211> LENGTH: 19
<212> TYPE: DNA
<213> ORGANISM: Human herpes virus 7
```

```
<400> SEQUENCE: 853
ttgcatagcc aaacaaaag                                            19

<210> SEQ ID NO 854
<211> LENGTH: 17
<212> TYPE: DNA
<213> ORGANISM: Homo sapiens

<400> SEQUENCE: 854
ttgcatagtc acaaaag                                              17

<210> SEQ ID NO 855
<211> LENGTH: 18
<212> TYPE: DNA
<213> ORGANISM: Human herpes virus 7

<400> SEQUENCE: 855
ccagatggaa gcacgttc                                             18

<210> SEQ ID NO 856
<211> LENGTH: 18
<212> TYPE: DNA
<213> ORGANISM: Homo sapiens

<400> SEQUENCE: 856
ccagagggat gcactttc                                             18

<210> SEQ ID NO 857
<211> LENGTH: 18
<212> TYPE: DNA
<213> ORGANISM: Human herpes virus 7

<400> SEQUENCE: 857
tagtagactg tcatcgta                                             18

<210> SEQ ID NO 858
<211> LENGTH: 19
<212> TYPE: DNA
<213> ORGANISM: Homo sapiens

<400> SEQUENCE: 858
tagtagaccg tatagcgta                                            19

<210> SEQ ID NO 859
<211> LENGTH: 23
<212> TYPE: DNA
<213> ORGANISM: Human herpes virus 7

<400> SEQUENCE: 859
actaatttca ttttggagat cag                                       23

<210> SEQ ID NO 860
<211> LENGTH: 22
<212> TYPE: DNA
<213> ORGANISM: Homo sapiens

<400> SEQUENCE: 860
actgatttct tttggtgttc ag                                        22

<210> SEQ ID NO 861
<211> LENGTH: 22
<212> TYPE: DNA
<213> ORGANISM: Human herpes virus 7
```

```
<400> SEQUENCE: 861
gaatgtggta agaagtttgt at                                          22

<210> SEQ ID NO 862
<211> LENGTH: 20
<212> TYPE: DNA
<213> ORGANISM: Homo sapiens

<400> SEQUENCE: 862
gaatgtaaag aagtatgtat                                             20

<210> SEQ ID NO 863
<211> LENGTH: 19
<212> TYPE: DNA
<213> ORGANISM: Human herpes virus 7

<400> SEQUENCE: 863
tgttttctat agaatcagt                                              19

<210> SEQ ID NO 864
<211> LENGTH: 18
<212> TYPE: DNA
<213> ORGANISM: Homo sapiens

<400> SEQUENCE: 864
tgtgttctct agatcagt                                               18

<210> SEQ ID NO 865
<211> LENGTH: 21
<212> TYPE: DNA
<213> ORGANISM: Human herpes virus 7

<400> SEQUENCE: 865
tcgatttttc acagaaatcc c                                           21

<210> SEQ ID NO 866
<211> LENGTH: 21
<212> TYPE: DNA
<213> ORGANISM: Homo sapiens

<400> SEQUENCE: 866
tccagttttc ccaggaatcc c                                           21

<210> SEQ ID NO 867
<211> LENGTH: 19
<212> TYPE: DNA
<213> ORGANISM: Human herpes virus 7

<400> SEQUENCE: 867
accaggtgac gtctagaca                                              19

<210> SEQ ID NO 868
<211> LENGTH: 20
<212> TYPE: DNA
<213> ORGANISM: Homo sapiens

<400> SEQUENCE: 868
aacaggtgac tggttagaca                                             20

<210> SEQ ID NO 869
<211> LENGTH: 19
<212> TYPE: DNA
<213> ORGANISM: Human herpes virus 7
```

```
<400> SEQUENCE: 869
gtgcgtcaca caactttt                                                   19

<210> SEQ ID NO 870
<211> LENGTH: 19
<212> TYPE: DNA
<213> ORGANISM: Homo sapiens

<400> SEQUENCE: 870
gtgcatcaca gaactttgt                                                  19

<210> SEQ ID NO 871
<211> LENGTH: 24
<212> TYPE: DNA
<213> ORGANISM: Human herpes virus 7

<400> SEQUENCE: 871
ctgcacaagt actaaatgct tgct                                            24

<210> SEQ ID NO 872
<211> LENGTH: 22
<212> TYPE: DNA
<213> ORGANISM: Homo sapiens

<400> SEQUENCE: 872
ctgcgcaagc tactgccttg ct                                              22

<210> SEQ ID NO 873
<211> LENGTH: 16
<212> TYPE: DNA
<213> ORGANISM: Human herpes virus 7

<400> SEQUENCE: 873
ttcataattc agaata                                                     16

<210> SEQ ID NO 874
<211> LENGTH: 18
<212> TYPE: DNA
<213> ORGANISM: Homo sapiens

<400> SEQUENCE: 874
ttcaagtaat tcaggata                                                   18

<210> SEQ ID NO 875
<211> LENGTH: 19
<212> TYPE: DNA
<213> ORGANISM: Human herpes virus 7

<400> SEQUENCE: 875
caagatgctt caatggttc                                                  19

<210> SEQ ID NO 876
<211> LENGTH: 20
<212> TYPE: DNA
<213> ORGANISM: Homo sapiens

<400> SEQUENCE: 876
caagctcgct tctatgggtc                                                 20

<210> SEQ ID NO 877
<211> LENGTH: 20
<212> TYPE: DNA
<213> ORGANISM: Human herpes virus 7
```

```
<400> SEQUENCE: 877
caggcttatt cccccccgtt                                                     20

<210> SEQ ID NO 878
<211> LENGTH: 21
<212> TYPE: DNA
<213> ORGANISM: Homo sapiens

<400> SEQUENCE: 878
caggctcagt cccctcccga t                                                   21

<210> SEQ ID NO 879
<211> LENGTH: 21
<212> TYPE: DNA
<213> ORGANISM: Human herpes virus 7

<400> SEQUENCE: 879
aacaaacatg atgaacttat t                                                   21

<210> SEQ ID NO 880
<211> LENGTH: 21
<212> TYPE: DNA
<213> ORGANISM: Homo sapiens

<400> SEQUENCE: 880
aacaaacatg gtgcacttct t                                                   21

<210> SEQ ID NO 881
<211> LENGTH: 20
<212> TYPE: DNA
<213> ORGANISM: Human herpes virus 7

<400> SEQUENCE: 881
agaacagccg ttctcattgt                                                     20

<210> SEQ ID NO 882
<211> LENGTH: 20
<212> TYPE: DNA
<213> ORGANISM: Homo sapiens

<400> SEQUENCE: 882
agaccatggg ttctcattgt                                                     20

<210> SEQ ID NO 883
<211> LENGTH: 20
<212> TYPE: DNA
<213> ORGANISM: Human herpes virus 7

<400> SEQUENCE: 883
tgactatgaa tttgacagtc                                                     20

<210> SEQ ID NO 884
<211> LENGTH: 20
<212> TYPE: DNA
<213> ORGANISM: Homo sapiens

<400> SEQUENCE: 884
tgacctatga attgacagac                                                     20

<210> SEQ ID NO 885
<211> LENGTH: 21
<212> TYPE: DNA
<213> ORGANISM: Human herpes virus 7
```

```
<400> SEQUENCE: 885
acttgctctg tgaaacaatg t                                              21

<210> SEQ ID NO 886
<211> LENGTH: 21
<212> TYPE: DNA
<213> ORGANISM: Homo sapiens

<400> SEQUENCE: 886
acttgggcac tgaaacaatg t                                              21

<210> SEQ ID NO 887
<211> LENGTH: 21
<212> TYPE: DNA
<213> ORGANISM: Human herpes virus 7

<400> SEQUENCE: 887
cctgttctcc atgccctgcc t                                              21

<210> SEQ ID NO 888
<211> LENGTH: 21
<212> TYPE: DNA
<213> ORGANISM: Homo sapiens

<400> SEQUENCE: 888
cctgttctcc attacttggc t                                              21

<210> SEQ ID NO 889
<211> LENGTH: 18
<212> TYPE: DNA
<213> ORGANISM: Human herpes virus 7

<400> SEQUENCE: 889
tgatatgttt tattcggt                                                  18

<210> SEQ ID NO 890
<211> LENGTH: 20
<212> TYPE: DNA
<213> ORGANISM: Homo sapiens

<400> SEQUENCE: 890
tgatatgttt gatattgggt                                                20

<210> SEQ ID NO 891
<211> LENGTH: 21
<212> TYPE: DNA
<213> ORGANISM: Human herpes virus 7

<400> SEQUENCE: 891
ttttcagatt ctacaggggg a                                              21

<210> SEQ ID NO 892
<211> LENGTH: 21
<212> TYPE: DNA
<213> ORGANISM: Homo sapiens

<400> SEQUENCE: 892
ttatcagaat ctccaggggt a                                              21

<210> SEQ ID NO 893
<211> LENGTH: 20
<212> TYPE: DNA
<213> ORGANISM: Human herpes virus 7
```

```
<400> SEQUENCE: 893
gtggttcatt ttaaagggtt                                              20

<210> SEQ ID NO 894
<211> LENGTH: 20
<212> TYPE: DNA
<213> ORGANISM: Homo sapiens

<400> SEQUENCE: 894
gtgcttcctt ttagagggtt                                              20

<210> SEQ ID NO 895
<211> LENGTH: 21
<212> TYPE: DNA
<213> ORGANISM: Human herpes virus 7

<400> SEQUENCE: 895
tttgcagatt gaattatgat t                                            21

<210> SEQ ID NO 896
<211> LENGTH: 21
<212> TYPE: DNA
<213> ORGANISM: Homo sapiens

<400> SEQUENCE: 896
ttagcaggtt gtattatcat t                                            21

<210> SEQ ID NO 897
<211> LENGTH: 18
<212> TYPE: DNA
<213> ORGANISM: Human herpes virus 7

<400> SEQUENCE: 897
cttacactgt agtgtttg                                                18

<210> SEQ ID NO 898
<211> LENGTH: 18
<212> TYPE: DNA
<213> ORGANISM: Homo sapiens

<400> SEQUENCE: 898
cttacccagc agtgtttg                                                18

<210> SEQ ID NO 899
<211> LENGTH: 19
<212> TYPE: DNA
<213> ORGANISM: Human herpes virus 7

<400> SEQUENCE: 899
gtggttcatt ttaaagggt                                               19

<210> SEQ ID NO 900
<211> LENGTH: 19
<212> TYPE: DNA
<213> ORGANISM: Homo sapiens

<400> SEQUENCE: 900
gtgcttcctt ttagagggt                                               19

<210> SEQ ID NO 901
<211> LENGTH: 20
<212> TYPE: DNA
<213> ORGANISM: Human herpes virus 7
```

<400> SEQUENCE: 901
gtccatgtag tgcagcttta                                                    20

<210> SEQ ID NO 902
<211> LENGTH: 18
<212> TYPE: DNA
<213> ORGANISM: Homo sapiens

<400> SEQUENCE: 902
gtgcatctag tgcagtta                                                      18

<210> SEQ ID NO 903
<211> LENGTH: 21
<212> TYPE: DNA
<213> ORGANISM: Human herpes virus 7

<400> SEQUENCE: 903
aatagacatc ttccacaaaa a                                                  21

<210> SEQ ID NO 904
<211> LENGTH: 20
<212> TYPE: DNA
<213> ORGANISM: Homo sapiens

<400> SEQUENCE: 904
aatagtatct accacaataa                                                    20

<210> SEQ ID NO 905
<211> LENGTH: 19
<212> TYPE: DNA
<213> ORGANISM: Human herpes virus 7

<400> SEQUENCE: 905
tacagtttag ctgaagtac                                                     19

<210> SEQ ID NO 906
<211> LENGTH: 19
<212> TYPE: DNA
<213> ORGANISM: Homo sapiens

<400> SEQUENCE: 906
tacagtatag atgatgtac                                                     19

<210> SEQ ID NO 907
<211> LENGTH: 18
<212> TYPE: DNA
<213> ORGANISM: Human herpes virus 7

<400> SEQUENCE: 907
gtggaaataa tctctact                                                      18

<210> SEQ ID NO 908
<211> LENGTH: 18
<212> TYPE: DNA
<213> ORGANISM: Homo sapiens

<400> SEQUENCE: 908
gttgaaacaa tctctact                                                      18

<210> SEQ ID NO 909
<211> LENGTH: 19
<212> TYPE: DNA
<213> ORGANISM: Human herpes virus 7

-continued

```
<400> SEQUENCE: 909
caccaggtgt atgacacat                                              19

<210> SEQ ID NO 910
<211> LENGTH: 20
<212> TYPE: DNA
<213> ORGANISM: Homo sapiens

<400> SEQUENCE: 910
caccaccgtg tctgacactt                                             20

<210> SEQ ID NO 911
<211> LENGTH: 19
<212> TYPE: DNA
<213> ORGANISM: Human herpes virus 7

<400> SEQUENCE: 911
tttcagttag atgattaca                                              19

<210> SEQ ID NO 912
<211> LENGTH: 19
<212> TYPE: DNA
<213> ORGANISM: Homo sapiens

<400> SEQUENCE: 912
tttcagtcgg atgtttaca                                              19

<210> SEQ ID NO 913
<211> LENGTH: 22
<212> TYPE: DNA
<213> ORGANISM: Human herpes virus 7

<400> SEQUENCE: 913
gactgtaact ttttggatta ta                                          22

<210> SEQ ID NO 914
<211> LENGTH: 22
<212> TYPE: DNA
<213> ORGANISM: Homo sapiens

<400> SEQUENCE: 914
gattgtagcc ttttggagta ga                                          22

<210> SEQ ID NO 915
<211> LENGTH: 20
<212> TYPE: DNA
<213> ORGANISM: Human herpes virus 7

<400> SEQUENCE: 915
aaggccacgc tgtaaatgac                                             20

<210> SEQ ID NO 916
<211> LENGTH: 19
<212> TYPE: DNA
<213> ORGANISM: Homo sapiens

<400> SEQUENCE: 916
aaggcacgcg gtgaatgcc                                              19

<210> SEQ ID NO 917
<211> LENGTH: 18
<212> TYPE: DNA
<213> ORGANISM: Human herpes virus 7
```

```
<400> SEQUENCE: 917
tagatggcag cactatct                                              18

<210> SEQ ID NO 918
<211> LENGTH: 18
<212> TYPE: DNA
<213> ORGANISM: Homo sapiens

<400> SEQUENCE: 918
tagatggaag cactgtct                                              18

<210> SEQ ID NO 919
<211> LENGTH: 18
<212> TYPE: DNA
<213> ORGANISM: Human herpes virus 7

<400> SEQUENCE: 919
tattgcttat cttgatag                                              18

<210> SEQ ID NO 920
<211> LENGTH: 18
<212> TYPE: DNA
<213> ORGANISM: Homo sapiens

<400> SEQUENCE: 920
taatgctaat cgtgatag                                              18

<210> SEQ ID NO 921
<211> LENGTH: 22
<212> TYPE: DNA
<213> ORGANISM: Human herpes virus 7

<400> SEQUENCE: 921
aaaaatattt gtgattttcg cc                                         22

<210> SEQ ID NO 922
<211> LENGTH: 22
<212> TYPE: DNA
<213> ORGANISM: Homo sapiens

<400> SEQUENCE: 922
aaaagtaatt gtggtttttg cc                                         22

<210> SEQ ID NO 923
<211> LENGTH: 21
<212> TYPE: DNA
<213> ORGANISM: Human herpes virus 7

<400> SEQUENCE: 923
tagtaggtgt gcaggtagag t                                          21

<210> SEQ ID NO 924
<211> LENGTH: 21
<212> TYPE: DNA
<213> ORGANISM: Homo sapiens

<400> SEQUENCE: 924
tagtaggtgt ccagtaagtg t                                          21

<210> SEQ ID NO 925
<211> LENGTH: 18
<212> TYPE: DNA
<213> ORGANISM: Human herpes virus 7
```

```
<400> SEQUENCE: 925
aggctgtgtt agctgatt                                                    18

<210> SEQ ID NO 926
<211> LENGTH: 21
<212> TYPE: DNA
<213> ORGANISM: Homo sapiens

<400> SEQUENCE: 926
aggcagtgtc attagctgat t                                                21

<210> SEQ ID NO 927
<211> LENGTH: 20
<212> TYPE: DNA
<213> ORGANISM: Human herpes virus 7

<400> SEQUENCE: 927
atcgtttcaa aagatggtct                                                  20

<210> SEQ ID NO 928
<211> LENGTH: 18
<212> TYPE: DNA
<213> ORGANISM: Homo sapiens

<400> SEQUENCE: 928
atcgtctcaa atgagtct                                                    18

<210> SEQ ID NO 929
<211> LENGTH: 22
<212> TYPE: DNA
<213> ORGANISM: Human herpes virus 7

<400> SEQUENCE: 929
tttggatttt tctgcatcta ta                                               22

<210> SEQ ID NO 930
<211> LENGTH: 22
<212> TYPE: DNA
<213> ORGANISM: Homo sapiens

<400> SEQUENCE: 930
ttgggatcat tttgcatcca ta                                               22

<210> SEQ ID NO 931
<211> LENGTH: 19
<212> TYPE: DNA
<213> ORGANISM: Human herpes virus 7

<400> SEQUENCE: 931
agcatcacga tatattggc                                                   19

<210> SEQ ID NO 932
<211> LENGTH: 20
<212> TYPE: DNA
<213> ORGANISM: Homo sapiens

<400> SEQUENCE: 932
agcagcacag aaatattggc                                                  20

<210> SEQ ID NO 933
<211> LENGTH: 19
<212> TYPE: DNA
<213> ORGANISM: Human herpes virus 7
```

<400> SEQUENCE: 933
tcggtctcag tctcctcag                                          19

<210> SEQ ID NO 934
<211> LENGTH: 19
<212> TYPE: DNA
<213> ORGANISM: Homo sapiens

<400> SEQUENCE: 934
tcggtctgag gccctcag                                           19

<210> SEQ ID NO 935
<211> LENGTH: 21
<212> TYPE: DNA
<213> ORGANISM: Human herpes virus 7

<400> SEQUENCE: 935
tcatttggaa agaggtaaat g                                       21

<210> SEQ ID NO 936
<211> LENGTH: 21
<212> TYPE: DNA
<213> ORGANISM: Homo sapiens

<400> SEQUENCE: 936
tcatctgcaa agaagtaagt g                                       21

<210> SEQ ID NO 937
<211> LENGTH: 17
<212> TYPE: DNA
<213> ORGANISM: Human herpes virus 7

<400> SEQUENCE: 937
ataaagctag acacgaa                                            17

<210> SEQ ID NO 938
<211> LENGTH: 19
<212> TYPE: DNA
<213> ORGANISM: Homo sapiens

<400> SEQUENCE: 938
ataaagctag ataccgaa                                           19

<210> SEQ ID NO 939
<211> LENGTH: 20
<212> TYPE: DNA
<213> ORGANISM: Human herpes virus 7

<400> SEQUENCE: 939
cttcctcttc cacgcccaca                                         20

<210> SEQ ID NO 940
<211> LENGTH: 19
<212> TYPE: DNA
<213> ORGANISM: Homo sapiens

<400> SEQUENCE: 940
cttgctcgtc ccgcccgca                                          19

<210> SEQ ID NO 941
<211> LENGTH: 17
<212> TYPE: DNA
<213> ORGANISM: Human herpes virus 7

```
<400> SEQUENCE: 941
cacattacgt cagacct                                              17

<210> SEQ ID NO 942
<211> LENGTH: 19
<212> TYPE: DNA
<213> ORGANISM: Homo sapiens

<400> SEQUENCE: 942
cacattacac ggtcgacct                                            19

<210> SEQ ID NO 943
<211> LENGTH: 21
<212> TYPE: DNA
<213> ORGANISM: Human herpes virus 7

<400> SEQUENCE: 943
gttctaaagc aagatctgta a                                         21

<210> SEQ ID NO 944
<211> LENGTH: 20
<212> TYPE: DNA
<213> ORGANISM: Homo sapiens

<400> SEQUENCE: 944
gttcaaatcc agatctataa                                           20

<210> SEQ ID NO 945
<211> LENGTH: 18
<212> TYPE: DNA
<213> ORGANISM: Human herpes virus 7

<400> SEQUENCE: 945
ccagatggaa gcacgttc                                             18

<210> SEQ ID NO 946
<211> LENGTH: 18
<212> TYPE: DNA
<213> ORGANISM: Homo sapiens

<400> SEQUENCE: 946
ctagagggaa gcactttc                                             18

<210> SEQ ID NO 947
<211> LENGTH: 18
<212> TYPE: DNA
<213> ORGANISM: Human herpes virus 7

<400> SEQUENCE: 947
gtaaacaacc cggatgga                                             18

<210> SEQ ID NO 948
<211> LENGTH: 19
<212> TYPE: DNA
<213> ORGANISM: Homo sapiens

<400> SEQUENCE: 948
gtaaacatcc ccgactgga                                            19

<210> SEQ ID NO 949
<211> LENGTH: 19
<212> TYPE: DNA
<213> ORGANISM: Human herpes virus 7
```

-continued

```
<400> SEQUENCE: 949
gcgagcctgt gatccccac                                                      19

<210> SEQ ID NO 950
<211> LENGTH: 19
<212> TYPE: DNA
<213> ORGANISM: Homo sapiens

<400> SEQUENCE: 950
gggcgcctgt gatcccaac                                                      19

<210> SEQ ID NO 951
<211> LENGTH: 20
<212> TYPE: DNA
<213> ORGANISM: Human herpes virus 7

<400> SEQUENCE: 951
ctagtcctga ttcaaaaagt                                                     20

<210> SEQ ID NO 952
<211> LENGTH: 20
<212> TYPE: DNA
<213> ORGANISM: Homo sapiens

<400> SEQUENCE: 952
ctagtcctga ctcagccagt                                                     20

<210> SEQ ID NO 953
<211> LENGTH: 22
<212> TYPE: DNA
<213> ORGANISM: Human herpes virus 7

<400> SEQUENCE: 953
catcttacac gacagcattg ta                                                  22

<210> SEQ ID NO 954
<211> LENGTH: 22
<212> TYPE: DNA
<213> ORGANISM: Homo sapiens

<400> SEQUENCE: 954
catcttactg ggcagcattg ga                                                  22

<210> SEQ ID NO 955
<211> LENGTH: 17
<212> TYPE: DNA
<213> ORGANISM: Human herpes virus 7

<400> SEQUENCE: 955
tctggagggt agacttt                                                        17

<210> SEQ ID NO 956
<211> LENGTH: 18
<212> TYPE: DNA
<213> ORGANISM: Homo sapiens

<400> SEQUENCE: 956
tctggaggga agcacttt                                                       18

<210> SEQ ID NO 957
<211> LENGTH: 19
<212> TYPE: DNA
<213> ORGANISM: Human herpes virus 7
```

```
<400> SEQUENCE: 957
ggtactagtt tatcctgtt                                                    19

<210> SEQ ID NO 958
<211> LENGTH: 19
<212> TYPE: DNA
<213> ORGANISM: Homo sapiens

<400> SEQUENCE: 958
ggtagtagtt tgtgctgtt                                                    19

<210> SEQ ID NO 959
<211> LENGTH: 23
<212> TYPE: DNA
<213> ORGANISM: Human herpes virus 7

<400> SEQUENCE: 959
tcagtggcct tgaaagaact agg                                               23

<210> SEQ ID NO 960
<211> LENGTH: 21
<212> TYPE: DNA
<213> ORGANISM: Homo sapiens

<400> SEQUENCE: 960
tcagtgcatg acagaacttg g                                                 21

<210> SEQ ID NO 961
<211> LENGTH: 20
<212> TYPE: DNA
<213> ORGANISM: Human herpes virus 7

<400> SEQUENCE: 961
ggttattgga aatgagattt                                                   20

<210> SEQ ID NO 962
<211> LENGTH: 20
<212> TYPE: DNA
<213> ORGANISM: Homo sapiens

<400> SEQUENCE: 962
ggttcctggg gatgggattt                                                   20

<210> SEQ ID NO 963
<211> LENGTH: 22
<212> TYPE: DNA
<213> ORGANISM: Human herpes virus 7

<400> SEQUENCE: 963
agtaagttct tcaggacaac ac                                                22

<210> SEQ ID NO 964
<211> LENGTH: 23
<212> TYPE: DNA
<213> ORGANISM: Homo sapiens

<400> SEQUENCE: 964
agtatgttct tccaggacag aac                                               23

<210> SEQ ID NO 965
<211> LENGTH: 20
<212> TYPE: DNA
<213> ORGANISM: Human herpes virus 7
```

-continued

```
<400> SEQUENCE: 965
atggagataa gaaatataaa                                                    20

<210> SEQ ID NO 966
<211> LENGTH: 19
<212> TYPE: DNA
<213> ORGANISM: Homo sapiens

<400> SEQUENCE: 966
atggagatag atatagaaa                                                     19

<210> SEQ ID NO 967
<211> LENGTH: 18
<212> TYPE: DNA
<213> ORGANISM: Human herpes virus 7

<400> SEQUENCE: 967
cttcagttcc gtgtctcc                                                      18

<210> SEQ ID NO 968
<211> LENGTH: 19
<212> TYPE: DNA
<213> ORGANISM: Homo sapiens

<400> SEQUENCE: 968
ctacagtgca cgtgtctcc                                                     19

<210> SEQ ID NO 969
<211> LENGTH: 17
<212> TYPE: DNA
<213> ORGANISM: Human herpes virus 7

<400> SEQUENCE: 969
tccatttgtt ttgtgga                                                       17

<210> SEQ ID NO 970
<211> LENGTH: 21
<212> TYPE: DNA
<213> ORGANISM: Homo sapiens

<400> SEQUENCE: 970
tccatttgtt ttgatgatgg a                                                  21

<210> SEQ ID NO 971
<211> LENGTH: 22
<212> TYPE: DNA
<213> ORGANISM: Human herpes virus 7

<400> SEQUENCE: 971
cagggcaaaa atattgacaa ag                                                 22

<210> SEQ ID NO 972
<211> LENGTH: 22
<212> TYPE: DNA
<213> ORGANISM: Homo sapiens

<400> SEQUENCE: 972
cagtgcaata gtattgtcaa ag                                                 22

<210> SEQ ID NO 973
<211> LENGTH: 20
<212> TYPE: DNA
<213> ORGANISM: Human herpes virus 7
```

```
<400> SEQUENCE: 973
gaaaatgcat tgcttttaga                                              20

<210> SEQ ID NO 974
<211> LENGTH: 19
<212> TYPE: DNA
<213> ORGANISM: Homo sapiens

<400> SEQUENCE: 974
gaaagtgctt ccttttaga                                               19

<210> SEQ ID NO 975
<211> LENGTH: 20
<212> TYPE: DNA
<213> ORGANISM: Human herpes virus 7

<400> SEQUENCE: 975 agttttcag tggcgagttt                                               20

<210> SEQ ID NO 976
<211> LENGTH: 20
<212> TYPE: DNA
<213> ORGANISM: Homo sapiens

<400> SEQUENCE: 976
agttcttcag tggcaagctt                                              20

<210> SEQ ID NO 977
<211> LENGTH: 19
<212> TYPE: DNA
<213> ORGANISM: Human herpes virus 7

<400> SEQUENCE: 977
tgaaatttta gaccaatag                                               19

<210> SEQ ID NO 978
<211> LENGTH: 21
<212> TYPE: DNA
<213> ORGANISM: Homo sapiens

<400> SEQUENCE: 978
tgaaatgttt aggaccacta g                                            21

<210> SEQ ID NO 979
<211> LENGTH: 21
<212> TYPE: DNA
<213> ORGANISM: Human herpes virus 7

<400> SEQUENCE: 979
ctgtcgaact ttccaccgtc a                                            21

<210> SEQ ID NO 980
<211> LENGTH: 20
<212> TYPE: DNA
<213> ORGANISM: Homo sapiens

<400> SEQUENCE: 980
ctatagaact ttcccccctca                                             20

<210> SEQ ID NO 981
<211> LENGTH: 19
<212> TYPE: DNA
<213> ORGANISM: Human herpes virus 7
```

```
<400> SEQUENCE: 981
cttttgccac aactctcaa                                                    19

<210> SEQ ID NO 982
<211> LENGTH: 19
<212> TYPE: DNA
<213> ORGANISM: Homo sapiens

<400> SEQUENCE: 982
ctgttgccac taacctcaa                                                    19

<210> SEQ ID NO 983
<211> LENGTH: 21
<212> TYPE: DNA
<213> ORGANISM: Human herpes virus 7

<400> SEQUENCE: 983
caatcgaacg ttgataagta c                                                 21

<210> SEQ ID NO 984
<211> LENGTH: 20
<212> TYPE: DNA
<213> ORGANISM: Homo sapiens

<400> SEQUENCE: 984
ccatcgaccg ttgattgtac                                                   20

<210> SEQ ID NO 985
<211> LENGTH: 18
<212> TYPE: DNA
<213> ORGANISM: Human herpes virus 7

<400> SEQUENCE: 985
acattcacct ggcggtga                                                     18

<210> SEQ ID NO 986
<211> LENGTH: 19
<212> TYPE: DNA
<213> ORGANISM: Homo sapiens

<400> SEQUENCE: 986
acattcaacc tgtcggtga                                                    19

<210> SEQ ID NO 987
<211> LENGTH: 18
<212> TYPE: DNA
<213> ORGANISM: Human herpes virus 7

<400> SEQUENCE: 987
ccagatggaa gcacgttc                                                     18

<210> SEQ ID NO 988
<211> LENGTH: 18
<212> TYPE: DNA
<213> ORGANISM: Homo sapiens

<400> SEQUENCE: 988
ctagagggaa gcactttc                                                     18

<210> SEQ ID NO 989
<211> LENGTH: 21
<212> TYPE: DNA
<213> ORGANISM: Human herpes virus 7
```

<400> SEQUENCE: 989
tatagactga tacgctttct g                                    21

<210> SEQ ID NO 990
<211> LENGTH: 21
<212> TYPE: DNA
<213> ORGANISM: Homo sapiens

<400> SEQUENCE: 990
tctagaggga agcgctttct g                                    21

<210> SEQ ID NO 991
<211> LENGTH: 25
<212> TYPE: DNA
<213> ORGANISM: Human herpes virus 7

<400> SEQUENCE: 991
aggctgcatc ttttcagtga agcta                                25

<210> SEQ ID NO 992
<211> LENGTH: 20
<212> TYPE: DNA
<213> ORGANISM: Homo sapiens

<400> SEQUENCE: 992
aggtgcatct agtgcagata                                      20

<210> SEQ ID NO 993
<211> LENGTH: 18
<212> TYPE: DNA
<213> ORGANISM: Human herpes virus 7

<400> SEQUENCE: 993
aaagtgctca agtaagta                                        18

<210> SEQ ID NO 994
<211> LENGTH: 21
<212> TYPE: DNA
<213> ORGANISM: Homo sapiens

<400> SEQUENCE: 994
aaagtgctca tagtgcaggt a                                    21

<210> SEQ ID NO 995
<211> LENGTH: 18
<212> TYPE: DNA
<213> ORGANISM: Human herpes virus 7

<400> SEQUENCE: 995
atgagttaat tgtaaatg                                        18

<210> SEQ ID NO 996
<211> LENGTH: 19
<212> TYPE: DNA
<213> ORGANISM: Homo sapiens

<400> SEQUENCE: 996
atgagctcat tgtaatatg                                       19

<210> SEQ ID NO 997
<211> LENGTH: 21
<212> TYPE: DNA
<213> ORGANISM: Human herpes virus 7

<400> SEQUENCE: 997
tgattcagaa gacctgcttc t                                              21

<210> SEQ ID NO 998
<211> LENGTH: 20
<212> TYPE: DNA
<213> ORGANISM: Homo sapiens

<400> SEQUENCE: 998
tgatccagga acctgcctct                                                20

<210> SEQ ID NO 999
<211> LENGTH: 20
<212> TYPE: DNA
<213> ORGANISM: Human herpes virus 7

<400> SEQUENCE: 999
aagcttgtat atacggaatg                                                20

<210> SEQ ID NO 1000
<211> LENGTH: 21
<212> TYPE: DNA
<213> ORGANISM: Homo sapiens

<400> SEQUENCE: 1000
aagcttgtat ctataggtat g                                              21

<210> SEQ ID NO 1001
<211> LENGTH: 21
<212> TYPE: DNA
<213> ORGANISM: Human herpes virus 7

<400> SEQUENCE: 1001
tatagactga tacgctttct g                                              21

<210> SEQ ID NO 1002
<211> LENGTH: 21
<212> TYPE: DNA
<213> ORGANISM: Homo sapiens

<400> SEQUENCE: 1002
tctagaggga agcgctttct g                                              21

<210> SEQ ID NO 1003
<211> LENGTH: 18
<212> TYPE: DNA
<213> ORGANISM: Human herpes virus 7

<400> SEQUENCE: 1003
caatagactg cactttgg                                                  18

<210> SEQ ID NO 1004
<211> LENGTH: 18
<212> TYPE: DNA
<213> ORGANISM: Homo sapiens

<400> SEQUENCE: 1004
cagtagtctg cacattgg                                                  18

<210> SEQ ID NO 1005
<211> LENGTH: 19
<212> TYPE: DNA
<213> ORGANISM: Human herpes virus 7

```
<400> SEQUENCE: 1005
tcctcatctc ccacttccc                                              19

<210> SEQ ID NO 1006
<211> LENGTH: 19
<212> TYPE: DNA
<213> ORGANISM: Homo sapiens

<400> SEQUENCE: 1006
tcctcttctc cctcctccc                                              19

<210> SEQ ID NO 1007
<211> LENGTH: 19
<212> TYPE: DNA
<213> ORGANISM: Human herpes virus 7

<400> SEQUENCE: 1007
cttgaagtac cgaatttgt                                              19

<210> SEQ ID NO 1008
<211> LENGTH: 19
<212> TYPE: DNA
<213> ORGANISM: Homo sapiens

<400> SEQUENCE: 1008
cctgtagaac cgaatttgt                                              19

<210> SEQ ID NO 1009
<211> LENGTH: 19
<212> TYPE: DNA
<213> ORGANISM: Human herpes virus 7

<400> SEQUENCE: 1009
aaaatggttc tttagtagt                                              19

<210> SEQ ID NO 1010
<211> LENGTH: 20
<212> TYPE: DNA
<213> ORGANISM: Homo sapiens

<400> SEQUENCE: 1010
aaaatggttc cctttagagt                                             20

<210> SEQ ID NO 1011
<211> LENGTH: 22
<212> TYPE: DNA
<213> ORGANISM: Human herpes virus 7

<400> SEQUENCE: 1011
tcctatggac atatacattt tt                                          22

<210> SEQ ID NO 1012
<211> LENGTH: 20
<212> TYPE: DNA
<213> ORGANISM: Homo sapiens

<400> SEQUENCE: 1012
tcctatgcat atacttcttt                                             20

<210> SEQ ID NO 1013
<211> LENGTH: 20
<212> TYPE: DNA
<213> ORGANISM: Human herpes virus 7
```

-continued

<400> SEQUENCE: 1013
ggaatggaag cacttcatta                                              20

<210> SEQ ID NO 1014
<211> LENGTH: 19
<212> TYPE: DNA
<213> ORGANISM: Homo sapiens

<400> SEQUENCE: 1014
gcaatgtaag cacttctta                                               19

<210> SEQ ID NO 1015
<211> LENGTH: 19
<212> TYPE: DNA
<213> ORGANISM: Human herpes virus 7

<400> SEQUENCE: 1015
tgacaactct ttgagttaa                                               19

<210> SEQ ID NO 1016
<211> LENGTH: 19
<212> TYPE: DNA
<213> ORGANISM: Homo sapiens

<400> SEQUENCE: 1016
tgacacctct ttgggtgaa                                               19

<210> SEQ ID NO 1017
<211> LENGTH: 23
<212> TYPE: DNA
<213> ORGANISM: Human herpes virus 7

<400> SEQUENCE: 1017
tattgctcta agactacacg aag                                          23

<210> SEQ ID NO 1018
<211> LENGTH: 22
<212> TYPE: DNA
<213> ORGANISM: Homo sapiens

<400> SEQUENCE: 1018
tattgcttaa gaatacgcgt ag                                           22

<210> SEQ ID NO 1019
<211> LENGTH: 18
<212> TYPE: DNA
<213> ORGANISM: Human herpes virus 7

<400> SEQUENCE: 1019
caatagactg cactttgg                                                18

<210> SEQ ID NO 1020
<211> LENGTH: 18
<212> TYPE: DNA
<213> ORGANISM: Homo sapiens

<400> SEQUENCE: 1020
cagtagtctg cacattgg                                                18

<210> SEQ ID NO 1021
<211> LENGTH: 22
<212> TYPE: DNA
<213> ORGANISM: Human herpes virus 7

```
<400> SEQUENCE: 1021
atagtcattg tgaatgtctt tc                                              22

<210> SEQ ID NO 1022
<211> LENGTH: 20
<212> TYPE: DNA
<213> ORGANISM: Homo sapiens

<400> SEQUENCE: 1022
agagtcttgt gatgtcttgc                                                 20

<210> SEQ ID NO 1023
<211> LENGTH: 16
<212> TYPE: DNA
<213> ORGANISM: Human herpes virus 7

<400> SEQUENCE: 1023
tctgtcctct gcgtag                                                     16

<210> SEQ ID NO 1024
<211> LENGTH: 18
<212> TYPE: DNA
<213> ORGANISM: Homo sapiens

<400> SEQUENCE: 1024
tgtgtccttt ctgcgtag                                                   18

<210> SEQ ID NO 1025
<211> LENGTH: 20
<212> TYPE: DNA
<213> ORGANISM: Human herpes virus 7

<400> SEQUENCE: 1025
tagataatta atttggtacc                                                 20

<210> SEQ ID NO 1026
<211> LENGTH: 19
<212> TYPE: DNA
<213> ORGANISM: Homo sapiens

<400> SEQUENCE: 1026
tagataaaat attggtacc                                                  19

<210> SEQ ID NO 1027
<211> LENGTH: 17
<212> TYPE: DNA
<213> ORGANISM: Human herpes virus 7

<400> SEQUENCE: 1027
atctaaggaa ggtgtgg                                                    17

<210> SEQ ID NO 1028
<211> LENGTH: 18
<212> TYPE: DNA
<213> ORGANISM: Homo sapiens

<400> SEQUENCE: 1028
atgtaaggaa gtgtgtgg                                                   18

<210> SEQ ID NO 1029
<211> LENGTH: 22
<212> TYPE: DNA
<213> ORGANISM: Human herpes virus 7
```

<400> SEQUENCE: 1029
tggtaatgtg acaattggtg tt                                    22

<210> SEQ ID NO 1030
<211> LENGTH: 20
<212> TYPE: DNA
<213> ORGANISM: Homo sapiens

<400> SEQUENCE: 1030
tggagtgtga caatggtgtt                                       20

<210> SEQ ID NO 1031
<211> LENGTH: 17
<212> TYPE: DNA
<213> ORGANISM: Human herpes virus 7

<400> SEQUENCE: 1031
gtgcattgta attcatt                                          17

<210> SEQ ID NO 1032
<211> LENGTH: 18
<212> TYPE: DNA
<213> ORGANISM: Homo sapiens

<400> SEQUENCE: 1032
gtgcattgta gttgcatt                                         18

<210> SEQ ID NO 1033
<211> LENGTH: 18
<212> TYPE: DNA
<213> ORGANISM: Human herpes virus 7

<400> SEQUENCE: 1033
agatgttgcc cgtgaatt                                         18

<210> SEQ ID NO 1034
<211> LENGTH: 21
<212> TYPE: DNA
<213> ORGANISM: Homo sapiens

<400> SEQUENCE: 1034
agaggttgcc cttggtgaat t                                     21

<210> SEQ ID NO 1035
<211> LENGTH: 22
<212> TYPE: DNA
<213> ORGANISM: Human herpes virus 7

<400> SEQUENCE: 1035
tcatacacga agcccttcct ct                                    22

<210> SEQ ID NO 1036
<211> LENGTH: 19
<212> TYPE: DNA
<213> ORGANISM: Homo sapiens

<400> SEQUENCE: 1036
tcatacacgg ctctcctct                                        19

<210> SEQ ID NO 1037
<211> LENGTH: 18
<212> TYPE: DNA
<213> ORGANISM: Human herpes virus 7

<400> SEQUENCE: 1037
tatgacactg aaagaatt                                                    18

<210> SEQ ID NO 1038
<211> LENGTH: 18
<212> TYPE: DNA
<213> ORGANISM: Homo sapiens

<400> SEQUENCE: 1038
tatggcactg gtagaatt                                                    18

<210> SEQ ID NO 1039
<211> LENGTH: 21
<212> TYPE: DNA
<213> ORGANISM: Human herpes virus 7

<400> SEQUENCE: 1039
ggtggtttat gcaaattttc a                                                21

<210> SEQ ID NO 1040
<211> LENGTH: 21
<212> TYPE: DNA
<213> ORGANISM: Homo sapiens

<400> SEQUENCE: 1040
ggtggtttac aaagtaattc a                                                21

<210> SEQ ID NO 1041
<211> LENGTH: 19
<212> TYPE: DNA
<213> ORGANISM: Human herpes virus 7

<400> SEQUENCE: 1041
caatattact tttgatatg                                                   19

<210> SEQ ID NO 1042
<211> LENGTH: 19
<212> TYPE: DNA
<213> ORGANISM: Homo sapiens

<400> SEQUENCE: 1042
cattattact tttggtacg                                                   19

<210> SEQ ID NO 1043
<211> LENGTH: 19
<212> TYPE: DNA
<213> ORGANISM: Human herpes virus 7

<400> SEQUENCE: 1043
ctatagaatc aacttctttt                                                  19

<210> SEQ ID NO 1044
<211> LENGTH: 20
<212> TYPE: DNA
<213> ORGANISM: Homo sapiens

<400> SEQUENCE: 1044
ctatacaatc tactgtcttt                                                  20

<210> SEQ ID NO 1045
<211> LENGTH: 21
<212> TYPE: DNA
<213> ORGANISM: Human herpes virus 7

```
<400> SEQUENCE: 1045
tatagactga tacgctttct g                                              21

<210> SEQ ID NO 1046
<211> LENGTH: 21
<212> TYPE: DNA
<213> ORGANISM: Homo sapiens

<400> SEQUENCE: 1046
tctagaggga agcgctttct g                                              21

<210> SEQ ID NO 1047
<211> LENGTH: 21
<212> TYPE: DNA
<213> ORGANISM: Human herpes virus 7

<400> SEQUENCE: 1047
agagagtgtg tgacagtgtg t                                              21

<210> SEQ ID NO 1048
<211> LENGTH: 21
<212> TYPE: DNA
<213> ORGANISM: Homo sapiens

<400> SEQUENCE: 1048
agtgtgtgtg tgtgagtgtg t                                              21

<210> SEQ ID NO 1049
<211> LENGTH: 20
<212> TYPE: DNA
<213> ORGANISM: Human herpes virus 7

<400> SEQUENCE: 1049
gggttttcag ggacatatga                                                20

<210> SEQ ID NO 1050
<211> LENGTH: 20
<212> TYPE: DNA
<213> ORGANISM: Homo sapiens

<400> SEQUENCE: 1050
gggttttgag ggcgagatga                                                20

<210> SEQ ID NO 1051
<211> LENGTH: 19
<212> TYPE: DNA
<213> ORGANISM: Human herpes virus 7

<400> SEQUENCE: 1051
caacattaac tgttgctga                                                 19

<210> SEQ ID NO 1052
<211> LENGTH: 21
<212> TYPE: DNA
<213> ORGANISM: Homo sapiens

<400> SEQUENCE: 1052
cagtattaac tgtgctgctg a                                              21

<210> SEQ ID NO 1053
<211> LENGTH: 21
<212> TYPE: DNA
<213> ORGANISM: Human herpes virus 7
```

```
<400> SEQUENCE: 1053
tatagactga tacgctttct g                                          21

<210> SEQ ID NO 1054
<211> LENGTH: 21
<212> TYPE: DNA
<213> ORGANISM: Homo sapiens

<400> SEQUENCE: 1054
tctagaggga agcgctttct g                                          21

<210> SEQ ID NO 1055
<211> LENGTH: 20
<212> TYPE: DNA
<213> ORGANISM: Human herpes virus 7

<400> SEQUENCE: 1055
actgttgtca tatgcactct                                            20

<210> SEQ ID NO 1056
<211> LENGTH: 22
<212> TYPE: DNA
<213> ORGANISM: Homo sapiens

<400> SEQUENCE: 1056
actgttgcta atatgcaact ct                                         22

<210> SEQ ID NO 1057
<211> LENGTH: 20
<212> TYPE: DNA
<213> ORGANISM: Human herpes virus 7

<400> SEQUENCE: 1057
aacaataaag caaatctgtg                                            20

<210> SEQ ID NO 1058
<211> LENGTH: 20
<212> TYPE: DNA
<213> ORGANISM: Homo sapiens

<400> SEQUENCE: 1058
aacatcacag caagtctgtg                                            20

<210> SEQ ID NO 1059
<211> LENGTH: 17
<212> TYPE: DNA
<213> ORGANISM: Human herpes virus 7

<400> SEQUENCE: 1059
acaaaggtaa ccatttc                                               17

<210> SEQ ID NO 1060
<211> LENGTH: 18
<212> TYPE: DNA
<213> ORGANISM: Homo sapiens

<400> SEQUENCE: 1060
acaaagggaa gccctttc                                              18

<210> SEQ ID NO 1061
<211> LENGTH: 22
<212> TYPE: DNA
<213> ORGANISM: Human herpes virus 7
```

```
<400> SEQUENCE: 1061
tgtagggttt cctaatatgt gg                                              22

<210> SEQ ID NO 1062
<211> LENGTH: 22
<212> TYPE: DNA
<213> ORGANISM: Homo sapiens

<400> SEQUENCE: 1062
tgtagtgttt cctactttat gg                                              22

<210> SEQ ID NO 1063
<211> LENGTH: 18
<212> TYPE: DNA
<213> ORGANISM: Human herpes virus 7

<400> SEQUENCE: 1063
ttaccgtaca ctgctgaa                                                   18

<210> SEQ ID NO 1064
<211> LENGTH: 18
<212> TYPE: DNA
<213> ORGANISM: Homo sapiens

<400> SEQUENCE: 1064
ttaccggaca gtgctgga                                                   18

<210> SEQ ID NO 1065
<211> LENGTH: 20
<212> TYPE: DNA
<213> ORGANISM: Human herpes virus 7

<400> SEQUENCE: 1065
ttcaaacggt attttattga                                                 20

<210> SEQ ID NO 1066
<211> LENGTH: 19
<212> TYPE: DNA
<213> ORGANISM: Homo sapiens

<400> SEQUENCE: 1066
ttcaacgggt atttattga                                                  19

<210> SEQ ID NO 1067
<211> LENGTH: 19
<212> TYPE: DNA
<213> ORGANISM: Human herpes virus 7

<400> SEQUENCE: 1067
ccgtctcatt ttttatagc                                                  19

<210> SEQ ID NO 1068
<211> LENGTH: 21
<212> TYPE: DNA
<213> ORGANISM: Homo sapiens

<400> SEQUENCE: 1068
ccgtctcagt tactttatag c                                               21

<210> SEQ ID NO 1069
<211> LENGTH: 24
<212> TYPE: DNA
<213> ORGANISM: Human herpes virus 7
```

<400> SEQUENCE: 1069
tgcaaacatc attgcacaca ggaa                                          24

<210> SEQ ID NO 1070
<211> LENGTH: 21
<212> TYPE: DNA
<213> ORGANISM: Homo sapiens

<400> SEQUENCE: 1070
tgtaaacatc cttgactgga a                                             21

<210> SEQ ID NO 1071
<211> LENGTH: 17
<212> TYPE: DNA
<213> ORGANISM: GB virus C

<400> SEQUENCE: 1071
gtgttcagcg gaccatg                                                  17

<210> SEQ ID NO 1072
<211> LENGTH: 19
<212> TYPE: DNA
<213> ORGANISM: Homo sapiens

<400> SEQUENCE: 1072
gtgttcacag cggaccttg                                                19

<210> SEQ ID NO 1073
<211> LENGTH: 18
<212> TYPE: DNA
<213> ORGANISM: GB virus C

<400> SEQUENCE: 1073
gacagtagca taactgaa                                                 18

<210> SEQ ID NO 1074
<211> LENGTH: 18
<212> TYPE: DNA
<213> ORGANISM: Homo sapiens

<400> SEQUENCE: 1074
gacagattga taactgaa                                                 18

<210> SEQ ID NO 1075
<211> LENGTH: 19
<212> TYPE: DNA
<213> ORGANISM: GB virus C

<400> SEQUENCE: 1075
cttacctttg aatgtgaca                                                19

<210> SEQ ID NO 1076
<211> LENGTH: 18
<212> TYPE: DNA
<213> ORGANISM: Homo sapiens

<400> SEQUENCE: 1076
ctgacctatg aattgaca                                                 18

<210> SEQ ID NO 1077
<211> LENGTH: 19
<212> TYPE: DNA
<213> ORGANISM: GB virus C

```
<400> SEQUENCE: 1077
acaactgcat gctcttggg                                              19

<210> SEQ ID NO 1078
<211> LENGTH: 18
<212> TYPE: DNA
<213> ORGANISM: Homo sapiens

<400> SEQUENCE: 1078
acaagtcagg ctcttggg                                               18

<210> SEQ ID NO 1079
<211> LENGTH: 17
<212> TYPE: DNA
<213> ORGANISM: GB virus C

<400> SEQUENCE: 1079
tactatgcct caggcac                                                17

<210> SEQ ID NO 1080
<211> LENGTH: 15
<212> TYPE: DNA
<213> ORGANISM: Homo sapiens

<400> SEQUENCE: 1080
tactccctca ggcac                                                  15

<210> SEQ ID NO 1081
<211> LENGTH: 21
<212> TYPE: DNA
<213> ORGANISM: GB virus C

<400> SEQUENCE: 1081
aatgtggcac cctctgaggt t                                           21

<210> SEQ ID NO 1082
<211> LENGTH: 22
<212> TYPE: DNA
<213> ORGANISM: Homo sapiens

<400> SEQUENCE: 1082
aaagtgcatc cttttagagg tt                                          22

<210> SEQ ID NO 1083
<211> LENGTH: 22
<212> TYPE: DNA
<213> ORGANISM: GB virus C

<400> SEQUENCE: 1083
aaagtgggaa agtgagtttt gg                                          22

<210> SEQ ID NO 1084
<211> LENGTH: 19
<212> TYPE: DNA
<213> ORGANISM: Homo sapiens

<400> SEQUENCE: 1084
aaagtaattg tggttttgg                                              19

<210> SEQ ID NO 1085
<211> LENGTH: 19
<212> TYPE: DNA
<213> ORGANISM: GB virus C
```

```
<400> SEQUENCE: 1085
gtccttctct ttggcctgt                                              19

<210> SEQ ID NO 1086
<211> LENGTH: 19
<212> TYPE: DNA
<213> ORGANISM: Homo sapiens

<400> SEQUENCE: 1086
gtgcttccct ttggactgt                                              19

<210> SEQ ID NO 1087
<211> LENGTH: 17
<212> TYPE: DNA
<213> ORGANISM: GB virus C

<400> SEQUENCE: 1087
aggatgtgaa tcatttg                                                17

<210> SEQ ID NO 1088
<211> LENGTH: 18
<212> TYPE: DNA
<213> ORGANISM: Homo sapiens

<400> SEQUENCE: 1088
agaatgatga atcattag                                               18

<210> SEQ ID NO 1089
<211> LENGTH: 22
<212> TYPE: DNA
<213> ORGANISM: GB virus C

<400> SEQUENCE: 1089
cgcgcctggc gtctgccctc ct                                          22

<210> SEQ ID NO 1090
<211> LENGTH: 20
<212> TYPE: DNA
<213> ORGANISM: Homo sapiens

<400> SEQUENCE: 1090
cgagcctggg tctccctctt                                             20

<210> SEQ ID NO 1091
<211> LENGTH: 20
<212> TYPE: DNA
<213> ORGANISM: GB virus C

<400> SEQUENCE: 1091
acattcgagg tggacacttc                                             20

<210> SEQ ID NO 1092
<211> LENGTH: 18
<212> TYPE: DNA
<213> ORGANISM: Homo sapiens

<400> SEQUENCE: 1092
acattcgcgg tgcacttc                                               18

<210> SEQ ID NO 1093
<211> LENGTH: 20
<212> TYPE: DNA
<213> ORGANISM: GB virus C
```

```
<400> SEQUENCE: 1093
gcacttatct cggttactga                                               20

<210> SEQ ID NO 1094
<211> LENGTH: 18
<212> TYPE: DNA
<213> ORGANISM: Homo sapiens

<400> SEQUENCE: 1094
gcacttgtct cggtctga                                                 18

<210> SEQ ID NO 1095
<211> LENGTH: 20
<212> TYPE: DNA
<213> ORGANISM: GB virus C

<400> SEQUENCE: 1095
ctccacttgg cttgctgagt                                               20

<210> SEQ ID NO 1096
<211> LENGTH: 20
<212> TYPE: DNA
<213> ORGANISM: Homo sapiens

<400> SEQUENCE: 1096
ctctacttgt ccttctgagt                                               20

<210> SEQ ID NO 1097
<211> LENGTH: 20
<212> TYPE: DNA
<213> ORGANISM: GB virus C

<400> SEQUENCE: 1097
tgcttcgaca gtagcataac                                               20

<210> SEQ ID NO 1098
<211> LENGTH: 19
<212> TYPE: DNA
<213> ORGANISM: Homo sapiens

<400> SEQUENCE: 1098
tgtttccaca gtgcatcac                                                19

<210> SEQ ID NO 1099
<211> LENGTH: 18
<212> TYPE: DNA
<213> ORGANISM: GB virus C

<400> SEQUENCE: 1099
agtcgctgcc tctgtggc                                                 18

<210> SEQ ID NO 1100
<211> LENGTH: 18
<212> TYPE: DNA
<213> ORGANISM: Homo sapiens

<400> SEQUENCE: 1100
agcagctgcc tctgaggc                                                 18

<210> SEQ ID NO 1101
<211> LENGTH: 18
<212> TYPE: DNA
<213> ORGANISM: GB virus C
```

```
<400> SEQUENCE: 1101
tgccagcctt ttgccaag                                              18

<210> SEQ ID NO 1102
<211> LENGTH: 18
<212> TYPE: DNA
<213> ORGANISM: Homo sapiens

<400> SEQUENCE: 1102
tgccaccctt ttccccag                                              18

<210> SEQ ID NO 1103
<211> LENGTH: 17
<212> TYPE: DNA
<213> ORGANISM: GB virus C

<400> SEQUENCE: 1103
ctgctggccc gagaccg                                               17

<210> SEQ ID NO 1104
<211> LENGTH: 21
<212> TYPE: DNA
<213> ORGANISM: Homo sapiens

<400> SEQUENCE: 1104
ctgccctggc ccgagggacc g                                          21

<210> SEQ ID NO 1105
<211> LENGTH: 20
<212> TYPE: DNA
<213> ORGANISM: GB virus C

<400> SEQUENCE: 1105
tcctgcggca cctgtgtgag                                            20

<210> SEQ ID NO 1106
<211> LENGTH: 21
<212> TYPE: DNA
<213> ORGANISM: Homo sapiens

<400> SEQUENCE: 1106
tccttggaac ctaggtgtga g                                          21

<210> SEQ ID NO 1107
<211> LENGTH: 20
<212> TYPE: DNA
<213> ORGANISM: GB virus C

<400> SEQUENCE: 1107
gcagtgcgtc atgggtttac                                            20

<210> SEQ ID NO 1108
<211> LENGTH: 19
<212> TYPE: DNA
<213> ORGANISM: Homo sapiens

<400> SEQUENCE: 1108
gcagcacatc atggtttac                                             19

<210> SEQ ID NO 1109
<211> LENGTH: 20
<212> TYPE: DNA
<213> ORGANISM: GB virus C
```

<400> SEQUENCE: 1109
gtgctgtact ttagatggtt                                          20

<210> SEQ ID NO 1110
<211> LENGTH: 20
<212> TYPE: DNA
<213> ORGANISM: Homo sapiens

<400> SEQUENCE: 1110
gtgcttcctt ttagagggtt                                          20

<210> SEQ ID NO 1111
<211> LENGTH: 19
<212> TYPE: DNA
<213> ORGANISM: GB virus C

<400> SEQUENCE: 1111
agattccctt ttatgggca                                           19

<210> SEQ ID NO 1112
<211> LENGTH: 20
<212> TYPE: DNA
<213> ORGANISM: Homo sapiens

<400> SEQUENCE: 1112
agattctcct tctatgagta                                          20

<210> SEQ ID NO 1113
<211> LENGTH: 16
<212> TYPE: DNA
<213> ORGANISM: GB virus C

<400> SEQUENCE: 1113
tgttgacaag ctcttc                                              16

<210> SEQ ID NO 1114
<211> LENGTH: 18
<212> TYPE: DNA
<213> ORGANISM: Homo sapiens

<400> SEQUENCE: 1114
tgttgaaaca atctctac                                            18

<210> SEQ ID NO 1115
<211> LENGTH: 17
<212> TYPE: DNA
<213> ORGANISM: GB virus C

<400> SEQUENCE: 1115
ggacgtctgg ctgggct                                             17

<210> SEQ ID NO 1116
<211> LENGTH: 20
<212> TYPE: DNA
<213> ORGANISM: Homo sapiens

<400> SEQUENCE: 1116
ggatccgtct gagcttggct                                          20

<210> SEQ ID NO 1117
<211> LENGTH: 19
<212> TYPE: DNA
<213> ORGANISM: GB virus C

```
<400> SEQUENCE: 1117
gattgggcct tggaggaga                                                  19

<210> SEQ ID NO 1118
<211> LENGTH: 22
<212> TYPE: DNA
<213> ORGANISM: Homo sapiens

<400> SEQUENCE: 1118
gattgtagcc ttttggagta ga                                              22

<210> SEQ ID NO 1119
<211> LENGTH: 20
<212> TYPE: DNA
<213> ORGANISM: GB virus C

<400> SEQUENCE: 1119
agggcacgca gtaggaatgc                                                 20

<210> SEQ ID NO 1120
<211> LENGTH: 18
<212> TYPE: DNA
<213> ORGANISM: Homo sapiens

<400> SEQUENCE: 1120
aaggcacgcg gtgaatgc                                                   18

<210> SEQ ID NO 1121
<211> LENGTH: 20
<212> TYPE: DNA
<213> ORGANISM: GB virus C

<400> SEQUENCE: 1121
tggaggaggt cgttgaggtg                                                 20

<210> SEQ ID NO 1122
<211> LENGTH: 19
<212> TYPE: DNA
<213> ORGANISM: Homo sapiens

<400> SEQUENCE: 1122
tggagtaggt cattgggtg                                                  19

<210> SEQ ID NO 1123
<211> LENGTH: 21
<212> TYPE: DNA
<213> ORGANISM: GB virus C

<400> SEQUENCE: 1123
gtgctgtgtg atggcgggtg a                                               21

<210> SEQ ID NO 1124
<211> LENGTH: 20
<212> TYPE: DNA
<213> ORGANISM: Homo sapiens

<400> SEQUENCE: 1124
gtgcgtgtga cagcggctga                                                 20

<210> SEQ ID NO 1125
<211> LENGTH: 22
<212> TYPE: DNA
<213> ORGANISM: GB virus C
```

```
<400> SEQUENCE: 1125
tcgggatcct gacttacatc ca                                              22

<210> SEQ ID NO 1126
<211> LENGTH: 20
<212> TYPE: DNA
<213> ORGANISM: Homo sapiens

<400> SEQUENCE: 1126
ttgggatcat tttgcatcca                                                 20

<210> SEQ ID NO 1127
<211> LENGTH: 24
<212> TYPE: DNA
<213> ORGANISM: GB virus C

<400> SEQUENCE: 1127
tgccctaacg gccctgggt gtgg                                             24

<210> SEQ ID NO 1128
<211> LENGTH: 21
<212> TYPE: DNA
<213> ORGANISM: Homo sapiens

<400> SEQUENCE: 1128
tgccctaaat gcccttctg g                                                21

<210> SEQ ID NO 1129
<211> LENGTH: 19
<212> TYPE: DNA
<213> ORGANISM: GB virus C

<400> SEQUENCE: 1129
ggcagtcctt ctgctcctt                                                  19

<210> SEQ ID NO 1130
<211> LENGTH: 21
<212> TYPE: DNA
<213> ORGANISM: Homo sapiens

<400> SEQUENCE: 1130
ggcagggctt ctgagctcct t                                               21

<210> SEQ ID NO 1131
<211> LENGTH: 22
<212> TYPE: DNA
<213> ORGANISM: GB virus C

<400> SEQUENCE: 1131
tgtgggcatg atacaactgc tt                                              22

<210> SEQ ID NO 1132
<211> LENGTH: 20
<212> TYPE: DNA
<213> ORGANISM: Homo sapiens

<400> SEQUENCE: 1132
tgtgggatgg taaaccgctt                                                 20

<210> SEQ ID NO 1133
<211> LENGTH: 19
<212> TYPE: DNA
<213> ORGANISM: GB virus C
```

<400> SEQUENCE: 1133
gggttgactt ggcagacct                                                19

<210> SEQ ID NO 1134
<211> LENGTH: 20
<212> TYPE: DNA
<213> ORGANISM: Homo sapiens

<400> SEQUENCE: 1134
gggtttacgt tgggagaact                                               20

<210> SEQ ID NO 1135
<211> LENGTH: 20
<212> TYPE: DNA
<213> ORGANISM: GB virus C

<400> SEQUENCE: 1135
gactttgtat ttgtcctgtt                                               20

<210> SEQ ID NO 1136
<211> LENGTH: 21
<212> TYPE: DNA
<213> ORGANISM: Homo sapiens

<400> SEQUENCE: 1136
gaggtagtag tttgtgctgt t                                             21

<210> SEQ ID NO 1137
<211> LENGTH: 16
<212> TYPE: DNA
<213> ORGANISM: GB virus C

<400> SEQUENCE: 1137
cttctctttg gcctgt                                                   16

<210> SEQ ID NO 1138
<211> LENGTH: 20
<212> TYPE: DNA
<213> ORGANISM: Homo sapiens

<400> SEQUENCE: 1138
cttctctgtt ttggccatgt                                               20

<210> SEQ ID NO 1139
<211> LENGTH: 20
<212> TYPE: DNA
<213> ORGANISM: GB virus C

<400> SEQUENCE: 1139
acagtgcact gtgatctgaa                                               20

<210> SEQ ID NO 1140
<211> LENGTH: 20
<212> TYPE: DNA
<213> ORGANISM: Homo sapiens

<400> SEQUENCE: 1140
acagtactgt gataactgaa                                               20

<210> SEQ ID NO 1141
<211> LENGTH: 17
<212> TYPE: DNA
<213> ORGANISM: GB virus C

```
<400> SEQUENCE: 1141 ggggtttcc ctctctc                                                       17

<210> SEQ ID NO 1142
<211> LENGTH: 18
<212> TYPE: DNA
<213> ORGANISM: Homo sapiens

<400> SEQUENCE: 1142
gggtgtttct ctcatctc                                                     18

<210> SEQ ID NO 1143
<211> LENGTH: 18
<212> TYPE: DNA
<213> ORGANISM: GB virus C

<400> SEQUENCE: 1143
ggagggtggg cggctgtg                                                     18

<210> SEQ ID NO 1144
<211> LENGTH: 18
<212> TYPE: DNA
<213> ORGANISM: Homo sapiens

<400> SEQUENCE: 1144
ggagggacgg gggctgtg                                                     18

<210> SEQ ID NO 1145
<211> LENGTH: 21
<212> TYPE: DNA
<213> ORGANISM: GB virus C

<400> SEQUENCE: 1145
acagtgcact gtgatctgaa g                                                 21

<210> SEQ ID NO 1146
<211> LENGTH: 19
<212> TYPE: DNA
<213> ORGANISM: Homo sapiens

<400> SEQUENCE: 1146
acagtgcacg tgtctccag                                                    19

<210> SEQ ID NO 1147
<211> LENGTH: 20
<212> TYPE: DNA
<213> ORGANISM: GB virus C

<400> SEQUENCE: 1147
tcgacgcgtt ggattgggcc                                                   20

<210> SEQ ID NO 1148
<211> LENGTH: 18
<212> TYPE: DNA
<213> ORGANISM: Homo sapiens

<400> SEQUENCE: 1148
tcgaccgttg attgtacc                                                     18

<210> SEQ ID NO 1149
<211> LENGTH: 18
<212> TYPE: DNA
<213> ORGANISM: GB virus C
```

```
<400> SEQUENCE: 1149 accccctgacc tttgcctg                                                  18

<210> SEQ ID NO 1150
<211> LENGTH: 18
<212> TYPE: DNA
<213> ORGANISM: Homo sapiens

<400> SEQUENCE: 1150
accactgacc gttgactg                                                   18

<210> SEQ ID NO 1151
<211> LENGTH: 20
<212> TYPE: DNA
<213> ORGANISM: GB virus C

<400> SEQUENCE: 1151
agaccaggcc acgcctcagc                                                 20

<210> SEQ ID NO 1152
<211> LENGTH: 21
<212> TYPE: DNA
<213> ORGANISM: Homo sapiens

<400> SEQUENCE: 1152
agacctggcc cagacctcag c                                               21

<210> SEQ ID NO 1153
<211> LENGTH: 20
<212> TYPE: DNA
<213> ORGANISM: GB virus C

<400> SEQUENCE: 1153
tgggaggcat ggtggttact                                                 20

<210> SEQ ID NO 1154
<211> LENGTH: 19
<212> TYPE: DNA
<213> ORGANISM: Homo sapiens

<400> SEQUENCE: 1154
tgggaggtgg atgtttact                                                  19

<210> SEQ ID NO 1155
<211> LENGTH: 21
<212> TYPE: DNA
<213> ORGANISM: GB virus C

<400> SEQUENCE: 1155
aagaccggaa ggaggagaag g                                               21

<210> SEQ ID NO 1156
<211> LENGTH: 19
<212> TYPE: DNA
<213> ORGANISM: Homo sapiens

<400> SEQUENCE: 1156
aagacgggag gaaagaagg                                                  19

<210> SEQ ID NO 1157
<211> LENGTH: 20
<212> TYPE: DNA
<213> ORGANISM: GB virus C
```

<400> SEQUENCE: 1157
aacaccttgt acttgccagg                                    20

<210> SEQ ID NO 1158
<211> LENGTH: 19
<212> TYPE: DNA
<213> ORGANISM: Homo sapiens

<400> SEQUENCE: 1158
aacgcctgtt cttgccagg                                     19

<210> SEQ ID NO 1159
<211> LENGTH: 21
<212> TYPE: DNA
<213> ORGANISM: GB virus C

<400> SEQUENCE: 1159
actggcccct cttggtgggt g                                  21

<210> SEQ ID NO 1160
<211> LENGTH: 19
<212> TYPE: DNA
<213> ORGANISM: Homo sapiens

<400> SEQUENCE: 1160
actgacacct ctttgggtg                                     19

<210> SEQ ID NO 1161
<211> LENGTH: 17
<212> TYPE: DNA
<213> ORGANISM: GB virus C

<400> SEQUENCE: 1161
gcatcattgg acacggc                                       17

<210> SEQ ID NO 1162
<211> LENGTH: 17
<212> TYPE: DNA
<213> ORGANISM: Homo sapiens

<400> SEQUENCE: 1162
gcagcattgt acagggc                                       17

<210> SEQ ID NO 1163
<211> LENGTH: 18
<212> TYPE: DNA
<213> ORGANISM: GB virus C

<400> SEQUENCE: 1163
tgtctgggac ctgtggga                                      18

<210> SEQ ID NO 1164
<211> LENGTH: 18
<212> TYPE: DNA
<213> ORGANISM: Homo sapiens

<400> SEQUENCE: 1164
tgtctgcttc ctgtggga                                      18

<210> SEQ ID NO 1165
<211> LENGTH: 17
<212> TYPE: DNA
<213> ORGANISM: GB virus C -continued

```
<400> SEQUENCE: 1165
ggcacggttc actaggc                                                    17

<210> SEQ ID NO 1166
<211> LENGTH: 18
<212> TYPE: DNA
<213> ORGANISM: Homo sapiens

<400> SEQUENCE: 1166
ggcacggtgt cagcaggc                                                   18

<210> SEQ ID NO 1167
<211> LENGTH: 17
<212> TYPE: DNA
<213> ORGANISM: GB virus C

<400> SEQUENCE: 1167
gtgggtctta agagaag                                                    17

<210> SEQ ID NO 1168
<211> LENGTH: 18
<212> TYPE: DNA
<213> ORGANISM: Homo sapiens

<400> SEQUENCE: 1168
gtgagtctct aagaaaag                                                   18

<210> SEQ ID NO 1169
<211> LENGTH: 20
<212> TYPE: DNA
<213> ORGANISM: GB virus C

<400> SEQUENCE: 1169
catctccctg cggacagtgc                                                 20

<210> SEQ ID NO 1170
<211> LENGTH: 18
<212> TYPE: DNA
<213> ORGANISM: Homo sapiens

<400> SEQUENCE: 1170
catcttaccg gacagtgc                                                   18

<210> SEQ ID NO 1171
<211> LENGTH: 20
<212> TYPE: DNA
<213> ORGANISM: GB virus C

<400> SEQUENCE: 1171
aggaatgctc gtgtctgtgc                                                 20

<210> SEQ ID NO 1172
<211> LENGTH: 19
<212> TYPE: DNA
<213> ORGANISM: Homo sapiens

<400> SEQUENCE: 1172
aggaatgttc cttctttgc                                                  19

<210> SEQ ID NO 1173
<211> LENGTH: 19
<212> TYPE: DNA
<213> ORGANISM: Human immunodeficiency virus 1
```

<400> SEQUENCE: 1173
tagaagagaa ggctttcag                                                19

<210> SEQ ID NO 1174
<211> LENGTH: 19
<212> TYPE: DNA
<213> ORGANISM: Homo sapiens

<400> SEQUENCE: 1174
tagagggaag cgctttctg                                                19

<210> SEQ ID NO 1175
<211> LENGTH: 19
<212> TYPE: DNA
<213> ORGANISM: Human immunodeficiency virus 1

<400> SEQUENCE: 1175
tagaagagaa ggctttcag                                                19

<210> SEQ ID NO 1176
<211> LENGTH: 19
<212> TYPE: DNA
<213> ORGANISM: Homo sapiens

<400> SEQUENCE: 1176
tagagggaag cgctttctg                                                19

<210> SEQ ID NO 1177
<211> LENGTH: 20
<212> TYPE: DNA
<213> ORGANISM: Human immunodeficiency virus 1

<400> SEQUENCE: 1177
ggttaaggcc aggggggaaag                                              20

<210> SEQ ID NO 1178
<211> LENGTH: 20
<212> TYPE: DNA
<213> ORGANISM: Homo sapiens

<400> SEQUENCE: 1178
ggtacaggcc tgggggacag                                               20

<210> SEQ ID NO 1179
<211> LENGTH: 19
<212> TYPE: DNA
<213> ORGANISM: Human immunodeficiency virus 1

<400> SEQUENCE: 1179
accacacaca aggctactt                                                19

<210> SEQ ID NO 1180
<211> LENGTH: 18
<212> TYPE: DNA
<213> ORGANISM: Homo sapiens

<400> SEQUENCE: 1180
atcacacaaa ggcaactt                                                 18

<210> SEQ ID NO 1181
<211> LENGTH: 20
<212> TYPE: DNA
<213> ORGANISM: Human immunodeficiency virus 1

-continued

```
<400> SEQUENCE: 1181
gggagcagca ggaagcacta                                              20

<210> SEQ ID NO 1182
<211> LENGTH: 19
<212> TYPE: DNA
<213> ORGANISM: Homo sapiens

<400> SEQUENCE: 1182
gggagctgtg gaagcagta                                               19

<210> SEQ ID NO 1183
<211> LENGTH: 23
<212> TYPE: DNA
<213> ORGANISM: Human immunodeficiency virus 1

<400> SEQUENCE: 1183
caaatattac agggctgcta tta                                          23

<210> SEQ ID NO 1184
<211> LENGTH: 22
<212> TYPE: DNA
<213> ORGANISM: Homo sapiens

<400> SEQUENCE: 1184
ccaatattac tgtgctgctt ta                                           22

<210> SEQ ID NO 1185
<211> LENGTH: 22
<212> TYPE: DNA
<213> ORGANISM: Human immunodeficiency virus 1

<400> SEQUENCE: 1185
cataaagaaa aaagacagta ct                                           22

<210> SEQ ID NO 1186
<211> LENGTH: 21
<212> TYPE: DNA
<213> ORGANISM: Homo sapiens

<400> SEQUENCE: 1186
cataaagtag aaagcactac t                                            21

<210> SEQ ID NO 1187
<211> LENGTH: 20
<212> TYPE: DNA
<213> ORGANISM: Human immunodeficiency virus 1

<400> SEQUENCE: 1187
cctattgaga ctgtaccagt                                              20

<210> SEQ ID NO 1188
<211> LENGTH: 20
<212> TYPE: DNA
<213> ORGANISM: Homo sapiens

<400> SEQUENCE: 1188
cctactgagc tgatatcagt                                              20

<210> SEQ ID NO 1189
<211> LENGTH: 20
<212> TYPE: DNA
<213> ORGANISM: Human immunodeficiency virus 1
```

```
<400> SEQUENCE: 1189
gaggtagtaa ttagatctgt                                               20

<210> SEQ ID NO 1190
<211> LENGTH: 20
<212> TYPE: DNA
<213> ORGANISM: Homo sapiens

<400> SEQUENCE: 1190
gaggtagtag tttgtgctgt                                               20

<210> SEQ ID NO 1191
<211> LENGTH: 19
<212> TYPE: DNA
<213> ORGANISM: Human immunodeficiency virus 1

<400> SEQUENCE: 1191
tgaaaatcca tacaatact                                                19

<210> SEQ ID NO 1192
<211> LENGTH: 19
<212> TYPE: DNA
<213> ORGANISM: Homo sapiens

<400> SEQUENCE: 1192
tgcaaatcca tgcaaaact                                                19

<210> SEQ ID NO 1193
<211> LENGTH: 20
<212> TYPE: DNA
<213> ORGANISM: Human immunodeficiency virus 1

<400> SEQUENCE: 1193
actgggtctc tctggttaga                                               20

<210> SEQ ID NO 1194
<211> LENGTH: 21
<212> TYPE: DNA
<213> ORGANISM: Homo sapiens

<400> SEQUENCE: 1194
actggctcct ttctgggtag a                                             21

<210> SEQ ID NO 1195
<211> LENGTH: 17
<212> TYPE: DNA
<213> ORGANISM: Human immunodeficiency virus 1

<400> SEQUENCE: 1195
ctgttgactc agattgg                                                  17

<210> SEQ ID NO 1196
<211> LENGTH: 18
<212> TYPE: DNA
<213> ORGANISM: Homo sapiens

<400> SEQUENCE: 1196
ctgtggactc agttctgg                                                 18

<210> SEQ ID NO 1197
<211> LENGTH: 19
<212> TYPE: DNA
<213> ORGANISM: Human immunodeficiency virus 1
```

```
<400> SEQUENCE: 1197
gctcaatgcc acagccata                                               19

<210> SEQ ID NO 1198
<211> LENGTH: 19
<212> TYPE: DNA
<213> ORGANISM: Homo sapiens

<400> SEQUENCE: 1198
gctcatgcac acacccaca                                               19

<210> SEQ ID NO 1199
<211> LENGTH: 20
<212> TYPE: DNA
<213> ORGANISM: Human immunodeficiency virus 1

<400> SEQUENCE: 1199
tggaagaaat ctgttgactc                                              20

<210> SEQ ID NO 1200
<211> LENGTH: 20
<212> TYPE: DNA
<213> ORGANISM: Homo sapiens

<400> SEQUENCE: 1200
tgggagaagg ctgtttactc                                              20

<210> SEQ ID NO 1201
<211> LENGTH: 17
<212> TYPE: DNA
<213> ORGANISM: Human immunodeficiency virus 1

<400> SEQUENCE: 1201
atcaaaagac ttaatag                                                 17

<210> SEQ ID NO 1202
<211> LENGTH: 18
<212> TYPE: DNA
<213> ORGANISM: Homo sapiens

<400> SEQUENCE: 1202
atcaacagac attaattg                                                18

<210> SEQ ID NO 1203
<211> LENGTH: 21
<212> TYPE: DNA
<213> ORGANISM: Human immunodeficiency virus 1

<400> SEQUENCE: 1203
aggagcttaa gaatgaagct g                                            21

<210> SEQ ID NO 1204
<211> LENGTH: 20
<212> TYPE: DNA
<213> ORGANISM: Homo sapiens

<400> SEQUENCE: 1204
aggagcttac aatctagctg                                              20

<210> SEQ ID NO 1205
<211> LENGTH: 22
<212> TYPE: DNA
<213> ORGANISM: Human immunodeficiency virus 1
```

```
<400> SEQUENCE: 1205
agtgcagcag cagaacaatt tg                                              22

<210> SEQ ID NO 1206
<211> LENGTH: 19
<212> TYPE: DNA
<213> ORGANISM: Homo sapiens

<400> SEQUENCE: 1206
agtgcatcac agaactttg                                                  19

<210> SEQ ID NO 1207
<211> LENGTH: 21
<212> TYPE: DNA
<213> ORGANISM: Human immunodeficiency virus 1

<400> SEQUENCE: 1207
ccttggaatg ctagttggag t                                               21

<210> SEQ ID NO 1208
<211> LENGTH: 21
<212> TYPE: DNA
<213> ORGANISM: Homo sapiens

<400> SEQUENCE: 1208
ccttggaacc taggtgtgag t                                               21

<210> SEQ ID NO 1209
<211> LENGTH: 20
<212> TYPE: DNA
<213> ORGANISM: Human immunodeficiency virus 1

<400> SEQUENCE: 1209
gcagcagcag aacaatttgc                                                 20

<210> SEQ ID NO 1210
<211> LENGTH: 19
<212> TYPE: DNA
<213> ORGANISM: Homo sapiens

<400> SEQUENCE: 1210
gcagcacaga aatattggc                                                  19

<210> SEQ ID NO 1211
<211> LENGTH: 18
<212> TYPE: DNA
<213> ORGANISM: Human immunodeficiency virus 1

<400> SEQUENCE: 1211
tagagtgcat ccagtgca                                                   18

<210> SEQ ID NO 1212
<211> LENGTH: 18
<212> TYPE: DNA
<213> ORGANISM: Homo sapiens

<400> SEQUENCE: 1212
taaggtgcat ctagtgca                                                   18

<210> SEQ ID NO 1213
<211> LENGTH: 20
<212> TYPE: DNA
<213> ORGANISM: Human immunodeficiency virus 1
```

-continued

<400> SEQUENCE: 1213
caactcacag tctggggcat                                              20

<210> SEQ ID NO 1214
<211> LENGTH: 18
<212> TYPE: DNA
<213> ORGANISM: Homo sapiens

<400> SEQUENCE: 1214
caaatcacag tctgccat                                                18

<210> SEQ ID NO 1215
<211> LENGTH: 16
<212> TYPE: DNA
<213> ORGANISM: Human immunodeficiency virus 1

<400> SEQUENCE: 1215
gtgtggaaaa tctcta                                                  16

<210> SEQ ID NO 1216
<211> LENGTH: 18
<212> TYPE: DNA
<213> ORGANISM: Homo sapiens

<400> SEQUENCE: 1216
gtgttgaaac aatctcta                                                18

<210> SEQ ID NO 1217
<211> LENGTH: 19
<212> TYPE: DNA
<213> ORGANISM: Human immunodeficiency virus 1

<400> SEQUENCE: 1217
attgaaccat taggagtag                                               19

<210> SEQ ID NO 1218
<211> LENGTH: 20
<212> TYPE: DNA
<213> ORGANISM: Homo sapiens

<400> SEQUENCE: 1218
attgtagcct tttggagtag                                              20

<210> SEQ ID NO 1219
<211> LENGTH: 19
<212> TYPE: DNA
<213> ORGANISM: Human immunodeficiency virus 1

<400> SEQUENCE: 1219
gcaggatatg ttactaata                                               19

<210> SEQ ID NO 1220
<211> LENGTH: 18
<212> TYPE: DNA
<213> ORGANISM: Homo sapiens

<400> SEQUENCE: 1220
gcaatatgtt cctgaata                                                18

<210> SEQ ID NO 1221
<211> LENGTH: 20
<212> TYPE: DNA
<213> ORGANISM: Human immunodeficiency virus 1

```
<400> SEQUENCE: 1221
agcaaccctc tattgtgtgc                                           20

<210> SEQ ID NO 1222
<211> LENGTH: 20
<212> TYPE: DNA
<213> ORGANISM: Homo sapiens

<400> SEQUENCE: 1222
agcaaacatt tattgtgtgc                                           20

<210> SEQ ID NO 1223
<211> LENGTH: 20
<212> TYPE: DNA
<213> ORGANISM: Human immunodeficiency virus 1

<400> SEQUENCE: 1223
aagaacctcc attcctttgg                                           20

<210> SEQ ID NO 1224
<211> LENGTH: 20
<212> TYPE: DNA
<213> ORGANISM: Homo sapiens

<400> SEQUENCE: 1224
aagaacctca gttgcttttg                                           20

<210> SEQ ID NO 1225
<211> LENGTH: 20
<212> TYPE: DNA
<213> ORGANISM: Human immunodeficiency virus 1

<400> SEQUENCE: 1225
attggatgac agaaaccttg                                           20

<210> SEQ ID NO 1226
<211> LENGTH: 18
<212> TYPE: DNA
<213> ORGANISM: Homo sapiens

<400> SEQUENCE: 1226
agtgcatgac agaacttg                                             18

<210> SEQ ID NO 1227
<211> LENGTH: 20
<212> TYPE: DNA
<213> ORGANISM: Human immunodeficiency virus 1

<400> SEQUENCE: 1227
tcagatttac ccagggatta                                           20

<210> SEQ ID NO 1228
<211> LENGTH: 18
<212> TYPE: DNA
<213> ORGANISM: Homo sapiens

<400> SEQUENCE: 1228
tcacattgcc agggatta                                             18

<210> SEQ ID NO 1229
<211> LENGTH: 20
<212> TYPE: DNA
<213> ORGANISM: Human immunodeficiency virus 1
```

```
<400> SEQUENCE: 1229
gctcctgggg atttggggtt                                                  20

<210> SEQ ID NO 1230
<211> LENGTH: 18
<212> TYPE: DNA
<213> ORGANISM: Homo sapiens

<400> SEQUENCE: 1230
gttcctgggg atgggatt                                                    18

<210> SEQ ID NO 1231
<211> LENGTH: 20
<212> TYPE: DNA
<213> ORGANISM: Human immunodeficiency virus 1

<400> SEQUENCE: 1231
tgggagtttg ttaatacccc                                                  20

<210> SEQ ID NO 1232
<211> LENGTH: 21
<212> TYPE: DNA
<213> ORGANISM: Homo sapiens

<400> SEQUENCE: 1232
tgtcagtttg tcaaataccc c                                                21

<210> SEQ ID NO 1233
<211> LENGTH: 18
<212> TYPE: DNA
<213> ORGANISM: Human immunodeficiency virus 1

<400> SEQUENCE: 1233
tagagtgcat ccagtgca                                                    18

<210> SEQ ID NO 1234
<211> LENGTH: 18
<212> TYPE: DNA
<213> ORGANISM: Homo sapiens

<400> SEQUENCE: 1234
taaggtgcat ctagtgca                                                    18

<210> SEQ ID NO 1235
<211> LENGTH: 19
<212> TYPE: DNA
<213> ORGANISM: Human immunodeficiency virus 1

<400> SEQUENCE: 1235
tagaagagaa ggctttcag                                                   19

<210> SEQ ID NO 1236
<211> LENGTH: 19
<212> TYPE: DNA
<213> ORGANISM: Homo sapiens

<400> SEQUENCE: 1236
tagagggaag cgctttctg                                                   19

<210> SEQ ID NO 1237
<211> LENGTH: 19
<212> TYPE: DNA
<213> ORGANISM: Human immunodeficiency virus 1
```

<400> SEQUENCE: 1237
ttgggtcagg gagtctcca                                            19

<210> SEQ ID NO 1238
<211> LENGTH: 21
<212> TYPE: DNA
<213> ORGANISM: Homo sapiens

<400> SEQUENCE: 1238
ttggttcagg gagggtcccc a                                         21

<210> SEQ ID NO 1239
<211> LENGTH: 19
<212> TYPE: DNA
<213> ORGANISM: Human immunodeficiency virus 1

<400> SEQUENCE: 1239
tagaagagaa ggctttcag                                            19

<210> SEQ ID NO 1240
<211> LENGTH: 19
<212> TYPE: DNA
<213> ORGANISM: Homo sapiens

<400> SEQUENCE: 1240
tagagggaag cgctttctg                                            19

<210> SEQ ID NO 1241
<211> LENGTH: 20
<212> TYPE: DNA
<213> ORGANISM: Human immunodeficiency virus 1

<400> SEQUENCE: 1241
ggcacacagc cagaaattgc                                           20

<210> SEQ ID NO 1242
<211> LENGTH: 19
<212> TYPE: DNA
<213> ORGANISM: Homo sapiens

<400> SEQUENCE: 1242
ggcaccagcc aggcattgc                                            19

<210> SEQ ID NO 1243
<211> LENGTH: 19
<212> TYPE: DNA
<213> ORGANISM: Human immunodeficiency virus 1

<400> SEQUENCE: 1243
agaatggagg aaaaagaga                                            19

<210> SEQ ID NO 1244
<211> LENGTH: 20
<212> TYPE: DNA
<213> ORGANISM: Homo sapiens

<400> SEQUENCE: 1244
agacgggagg aaagaaggga                                           20

<210> SEQ ID NO 1245
<211> LENGTH: 20
<212> TYPE: DNA
<213> ORGANISM: Human immunodeficiency virus 1

```
<400> SEQUENCE: 1245
ctgcatataa gcagctgctt                                                 20

<210> SEQ ID NO 1246
<211> LENGTH: 20
<212> TYPE: DNA
<213> ORGANISM: Homo sapiens

<400> SEQUENCE: 1246
ctgcaatgta agcacttctt                                                 20

<210> SEQ ID NO 1247
<211> LENGTH: 23
<212> TYPE: DNA
<213> ORGANISM: Human immunodeficiency virus 1

<400> SEQUENCE: 1247
atataataca gtagcaaccc tct                                             23

<210> SEQ ID NO 1248
<211> LENGTH: 20
<212> TYPE: DNA
<213> ORGANISM: Homo sapiens

<400> SEQUENCE: 1248
atattataca gtcaacctct                                                 20

<210> SEQ ID NO 1249
<211> LENGTH: 20
<212> TYPE: DNA
<213> ORGANISM: Human immunodeficiency virus 1

<400> SEQUENCE: 1249
aacaaattca gctaccataa                                                 20

<210> SEQ ID NO 1250
<211> LENGTH: 21
<212> TYPE: DNA
<213> ORGANISM: Homo sapiens

<400> SEQUENCE: 1250
aacaaatccc agtctaccta a                                               21

<210> SEQ ID NO 1251
<211> LENGTH: 18
<212> TYPE: DNA
<213> ORGANISM: Human immunodeficiency virus 1

<400> SEQUENCE: 1251
aagtgttaga gtggaggt                                                   18

<210> SEQ ID NO 1252
<211> LENGTH: 19
<212> TYPE: DNA
<213> ORGANISM: Homo sapiens

<400> SEQUENCE: 1252
aagtgcttat agtgcaggt                                                  19

<210> SEQ ID NO 1253
<211> LENGTH: 20
<212> TYPE: DNA
<213> ORGANISM: Human immunodeficiency virus 1
```

<400> SEQUENCE: 1253
gtggtatata aaattattca                                               20

<210> SEQ ID NO 1254
<211> LENGTH: 20
<212> TYPE: DNA
<213> ORGANISM: Homo sapiens

<400> SEQUENCE: 1254
gtggtttaca aagtaattca                                               20

<210> SEQ ID NO 1255
<211> LENGTH: 19
<212> TYPE: DNA
<213> ORGANISM: Human immunodeficiency virus 1

<400> SEQUENCE: 1255
tagaagagaa ggctttcag                                                19

<210> SEQ ID NO 1256
<211> LENGTH: 19
<212> TYPE: DNA
<213> ORGANISM: Homo sapiens

<400> SEQUENCE: 1256
tagagggaag cgctttctg                                                19

<210> SEQ ID NO 1257
<211> LENGTH: 19
<212> TYPE: DNA
<213> ORGANISM: Human immunodeficiency virus 1

<400> SEQUENCE: 1257
cagaagacag tggcaatga                                                19

<210> SEQ ID NO 1258
<211> LENGTH: 19
<212> TYPE: DNA
<213> ORGANISM: Homo sapiens

<400> SEQUENCE: 1258
ctgcagacag tggcaatca                                                19

<210> SEQ ID NO 1259
<211> LENGTH: 17
<212> TYPE: DNA
<213> ORGANISM: Human immunodeficiency virus 1

<400> SEQUENCE: 1259
attttgtgca tcagatg                                                  17

<210> SEQ ID NO 1260
<211> LENGTH: 18
<212> TYPE: DNA
<213> ORGANISM: Homo sapiens

<400> SEQUENCE: 1260
attattgtac atcggatg                                                 18

<210> SEQ ID NO 1261
<211> LENGTH: 18
<212> TYPE: DNA
<213> ORGANISM: Human immunodeficiency virus 1

```
<400> SEQUENCE: 1261
aatacatgga tgatttgt                                              18

<210> SEQ ID NO 1262
<211> LENGTH: 18
<212> TYPE: DNA
<213> ORGANISM: Homo sapiens

<400> SEQUENCE: 1262
aatacatggt tgatctttt                                             18

<210> SEQ ID NO 1263
<211> LENGTH: 18
<212> TYPE: DNA
<213> ORGANISM: Human immunodeficiency virus 1

<400> SEQUENCE: 1263
aaccccactc tgtgttag                                              18

<210> SEQ ID NO 1264
<211> LENGTH: 19
<212> TYPE: DNA
<213> ORGANISM: Homo sapiens

<400> SEQUENCE: 1264
aaccacactg tggtgttag                                             19

<210> SEQ ID NO 1265
<211> LENGTH: 18
<212> TYPE: DNA
<213> ORGANISM: Human immunodeficiency virus 1

<400> SEQUENCE: 1265
tgtaacacct cagtcatt                                              18

<210> SEQ ID NO 1266
<211> LENGTH: 20
<212> TYPE: DNA
<213> ORGANISM: Homo sapiens

<400> SEQUENCE: 1266
tgcaacttac ctgagtcatt                                            20

<210> SEQ ID NO 1267
<211> LENGTH: 19
<212> TYPE: DNA
<213> ORGANISM: Human immunodeficiency virus 1

<400> SEQUENCE: 1267
tgtaaactcc ttagaggaa                                             19

<210> SEQ ID NO 1268
<211> LENGTH: 21
<212> TYPE: DNA
<213> ORGANISM: Homo sapiens

<400> SEQUENCE: 1268
tgtaaacatc cttgactgga a                                          21

<210> SEQ ID NO 1269
<211> LENGTH: 17
<212> TYPE: DNA
<213> ORGANISM: Human immunodeficiency virus 1
```

-continued

```
<400> SEQUENCE: 1269
aaaaagggct gttggaa                                                   17

<210> SEQ ID NO 1270
<211> LENGTH: 18
<212> TYPE: DNA
<213> ORGANISM: Homo sapiens

<400> SEQUENCE: 1270
acacagggct gttgtgaa                                                  18

<210> SEQ ID NO 1271
<211> LENGTH: 19
<212> TYPE: DNA
<213> ORGANISM: Human immunodeficiency virus 1

<400> SEQUENCE: 1271
tagaagagaa ggcttttcag                                                19

<210> SEQ ID NO 1272
<211> LENGTH: 19
<212> TYPE: DNA
<213> ORGANISM: Homo sapiens

<400> SEQUENCE: 1272
tagagggaag cgctttctg                                                 19

<210> SEQ ID NO 1273
<211> LENGTH: 19
<212> TYPE: DNA
<213> ORGANISM: Human immunodeficiency virus 1

<400> SEQUENCE: 1273
tagaagagaa ggctttcag                                                 19

<210> SEQ ID NO 1274
<211> LENGTH: 19
<212> TYPE: DNA
<213> ORGANISM: Homo sapiens

<400> SEQUENCE: 1274
tagagggaag cgctttctg                                                 19

<210> SEQ ID NO 1275
<211> LENGTH: 19
<212> TYPE: DNA
<213> ORGANISM: Human immunodeficiency virus 1

<400> SEQUENCE: 1275
tagaagagaa ggctttcag                                                 19

<210> SEQ ID NO 1276
<211> LENGTH: 19
<212> TYPE: DNA
<213> ORGANISM: Homo sapiens

<400> SEQUENCE: 1276
tagagggaag cgctttctg                                                 19

<210> SEQ ID NO 1277
<211> LENGTH: 20
<212> TYPE: DNA
<213> ORGANISM: Human immunodeficiency virus 1
```

```
<400> SEQUENCE: 1277
ggttaaggcc aggggggaaag                                              20

<210> SEQ ID NO 1278
<211> LENGTH: 20
<212> TYPE: DNA
<213> ORGANISM: Homo sapiens

<400> SEQUENCE: 1278
ggtacaggcc tgggggacag                                               20

<210> SEQ ID NO 1279
<211> LENGTH: 19
<212> TYPE: DNA
<213> ORGANISM: Human immunodeficiency virus 1

<400> SEQUENCE: 1279
accacacaca aggctactt                                                19

<210> SEQ ID NO 1280
<211> LENGTH: 18
<212> TYPE: DNA
<213> ORGANISM: Homo sapiens

<400> SEQUENCE: 1280
atcacacaaa ggcaactt                                                 18

<210> SEQ ID NO 1281
<211> LENGTH: 20
<212> TYPE: DNA
<213> ORGANISM: Human immunodeficiency virus 1

<400> SEQUENCE: 1281
gggagcagca ggaagcacta                                               20

<210> SEQ ID NO 1282
<211> LENGTH: 19
<212> TYPE: DNA
<213> ORGANISM: Homo sapiens

<400> SEQUENCE: 1282
gggagctgtg gaagcagta                                                19

<210> SEQ ID NO 1283
<211> LENGTH: 23
<212> TYPE: DNA
<213> ORGANISM: Human immunodeficiency virus 1

<400> SEQUENCE: 1283
caaatattac agggctgcta tta                                           23

<210> SEQ ID NO 1284
<211> LENGTH: 22
<212> TYPE: DNA
<213> ORGANISM: Homo sapiens

<400> SEQUENCE: 1284
ccaatattac tgtgctgctt ta                                            22

<210> SEQ ID NO 1285
<211> LENGTH: 22
<212> TYPE: DNA
<213> ORGANISM: Human immunodeficiency virus 1
```

```
<400> SEQUENCE: 1285
cataaagaaa aaagacagta ct                                          22

<210> SEQ ID NO 1286
<211> LENGTH: 21
<212> TYPE: DNA
<213> ORGANISM: Homo sapiens

<400> SEQUENCE: 1286
cataaagtag aaagcactac t                                           21

<210> SEQ ID NO 1287
<211> LENGTH: 20
<212> TYPE: DNA
<213> ORGANISM: Human immunodeficiency virus 1

<400> SEQUENCE: 1287
cctattgaga ctgtaccagt                                             20

<210> SEQ ID NO 1288
<211> LENGTH: 20
<212> TYPE: DNA
<213> ORGANISM: Homo sapiens

<400> SEQUENCE: 1288
cctactgagc tgatatcagt                                             20

<210> SEQ ID NO 1289
<211> LENGTH: 20
<212> TYPE: DNA
<213> ORGANISM: Human immunodeficiency virus 1

<400> SEQUENCE: 1289
gaggtagtaa ttagatctgt                                             20

<210> SEQ ID NO 1290
<211> LENGTH: 20
<212> TYPE: DNA
<213> ORGANISM: Homo sapiens

<400> SEQUENCE: 1290
gaggtagtaa ttagatctgt                                             20

<210> SEQ ID NO 1291
<211> LENGTH: 19
<212> TYPE: DNA
<213> ORGANISM: Human immunodeficiency virus 1

<400> SEQUENCE: 1291
tgaaaatcca tacaatact                                              19

<210> SEQ ID NO 1292
<211> LENGTH: 19
<212> TYPE: DNA
<213> ORGANISM: Homo sapiens

<400> SEQUENCE: 1292
tgcaaatcca tgcaaaact                                              19

<210> SEQ ID NO 1293
<211> LENGTH: 20
<212> TYPE: DNA
<213> ORGANISM: Human immunodeficiency virus 1
```

-continued

```
<400> SEQUENCE: 1293
actgggtctc tctggttaga                                              20

<210> SEQ ID NO 1294
<211> LENGTH: 21
<212> TYPE: DNA
<213> ORGANISM: Homo sapiens

<400> SEQUENCE: 1294
actggctcct ttctgggtag a                                            21

<210> SEQ ID NO 1295
<211> LENGTH: 17
<212> TYPE: DNA
<213> ORGANISM: Human immunodeficiency virus 1

<400> SEQUENCE: 1295
ctgttgactc agattgg                                                 17

<210> SEQ ID NO 1296
<211> LENGTH: 18
<212> TYPE: DNA
<213> ORGANISM: Homo sapiens

<400> SEQUENCE: 1296
ctgtggactc agttctgg                                                18

<210> SEQ ID NO 1297
<211> LENGTH: 19
<212> TYPE: DNA
<213> ORGANISM: Human immunodeficiency virus 1

<400> SEQUENCE: 1297
gctcaatgcc acagccata                                               19

<210> SEQ ID NO 1298
<211> LENGTH: 19
<212> TYPE: DNA
<213> ORGANISM: Homo sapiens

<400> SEQUENCE: 1298
gctcatgcac acacccaca                                               19

<210> SEQ ID NO 1299
<211> LENGTH: 20
<212> TYPE: DNA
<213> ORGANISM: Human immunodeficiency virus 1

<400> SEQUENCE: 1299
tggaagaaat ctgttgactc                                              20

<210> SEQ ID NO 1300
<211> LENGTH: 20
<212> TYPE: DNA
<213> ORGANISM: Homo sapiens

<400> SEQUENCE: 1300
tgggagaagg ctgtttactc                                              20

<210> SEQ ID NO 1301
<211> LENGTH: 17
<212> TYPE: DNA
<213> ORGANISM: Human immunodeficiency virus 1
```

```
<400> SEQUENCE: 1301
atcaaaagac ttaatag                                                  17

<210> SEQ ID NO 1302
<211> LENGTH: 18
<212> TYPE: DNA
<213> ORGANISM: Homo sapiens

<400> SEQUENCE: 1302
atcaacagac attaattg                                                 18

<210> SEQ ID NO 1303
<211> LENGTH: 21
<212> TYPE: DNA
<213> ORGANISM: Human immunodeficiency virus 1

<400> SEQUENCE: 1303
aggagcttaa gaatgaagct g                                             21

<210> SEQ ID NO 1304
<211> LENGTH: 20
<212> TYPE: DNA
<213> ORGANISM: Homo sapiens

<400> SEQUENCE: 1304
aggagcttac aatctagctg                                               20

<210> SEQ ID NO 1305
<211> LENGTH: 22
<212> TYPE: DNA
<213> ORGANISM: Human immunodeficiency virus 1

<400> SEQUENCE: 1305
agtgcagcag cagaacaatt tg                                            22

<210> SEQ ID NO 1306
<211> LENGTH: 19
<212> TYPE: DNA
<213> ORGANISM: Homo sapiens

<400> SEQUENCE: 1306
agtgcatcac agaactttg                                                19

<210> SEQ ID NO 1307
<211> LENGTH: 21
<212> TYPE: DNA
<213> ORGANISM: Human immunodeficiency virus 1

<400> SEQUENCE: 1307
ccttggaatg ctagttggag t                                             21

<210> SEQ ID NO 1308
<211> LENGTH: 21
<212> TYPE: DNA
<213> ORGANISM: Homo sapiens

<400> SEQUENCE: 1308
ccttggaacc taggtgtgag t                                             21

<210> SEQ ID NO 1309
<211> LENGTH: 20
<212> TYPE: DNA
<213> ORGANISM: Human immunodeficiency virus 1
```

<400> SEQUENCE: 1309
gcagcagcag aacaatttgc                                              20

<210> SEQ ID NO 1310
<211> LENGTH: 20
<212> TYPE: DNA
<213> ORGANISM: Homo sapiens

<400> SEQUENCE: 1310
gcagcagcag aacaatttgc                                              20

<210> SEQ ID NO 1311
<211> LENGTH: 18
<212> TYPE: DNA
<213> ORGANISM: Human immunodeficiency virus 1

<400> SEQUENCE: 1311
tagagtgcat ccagtgca                                                18

<210> SEQ ID NO 1312
<211> LENGTH: 18
<212> TYPE: DNA
<213> ORGANISM: Homo sapiens

<400> SEQUENCE: 1312
taaggtgcat ctagtgca                                                18

<210> SEQ ID NO 1313
<211> LENGTH: 20
<212> TYPE: DNA
<213> ORGANISM: Human immunodeficiency virus 1

<400> SEQUENCE: 1313
caactcacag tctggggcat                                              20

<210> SEQ ID NO 1314
<211> LENGTH: 18
<212> TYPE: DNA
<213> ORGANISM: Homo sapiens

<400> SEQUENCE: 1314
caaatcacag tctgccat                                                18

<210> SEQ ID NO 1315
<211> LENGTH: 16
<212> TYPE: DNA
<213> ORGANISM: Human immunodeficiency virus 1

<400> SEQUENCE: 1315
gtgtggaaaa tctcta                                                  16

<210> SEQ ID NO 1316
<211> LENGTH: 18
<212> TYPE: DNA
<213> ORGANISM: Homo sapiens

<400> SEQUENCE: 1316
gtgttgaaac aatctcta                                                18

<210> SEQ ID NO 1317
<211> LENGTH: 19
<212> TYPE: DNA
<213> ORGANISM: Human immunodeficiency virus 1

```
<400> SEQUENCE: 1317
attgaaccat taggagtag                                                  19

<210> SEQ ID NO 1318
<211> LENGTH: 20
<212> TYPE: DNA
<213> ORGANISM: Homo sapiens

<400> SEQUENCE: 1318
attgtaacca ttaggagtag                                                 20

<210> SEQ ID NO 1319
<211> LENGTH: 19
<212> TYPE: DNA
<213> ORGANISM: Human immunodeficiency virus 1

<400> SEQUENCE: 1319
gcaggatatg ttactaata                                                  19

<210> SEQ ID NO 1320
<211> LENGTH: 18
<212> TYPE: DNA
<213> ORGANISM: Homo sapiens

<400> SEQUENCE: 1320
gcaatatgtt cctgaata                                                   18

<210> SEQ ID NO 1321
<211> LENGTH: 20
<212> TYPE: DNA
<213> ORGANISM: Human immunodeficiency virus 1

<400> SEQUENCE: 1321
agcaaccctc tattgtgtgc                                                 20

<210> SEQ ID NO 1322
<211> LENGTH: 20
<212> TYPE: DNA
<213> ORGANISM: Homo sapiens

<400> SEQUENCE: 1322
agcaaacatt tattgtgtgc                                                 20

<210> SEQ ID NO 1323
<211> LENGTH: 20
<212> TYPE: DNA
<213> ORGANISM: Human immunodeficiency virus 1

<400> SEQUENCE: 1323
aagaacctcc attcctttgg                                                 20

<210> SEQ ID NO 1324
<211> LENGTH: 20
<212> TYPE: DNA
<213> ORGANISM: Homo sapiens

<400> SEQUENCE: 1324
aagaacctca gttgcttttg                                                 20

<210> SEQ ID NO 1325
<211> LENGTH: 20
<212> TYPE: DNA
<213> ORGANISM: Human immunodeficiency virus 1
```

```
<400> SEQUENCE: 1325
attggatgac agaaaccttg                                              20

<210> SEQ ID NO 1326
<211> LENGTH: 18
<212> TYPE: DNA
<213> ORGANISM: Homo sapiens

<400> SEQUENCE: 1326
agtgcatgac agaacttg                                                18

<210> SEQ ID NO 1327
<211> LENGTH: 20
<212> TYPE: DNA
<213> ORGANISM: Human immunodeficiency virus 1

<400> SEQUENCE: 1327
tcagatttac ccagggatta                                              20

<210> SEQ ID NO 1328
<211> LENGTH: 18
<212> TYPE: DNA
<213> ORGANISM: Homo sapiens

<400> SEQUENCE: 1328
tcacattgcc agggatta                                                18

<210> SEQ ID NO 1329
<211> LENGTH: 20
<212> TYPE: DNA
<213> ORGANISM: Human immunodeficiency virus 1

<400> SEQUENCE: 1329
gctcctgggg atttggggtt                                              20

<210> SEQ ID NO 1330
<211> LENGTH: 18
<212> TYPE: DNA
<213> ORGANISM: Homo sapiens

<400> SEQUENCE: 1330
gttcctgggg atgggatt                                                18

<210> SEQ ID NO 1331
<211> LENGTH: 20
<212> TYPE: DNA
<213> ORGANISM: Human immunodeficiency virus 1

<400> SEQUENCE: 1331
tgggagtttg ttaataccccc                                             20

<210> SEQ ID NO 1332
<211> LENGTH: 21
<212> TYPE: DNA
<213> ORGANISM: Homo sapiens

<400> SEQUENCE: 1332
tgtcagtttg tcaaataccc c                                            21

<210> SEQ ID NO 1333
<211> LENGTH: 18
<212> TYPE: DNA
<213> ORGANISM: Human immunodeficiency virus 1
```

```
<400> SEQUENCE: 1333
tagagtgcat ccagtgca                                                 18

<210> SEQ ID NO 1334
<211> LENGTH: 18
<212> TYPE: DNA
<213> ORGANISM: Homo sapiens

<400> SEQUENCE: 1334
taaggtgcat ctagtgca                                                 18

<210> SEQ ID NO 1335
<211> LENGTH: 19
<212> TYPE: DNA
<213> ORGANISM: Human immunodeficiency virus 1

<400> SEQUENCE: 1335
tagaagagaa ggctttcag                                                19

<210> SEQ ID NO 1336
<211> LENGTH: 19
<212> TYPE: DNA
<213> ORGANISM: Homo sapiens

<400> SEQUENCE: 1336
tagagggaag cgctttctg                                                19

<210> SEQ ID NO 1337
<211> LENGTH: 19
<212> TYPE: DNA
<213> ORGANISM: Human immunodeficiency virus 1

<400> SEQUENCE: 1337
ttgggtcagg gagtctcca                                                19

<210> SEQ ID NO 1338
<211> LENGTH: 21
<212> TYPE: DNA
<213> ORGANISM: Homo sapiens

<400> SEQUENCE: 1338
ttgggtcagg gagggtctcc a                                             21

<210> SEQ ID NO 1339
<211> LENGTH: 19
<212> TYPE: DNA
<213> ORGANISM: Human immunodeficiency virus 1

<400> SEQUENCE: 1339
tagaagagaa ggctttcag                                                19

<210> SEQ ID NO 1340
<211> LENGTH: 19
<212> TYPE: DNA
<213> ORGANISM: Homo sapiens

<400> SEQUENCE: 1340
tagagggaag cgctttctg                                                19

<210> SEQ ID NO 1341
<211> LENGTH: 20
<212> TYPE: DNA
<213> ORGANISM: Human immunodeficiency virus 1
```

<400> SEQUENCE: 1341
ggcacacagc cagaaattgc                                                 20

<210> SEQ ID NO 1342
<211> LENGTH: 19
<212> TYPE: DNA
<213> ORGANISM: Homo sapiens

<400> SEQUENCE: 1342
ggcaccagcc aggcattgc                                                  19

<210> SEQ ID NO 1343
<211> LENGTH: 19
<212> TYPE: DNA
<213> ORGANISM: Human immunodeficiency virus 1

<400> SEQUENCE: 1343
agaatggagg aaaaagaga                                                  19

<210> SEQ ID NO 1344
<211> LENGTH: 20
<212> TYPE: DNA
<213> ORGANISM: Homo sapiens

<400> SEQUENCE: 1344
agacgggagg aaagaaggga                                                 20

<210> SEQ ID NO 1345
<211> LENGTH: 20
<212> TYPE: DNA
<213> ORGANISM: Human immunodeficiency virus 1

<400> SEQUENCE: 1345
ctgcatataa gcagctgctt                                                 20

<210> SEQ ID NO 1346
<211> LENGTH: 20
<212> TYPE: DNA
<213> ORGANISM: Homo sapiens

<400> SEQUENCE: 1346
ctgcaatgta agcacttctt                                                 20

<210> SEQ ID NO 1347
<211> LENGTH: 23
<212> TYPE: DNA
<213> ORGANISM: Human immunodeficiency virus 1

<400> SEQUENCE: 1347
atataataca gtagcaaccc tct                                             23

<210> SEQ ID NO 1348
<211> LENGTH: 20
<212> TYPE: DNA
<213> ORGANISM: Homo sapiens

<400> SEQUENCE: 1348
atattataca gtcaacctct                                                 20

<210> SEQ ID NO 1349
<211> LENGTH: 20
<212> TYPE: DNA
<213> ORGANISM: Human immunodeficiency virus 1

```
<400> SEQUENCE: 1349
aacaaattca gctaccataa                                              20

<210> SEQ ID NO 1350
<211> LENGTH: 21
<212> TYPE: DNA
<213> ORGANISM: Homo sapiens

<400> SEQUENCE: 1350
aacaaatccc agtctaccta a                                            21

<210> SEQ ID NO 1351
<211> LENGTH: 18
<212> TYPE: DNA
<213> ORGANISM: Human immunodeficiency virus 1

<400> SEQUENCE: 1351
aagtgttaga gtggaggt                                                18

<210> SEQ ID NO 1352
<211> LENGTH: 19
<212> TYPE: DNA
<213> ORGANISM: Homo sapiens

<400> SEQUENCE: 1352
aagtgcttat agtgcaggt                                               19

<210> SEQ ID NO 1353
<211> LENGTH: 20
<212> TYPE: DNA
<213> ORGANISM: Human immunodeficiency virus 1

<400> SEQUENCE: 1353
gtggtatata aaattattca                                              20

<210> SEQ ID NO 1354
<211> LENGTH: 20
<212> TYPE: DNA
<213> ORGANISM: Homo sapiens

<400> SEQUENCE: 1354
gtggtttaca aagtaattca                                              20

<210> SEQ ID NO 1355
<211> LENGTH: 19
<212> TYPE: DNA
<213> ORGANISM: Human immunodeficiency virus 1

<400> SEQUENCE: 1355
tagaagagaa ggctttcag                                               19

<210> SEQ ID NO 1356
<211> LENGTH: 19
<212> TYPE: DNA
<213> ORGANISM: Homo sapiens

<400> SEQUENCE: 1356
tagagggaag cgctttctg                                               19

<210> SEQ ID NO 1357
<211> LENGTH: 19
<212> TYPE: DNA
<213> ORGANISM: Human immunodeficiency virus 1
```

<400> SEQUENCE: 1357
cagaagacag tggcaatga                                            19

<210> SEQ ID NO 1358
<211> LENGTH: 19
<212> TYPE: DNA
<213> ORGANISM: Homo sapiens

<400> SEQUENCE: 1358
ctgcagacag tggcaatca                                            19

<210> SEQ ID NO 1359
<211> LENGTH: 17
<212> TYPE: DNA
<213> ORGANISM: Human immunodeficiency virus 1

<400> SEQUENCE: 1359
attttgtgca tcagatg                                              17

<210> SEQ ID NO 1360
<211> LENGTH: 18
<212> TYPE: DNA
<213> ORGANISM: Homo sapiens

<400> SEQUENCE: 1360
attattgtac atcggatg                                             18

<210> SEQ ID NO 1361
<211> LENGTH: 18
<212> TYPE: DNA
<213> ORGANISM: Human immunodeficiency virus 1

<400> SEQUENCE: 1361
aatacatgga tgatttgt                                             18

<210> SEQ ID NO 1362
<211> LENGTH: 18
<212> TYPE: DNA
<213> ORGANISM: Homo sapiens

<400> SEQUENCE: 1362
aatacatggt tgatcttt                                             18

<210> SEQ ID NO 1363
<211> LENGTH: 18
<212> TYPE: DNA
<213> ORGANISM: Human immunodeficiency virus 1

<400> SEQUENCE: 1363
aaccccactc tgtgttag                                             18

<210> SEQ ID NO 1364
<211> LENGTH: 19
<212> TYPE: DNA
<213> ORGANISM: Homo sapiens

<400> SEQUENCE: 1364
aaccacactg tggtgttag                                            19

<210> SEQ ID NO 1365
<211> LENGTH: 18
<212> TYPE: DNA
<213> ORGANISM: Human immunodeficiency virus 1

```
<400> SEQUENCE: 1365
tgtaacacct cagtcatt                                                    18

<210> SEQ ID NO 1366
<211> LENGTH: 20
<212> TYPE: DNA
<213> ORGANISM: Homo sapiens

<400> SEQUENCE: 1366
tgcaacttac ctgagtcatt                                                  20

<210> SEQ ID NO 1367
<211> LENGTH: 19
<212> TYPE: DNA
<213> ORGANISM: Human immunodeficiency virus 1

<400> SEQUENCE: 1367
tgtaaactcc ttagaggaa                                                   19

<210> SEQ ID NO 1368
<211> LENGTH: 21
<212> TYPE: DNA
<213> ORGANISM: Homo sapiens

<400> SEQUENCE: 1368
tgtaaacatc cttgactgga a                                                21

<210> SEQ ID NO 1369
<211> LENGTH: 17
<212> TYPE: DNA
<213> ORGANISM: Human immunodeficiency virus 1

<400> SEQUENCE: 1369
aaaaagggct gttggaa                                                     17

<210> SEQ ID NO 1370
<211> LENGTH: 18
<212> TYPE: DNA
<213> ORGANISM: Homo sapiens

<400> SEQUENCE: 1370
acacagggct gttgtgaa                                                    18

<210> SEQ ID NO 1371
<211> LENGTH: 19
<212> TYPE: DNA
<213> ORGANISM: Human immunodeficiency virus 1

<400> SEQUENCE: 1371
tagaagagaa ggctttcag                                                   19

<210> SEQ ID NO 1372
<211> LENGTH: 19
<212> TYPE: DNA
<213> ORGANISM: Homo sapiens

<400> SEQUENCE: 1372
tagagggaag cgctttctg                                                   19

<210> SEQ ID NO 1373
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1373
gaggtagtaa ttagatctgt                                                   20

<210> SEQ ID NO 1374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1374
gaggtagtaa ttagatctgt                                                   20

<210> SEQ ID NO 1375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1375
acagatctaa ttactacctc                                                   20

<210> SEQ ID NO 1376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1376
gcagcagcag aacaatttgc                                                   20

<210> SEQ ID NO 1377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1377
gcagcagcag aacaatttgc                                                   20

<210> SEQ ID NO 1378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1378
gcaaattgtt ctgctgctgc                                                   20

<210> SEQ ID NO 1379
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1379
attgtaacca ttaggagtag                                                    20

<210> SEQ ID NO 1380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1380
attgtaacca ttaggagtag                                                    20

<210> SEQ ID NO 1381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1381
ctactcctaa tggttacaat                                                    20

<210> SEQ ID NO 1382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1382
ttgggtcagg gagggtctcc a                                                  21

<210> SEQ ID NO 1383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1383
ttgggtcagg gagggtctcc a                                                  21

<210> SEQ ID NO 1384
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1384
tggagactcc ctgacccaa                                                     19

<210> SEQ ID NO 1385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1385
gcagcagcag aacaatttgc                                               20

<210> SEQ ID NO 1386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1386
gcaaattgtt ctgctgctgc                                               20

<210> SEQ ID NO 1387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1387
gcagcagcag aacaatttgc                                               20

<210> SEQ ID NO 1388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1388
gcagcagcag aacaatttgc                                               20

<210> SEQ ID NO 1389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1389
gcaaattgtt ctgctgctgc                                               20

<210> SEQ ID NO 1390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1390
attgtaacca ttaggagtag                                               20

<210> SEQ ID NO 1391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1391
```
ctactcctaa tggttacaat                                                20

<210> SEQ ID NO 1392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1392
attgtaacca ttaggagtag                                                20

<210> SEQ ID NO 1393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1393
attgtaacca ttaggagtag                                                20

<210> SEQ ID NO 1394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1394
ctactcctaa tggttacaat                                                20

<210> SEQ ID NO 1395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1395
gaggtagtaa ttagatctgt                                                20

<210> SEQ ID NO 1396
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1396
acagatctaa ttactacctc                                                20

<210> SEQ ID NO 1397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1397
gaggtagtaa ttagatctgt                                                20

```
<210> SEQ ID NO 1398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1398
gaggtagtaa ttagatctgt                                                   20

<210> SEQ ID NO 1399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1399
acagatctaa ttactacctc                                                   20

<210> SEQ ID NO 1400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1400
ttgggtcagg gaccgtctcc a                                                 21

<210> SEQ ID NO 1401
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1401
tggagacggt ccctgaccca a                                                 21

<210> SEQ ID NO 1402
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1402
ttggctcagg gaccgtctcc a                                                 21

<210> SEQ ID NO 1403
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1403
ttgggtcagg gaccgtctcc a                                                 21

<210> SEQ ID NO 1404
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1404
tggagacggt ccctgaccca a                                              21
```

MIRNA TRIPLEX FORMATIONS FOR THE DOWNREGULATION OF VIRAL REPLICATION

PRIORITY

The instant application claims the benefit in U.S. Provisional Application Ser. No. 61/137,744 filed Aug. 1, 2008, the entire contents of which are incorporated by reference herein.

BACKGROUND OF THE INVENTION

1) Field of the Invention

The present invention relates to miRNA triplex formations capable of downregulating viral replication. More particularly, the present invention relates to the discovery of miRNAs having high homology with both HIV-1 and a co-infecting virus such as HHV-6, HHV-7, or GVB-C, and the use of such mutually homologous miRNAs to form stable triplex molecules effective in the downregulation and/or inhibition of viral replication.

2) Description of Related Art

The general concept of harnessing RNA interference to silence gene replication/transcription/expression for therapeutic benefit is known in the art, as is the idea of using single-stranded interfering RNA molecules (e.g., antisense RNA, small interfering RNA (siRNA), microRNAs (miRNA)) to silence expression of viral genes, for example, as part of a component in an antiviral therapy. Further efforts in the prior art to control viral replication include the use of attenuated viral mutants or viral sequences, subunits or particles that can be used to generate a protective immune response against live virus (i.e., viral particles that are sufficiently "virus" looking to stimulate host immune system to generate protective antibodies but sufficiently disabled or incomplete to prevent onset of negative viral effects). Also, considerable attention has been directed towards the use of proteins, peptides or chemicals having therapeutic antiviral potential that operate by inhibiting an essential viral activity in vivo, acting on the virus itself to forestall/inhibit/prevent its negative consequences. None of these efforts involve the use of stable triplex formations to inhibit viral replication; rather, they utilize completely different mechanisms. Further, the prior art is replete with other efforts directed towards the use of viral sequences having utility in the context of the construction of viral vectors for the delivery of genes or proteins of interest (i.e., in the context of gene therapy) or in the context of a vaccine adjuvant.

For example, U.S. Pat. No. 6,682,907 describes the use of triplex structure DNA in transferring nucleotide sequences. The structure of the DNA triplex formed during reverse transcription in this process enables, or at least contributes, to the entry of the retroviral genome into the cell nucleus, thus allowing infection of non mitotic cells. The invention concerns a nucleotide sequence of retroviral or retroviral-like origin, which can be prepared synthetically, comprising cPPT and CTS regions which are cis-acting in reverse transcription in general, and in particular two associated polynucleotides when they are placed in the normal retroviral genome, each polynucleotide containing at least 10 nucleotides. The vector of the invention contains a transgene inserted under the control of viral or non viral sequences regulating transcription or expression. Ultimately, the triplex formation with HIV in this invention is intended to promote an immune response in the body, and does not disclose specific sequences that effect HIV replication by forming stable triplexes in vivo.

U.S. Pat. No. 6,555,342 describes a fusion protein delivery system and uses thereof. Ultimately, this invention demonstrated that Vpr and Vpx can serve as vehicles to deliver functionally active enzymes to the HIV virion, including those that may exert an antiviral activity such as SN. However, there is no discussion of using the specific miRNA or siRNA sequences identified in the present invention to form stable triplexes to inhibit HIV replication.

U.S. Pat. No. 6,531,123 describes lentiviral vectors and contemplates attenuated lentiviruses, and improved viral packaging and transducing vectors derived from lentiviruses, especially HIV-1, useful for the delivery of nonlentiviral genes to target cells. It also contemplates the use of these vectors in delivering transgenes to target cells, especially nondividing cells, in organisms, especially humans. However, there is no discussion of using the specific miRNA or siRNA sequences identified in the present invention to form stable triplexes to inhibit HIV replication.

U.S. Patent No. 20070099858 describes small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating or that mediate RNA interference (RNAi) against influenza virus gene expression. However, there is no disclosure of using miRNA to form triplex formation to inhibit the HIV.

U.S. Patent No. 20030175693 describes an HIV recombinant vaccine. The invention encompasses recombinant HIV and SIV viruses containing heterologous transcriptional regulatory elements in the U3 region of the virus. In particular embodiments, the recombinant virus has decreased replication in vivo and the virus has a protective effect when administered to a host. The recombinant virus can have heterologous transcriptional regulatory elements that replace the HIV region corresponding to the NFKB/Sp1/TATA Box/initiation region (−114 to +1) or corresponding to the NFKB/Sp1/TAR region (−114 to +93) of the SIVmac239 long terminal repeat. However, there is no disclosure of using miRNA to form triplex formation to inhibit the HIV.

In each instance, the prior art fails to teach the use of specific miRNA sequences such as those identified in the instant application to form stable triplexes with HIV to inhibit HIV replication in accordance with the teachings of the present invention. Thus, although the present invention arises in view of the noted background, it nevertheless diverges therefrom in the discovery of specific miRNA sequences capable of forming with the HIV-1 genome stable triplexes that inhibit HIV-1 replication in vivo. These miRNA sequences find utility in the context of pharmaceutical compositions for use in the treatment and prevention of the HIV, and given the conserved nature of many viral genomes, may be reasonably extended to the treatment of other viruses, particularly retroviruses, more particularly lentiviruses such as SIV etc.

Accordingly, it is an object of the present invention to provide mutually homologous miRNAs give rise to the creation of stable triplex formations with a viral genome, such as the HIV-1 genome, to effect the downregulation of viral replication in vivo.

SUMMARY OF THE INVENTION

The above objective is accomplished according to the present invention by providing an isolated nucleic acid molecule selected from the group consisting of: (a) a nucleotide sequence selected from among SEQ ID NOs: 1273-1372; (b) a nucleotide sequence consisting of the complement of a nucleotide sequence of (a); and (c) a nucleotide sequence consisting of 15-25 nucleotides having a sequence identity of at least 90% to a nucleotide sequence of (a) or (b).

In a further embodiment, the nucleic acid molecule is (a) a nucleotide sequence selected from among SEQ ID NOs: 1289-1290, 1309-1310, 1317-1318, and 1337-1338; (b) a nucleotide sequence consisting of the complement of a nucleotide sequence of (a); or (c) a nucleotide sequence consisting of 15-25 nucleotides having a sequence identity of at least 90% to a nucleotide sequence of (a) or (b).

In a further embodiment, the nucleic acid molecule is selected from the group consisting of RNA, DNA and modified nucleotide molecules.

In a further embodiment, the nucleic acid molecule is single-stranded.

In a further embodiment, the nucleic acid molecule is at least partially double-stranded.

In a further embodiment, the nucleic acid molecule is an miRNA.

In a further embodiment, the nucleic acid molecule is an siRNA.

In a further embodiment, the nucleic acid molecule comprises at least one modified nucleotide. Preferably, nucleotide is a 2' modified nucleotide.

In a further embodiment, the nucleotide sequence of (c) has an identity of at least 95% to a nucleotide sequence of (a) or (b).

In a further embodiment, the nucleotide sequence in part (c) further comprises a uridine (U) or adenosine (A).

In a further embodiment, the nucleotide sequence of (c) consists of 19-25 nucleotides.

In a further embodiment, the nucleotide sequence of (c) consists of 21-23 nucleotides.

The above objective is further accomplished according to the present invention by providing a recombinant expression vector comprising the nucleic acid molecule expressed above.

The above objective is further accomplished according to the present invention by providing a composition comprising at least one nucleic acid molecule as expressed above in combination with a pharmaceutically acceptable carrier.

In a further embodiment, the pharmaceutically acceptable carrier is suitable for diagnostic applications.

In a further embodiment, the pharmaceutically acceptable carrier is suitable for therapeutic applications.

The above objective is further accomplished according to the present invention by providing a method of inhibiting replication of a virus in a target cell, said method comprising the steps of: (a) introducing into a target cell infected with the virus an homologous small double stranded RNA comprising a nucleic acid molecule as set forth above and (b) allowing the homologous small double stranded RNA to hybridize with the viral genome.

In a further embodiment, the hybridization of step (b) results in the formation of a stable triplex molecule.

In a further embodiment, the homologous small double stranded RNA is contained within a recombinant vector.

In a further embodiment, the virus is one of a retrovirus, lentivirus, HIV, HIV-1, and HERV.

In a further embodiment, the viral genome comprises a proviral or preintegration version of the virus.

The above objective is further accomplished according to the present invention by providing a method of reducing the level of HIV-1 replication in a target cell, said method comprising the steps of: (a) introducing into a target cell infected with the virus an homologous small double stranded RNA at least 80% complementary to a portion of the HIV-1 genome, the homologous small double stranded RNA comprising a nucleic acid molecule as set forth in claims 1 or 2; and (b) allowing the homologous small double stranded RNA to hybridize with the HIV-1 genome or a proviral or preintegration version thereof.

In a further embodiment, the hybridization of step (b) results in the formation of a stable triplex molecule.

In a further embodiment, the homologous small double stranded RNA is an miRNA or an siRNA.

In a further embodiment, the target cell is in vitro.

In a further embodiment, the target cell is in vivo.

In a further embodiment, the method comprises administering a recombinant vector carrying the homologous small double stranded RNA to a subject comprising said target cell.

In a further embodiment, the method comprises treating said subject for an HIV-1 mediated disease condition.

The above objective is further accomplished according to the present invention by providing a method of inhibiting replication of a virus in a cell comprising the steps of: (a) stimulating the expression of an endogenous antisense sequence comprising a nucleotide sequence as set forth in claims 1 or 2 and (b) inducing the endogenous miRNA to hybridize with the viral genome.

In a further embodiment, the endogenous antisense sequence comprises a primary miRNA transcript.

In a further embodiment, the endogenous antisense sequence comprises a stem loop pre-miRNA transcript. In a further embodiment, the viral genome comprises a proviral or preintegration version of the virus.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows sequences of the HIV-1 duplexes and third strand homologous oligonucleotides (representing one strand of homologous small RNA). FIG. 1 discloses SEQ ID NOS 1373-1384, respectively, in order of appearance;

FIG. 2 discloses SEQ ID NOS 1385-1404, respectively, in order of appearance from left to right;

DETAILED DESCRIPTION OF A PREFERRED EMBODIMENT

Figure 2:
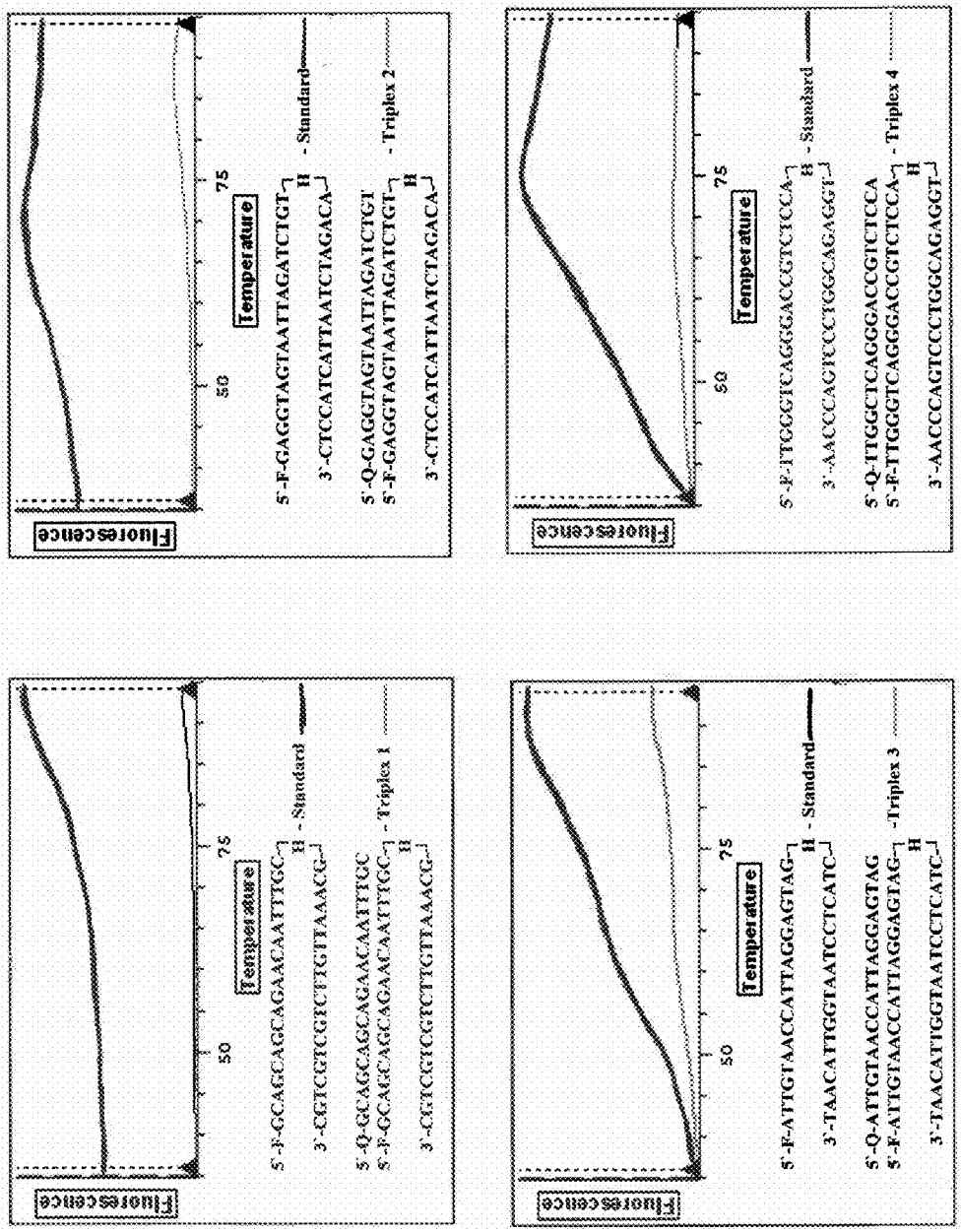
FIG. 2 shows fluorescence melting profiles for sequence numbers 1-4 in FIG. 1.

With reference to the Figures, the invention will now be described in more detail. Although methods and materials similar or equivalent to those described herein can be used in the practice or testing of embodiments of the present invention, the preferred methods and materials are now described. However, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

Definitions:

As used herein and in the appended claims, the singular forms "a", "an", and "the" include plural reference unless the context clearly dictates otherwise. Thus, for example, reference to a "molecule" is a reference to one or more molecules and equivalents thereof known to those skilled in the art, and so forth.

As used herein, the term "organism" refers to any living entity composed of at least one cell. A living organism can be as simple as, for example, a single eukaryotic cell or as complex as a mammal, including a human being.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). The term "biological sample" further refers to a homogenate, lysate, extract, cell culture or tissue culture prepared from a whole organism or a subset of its cells, tissues or component parts, or a fraction or portion thereof. Lastly, "biological sample" refers to a medium, such as a nutrient broth or gel in which an organism has been propagated, which contains cellular components, such as proteins or polynucleotides.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents.

The terms "polypeptide", "peptide", and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The terms "polynucleotides", "oligonucleotides" "nucleotides", "nucleic acids", and "nucleic acid molecules" are used interchangeably herein to refer to a polymer of nucleic acid residues linked by ester bonding, and, unless otherwise specifically indicated, are similarly to the amino acids referred to by their commonly accepted single-letter codes (triple codon system). Similar to the amino acids, they encompass both naturally-occurring and non-naturally occurring nucleic acid polymers. The polynucleotide or oligonucleotide may be composed of DNA, RNA or a combination thereof.

In the context of the present invention, nucleic acid homology is deemed "substantially identical" where they have between about 70% and about 80% or more preferably, between about 81% and about 90%, or even more preferably, between about 91% and about 99%, sequence identity along their entirety.

The term "isolated" is used herein to refer to a molecule separated from its native environment (i.e., in a non-naturally occurring form). The term "purified" is used herein to refer to a molecule in a form substantially free from contaminants.

The present invention relates to inhibitory molecules that are complementary to a nucleotide sequence within a viral genome, particularly the HIV-1 genome. The inhibitory molecules of the present invention act by binding to/hybridizing with the viral genome to form a stable triplex (or multiplex) therewith, thereby inhibiting the replication of the genome and the subsequent transcription and/or translation of the genes contained therein. As such, the inhibitory molecules of the present invention find utility in the treatment and prevention of viral infection, particularly HIV-1 infection. An inhibitory molecule of the present invention can be directly or indirectly introduced into a subject, into a tissue or cell thereof, in a form that is capable of binding to the viral genome. Alternatively, it can be carried in a vector.

The term "inhibitory molecules" as used herein encompasses both nucleotides that are entirely complementary to the target sequence and those having a mismatch of one or more nucleotides, so long as the inhibitory molecules can specifically hybridize to the target sequences of the viral genome. The inhibitory molecules of the present invention include oligonucleotides that have a sequence identity of at least 70%, 75%, 80%, 85%, 90%, 95%, 96%, 97%, 98%, 99% or higher over a span of at least 10 continuous nucleotides. Algorithms known in the art can be used to determine the sequence identity. The inhibitory molecules of present invention include modified oligonucleotides. For example, thioated oligonucleotides can be used to confer nuclease resistance to an oligonucleotide.

The inhibitory molecules of the present invention are preferably directed against the HIV-1 genome. However, given the high degree of sequence conservation among retroviruses, such inhibitory molecules may also find utility in connection with other of viruses, more particularly retroviruses including Human endogenous retroviruses (HERVs), more particularly lentiviruses, examples of which include, but not limited to, FIV (feline immunodeficiency virus), SIV (simian immunodeficiency virus), HIV-1, and HIV-2.

The inhibitory molecules of the present invention may contain one or more modified nucleotides and/or non-phosphodiester linkages. Chemical modifications well known in the art are capable of increasing stability, availability, and/or cell uptake of the double-stranded molecule. The skilled person will be aware of other types of chemical modification which may be incorporated into the present molecules (WO03/070744; WO2005/045037). In one embodiment, modifications can be used to provide improved resistance to degradation or improved uptake. Examples of such modifications include phosphorothioate linkages, 2'-O-methyl ribonucleotides (especially on the sense strand of a double-stranded molecule), 2'-deoxy-fluoro ribonucleotides, 2'-deoxy ribonucleotides, "universal base" nucleotides, 5'-C-methyl nucleotides, and inverted deoxyabasic residue incorporation (US20060122137).

In another embodiment, modifications can be used to enhance the stability or to increase targeting efficiency of the inhibitory molecule. Modifications include chemical cross linking between two complementary strands of a double-stranded molecule, chemical modification of a 3' or 5' terminus of a strand of a double-stranded molecule, sugar modifications, nucleobase modifications and/or backbone modifications, 2-fluoro modified ribonucleotides and 2'-deoxy ribonucleotides (WO2004/029212). In another embodiment, modifications can be used to increased or decreased affinity for the complementary nucleotides in the target sequence and/or in the complementary molecule strand (WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyi, or 7-alkenyi purine. In another embodiment, when the double-stranded molecule is a double-stranded molecule with a 3' overhang, the 3'-terminal nucleotide overhanging nucleotides may be replaced by deoxyribonucleotides (Elbashir S M et al., Genes Dev Jan. 15, 2001 15(2): 188-200). For further details, published documents such as US20060234970 are available. The present invention is not limited to these examples and any known chemical modifications may be employed for the double-stranded molecules of the present invention so long as the resulting molecule retains the ability to bind to the viral genome and inhibit replication thereof.

As used herein, the term "siRNA", also known as small interfering RNA (siRNA), short interfering RNA or silencing RNA, refers to a class of inhibitory molecules that are typically 20-25 nucleotide-long double stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

As used herein, the term "miRNA", also known as microRNA, refers to double-stranded RNA molecules, typically of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

As noted above, the inhibitory molecules of the present invention are capable of binding to viral genome sequences, forming a stable triplex (or multiplex) therewith so as to inhibit replication thereof. This binding results from hybridization of complementary sequences. Nucleic acid hybridization is affected by conditions such as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. (See e.g., Wetmur & Davidson, 1968). Determining appropriate hybridization conditions to identify and/or isolate sequences containing high levels of identity is well known in the art. (See e.g., Sambrook et al., 1989). Representative moderate stringency conditions comprise, for example, hybridization at 50° C. and in 10×SSC (0.9 M NaCl/0.09 M sodium citrate), wherein the hybridized nucleic acid molecules remain bound when subjected to washing at 55° C. in 1×SSC. Sequence identity can be further determined by hybridization under more stringent conditions, for example, at 50° C. or higher and 0.1×SSC (9 mM mM sodium citrate), as described below. Typically, under "stringent conditions" a probe will hybridize specifically to its target sequence, but to no other sequences.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another representative stringent hybridization scheme uses 50% formamide, 4×SSC at 42° C. As used herein, the term "stringent conditions" can also mean conditions of high stringency, for example 6×SSC, 0.2% polyvinylpyrrolidone, 0.2% Ficoll, 0.2% bovine serum albumin, 0.1% sodium dodecyl sulfate, 100 µg/mL salmon sperm DNA and 15% formamide at 68° C.

Pharmaceutical Formulations:

The inhibitory molecules of the present invention may serve as drugs themselves or candidates for the development of drugs that inhibit the replication of HIV-1 and can be applied to the treatment or prevention of HIV-1 and other viral disorders.

When administrating one or more inhibitory molecules of the present invention as a pharmaceutical composition for humans and other mammals, including without limitation, mice, rats, hamsters, guinea-pigs, rabbits, cats, dogs, sheep, pigs, cattle, monkeys, baboons, and chimpanzees, the isolated molecules can be directly administered, either singly or in a cocktail combination, or can be formulated into a dosage form using known pharmaceutical preparation methods. For example, according to the needs of the patient, the inhibitory molecules of the present invention can be made into an external preparation, for example, a liniment or a poultice, by admixing it with a suitable base material which is inactive against the nucleic acid. Alternatively, the inhibitory molecules of the present invention or pharmaceutical formulations thereof can be taken orally, such as in the form of sugar-coated tablets, capsules, elixirs and microcapsules, or non-orally, such as in the form of injections of sterile solutions or suspensions with water or any other pharmaceutically acceptable liquid. Likewise, the molecules can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Also, as needed, the inhibitory molecules of the present invention can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by conventional methods.

The inhibitory molecules of the present invention can be given to the patient by direct application onto the ailing site or by injection into a blood vessel so that it will reach the site of ailment. In addition, a molecule-mounting medium can also be used to increase durability and membrane-permeability. Examples include, but are not limited to, liposomes, poly-L-lysine, lipids, cholesterol, lipofectin or derivatives of these.

Examples of additives that can be admixed into tablets and capsules include, but are not limited to, binders, including gelatin, corn starch, tragacanth gum and arabic gum; excipients, including crystalline cellulose; swelling agents, including corn starch, gelatin and alginic acid; lubricants, including magnesium stearate; sweeteners, including sucrose, lactose or saccharin; and flavoring agents, including peppermint, spearmint, Gaultheria adenothrix oil and cherry. When the unit-dose form is a capsule, a liquid carrier, including an oil, can be further included in the above ingredients. Sterile composites for injection can be formulated following normal drug implementations using vehicles, for example, distilled water or saline solution, suitable for injection.

Physiological saline, glucose, and other isotonic liquids, including adjuvants, such as D-sorbitol, D-mannose, D-mannitol, and sodium chloride, can be used as aqueous solutions for injection. These can be used in conjunction with suitable solubilizers, for example, alcohols including ethanol; polyalcohols, including propylene glycol and polyethylene glycol; and non-ionic surfactants, including Polysorbate 80 (TM) and HCO-50.

Sesame oil or soy-bean oil can be used as an oleaginous liquid, can be used in conjunction with benzyl benzoate or benzyl alcohol as a solubilizer, and can be formulated with a buffer, including phosphate buffer and sodium acetate buffer; a pain-killer, including procaine hydrochloride; a stabilizer, including benzyl alcohol and phenol; and/or an anti-oxidant. A prepared injection can be filled into a suitable ampoule.

Methods well known to those skilled in the art can be used to administer the molecules and pharmaceutical compositions of the present invention to patients, for example as an intra-arterial, intravenous, or percutaneous injection or as an intranasal, transbronchial, intramuscular or oral administration. When the active agent is a nucleic acid or encodable by a nucleic acid (as is the case herein), the nucleic acid molecule can be inserted into a vector for gene therapy and the vector administered to a patient to perform the therapy. In either context, the dosage and method of administration may vary according to the body-weight, age, and symptoms of the patient; however, one skilled in the art can suitably adjust the requisite dosage according to the patient's condition using routine optimization procedures.

For example, although the dose of inhibitory molecule needed to bind to a target viral genome, form a stable triplex therewith, and subsequently inhibit replication thereof depends on a number of factors, the dose is generally about 0.1 mg to about 100 mg per day, preferably about 1.0 mg to about 50 mg per day and more preferably about 1.0 mg to about 20 mg per day, when administered orally to a normal adult human (weighing about 60 kg).

When administering a molecule or pharmaceutical composition of the present invention parenterally, in the form of an injection to a normal adult human (weighing about 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount can be routinely calculated by converting to 60 kg of body-weight.

Hereinafter, the present invention is described in more detail by reference to the Examples detailed herein below. However, the following materials, methods and examples only illustrate aspects of the invention and in no way are intended to limit the scope of the present invention. As such, methods and materials similar or equivalent to those described herein can be used in the practice or testing of the present invention.

Analysis and Examples:

Human immunodeficiency virus type 1 (HIV-1) infection is often accompanied by co-infection with other pathogens that generally result in accelerating the progression of the disease and in early development of AIDS[1]. However, sometimes certain co-infections can have beneficial effects[2-6]. Several reports have documented the beneficial effects of two genetically related human herpes viruses-HHV-6, HHV-7- and GBV-C (a Hepatitis C virus related virus that is non-pathogenic but belongs to Flavivirus family) co-infections in HIV-1-infected individuals in terms of significantly longer survival and better prognosis[7]. However, some reports have contradicted such findings with the result that this issue remains controversial[9-10]. During the course of viral infections viruses from similar species compete with each other to gain access to the host replication machinery, causing one type of virus to eventually block the entry of the competing virus into the host cell by receptor modulation or by intracellular interference in its replication inside the cell by various mechanisms[10]. On the other hand, viruses from heterologous species can co-infect cells cooperatively where one virus provides another with a useful protein that it co-opts for its own use[11]. Rarely, one type of virus becomes dependent on another virus. One such example is hepatitis Delta, which requires the presence of hepatitis B virus in order to replicate. Viruses also interact with each other directly at molecular levels[10].

In order to evaluate the intracellular mechanisms at molecular levels of the reported beneficial effects of HHV-6,-7 and GBV-C viruses it was considered that such effects might be caused by the activation of mutually homologous endogenous miRNAs that can interfere with replication of both types of viruses (i.e. HIV-1 and co-infecting HHV-6A/B, or HHV-7 or GBV-C). In recent years, miRNAs have been shown to block replication of various pathogenic viruses in plants, warms and eukaryotic organisms[12-14]. The discovery of virally encoded miRNAs has attracted immense attention towards the possibility of miRNA as a critical modulator of viral pathogenecity and host susceptibility in higher eukaryotes[13-15] When eukaryotic cells encounter double-stranded miRNA, transcripts of homologous mRNAs are silenced through RNA interference[12-14] or triplex forming complexes (TF) between the nucleic acids[16-17].

There is growing evidence to support the concept that miRNAs of the vertebrate host may regulate the viral life cycle, viral tropism, and the pathogenesis of viral diseases[11-14,16-18]. For example, human miR-32 has been shown to have a direct negative effect on the replication of the retrovirus primate foamy virus type 1 (PFV-1) by downregulating the replication-essential viral proteins encoded by open reading frame 2 (ORF2)[19]. As the evolutionary process would dictate, pathogenic viruses have also evolved numerous countering mechanisms that can neutralize the host miRNA-based defenses[17,20].

In recent years, several reports have documented a better prognosis for HIV-1-infected patients co-infected with HHV-6, HHV-7 or GBV-C who may live three times longer as compared to those without these co-infections. Recent studies have also identified anti-viral roles of host microRNAs (miRNAs) in plants, worms, and mammals.

In order to evaluate whether the apparent beneficial effects of the co-infecting viruses are due to mutually homologous miRNAs, a computational analysis was done of miRNAs that have significant homologies to both HIV-1 and the co-infecting viruses. Constructs of such miRNAs were obtained and introduced into Hela-CD4+ cells to give rise to the development of stably transfected cell lines each expressing a particular miRNA.

As detailed herein below, it was determined that 50 miRNAs showed >80% homology to HIV-1 and, among these, 11 mutually targeted co-infecting viruses. As a result, 12 miRNAs were synthesized, 11 with significant mutual homologies and one with no homology to co-infecting viruses but with >90% homology to HIV-1 alone. Further, miRNAs were selected for their ability to form triplexes using a tool that detects C+·GC and T.AT triplets, factors suggested in the art to impart greater stability between miRNA and HIV-1 provirus. The stability of such miRNA triplexes was measured in vitro. In addition, triplex-forming miRNAs were detected using triplex specific monoclonal antibodies. Next, stably transfected Hela-CD4+cell lines were developed expressing each of the miRNAs utilizing pSuper vector. Referring to Table 1, all 12 miRNAs exhibited a significant inhibition of HIV-1 (P>0.001) as measured by HIV-1p24 ELISA and Real Time PCR (>90%; p>0.001) as compared to mock transfected control. Accordingly, the present invention provides a new miRNA-based therapeutic strategy for HIV-1 using a molecular mechanism by which the co-infecting viruses impart resistance to HIV-1.

In developing the present invention, it was hypothesized that since HHV-6, HHV-7 and GBV-C are non-pathogenic viruses, a co-infection with these viruses might activate miRNA-based antiviral immunity[12,17]. Since a single miRNA can share homology to several targets, it is theoretically possible that the co-infecting viruses are activating protective miRNAs that are mutually homologous with HIV-1 and quelling their replications in uninfected target cells making them resistant to HIV-1 infection. Of note, all three co-infecting viruses primarily infect CD4+ T-lymphocytes it is possible that they are interfering with HIV-1 replication[3,5,7].

Therefore, *Homo sapiens* miRNAs were first computationally analyzed for possible homologies to all four viral genomes by utilizing the Sanger miRNA Database[21]. This identified several miRNAs that have significant (>70%) sequence homologies with HHV-6 (A and B types), HHV-7 and GBV-C and HIV-1 (Tables 1-3). Fifty miRNAs showed >80% homology to HIV-1 sequences (Table 4). Currently, Sanger human miRNAs database contains 733 miRNAs (has-miRs). After tabulating all the miRNAs that target the two most common HIV-1 strains (accessions #s:NC_001722 and AF033819), HHV-6 (NC_001664 and NC_000898), HHV-7 (NC_001716) and GBV-C (NC_001710), all the miRNA that share significant mutual homologies to HIV-1 (>60%) were again tabulated. Table 1 shows selected sequences of miRNAs sequence alignments from the miRNAs that demonstrate homology to HIV-1 and exhibited significant to HHV-6, HHV-7 and GBV-C viruses (see all the sequences in Table 4).

In order to explore the molecular mechanisms of the observed protective roles of these co-infecting viruses via miRNA, a mathematical algorithm was developed to identify the miRNAs that would form stable nucleic acid complexes with HIV-1[24,28]. Previously, it was hypothesized that some of the relatively high sequence homologous miRNAs may develop stable triplexes forming complexes (TF) with HIV-1[16,17]. Recent evidence supports the notion that some miRNAs may mediate the silencing by TF[24]. Roberts and Crothers[22] have shown that $C^+$·GC and T.AT triplets impart a greater triplex stability. Several investigators have confirmed this observation and have demonstrated that the most stable triplexes contain alternating $C^+$·GC and T·AT triplets[22-23]. Two main structural motifs have been defined in which the third strand runs either parallel or antiparallel to the duplex purine strand. Antiparallel triplexes contain G·GC, A·AT and T·AT triplets while parallel triplexes contain $C^+$·GC and T·AT triplets.

It was reasoned that the presence of mutually homologous miRNAs, as naturally occurring phenomenon, provides for the formation of intermolecular triplexes and offers a unique opportunity for targeting HIV-1 proviral sequences by miRNAs. This has the potential for use in anti-HIV-1 therapy[17]. DNA triple helices are formed by the binding of synthetic oligonucleotides within the major groove of duplex DNA, where they make specific hydrogen bond interactions with groups on the exposed faces of the purine bases. Based on these reports and several experimental data that $C^+$·GC and T·AT triplets motifs favor TF, a java-based tool was developed that can predict the third strand sequence, representing miRNA, that can form the stable triplex with duplex DNA sequences[16,17] representing HIV-1 provirus. The tool was utilized to determine if any of the 50 miRNAs that exhibited >80% homologies to HIV-1 and the other beneficial co-infecting viruses sequences could be candidate for TF[31].

As shown in Table 4, 11/50 sequences made good candidates for TF on the basis of the algorithm that looks for $C^+$·GC+T·AT triplet motifs and multiple alignment with more than one co-infecting viruses[2-6,31]. Triplex Stability Index or TSI is shown for all 50 miRNAs (highlighted in dark for $C^+$·GC and light for T·AT in Table 4). According to this data, 12 miRNAs were determined to be good candidates since they exhibited ~40% TSI. In addition to the TSI, consideration was given to the length of the homologous pairing (RNAi silencing requires at least 19 base pairs) and to the mutual homologies to the three co-infecting viruses (Table 1). Therefore, twelve candidate miRNAs were selected and listed in Table 1. Eleven miRNAs exhibited strong TF capability (35-52% TSI as shown in Table 1) but also showed significant homologies to one or more of the three co-infecting viruses (62-84%), the 12$^{th}$ one (hsa-miR-659) showed homologies to laboratory strains of HIV-1 only (pNL4.3, 42% TSI).

In order to measure the stabilities of the miRNA, four sets of representative sequences for TF were utilized, oligonucleotides were synthesized that represented four of ten miRNAs (FIG. 1) and dsDNA HIV-1 proviral sequences. In order to avoid any potential problems with misannealing, intramolecular duplexes were used in which the two strands were connected by a single hexaethylene glycol moiety (H). The intramolecular duplexes and their respective third strand oligonucleotides are shown in FIG. 1. This arrangement of fluorophore and quencher allowed us to increase the amount of the third strand without affecting the total fluorescence signal. The 20 mer sequences were chosen so as to generate triplexes with different arrangements of $C^+ \cdot GC$ and $T \cdot AT$ triplets and are based around repeats of $(CCT)_n$, $(CT)_n$, $(CTT)_n$ and $T_n$ as described previously[22-23].

Fluorescence melting profiles were determined using an MJ Research Chromo4 Real Time thermocycler with minor modifications[23]. The logic of this experiment is such that when a triplex is formed, the fluorophore and quencher are in close proximity and the fluorescence is quenched. Upon heating the triplex complex denatures, the fluorophore and quencher are separated and there is a large increase in fluorescence that is recorded by the scanning imaging system. Triplexes were prepared in 50 mmol $L^{-1}$ sodium acetate pH 5.0 containing 150 mmol $L^{-1}$ NaCl. Each sample (20 µl) contained 0.25 µmol $L^{-1}$ duplex DNA and 0.25 µmol $L^{-1}$ triplex-forming oligonucleotide, as described previously[23]. The complexes were denatured by heating to 95° C. at a rate of 0.1° C. $s^{-1}$ and maintained at this temperature for 5 min before cooling to 20° C. at 0.1° C. $s^{-1}$. Samples were then held at 20° C. for 10 min before melting again by heating to 95° C. at 0.1° C. $s^{-1}$. The fluorescence was recorded during both melting and annealing phases. The thermocycler excited the samples at 495 nm and measured the emission at 520 nm. Since this technique measures the changes in fluorescence that accompany the denaturation process of the fluorophore and quencher, the signal was most strongly affected by opening of the terminal Hoogsteen pairs rather than dissociation of the entire third strand. The FITC-labeled duplex strands were used as standards in each experimental variable. As shown in FIG. 2, under these conditions all four miRNAs formed stable TF and exhibited $T_m$ values of 82° C., 77° C., 62° C., and 53° C., respectively.

After establishing TF stabilities of four out of ten representative miRNAs, the potential anti-HIV-1 activities of all ten TF miRNAs in HeLa-CD4+ cell lines were tested. Twelve pSUPER-derived vectors (pSuper.neo.gfp[24,28]) designed to drive expression of each of the miRNAs sequences constructed hairpin (hp) sequences that upon transcription expressed specific miRNAs shown in Table 1. pSuper hairpin constructs were generated by annealing together DNA primers encoding the entire hairpin and ligating the double-stranded fragments directly into BglIll-HindIll-digested pSUPER. Twelve different shmiRNA constructs as shown in Table 1 were generated. The recombinant pSuper vectors were confirmed by restriction enzyme digestion by BglIll-HindIll. The correct samples were sequenced on ABI PRISM 3031 sequencer.

Figure 3:
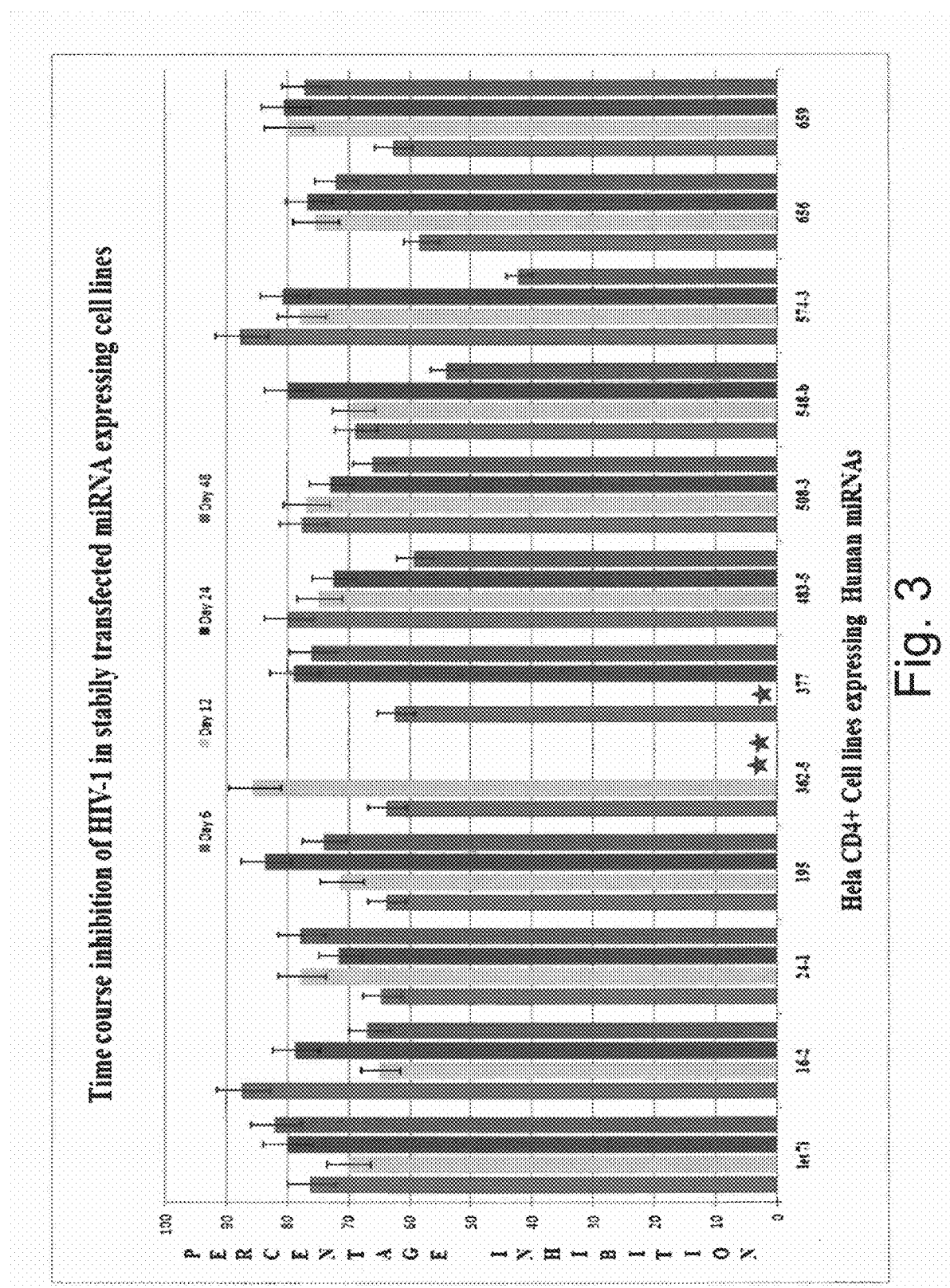
FIG. 3 shows inhibition of HIV-1 over time in stably transfected miRNA expressing cell lines.
Figure 4:
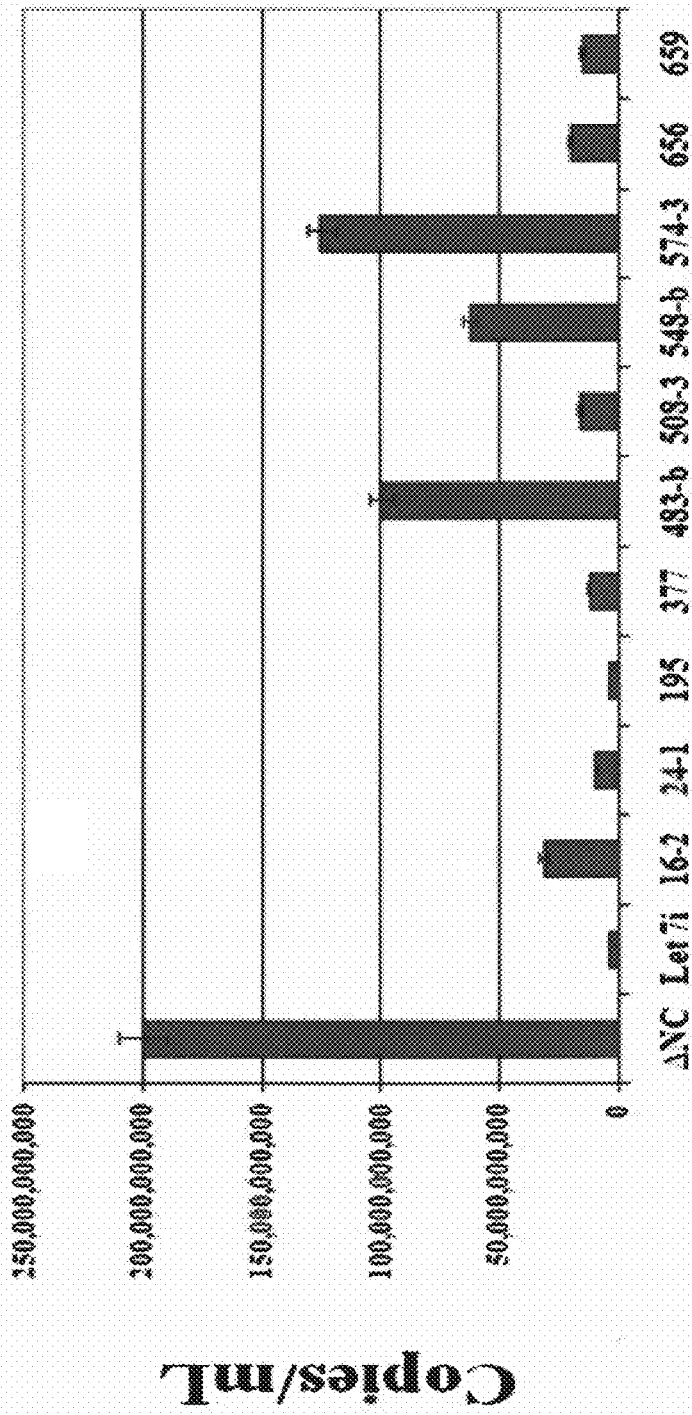
FIG. 4 shows the effects of HIV-1 homologous miRNA on viral replication.
Figure 5:
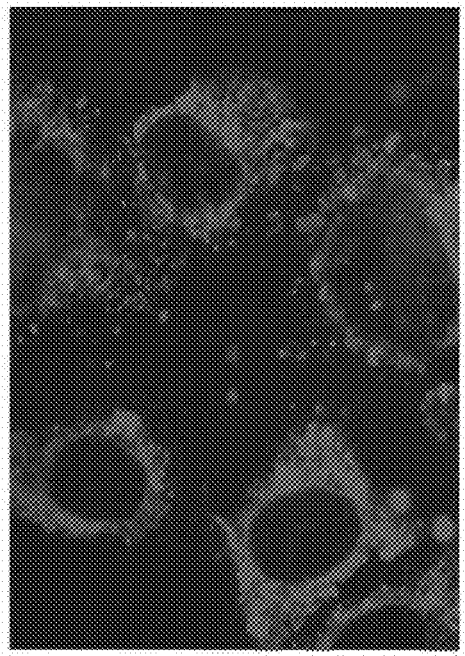
FIGS. 5A-5D show photos of stably transfected HeLa-CD4+ cell lines exhibiting triplex formations.
Figure 5:
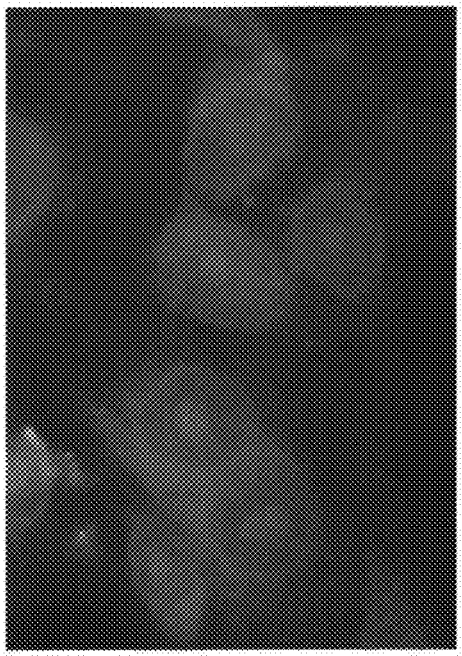
Figure 5:
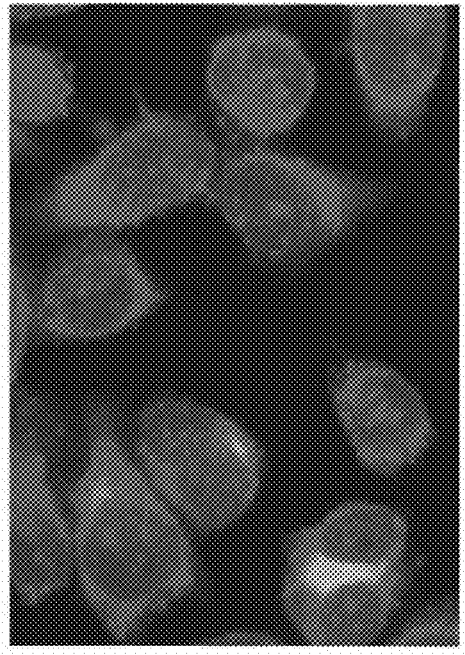
Figure 5:
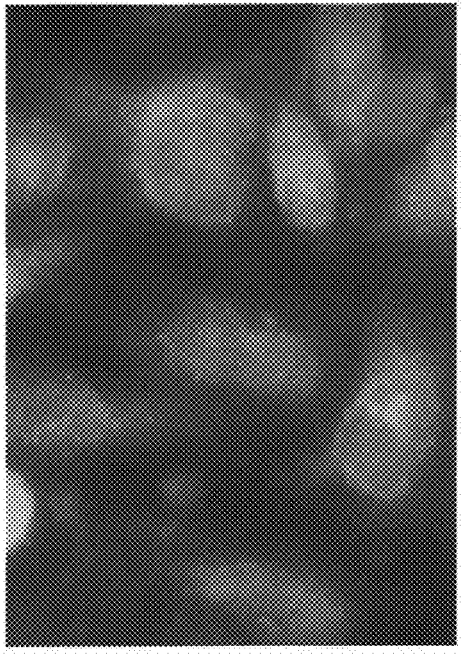

In order to determine the anti-HIV-1 activities of the vectors in vitro, stably transfected HeLa-CD4+ cell lines (NIH AIDS Research & Reagent Program; Cat #1022) were generated in selection media as described previously[25-26]. After four weeks of selection the resistant populations were characterized by observing under UV-Fluorescent microscope for green fluorescent cells (gfp) as well as PCR analyses (data not shown). As controls, nontransfected cells and cells transfected with the same plasmid backbone but without miRNA sequence was used (designated ΔNC: 30). The protective effects of each of the miRNAs and the backbone vector were evaluated by infecting each of the cell lines. Untransfected Hela-C4+ cell lines were used as controls. All cell lines were infected separately with HIV-1 NL-4-3 at a multiplicity of infection of 0.1 of cell-free viral stocks using the pNL4-3 isolates or cell lines were mock infected and then harvested 6, 12, 24, 48 days post-infection[25-26]. Filtered supernatants were used for HIV-1 p24 ELISA. Total RNA was harvested with TRIzol for the Real Time PCR for singly-spiced HIV-1 RNA[25-26]. As shown in FIG. 3 upon infection all cell lines expressing human miRNAs showed significant resistant to HIV-1 (p>0.001) and infection was reduced from ~60% to >80% in cell lines stably expressing miRNAs six days post infection. There were variations in the degree of inhibitions between days of harvests post infection, however, it was >60% in most cases except in miRNA-548-b and miRNA-574-3 where it was 53% and 42%, respectively on day 48 post infection. The p24 ELISA data were further confirmed by measuring the singly-spliced HIV-1 mRNA (FIG. 4).

In order to further determine if the observed HIV-1 inhibition is due to triplex formation (TF), two mAbs were utilized that can recognized TFs[27-28]. In all cases stably transfected HeLa-CD4+ cell lines exhibited clear evidence of TFs. Representative photographs are shown in FIGS. 5A-5D.

Methods:

Human microRNAs mature sequences were downloaded from the human mi RBase Sequences database (http://microrna.sanger.ac.uk/sequences/: (as of 28 Jan. 2008:20). Before analyses all the U of miRNAs were converted to T. For querying potential targets in the HIV-1, HHV-6A, HHV-6B, and GBV-C genomes we downloaded the full coding sequences of all four viruses (HIV-1 strains accession#s:NC_001722 and AF033819; HHV-6 accession # s: NC_001664 and NC_000898, HHV-7 accession # NC_001716 and GBV-C accession #NC_001710). The RefSeq validated reference sequences (http://ncbi.nlm.nih.gov) and the six representative strain sequences as identified by the International Committee on Taxonomy of Viruses (ICTV) (http://www.ncbi.nlm.nih.gov/ICTVdb/Ictv/fs_retro.htm) were utilized. Three well-established web links where used (http://microrna.sanger.ac.uk/, http://hiv-web.lanl.gov/content/hiv-db/mainpage.html, and http://www.ebi.ac.uk/) to predict homology for the 733 Homo sapiens microRNAs obtained from the miRBase Sequences, microRNA Registry. Sequence homologies of 733 Homo sapiens miRNAs versus HHV-6, -7 and GBV-C target genomes was explored using the local sequence alignment algorithms offered on the following well-established web sites: http://microrna.sanger.ac.uk/, http://hiv-web.lanl.gov/content/hiv-db/mainpage.html, and http://www.ebi.ac.uk/.

Oligodeoxyribonucleotides (Odn):

HPLC purified Odn were purchased from Sigma Genosys (The Woodlands, Tex., US). Fluorophore (flourescein isothiocyanate: FITC) was incorporated at 5'-end of the duplex DNA using FITC-cap-dU and the black-hole quencher-1 (BHQ-1) was attached at the 5' end of the third strand oligonucleotide as previously described[22-23]. In order to avoid any potential problems with misannealing, intramolecular duplexes were used in which the two strands were connected by a single hexaethylene glycol moiety (H) (FIG. 1). This arrangement of fluorophore and quencher allowed us to increase the amount of third strand without affecting the total fluorescence signal. The 20 mer sequences were chosen so as to generate triplexes with different arrangements of $C^+ \cdot GC$ and $T \cdot AT$ triplets and are based around repeats of $(CCT)_n$, $(CT)_n$, $(CTT)_n$ and $T_n$ as described previously[22-23].

Fluorescence Melting Curves of Intermolecular Triplexes:

Fluorescence melting profiles were determined using an MJ Research Chromo4 Real Time Thermocycler with minor modifications as set forth above and previously described[23]. The fluorescence was recorded during both melting and annealing phases. The thermocycler excited the samples at 495 nm and measured the emission at 520 nm. Since this technique measures the changes in fluorescence that accompany Denaturation process of the fluorophore and quencher, the signal was most strongly affected by opening of the terminal Hoogsteen pairs rather than dissociation of the entire third strand. However, simple separation of the termini leaves the fluorescent groups in close proximity, and dissociation of the entire third strand is a highly cooperative process. With this basic assumption, the fluorescence profiles provided a good approximation for the dissociation of the third strand. $T_m$ values were determined from the first derivatives of the melting profiles using the MJR Chrmo4 software and were reproducible to within 0.2° C. Unless otherwise stated, the $T_m$ values quoted refer to the second melting transition. The FITC-labelled duplex strands were used as standards in each experimental variable.

Designing and Construction of miRNA Expression Vector:

pSUPER-derived vectors (pSuper.gfp.neo[24,30]) designed to drive expression of each of the twelve miRNAs sequences in Table 1. The miRNA against HIV-1 was selected using the software available from OligoEngine. These sequences were arranged in the 64 base pair oligonucleotide in the form: BgIII site/19 bp Sense Strand/9 bp Stuffer/19 bp Antisense strand/Stuffer. A sequence exactly complementary to the 64 bp sequence was also obtained which had Hind Ill site at its terminal end. These two oligonucleotides were annealed to form a duplex oligonucleotide carrying BgIII and HindIII sites at their terminal sites for cloning into the pSuper Retro vector. The annealed oligonucleotide was cloned into the BgIII/HindIII sites of pSuper retro vector. Positive clones were confirmed by sequencing on ABI PRISM 3031 sequencer as well as by restriction enzyme digestion by BgIII-HindIII. Thirteen different shmiRNA constructs were generated, 12 expressed respective duplex miRNA and one was used as control that contained empty vector without miRNA (Table 1). Each oligonucleotide is placed downstream of H1 promoter's TATA box and it generates a duplex miRNA which is predicted to form a stem-loop precursor transcript which is then cleaved in the cell to produce a functional mature 20-21 bp miRNA.

Intracellular Expression of shmiRNAs:

HeLa-C4+ cell line (NIH AIDS Research & Reagent Program; Cat #1022) were used to develop stably transfection cell lines. The cells were cultured in RPMI-1640 supplemented with 10% fetal calf serum and penicillin-streptomycin (100units/ml). The transfection were carried out when cells were ~70% confluent at $1.10^6$ cells per 25 mL flask. Cells were transfected with each of the pSuper vectors, separately, by use of lipofectamine (Invitrogen) with a total of 50 ng of DNA per flask in serum-free RPMI-1640. 48 hours post-transfection, the medium was changed to neomycin-containing medium (100 units/ml) for selection. After 4 weeks in selection, resistant cell populations and clones were characterized. As controls, non-transfected cells and cells transfected with the same vector backbone but without the 64 bp miRNA hp was utilized (designated as C).

HIV-1 Infection Experiments:

Initial studies were conducted using the HIV-1 strain pNL4-3. Viral stock was prepared as described previously[25-26]. Infections of the HeLa-CD4+ lines with HIV-1 were performed by incubating equivalent of 1,000 ng of cell-free viral stocks with the various cell lines for 12 hrs at 37° C. After incubation the cell were washed 6 time with serum free medium to remove extracellular virions and then cells were cultures in complete medium for 5-days and supernatants were analyzed for the amount of HIV-1 p24 by ELISA assay. Cells were harvested at the same time and after multiple washes by centrifugations, cell pallets were used for total RNA isolated.

Indirect Immunofluorescence:

HeLa-CD4 cells were examined for triplex formation (TF) by utilizing two murine monoclonal antibodies (mAbs), Jel 318 and Jel 466[27]. mAbs were mixed in equal volume, at 2 µg/mL. These anti-triplex mAbs can recognize triplexes between any combinations of DNAs and RNAs, but more strongly between dsDNA and ssRNA[27-28]. A fluorescent conjugated secondary antibody for mouse antibody was used for staining triplexes[25].

Quantitative Real Time PCR:

Total RNA was extracted using Qiagen RNeasy Total RNA isolation kit with DNase I treatment to ensure complete removal of residual DNA. RNA was quantified in the Nano-Drop 1000 Spectrophotometer (3.1.0 software, NanoDrop Technologies Inc. IScript cDNA synthesis kit (Biorad) was used to perform the reverse transcriptase reaction, 100 ng of total RNA was used in the cDNA synthesis reaction. QRT-PCR was performed using SYBR®GREEN PCR Master Mix and a Chromo4™ System (Bio-Rad Laboratories, Hercules, Calif.). Each PCR reaction consisted of 5.0 µL of 5.0 ng of cDNA, 1.0 µL of 200 nM each of the respective primers (forward and reverse primers: 12.5 µL of SYBR®GREEN and 5.5 µL of nuclease free water. The following primers were used, Forward: 5'-CTCTCGACGCAGGACTCGGC-3' (SEQ ID NO: 1), Reverse, 5'-CCTTCCCCCTGGCCTTAACCG-3'[29] (SEQ ID NO: 2). 1:10 dilution of the cDNA synthesis reaction was used in the real time PCR for mRNA expression analysis. The following program: Amplification was carried out as follows: one cycle of 10 min at 95° C. (hot-start PCR) followed by 40 cycles in three steps each (95° C. for 15 sec, 60° C. for 1 minute, 72° C. for 45 sec) and one cycle of 10 min at 72° C. Melting temperature analysis was performed by slow increase in temperature (0.2° C./2 sec) from 45° C.-95° C. Standard curves for unspliced was performed using serial dilutions derived from DNA of pNL4-3 (80, 40, 20, 10, 5.0, 2.5, 1.25, 0.625, 0.3125 and 0.156 ng/µL). All samples were assayed in triplicates.

Data Analysis:

The significance of differences in relative gene expression numbers $C_t(C_{t((Cyclo)}-C_{t(target\ gene)})$ measured by real time quantitative PCR was calculated using a two-tailed Student's t test. Probability values less than 0.05 were considered significant[27].

Accordingly, a new method has been devised that mimics processes in co-infected individuals which explain the apparent beneficial effects. Evaluation of the regulatory effects of miRNAs on viral replication by analyzing the mutually homologous miRNAs-first by gene alignment tool and then by evaluating their effect in vitro by stably transfected cell lines, results in highly effective anti-HIV-1 miRNA based therapies.

All publications, patent applications, patents and other references mentioned herein are incorporated by reference in their entirety.

While a preferred embodiment of the invention has been described using specific terms, such description is for illustrative purposes only, and it is to be understood that changes and variations may be made without departing from the spirit or scope of the following claims. Through routine experimentation, one skilled in the art will readily recognize that various changes and modifications can be made therein without departing from the spirit and scope of the invention. Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

REFERENCES

1. Karp, C L, Auwaerter, P. G. Coinfection with HIV and tropical infectious diseases. II. Helminthic, fungal, bacterial and viral pathogens. Clin Infect Dis. 2007; 45:1214-20.

2. Lisco, A. Grivel J C, Biancotto A, et al. Viral interactions in human lymphoid tissue: Human herpesvirus 7 suppresses the replication of CCR5-tropic human immunodeficiency virus type 1 via CD4 modulation. J Virol. 2007; 81:708-17
3. Frenkel, N, Schirmer E C, Wyatt L S et al. Isolation of a new herpesvirus from human CD4+ T cells. Proc. Natl. Acad. Sci. USA 1990; 87:748-752
4. Lusso P, Secchiero P, Crowley R W, Garzino-Demo A, Berneman Z N, Gallo R C. CD4 is a critical component of the receptor for human herpesvirus 7: Interference with human immunodeficiency virus. Proc. Natl. Acad. Sci. USA 1994; 91:3872-3876.
5. Glushakova, S., Baibakov, B., Margolis, L. B. & Zimmerberg, J. Infection of human tonsil histocultures: a model for HIV pathogenesis. Nat. Med. 1995; 1:1320-1322.
6. Gimenez-Barcons M, Ribera M, Llano A, Clotet B, Este J A, Martinez M A. et al. Analysis of chemokine and cytokine expression in patients with HIV and GB virus type C coinfection. Clin Infect Dis. 2005; 40:1342-9.
7. Xiang J, Wünschmann S, Diekema D J, Klinzman D, Patrick K D, George S L, Stapleton J T. Effect of coinfection with GB virus C on survival among patients with HIV infection. N Engl J Med. 2001; 345:707-14.
8. Ryt-Hansen, R., Katzenstein, T. L., Gerstoft, J. & Eugen-Olsen, J. No influence of GB virus C on disease progression in a Danish cohort of HIV-infected men. AIDS Res Hum Retroviruses. 2006; 22:496-8.
9. Vignoli, M., Furlini, G., Re, M. C., Ramazzotti, E. & La Placa, M. Modulation of CD4, CXCR-4 and CCR-5 makes human hematopoietic progenitor cell lines infected with human herpesvirus-6 susceptible to human immunodeficiency virus type 1. J Hematother Stem Cell Res. 2000; 9:39-45.
10. Taylor, J. M. Hepatitis delta virus. Virology. 2006; 344: 71-6.
11. Matzke, M. A., Mette, M. F. & Matzke, A. J. Transgene silencing by the host genome defense: Implications for the evolution of epigenetic control mechanisms in plants and vertebrates. Plant Mol Biol. 2000; 43:401-15.
12. Jose, A. M, & Hunter, C. P. Transport of Sequence-Specific RNA Interference Information Between Cells. Annual Review of Genetics 2007; 41:305-330.
13. Kidwell, M. G. & Lisch, D. R. Perspective: transposable elements, parasitic DNA and genome evolution. Evolution Int J Org Evolution 2001; 55:1-24.
14. Taganov, K. D., Boldin, M. P. & Baltimore, D. MicroRNAs and immunity: Tiny players in a big field. Immunity 2007; 2:133-7
15. Bartel, D. P. MicroRNAs: genomics, biogenesis, mechanism, and function. Cell. 2004; 116:281-297
16. Bagasra, O, Stir A E, Pirisi-Creek L, Creek K E, Bagasra Au, and Lee J. Role of miRNAs in regulation of lentiviral latency and persistence. Applied Immunochem and Molecular Morphology 2006; 14:166-90.
17. Bagasra, O. A unified concept of HIV-1 Latency. Expert Opin Biol Ther 2006; 6:1135-1149.
18. Hakim S T, Alsayari M, McLean D C et al. A large number of the primate MicroRNAs target lentiviruses, RE and endogenous retroviruses. BBRC 2008; 369:357-362.
19. Lecellier C H, Dunoyer P, Arar K et al. A cellular microRNA mediates antiviral defense in human cells. Science 2005; 308:557-560
20. Cullen, B. R. Viruses and microRNAs. Nat. Genet. 38, pp. 2006; S25-S30
21. Griffiths-Jones S, Saini H K, van Dongen S, Enright A J Nucleic Acids Res 2008; 236 (Database Issue):D154-D158
22. Roberts, R. W. & Crothers, D. M. Prediction of the stability of DNA triplexes. Proc Natl Acad Sci USA 1996; 93:4320-5
23. James, P. L., Brown, T. & Fox, K. R. Thermodynamic and kinetic stability of intermolecular triple helices containing different proportions of C+*GC and T*AT triplets. Nucleic Acids Res. 2003; 3:5598-606
24. Martianov I, Ramadass A, Serra Barros A, Chow N, Akoulitchev A. Repression of the human dihydrofolate reductase gene by a non-coding interfering transcript Nature 2007; 445:666-670.
25. Shaheen F, Duan L, Zhu M, Bagasra O, Pomerantz R J. Targeting of HIV-1 Reverse Transcriptase by Intracellular Expression of Single-Chain Variable Fragments (SFv) to Inhibit Early Stage of HIV-1 Replication. J. Virology 1996; 170:3392-4300.
26. Bagasra, O., K. Khalili, Seshamma, T., Taylor, J. P. & Pomerantz, R. J. Tar-Independent Replication of HIV-1 in Glial Cells. J Virology 1992; 66:7522-7528.
27. Agazie Y M, Burkholder G D, Lee J S. Triplex DNA in the nucleus: direct binding of triplex specific antibodies and their effect on transcription, replication and cell growth. Biochem J. 1996; 316: 461-466.
28. Raghavan S C, Chastain P, Lee J S, Hegde B G, Houston S, Langen R, Hsieh C L, Haworth I S, Lieber M R. Evidence for a triplex DNA conformation at the bcl-2 major breakpoint region of the t(14; 18) translocation. J Biol Chem. 2005; 280:22749-60.
29. Seshamma, T., Bagasra, O., Trono, D., Baltimore, D., Pomerantz, R. J. Blocked Early-Stage Latency in the Peripheral Blood Cells of Certain HIV-1-Infected Individuals. Proc Natl Acad Sci USA 1992; 89:10663-10667.
30. Krom Y D, Fallaux F J, Que I, Lowik C, van Dijk K W. Efficient in vivo knock-down of estrogen receptor alpha: Application of recombinant adenovirus vectors for delivery of short hairpin RNA. BMC Biotechnol. 2006; 6:11
31. Mahalingam K., O Bagasra. Bioinformatics Tools: Searching for Markers in DNA/RNA Sequences. Biocomp. Vol II {g 612-615. Proceedings of Computer Science Computer Engineering and Applied Computing" Jul. 14-21 2008.
32. Marmor, M, K. Hertzmark, S. M. Thomas, P. N. Halkitis, and M. Vogler. Resistance to HIV Infection. J Urban Health. 2006; 83(1): 5-17
33. Hattori J, Okumura N, Yamazaki Y, Uchiyama M, Hamaguchi M, Nishiyama Y, Kaneda T. Beneficial effect of GB virus C co-infection in Human Immunodeficiency Virus type 1-infected individuals. Microbiol Immunol. 2007; 51:193-200.
34. Grivel J C, Ito Y, Faga G et al. Suppression of CCR5- but not CXCR4-tropic HIV-1 in lymphoid tissue by human herpesvirus 6. Nat. Med. 2001; 7:1232-1235.
35. Saayman S, Barichievy S, Capovilla A, Morris K V, Arbuthnot P, Weinberg M S. The efficacy of generating three independent anti-HIV-1 siRNAs from a single U6 RNA Pol III-expressed long hairpin RNA. PLoSONE. 2008; 2; 3:e2602.

Tables:

TABLE 1

Human miRNA showing mutual homologies (>80%) with HIV clone pNL 4-3 & co-infecting viruses GBV-C (>70%), HHV-6 (>80%) and HHV-7 (>70%)

| No | Homology | SEQ ID NOS: | Sequence Alignment | | | Proportion & Triplex Stability Index | Common | Target |
|---|---|---|---|---|---|---|---|---|
| 1 | 89.5 | 3<br>4 | EMBOSS_001<br>8508 ACCACACACAAGGCTACTT<br>\|.\|\|\|\|\|\|\|\|\|\|\|\|\|.\|\|\|\|<br>1 ATCACACACAAGGCAACTT<br>hsa-miR-377 | 8526<br><br><br>19 | | 8/19 42% | HHV-6A (94.0)<br>HHV-6B (89.5)<br>HHV-7 (86.7) | pNL (nef)<br>HHV-6A (U34)<br>HHV-6B (U34)<br>HHV-7 (U7) |
| 2 | 85.7 | 5<br>6 | EMBOSS_001<br>1937 CCTATTGAGACTG-TACCAGT<br>\|\|\|\|.\|\|\|\|\|\|\|\|\| \|\|.\|\|\|\|<br>1 CCTACTGAGACTGATATCAGT<br>hsa-miR-24-1* | 1956<br><br><br>21 | | 9/21 42% | HHV-6A (88.9)<br>HHV-6B (80.0)<br>HHV-7 (77.8) | pNL (pol)<br>HHV-6B (U7)<br>HHV-7 (U57) |
| 3 | 86.4 | 7<br>8 | EMBOSS_001<br>7417 CCTTGGAATGCTAGTTG-GAGT<br>\|\|\|\|\|\|\|\|\|\|.\|\|\|\|.\|\| \|\|\|\|<br>1 CCTTGGAATCCTAGGTGTGAGT<br>hsa-miR-362-5 | 7437<br><br><br>22 | | 9/22 40% | GBV-C (77.3)<br>HHV-6A (85.0)<br>HHV-6B (80.0) | pNL (env)<br>HHV-6A (U39) |
| 4 | 80.0 | 9<br>10 | EMBOSS_001<br>2595 AAGAACCTCCATTCCTTTGG<br>\|\|\|\|\|\|\|\|\|\|\|..\|\|.\|\|\|\|.\|<br>1 AAGAACCTCAGTTGCTTTTG<br>hsa-miR-548b- | 2614<br><br><br>20 | | 10/20 50% | GBV-C (73.7)<br>HHV-6B (80.0) | pNL (pol)<br>GBV-C (gp1)<br>HHV-6B (U85) |
| 5 | 91.3 | 11<br>12 | EMBOSS_001<br>6932 CAAATATTACTGGGCTGCTATTA<br>\|.\|\|\|\|\|\|\|\|\|\|\|\|.\|\|\|\|\|\|\|\|\|\|<br>1 CCAATATTACTGTGCTGCTATTA<br>hsa-miR-16-2* | 6954<br><br><br>23 | | 12/23 52% | HHV-7 (76.0) | pNL (tat)<br>HHV-7 (U20) |
| 6 | 82.6 | 13<br>14 | EMBOSS_001<br>401 ATATAATACAATAGCAGTCCTCT<br>\|\|\|\|.\|\|\|\|\|.\|\|\|\|\|\|..\|\|\|\|<br>1 ATATTATACAGTAGCAACCCTCT<br>hsa-miR-656 | 423<br><br><br>23 | | 11/23 47% | GBV-C (77.8)<br>HHV-7 (100)<br>HHV-6B (81.0) | pNL (gag)<br>GBV-C (gp1)<br>HHV-7 (U82) |
| 7 | 85.0 | 15<br>16 | EMBOSS_001<br>8034 GCTCAATGC-CACAGCCATA<br>\|\|\|\|\|\|\|\|\| \|\|\|\|.\|\|\|.\|<br>1 GCTCAATGCACACACCCACA<br>hsa-miR-574-3 | 8052<br><br><br>20 | | 9/20 45% | HHV-7 (70.8) | pNL (env)<br>HHV-7 (U7) |
| 8 | 80.0 | 17<br>18 | EMBOSS_001<br>4679 AGAATGGAGGAAA-AAGAGA<br>\|\|\|..\|\|\|\|\|\|\|\| \|\|\|.\|\|<br>1 AGACGGGAGGAAAGAAGGGA<br>hsa-miR-483-b | 4697<br><br><br>20 | | 0/20 0% | HHV-7 (88.2) | pNL (vif)<br>HHV-7 (U58) |
| 9 | 94.7 | 19<br>20 | EMBOSS_001<br>6397 GATGTAGTAATTAGATCTG<br>\|\|.\|\|\|\|\|\|\|\|\|\|\|\|\|\|\|\|<br>1 GAGGTAGTAATTAGATCTG<br>hsa-let-7i | 6415<br><br><br>19 | | 7/19 36% | GBV-C (70.8)<br>HHV-6A (62.1)<br>HHV-6B (62.1)<br>HHV-7 (84.2) | pNL (tat)<br>HHV-6A (U42) |

TABLE 1-continued

Human miRNA showing mutual homologies (>80%) with HIV clone pNL

TABLE 1A-continued

Human miRNA Showing mutual Homologies (>=80%) with HHV-6A

| No. | Homo-logy | SEQ ID NOS: | Sequence Alignment Result | | | |
|---|---|---|---|---|---|---|
| 10 | 89.5 | 45<br>46 | EMBOSS_001<br>hsa-miR-509-3 | 89496<br>3 | ctgcaga-gtgg-aatcat<br>\|\|\|\|\|\|\|  \|\|\|\|  \|\|\|\|\|\|<br>CTGCAGACGTGGCAATCAT | 89512<br>21 |
| 11 | 80.0 | 47<br>48 | EMBOSS_001<br>hsa-miR-877 | 130704<br>1 | gaagaggagat--agcaggg<br>\|.\|\|\|\|\|\|\|\|\|\|  .\|\|\|\|\|\|<br>GTAGAGGAGATGGCGCAGGG | 130721<br>20 |
| 12 | 84.2 | 49<br>50 | EMBOSS_001<br>hsa-miR-642 | 19796<br>5 | ctctccaaatctgatcctg<br>\|\|\|\|\|\|\|\|\|\|\|.\|\| \|\|.\|\|<br>CTCTCCAAATGTG-TCTTG | 19814<br>22 |
| 13 | 80.0 | 51<br>52 | EMBOSS_001<br>hsa-miR-645 | 128530<br>1 | tctagttctgg-agtgctga<br>\|\|\|\|\| .\|\|\|\| \|.\|\|\|\|\|\|<br>TCTAG-GCTGGTACTGCTGA | 128548<br>19 |
| 14 | 83.3 | 53<br>54 | EMBOSS_001<br>hsa-miR-380 | 37123<br>5 | taatatagtccgtatctt<br>\|\|\|\|\|\|.\|\|\|\|..\|\|\|\|\|<br>TAATATGGTCCACATCTT | 37140<br>22 |
| 15 | 83.3 | 55<br>56 | EMBOSS_001<br>hsa-miR-16 | 113527<br>1 | taacggcaagtaaatatt<br>\|\|.\|.\|\|\|.\|\|\|\|\|\|\|\|\|<br>TAGCAGCACGTAAATATT | 113544<br>18 |
| 16 | 84.2 | 57<br>58 | EMBOSS_001<br>hsa-miR-27b* | 116999<br>1 | agag-ttacctgatttgtg<br>\|\|\|\| \|\|\|.\|\|\|\|\|\|.\|\|\|<br>AGAGCTTAGCTGATTGGTG | 117016<br>19 |
| 17 | 84.2 | 59<br>60 | EMBOSS_001<br>hsa-miR-187 | 110351<br>1 | ttgtgt-ttgttttgcagc<br>\|.\|\|\|\| \|\|\|\| .\|\|\|\|\|\|\|\|<br>TCGTGTCTTGTGTTGCAGC | 110368<br>19 |
| 18 | 82.6 | 61<br>62 | EMBOSS_001<br>hsa-miR-625 | 16443<br>1 | agggtggaaattgtcta-agtcc<br>\|\|\|\|  \|\|\|\|\|.\| \|\|\|\| \|\|\|\|\|<br>AGGG-GGAAAGT-TCTATAGTCC | 16464<br>21 |
| 19 | 81.0 | 63<br>64 | EMBOSS_001<br>hsa-miR-130b* | 1179<br>2 | ctctatctcctgtcgcactcc<br>\|\|\|\|.\|\| \|\|\|\|\|.\|\|\|\|\|.\|<br>CTCTTTC-CCTGTTGCACTAC | 1199<br>21 |
| 20 | 80.0 | 65<br>66 | EMBOSS_001<br>hsa-miR-766 | 151208<br>3 | tccagccccatagtttctgc<br>\|\|\|\|\|\|\|\|\|\|.\|\|..\|.\|\|<br>TCCAGCCCCACAGCCTCAGC | 151227<br>22 |
| 21 | 84.2 | 67<br>68 | EMBOSS_001<br>hsa-miR-550* | 63245<br>4 | cttactccttccggcacgt<br>\|\|\|\|\|\|\|\|.\|\|.\|\|\|\|\|.\|<br>CTTACTCCCTCAGGCACAT | 63263<br>22 |
| 22 | 85.0 | 69<br>70 | EMBOSS_001<br>hsa-miR-204 | 59050<br>3 | ccctttgt-aacctatccct<br>\|\|\|\|\|\|\|\| \|.\|\|\|\|.\|\|\|<br>CCCTTTGTCATCCTATGCCT | 59068<br>22 |
| 23 | 83.3 | 71<br>72 | EMBOSS_001<br>hsa-miR-563 | 67320<br>2 | gattgaca-acatttccc<br>\|.\|\|\|\|\|\| \|\|.\|\|\|\|\|\|<br>GGTTGACATACGTTTCCC | 67336<br>19 |
| 24* | 88.9* | 73<br>74 | EMBOSS_001<br>hsa-miR-377 | 54899<br>1 | atcacacaaaggaaattt<br>\|\|\|\|\|\|\|\|\|\|\|\|.\|\|.\|\|<br>ATCACACAAAGGCAACTT | 54916<br>18 |
| 25 | 80.0 | 75<br>76 | EMBOSS_001<br>hsa-miR-106b* | 103678<br>3 | gcactgttggggtatttggt<br>\|\|\|\|\|\|\|  \|\|\|\|\|.\|\|\|.\|<br>GCACTGT--GGGTACTTGCT | 103697<br>20 |
| 26 | 85.7 | 77<br>78 | EMBOSS_001<br>hsa-miR-923 | 86008<br>2 | tcagcgagagtgaaaagagac<br>\|\|\|\|\|\| \|\|\| \|\|\|\|\|\|\|\|.\|<br>TCAGCG-GAG-GAAAAGAAAC | 86028<br>20 |

TABLE 1A-continued

Human miRNA Showing mutual Homologies (>=80%) with HHV-6A

| No. | Homology | SEQ ID NOS: | Sequence Alignment Result |
|---|---|---|---|
| 27 | 80.0 | 79 80 | EMBOSS_001    91095 agcttgcagagggtgctgat   91114<br>              \|\|\|\| \|\|\|\|\|\|\|\|..\|\|\|\|\|<br>hsa-miR-127-5     5 AGCT--CAGAGGGCTCTGAT      22 |
| 28 | 80.0 | 81 82 | EMBOSS_001   122275 agtcacgaagatggcatagc  122294<br>              \|\|.\|\|.\|\|.\|.\|\|\|\|\|\|\|\|\|\|<br>hsa-miR-31        1 AGGCAAGATGCTGGCATAGC      20 |
| 29 | 81.8 | 83 84 | EMBOSS_001    66216 aaagttgagagacactctggct  66237<br>              \|\|\|\|\|\|..\|\|\|\|\|\|\|\|\|\|.\|.\|\|<br>hsa-miR-148a*     1 AAAGTTCTGAGACACTCCGACT    22 |
| 30 | 82.6 | 85 86 | EMBOSS_001   111599 actctgcagcttttttaacaagtt 111621<br>              \|.\|\|\|\|\|\|    \|\|\|\|\|\|.\|\|\|\|\|\|<br>hsa-miR-544       1 ATTCTGCA--TTTTTAGCAAGTT   21 |
| 31 | 81.0 | 87 88 | EMBOSS_001    14018 atgt--cgtggtccaataact   14036<br>              \|\|\|\|  \|.\|\|\|\|\|\|\|\|.\|\|\|\|\|<br>hsa-miR-379*      2 ATGTAACATGGTCCACTAACT     22 |
| 32* | 80.0* | 89 90 | EMBOSS_001    14917 gcctactgtgct-ctatctg   14935<br>              \|\|\|\|\|\|\|\|.\|\|\| .\|\|\|\|.\|<br>hsa-miR-24-1*     2 GCCTACTGAGCTGATATCAG      21 |
| 33 | 88.9 | 91 92 | EMBOSS_001    76922 ggcagagttttgttagct    76939<br>              \|\|\|\|\|.\|\|.\|\|\|\|\|\|\|\|\|<br>hsa-miR-449a      2 GGCAGTGTATTGTTAGCT        19 |
| 34* | 80.0* | 93 94 | EMBOSS_001     1367 tgccctgtggagactgca--tctgg 1389<br>              \|\|\|\|\|\|\|\|\|  \|\|\|\|  \|\|  \|\|\|\|\|<br>hsa-miR-146b-     1 TGCCCTGTG--GACT-CAGTTCTGG 22 |
| 35 | 80.0 | 95 96 | EMBOSS_001    91670 ccatcatacacgattccctgcctct 91694<br>              \|\|\|\|    \|\|\|\|\|   \|.\|\|\|\|\|\|\|\|\|\|<br>hsa-miR-885-5     2 CCAT--TACAC--TACCCTGCCTCT 22 |
| 36 | 80.0 | 97 98 | EMBOSS_001   148860 tgctgacatagcactttcgg  148879<br>              \|\|\|\|\|\|..\|\|\|\|\|\|\|\|\|\|.\|.\|<br>hsa-miR-93*       3 TGCTGAGCTAGCACTTCCCG      22 |
| 37 | 83.3 | 99 100 | EMBOSS_001     6526 aggcgagggctgcagcgggacccc 6549<br>              \|\|\|\|\| \|\|\|\| \|\|.\|\|\|\|\|\|\|.\|<br>hsa-miR-663       1 AGGCG-GGGC-GCCGCGGGACCGC  22 |
| 38 | 81.0 | 101 102 | EMBOSS_001    45889 tctccatagttgatgtactca   45909<br>              \|.\|\|\|\|\|\|\|.\|\|\|\|\| \|.\|\|\|<br>hsa-miR-587       1 TTTCCATAGGTGATG-AGTCA     20 |
| 49 | 84.2 | 103 104 | EMBOSS_001    72416 tgatgtagaaggttgttta   72434<br>              \|\|\|.\|\|\|\|.\|\|\|\|\|\|.\|\|<br>hsa-let-7e        1 TGAGGTAGGAGGTTGTATA       19 |
| 40 | 85.0 | 105 106 | EMBOSS_001    42527 atacgac--gct-cctttct   42543<br>              \|\|\|\|\|\|\|  \|\|\| \|\|\|\|\|\|\|<br>hsa-let-7d*       3 ATACGACCTGCTGCCTTTCT      22 |
| 41 | 82.6 | 107 108 | EMBOSS_001   105696 tggttta-cgtccctcaca-aca 105716<br>              \|\|\|\|\|\|\| \|\|\|\|\|    \|\|\|\| \|\|\|<br>hsa-miR-299-5     1 TGGTTTACCGTCC--CACATACA   21 |
| 42 | 81.0 | 109 110 | EMBOSS_001    59277 atttaccgacaacagccctgc   59297<br>              \|.\|\|\|\|.\|\|\|\|\|.\|\|\|\|.\|\|\|<br>hsa-miR-600       1 ACTTACAGACAAGAGCCTTGC     21 |
| 43 | 81.0 | 111 112 | EMBOSS_001    11896 tacagttgttaataaccagct   11916<br>              \|\|\|\|\|\|\|\|\|  .\|\|\|\|\|\|\|.\|<br>hsa-miR-582-5     2 TACAGTTGTT--CAACCAGTT     20 |

TABLE 1A-continued

Human miRNA Showing mutual Homologies (>=80%) with HHV-6A

| No. | Homology | SEQ ID NOS: | Sequence Alignment Result |
|---|---|---|---|
| 44 | 87.0 | 113 114 | EMBOSS_001    106312 caatgcaatgatattggtcaatg 106334<br>               ‖.‖‖‖‖‖‖‖‖‖‖‖ ‖‖‖‖‖.‖<br>hsa-miR-301b        1 CAGTGCAATGATATT-GTCAAAG     22 |
| 45 | 89.5 | 115 116 | EMBOSS_001     76921 aggcagagttttgttagct 76939<br>               ‖‖‖‖‖.‖‖.‖‖‖‖‖‖‖‖‖<br>hsa-miR-449b        1 AGGCAGTGTATTGTTAGCT     19 |
| 46 | 83.3 | 117 118 | EMBOSS_001     47701 tgtgaaacacttccatga 47718<br>               ‖‖.‖.‖‖‖.‖‖‖‖‖‖‖‖‖<br>hsa-miR-491-5       3 TGGGGAACCCTTCCATGA     20 |
| 47 | 81.0 | 119 120 | EMBOSS_001    150984 acggacgcgaagcgcgtgcag 151004<br>               ‖.‖‖‖‖.‖‖.‖‖‖ ‖‖‖‖‖‖<br>hsa-miR-92b*        1 AGGGACGGGACGCG-GTGCAG     20 |
| 48 | 81.8 | 121 122 | EMBOSS_001     68710 cagaaaccaccgtttcgttttc 68731<br>               ‖‖.‖‖‖‖‖‖‖.‖‖‖‖.‖‖‖.‖<br>hsa-miR-548d-       1 CAAAAACCACAGTTTCTTTTGC     22 |
| 49 | 81.8 | 123 124 | EMBOSS_001     98083 gagattttcaaaaatgtgcag 98104<br>               ‖‖‖.‖‖.‖‖‖‖.‖‖‖.‖‖‖‖‖<br>hsa-miR-590-5       1 GAGCTTATTCATAAAAGTGCAG     22 |
| 50 | 83.3 | 125 126 | EMBOSS_001     13663 cgccagagcggtgcactt 13680<br>               ‖.‖‖‖‖‖.‖.‖‖‖‖‖‖‖‖<br>hsa-miR-525-5       1 CTCCAGAGGGATGCACTT     18 |
| 51 | 84.2 | 127 128 | EMBOSS_001    145189 aataaaactgtggggccac 145207<br>               ‖.‖.‖‖‖‖‖‖‖‖‖‖.‖‖‖<br>hsa-miR-371-5       1 ACTCAAACTGTGGGGCAC     19 |
| 52 | 89.5 | 129 130 | EMBOSS_001     95153 gaggtgcttcgattttagg 95171<br>               ‖‖.‖‖‖‖‖‖‖‖‖‖.‖‖<br>hsa-miR-373         1 GAAGTGCTTCGATTTTGGG     19 |
| 53 | 80.0 | 131 132 | EMBOSS_001     17779 cagttttccacaaaaccct 17798<br>               ‖‖‖‖‖‖‖‖.‖‖‖..‖‖.‖‖‖‖<br>hsa-miR-145         4 CAGTTTTCCCAGGAATCCCT     23 |
| 54* | 80.0* | 133 134 | EMBOSS_001     72330 aatccatgaaacttaggttt 72349<br>               ‖‖‖‖‖.‖‖.‖‖‖.‖‖‖‖‖.‖<br>hsa-miR-362-5       1 AATCCTTGGAACCTAGGTGT     20 |
| 55 | 85.0 | 135 136 | EMBOSS_001    139247 gaatgtta--aagtatgtat 139264<br>               ‖‖‖‖‖‖.‖ ‖‖‖‖‖‖‖‖‖‖<br>hsa-miR-1           3 GAATGTAAAGAAGTATGTAT     22 |
| 56 | 83.3 | 137 138 | EMBOSS_001    121294 tgtgttcgctagctcatt 121311<br>               ‖‖‖‖‖‖‖‖.‖‖‖‖.‖‖‖.‖<br>hsa-miR-581         4 TGTGTTCTCTAGATCAGT     21 |
| 57 | 82.6 | 139 140 | EMBOSS_001    115986 tgttgtagaagattgtataagtt 116008<br>               ‖‖..‖‖‖‖.‖‖‖‖‖‖‖‖‖ ‖‖‖‖<br>hsa-let-7f          1 TGAGGTAGTAGATTGTAT-AGTT     22 |
| 58 | 81.8 | 141 142 | EMBOSS_001      6153 gtgtgcgg--atgttttctgct 6172<br>               ‖‖‖‖‖‖‖‖   ‖‖‖ .‖‖‖‖‖‖‖<br>hsa-miR-147b        1 GTGTGCGGAAATG-CTTCTGCT     22 |
| 59 | 84.2 | 143 144 | EMBOSS_001    132685 atttagtgagcatgatatt 132703<br>               ‖‖‖‖‖‖‖‖.‖...‖‖‖‖‖‖<br>hsa-miR-32*         3 ATTTAGTGTGTGTGATATT     21 |
| 60 | 82.6 | 145 146 | EMBOSS_001    137846 aattgtcttccatgttagactgt 137868<br>               ‖‖.‖‖ ‖‖‖‖‖‖‖‖‖‖.‖.‖‖‖<br>hsa-miR-302d        2 AAGTG-CTTCCATGTTTGAGTGT     23 |

TABLE 1A-continued

Human miRNA Showing mutual Homologies (>=80%) with HHV-6A

| No. | Homology | SEQ ID NOS: | Sequence Alignment Result | | | |
|---|---|---|---|---|---|---|
| 61 | 83.3 | 147 148 | EMBOSS_001<br>hsa-miR-296-5 | 4430<br>2 | gggcccgccctc-gtcct<br>\|\|\|\|\|\|.\|\|\|\|\| .\|\|\|\|<br>GGGCCCCCCCTCAATCCT | 4446<br>19 |
| 62 | 88.9 | 149 150 | EMBOSS_001<br>hsa-miR-590-3 | 73203<br>1 | tattttatgtaaaagct<br>\|\|.\|\|\|\|\|\|\|\|\|.\|\|\|\|\|<br>TAATTTTATGTATAAGCT | 73220<br>18 |
| 63 | 81.0 | 151 152 | EMBOSS_001<br>hsa-miR-591 | 81989<br>1 | agaccaagcggttgtcattt<br>\|\|\|\|\|\|.\| \|\|\|\|.\|\|\|\|\|.\|<br>AGACCATG-GGTTCTCATTGT | 82009<br>20 |
| 64 | 85.0 | 153 154 | EMBOSS_001<br>hsa-miR-34c-3 | 46431<br>2 | atcactta-gacacggccag<br>\|\|\|\|\|\|.\| .\|\|\|\|\|\|\|\|\|<br>ATCACTAACCACACGGCCAG | 46449<br>21 |
| 65 | 80.0 | 155 156 | EMBOSS_001<br>hsa-miR-767-3 | 75535<br>3 | tgatcatctcccatggttcc<br>\|\|.\|\|\|..\|\|\|\|\|\|\|\|\|.\|<br>TGCTCATACCCCATGGTTTC | 75554<br>22 |
| 66 | 81.0 | 157 158 | EMBOSS_001<br>hsa-miR-936 | 2291<br>1 | acaggagagcgagg--tcgca<br>\|\|\|\|.\|\|\|\|.\|\|\|\| \|\|\|\|\|<br>ACAGTAGAGGGAGGAATCGCA | 2309<br>21 |
| 67 | 81.8 | 159 160 | EMBOSS_001<br>hsa-miR-135a | 82706<br>5 | gcttttattccacttatgaga<br>\|\|\|\|\|\|\|\|\|\| \|\|\|\|.\|\|<br>GCTTTTTATTCC---TATGTGA | 82727<br>23 |
| 68 | 82.6 | 161 162 | EMBOSS_001<br>hsa-miR-605 | 147594<br>1 | taaa-cacatggtg-gttctcct<br>\|\|\|\| \|.\|\|\|\|\|\|\| .\|\|\|\|\|\|\|<br>TAAATCCCATGGTGCCTTCTCCT | 147614<br>23 |
| 69 | 81.0 | 163 164 | EMBOSS_001<br>hsa-miR-185* | 1735<br>1 | agggcggctggcttcccttg<br>\|\|\| \|\|\|\|\|\|\|\|\|.\|\|\|.\|\|<br>AGG--GGCTGGCTTTCCTCTG | 1755<br>19 |
| 70 | 85.0 | 165 166 | EMBOSS_001<br>hsa-miR-125b | 104219<br>4 | ctgagacccctaatttgtta<br>\|\|\|\|\|\| \|\|\|\|\|\|.\|\|\|\|.\|<br>CTGAGA-CCCTAACTTGTGA | 104238<br>22 |
| 71 | 81.8 | 167 168 | EMBOSS_001<br>hsa-miR-214* | 77520<br>1 | tgacggtctgcactt-ctgtgc<br>\|\|.\|.\|\|\|\| \|\|\|\|\| \|\|\|\|\|\|<br>TGCCTGTCTACACTTGCTGTGC | 77540<br>22 |
| 72 | 81.0 | 169 170 | EMBOSS_001<br>hsa-miR-323-5 | 8823<br>3 | gtggtcc---gcgcgtgtcgc<br>\|\|\|\|\|\|\| \|\|\|\|\| \|\|\|\|<br>GTGGTCCGTGGCGCGT-TCGC | 8840<br>22 |
| 73 | 80.0 | 171 172 | EMBOSS_001<br>hsa-miR-220b | 3224<br>1 | ccaccaccg---ctgacagt<br>\|\|\|\|\|\|\|\|\| \|\|\|\|\|\|.\|<br>CCACCACCGTGTCTGACACT | 3240<br>20 |
| 74 | 85.0 | 173 174 | EMBOSS_001<br>hsa-miR-505* | 33369<br>4 | agccagagtagtcttgatgt<br>\|\|\|\|\|\| \|.\|\|\|.\|\|\|\|\|\|\|<br>AGCCAG-GAAGTATTGATGT | 33388<br>22 |
| 75 | 81.0 | 175 176 | EMBOSS_001<br>hsa-miR-200c* | 21424<br>1 | cgtctctaccccgagtgttt<br>\|\|\|\|\| \|\|\|\|\|...\|\|\|\|\|\|\|<br>CGTCT-TACCCAGCAGTGTTT | 21444<br>20 |
| 76 | 84.2 | 177 178 | EMBOSS_001<br>hsa-miR-802 | 50705<br>1 | cagcaacaaaatttcatcc<br>\|\|\|.\|\|\|\|\|\|..\|\|\|\|\|\|\|\|<br>CAGTAACAAAGATTCATCC | 50723<br>19 |
| 77 | 85.0 | 179 180 | EMBOSS_001<br>hsa-miR-21* | 95571<br>3 | ataccagtcgatgtcgctgt<br>\|.\|\|\|\|\|\|\|\|\|\| .\|\|\|\|<br>ACACCAGTCGATG-GGCTGT | 95590<br>21 |

TABLE 1A-continued

Human miRNA Showing mutual Homologies (>=80%) with HHV-6A

| No. | Homology | SEQ ID NOS: | Sequence Alignment Result |
|---|---|---|---|
| 78 | 81.0 | 181 182 | EMBOSS_001    92213 tggcaacgggagacagttttg  92233<br>              \|.\|\|\|.\|\|\|\|\| \|\|\|\|\|\|.\|\|<br>hsa-miR-503       1 TAGCAGCGGGA-ACAGTTCTG     20 |
| 79 | 85.0 | 183 184 | EMBOSS_001    33369 agccagagtagtcttgatgt  33388<br>              \|\|\|\|\|\| \|.\|\|\|.\|\|\|\|\|\|\|\|<br>hsa-miR-505*      4 AGCCAG-GAAGTATTGATGT     22 |
| 80 | 80.0 | 185 186 | EMBOSS_001    66718 cgtacagtgattgatactgc  66737<br>              \|\|\|\|\|\| \|.\|\|\|.\|\|\|\|\|\|\|\|<br>hsa-miR-126       2 CGTACCGTGAGTAATAATGC     21 |
| 81 | 83.3 | 187 188 | EMBOSS_001    57607 ctaataggtttccattaa    57624<br>              \|\|\|.\|\|\|\|\|.\|\|\|\|.\|\|\|<br>hsa-miR-325       2 CTAGTAGGTGTCCAGTAA       19 |
| 82 | 83.3 | 189 190 | EMBOSS_001    74504 cccttagggtattggggt    74521<br>              \|\|\|.\|\|\|\|\|.\|\|\|\|\|.\|\|<br>hsa-miR-324-5     6 CCCCTAGGGCATTGGTGT       23 |
| 83 | 88.9 | 191 192 | EMBOSS_001     1891 tcctgctctcagggctcc     1908<br>              \|\|\|.\|.\|\|\|\|\|\|\|\|\|\|\|\|<br>hsa-miR-671-3     1 TCCGGTTCTCAGGGCTCC       18 |
| 84 | 81.0 | 193 194 | EMBOSS_001     1725 ctgtgcg-gggagggcggctg  1744<br>              \|\|\|\|\|\|\| \|.\|\|..\|\|\|\|\|\|\|<br>hsa-miR-210       1 CTGTGCGTGTGACAGCGGCTG    21 |
| 85 | 85.0 | 195 196 | EMBOSS_001   139297 aggtggaggtttctttggag 139316<br>              \|\|\|\| \|\|\|\| \|\|\|\|\|.\|\|\|\|<br>hsa-miR-125a-     3 AGGT-GAGG-TTCTTGGGAG     20 |
| 86 | 81.8 | 197 198 | EMBOSS_001   102320 aaattgattcccttaggtgggt 102341<br>              \|\|\|.\|\|.\|\|\|.\|\|\|.\|\|\|\|\|\|\|\|<br>hsa-miR-520d-     1 AAAGTGCTTCTCTTTGGTGGGT    22 |
| 87 | 81.0 | 199 200 | EMBOSS_001    11489 ctcgttcttgggccacctcag  11509<br>              \|\|\|\|.\|\|\|..\|\|\|\| \|\|\|\|\|\|<br>hsa-miR-423-3     3 CTCGGTCTGAGGCC-CCTCAG    22 |
| 88* | 82.6* | 201 202 | EMBOSS_001    37494 tcagaaaacgatttactgtgagc  37516<br>              \|\|\|\|.\|\|\|\| \|\|\|\|\|.\|\|\|\|.\|\|<br>hsa-miR-545       1 TCAGCAAAC-ATTTATTGTGTGC   22 |
| 89 | 81.0 | 203 204 | EMBOSS_001   128707 tctaga-tgtagaactttctg 128726<br>              \|\|\|\|\|\| .\|.\|\|.\|\|\|\|\|\|\|\|<br>hsa-miR-520c-     2 TCTAGAGGGAAGCACTTTCTG    22 |
| 90 | 81.0 | 205 206 | EMBOSS_001    79448 gttgggatcggt--cagtgtt  79466<br>              \|\|\|\|\|\|\|\|\|\|\|\|  \|\|.\|\|.\|<br>hsa-miR-92a-1     3 GTTGGGATCGGTTGCAATGCT    23 |
| 91 | 80.0 | 207 208 | EMBOSS_001    71482 ctagtctagattcatccagt   71501<br>              \|\|\|\|\|\|..\|\|.\|\|\|.\|\|\|\|\|<br>hsa-miR-554       2 CTAGTCCTGACTCAGCCAGT     21 |
| 92* | 80.0* | 209 210 | EMBOSS_001   126675 aataaccacatttggttttg 126694<br>              \|\|.\|\|\|\|.\|\|.\|\|\|.\|\|\|\|\|<br>hsa-miR-548b-     2 AAGAACCTCAGTTGCTTTTG     21 |
| 93 | 84.2 | 211 212 | EMBOSS_001    62994 ctccgacatcttttgcatta   63012<br>              \|\|\|\|.\|\|\|\|.\|\|.\|\|\|\|\|\|\|<br>hsa-miR-155*      1 CTCCTACATATTAGCATTA      19 |
| 94 | 85.0 | 213 214 | EMBOSS_001    89539 aacattttctggtatcgatg  89558<br>              \|\|\|\|.\|.\|\|\|\|\|\|\|\|.\|\|\|\|<br>hsa-miR-200a      2 AACACTGTCTGGTAACGATG     21 |

TABLE 1A-continued

Human miRNA Showing mutual Homologies (>=80%) with HHV-6A

| No. | Homology | SEQ ID NOS: | Sequence Alignment Result |
|---|---|---|---|
| 95 | 80.0 | 215<br>216 | EMBOSS_001      82436 acaga--cgattttagagga  82453<br>                       \|\|\|\|\|  \|\|\|\|\|.\|\|\|.\|\|\|<br>hsa-miR-10b*        1 ACAGATTCGATTCTAGGGGA     20 |
| 96 | 84.2 | 217<br>218 | EMBOSS_001      92268 ggaatt-ggggcagaaggc  92285<br>                       \|\|\|.\|\| \|\|\|.\|\|\|\|\|\|\|\|\|<br>hsa-miR-422a        4 GGACTTAGGGTCAGAAGGC     22 |
| 97 | 85.0 | 219<br>220 | EMBOSS_001      30111 tacagtact-cgatagctga 30129<br>                       \|\|\|\|\|\|\|\|\| .\|\|\|.\|\|\|\|<br>hsa-miR-101         1 TACAGTACTGTGATAACTGA    20 |
| 98 | 84.2 | 221<br>222 | EMBOSS_001      88645 tttaatatggcggcagttg  88663<br>                       \|\|\|\|\|.\|\|\|\|.\|\|\|\|.\|\|\|<br>hsa-miR-302d*       3 TTTAACATGGAGGCACTTG     21 |
| 99 | 80.0 | 223<br>224 | EMBOSS_001     122520 atgaagataattatggaaat 122539<br>                       \|\|\|.\|\|\|\|..\|\|\|.\|\|\|\|<br>hsa-miR-620         1 ATGGAGATAGATATAGAAAT    20 |
| 100 | 84.2 | 225<br>226 | EMBOSS_001      72416 tgatgtagaaggttgttta  72434<br>                       \|\|\|.\|\|\|\|.\|\|\|\|\|\|.\|\|<br>hsa-let-7a          1 TGAGGTAGTAGGTTGTATA     19 |
| 101 | 81.8 | 227<br>228 | EMBOSS_001      73429 gatggt-cttcttttagaggc 73449<br>                       \|\|..\|\| \|\|\|\|.\|\|\|\|\|\|\|\|\|<br>hsa-miR-526b*       1 GAAAGTGCTTCCTTTTAGAGGC  22 |
| 102 | 81.0 | 229<br>230 | EMBOSS_001     139104 ttcttcagtag--agacttta 139122<br>                       \|\|\|\|\|\|\|\|\|.\|  \|\| \|\|\|\|\|<br>hsa-miR-22*         3 TTCTTCAGTGGCAAG-CTTTA   22 |
| 103 | 80.0 | 231<br>232 | EMBOSS_001      87214 tgaattcctggacatggtga 87233<br>                       \|\|..\|\|\|\|\|\|\| \|\|\|\|.\|\|\|<br>hsa-miR-23b*        1 TGGGTTCCTGG-CATGCTGA    19 |
| 104 | 81.8 | 233<br>234 | EMBOSS_001     146268 tggatgtgctcct-cagttgtc 146288<br>                       \|\|\|\|\|\| \|\|\|\|\|\| \|\| \|\|\|\|<br>hsa-miR-432*        2 TGGATG-GCTCCTCCA--TGTC  20 |
| 105 | 83.3 | 235<br>236 | EMBOSS_001      74620 gctgacgtattttctgga   74637<br>                       \|\|\|\|\|.\|\|\|\|\|.\|\|.\|\|<br>hsa-miR-628-5       3 GCTGACATATTTACTAGA      20 |
| 106 | 89.5 | 237<br>238 | EMBOSS_001     142386 ccactgacctttaactgta 142404<br>                       \|\|\|\|\|\|\|\|\|.\|\|.\|\|\|\|\|\|<br>hsa-miR-181a-       2 CCACTGACCGTTGACTGTA     20 |
| 107 | 84.2 | 239<br>240 | EMBOSS_001     138716 aaaacg-taccactactga 138733<br>                       \|\|\|.\|\| \|\|\|\|\|.\|\|\|\|\|\|<br>hsa-miR-451         1 AAACCGTTACCATTACTGA     19 |
| 108 | 81.0 | 241<br>242 | EMBOSS_001       7509 aacatacttcctgtccgtgag 7529<br>                       \|\|\|\|\|.\|..\|\|\|\|\|\|.\|\|\|\|<br>hsa-miR-181c        1 AACATTCAACCTGTCGGTGAG   21 |
| 109 | 81.0 | 243<br>244 | EMBOSS_001      20802 cgagcag-tcacagtttcagt 20821<br>                       \|\|\|\|.\|\| \|\|\|\|\|\|\|\|.\| \|\|\|<br>hsa-miR-151-5       2 CGAGGAGCTCACAGTCT-AGT   21 |
| 110 | 82.6 | 245<br>246 | EMBOSS_001       1427 ggagagaacagagctggtcctga 1449<br>                       \|\|\|\|\|\|\|\| \|\| \|\|.\|.\|\|\|\|\|<br>hsa-miR-185         2 GGAGAGAA-AG-GCAGTTCCTGA  22 |
| 111 | 81.0 | 247<br>248 | EMBOSS_001     128707 tctaga-tgtagaactttctg 128726<br>                       \|\|\|\|\|\| .\|.\|\|.\|\|\|\|\|\|\|\|\|<br>hsa-miR-526a        2 TCTAGAGGGAAGCACTTTCTG   22 |

TABLE 1A-continued

Human miRNA Showing mutual Homologies (>=80%) with HHV-6A

| No. | Homology | SEQ ID NOS: | Sequence Alignment Result |
|---|---|---|---|
| 112 | 81.8 | 249 250 | EMBOSS_001    34065 acc-ggcataaaatttagttttt   34085<br>                    ||| ||||||||.|||.|||.|||<br>hsa-miR-221*      1 ACCTGGCATACAATGTAGATTT      22 |
| 113 | 85.7 | 251 252 | EMBOSS_001     2700 tcctcttcctcctcctccccg     2720<br>                     |||||||||..|||||||||.|<br>hsa-miR-877*      1 TCCTCTTCTCCCTCCTCCCAG       21 |
| 114 | 80.0 | 253 254 | EMBOSS_001   123263 tgggtgatggatgtgcactt    123282<br>                     ||||.|.||||||||..||||<br>hsa-miR-30b*      2 TGGGAGGTGGATGTTTACTT        21 |
| 115 | 85.0 | 255 256 | EMBOSS_001    96701 atgagttcattg-aatatca      96719<br>                     |||||.||||||  ||||||.|<br>hsa-miR-556-5     2 ATGAGCTCATTGTAATATGA        21 |
| 116 | 81.0 | 257 258 | EMBOSS_001   149873 ttcatatccatatattttttt   149893<br>                     |||.|||.||||||.||.|||<br>hsa-miR-202*      1 TTCCTATGCATATACTTCTTT       21 |
| 117 | 81.0 | 259 260 | EMBOSS_001     2693 ctcctcctcctcttcctcctc     2713<br>                     |.||.|||||||||  ||||||<br>hsa-miR-1224-     1 CCCCACCTCCTCT--CTCCTC       19 |
| 118 | 80.0 | 261 262 | EMBOSS_001    61000 acagtagtcaccggattggt     61019<br>                     ||||||||..|..||||||<br>hsa-miR-199a-     1 ACAGTAGTCTGCACATTGGT        20 |
| 119 | 85.0 | 263 264 | EMBOSS_001    51041 gacctaggcccgtacctcag     51060<br>                     ||||| |||||..||||||||<br>hsa-miR-631       2 GACCT-GGCCCAGACCTCAG        20 |
| 120 | 83.3 | 265 266 | EMBOSS_001   105414 aacacgaaaactgcttgcg     105431<br>                     ||||.|||||||||.||.|<br>hsa-miR-196a*     5 AACAAGAAACTGCCTGAG         22 |
| 121 | 84.2 | 267 268 | EMBOSS_001    74659 agtttatcagaatgatatt      74677<br>                     ||.|||||||||.||||.||<br>hsa-miR-21        2 AGCTTATCAGACTGATGTT        20 |
| 122 | 81.8 | 269 270 | EMBOSS_001     1887 ctg-ctcctgctctcagggctc     1907<br>                     ||| |||||..|| |||||||||<br>hsa-miR-345       2 CTGACTCCTAGTC-CAGGGCTC      22 |
| 123 | 81.0 | 271 272 | EMBOSS_001   133605 gtagactagtttgattatgtt   133625<br>                     |.||||||||  |||||.||||<br>hsa-miR-7         3 GAAGACTAG--TGATTTTGTT       21 |
| 124 | 85.0 | 273 274 | EMBOSS_001   124054 gcttccatctgttttagcag    124073<br>                     ||||||||  ||||||||||.||<br>hsa-miR-302b      6 GCTTCCA--TGTTTTAGTAG        23 |
| 125 | 80.0 | 275 276 | EMBOSS_001    77701 cgccgcgtcttgccaagtgg     77720<br>                     ||||...||||||||||.||<br>hsa-miR-614       4 CGCCTGTTCTTGCCAGGTGG        23 |
| 126 | 80.0 | 277 278 | EMBOSS_001    61000 acagtagtcaccggattggt     61019<br>                     ||||||||..|..||||||<br>hsa-miR-199b-     1 ACAGTAGTCTGCACATTGGT        20 |
| 127 | 81.8 | 279 280 | EMBOSS_001   132725 gaagttattttcgtggttgatt   132746<br>                     |||||   |.||||||||.||||<br>hsa-miR-382       1 GAAGT--TGTTCGTGGTGGATT      20 |
| 128 | 89.5 | 281 282 | EMBOSS_001    22262 gagtttcgtgatgtcttgc      22280<br>                     ||||.|.||||||||||||<br>hsa-miR-924       2 GAGTCTTGTGATGTCTTGC         20 |

TABLE 1A-continued

Human miRNA Showing mutual Homologies (>=80%) with HHV-6A

| No. | Homo-logy | SEQ ID NOS: | Sequence Alignment Result | | | |
|---|---|---|---|---|---|---|
| 129 | 84.2 | 283 284 | EMBOSS_001<br>hsa-miR-527 | 143602<br>3 | gagtttcgtgatgtcttgc<br>\|\|\|\|.\|.\|\|\|\|\|\|\|\|\|\|\|\|\|\|<br>GAGTCTTGTGATGTCTTGC | 143619<br>21 |
| 130 | 83.3 | 285 286 | EMBOSS_001<br>hsa-miR-485-3 | 11057<br>1 | gtcgtgcacggcactcct<br>\|\|\|.\|.\|\|\|\|\|\|.\|\|\|\|\|<br>GTCATACACGGCTCTCCT | 11074<br>18 |
| 131 | 81.8 | 287 288 | EMBOSS_001<br>hsa-miR-125b- | 112288<br>1 | acgggttagagatttttggaagc<br>\|\|\|\|\|\|\|\|\| \|.\|.\|\|\|\|.\|\|\|<br>ACGGGTTAG-GCTCTTGGGAGC | 112309<br>21 |
| 132 | 80.0 | 289 290 | EMBOSS_001<br>hsa-miR-455-3 | 18487<br>2 | cag-ccatcggcagatccac<br>\|\|\| \|\|\|\|.\|\|\|\|.\|\|.\|\|\|<br>CAGTCCATGGGCATATACAC | 18505<br>21 |
| 133 | 80.0 | 291 292 | EMBOSS_001<br>hsa-miR-300 | 3720<br>2 | atac--gcgccgactctctc<br>\|\|\|\| \|.\|\|.\|\|\|\|\|\|\|\|\|\|<br>ATACAAGGGCAGACTCTCTC | 3737<br>22 |
| 134 | 82.6 | 293 294 | EMBOSS_001<br>hsa-miR-196b | 79410<br>2 | aggtagtgcgtcctggtgttggg<br>\|\|\|\|\|\|\|\| .\|\|\|\|\|.\|\|\|\|\|\|\|<br>AGGTAGT--TTCCTGTTGTTGGG | 79432<br>22 |
| 135 | 81.0 | 295 296 | EMBOSS_001<br>hsa-miR-107 | 152252<br>2 | gtagcattcgacagggctgtc<br>\|.\|\|\|\|\|\|..\|\|\|\|\|\|\|\|\|.\|\|<br>GCAGCATTGTACAGGGCTATC | 152272<br>22 |
| 136 | 82.6 | 297 298 | EMBOSS_001<br>hsa-miR-219-2 | 124044<br>1 | agaattgtaggct-tccatctgt<br>\|\|\|\|\|\|\|\| \|\|\|\| ..\|\|\|\|\|\|\|<br>AGAATTGT-GGCTGGACATCTGT | 124065<br>22 |
| 137 | 85.7 | 299 300 | EMBOSS_001<br>hsa-miR-515-3 | 94864<br>3 | gtggtttcttttggagcagtt<br>\|\|\|..\|\|\|\|\|\|\|\|\|\|\|\| \|\|\|<br>GTGCCTTCTTTTGGAGC-GTT | 94884<br>22 |
| 138 | 81.0 | 301 302 | EMBOSS_001<br>hsa-let-7a* | 36977<br>1 | caatacaacctaccctctttc<br>\|.\|\|\|\|\|\|.\|\|\|\|..\|\|\|\|\|\|<br>CTATACAATCTACTGTCTTTC | 36997<br>21 |
| 139 | 81.0 | 303 304 | EMBOSS_001<br>hsa-miR-302b* | 48153<br>1 | attttaacattgaagt--ttt<br>\|.\|\|\|\|\|\|\|\|.\|\|\|\|\| \|\|\|<br>ACTTTAACATGGAAGTGCTTT | 48171<br>21 |
| 140* | 80.0* | 305 306 | EMBOSS_001<br>hsa-miR-369-3 | 117295<br>2 | ataataactggataatcttt<br>\|\|\|\|\|\|..\|\|\|.\|.\|\|\|\|\|\|<br>ATAATACATGGTTGATCTTT | 117314<br>21 |
| 141 | 80.0 | 307 308 | EMBOSS_001<br>hsa-miR-16-1* | 111324<br>3 | agtctta--tgtgctgccga<br>\|\|\|\|\|\|..\|\|\|.\|.\|\|\|\|\|<br>AGTATTAACTGTGCTGCTGA | 111341<br>22 |
| 142 | 83.3 | 309 310 | EMBOSS_001<br>hsa-miR-372 | 151325<br>2 | aagtgctgcgacattttagagtg<br>\|\|\|\|\|\|..\|\|\|.\|.\|\|\|\|\|\|<br>AAGTGCTGCGACATTT---GAGCG | 151348<br>22 |
| 143 | 81.8 | 311 312 | EMBOSS_001<br>hsa-miR-433 | 127772<br>1 | ataatgat-ggctc--cggtgt<br>\|\|.\|\|\|\|\| \|\|\|\|\| \|\|\|\|\|\|<br>ATCATGATGGGCTCCTCGGTGT | 127790<br>22 |
| 144 | 81.0 | 313 314 | EMBOSS_001<br>hsa-miR-505 | 147594<br>3 | taaacacatggtggttctcct<br>\|.\|\|\|\|\|.\|\|.\|\|\|\|\| \|\|\|\|<br>TCAACACTTGCTGGTT-TCCT | 147614<br>22 |
| 145 | 83.3 | 315 316 | EMBOSS_001<br>hsa-miR-497 | 117069<br>4 | ctgcacactgttgttttt<br>\|.\|\|\|\|\|\|\|\|\|.\|\|\|\|.\|<br>CAGCACACTGTGGTTTGT | 117086<br>21 |

TABLE 1A-continued

Human miRNA Showing mutual Homologies (>=80%) with HHV-6A

| No. | Homology | SEQ ID NOS: | Sequence Alignment Result | | | |
|---|---|---|---|---|---|---|
| 146 | 81.0 | 317 318 | EMBOSS_001<br>hsa-miR-551b | 20411<br>1 | gcgtccca-acttgttttctg<br>\|\|\|.\|\|\|\| \|\|\|\|.\|\|\|\|.\|<br>GCGACCCATACTTGGTTTCAG | 20430<br>21 |
| 147 | 84.2 | 319 320 | EMBOSS_001<br>hsa-miR-602 | 5368<br>2 | acacgggcg--agcggcgg<br>\|\|\|\|\|\|\|\|\| \|\|\|.\|\|\|\|<br>ACACGGGCGACAGCTGCGG | 5384<br>20 |
| 148 | 85.0 | 321 322 | EMBOSS_001<br>hsa-miR-95 | 132678<br>3 | cgacggg-atttagtgagca<br>\|.\|\|\|\|\| \|\|\|\|\|.\|\|\|\|\|\|<br>CAACGGGTATTTATTGAGCA | 132696<br>22 |
| 149 | 82.6 | 323 324 | EMBOSS_001<br>hsa-miR-340* | 15968<br>1 | tccgtctcagtgtcacttatata<br>\|\|\|\|\|\|\|\|\| \|\|.\|\|\|\| \|\|\|\|<br>TCCGTCTCA--GTTACTT-TATA | 15990<br>20 |
| 150 | 81.0 | 325 326 | EMBOSS_001<br>hsa-miR-541 | 108173<br>2 | ggt-ggcaccgaatccggaat<br>\|\|\| \|\|\|\|\|.\|\|\|\|\| \|\|\|.\|<br>GGTGGGCACAGAATCTGGACT | 108192<br>22 |
| 151 | 84.2 | 327 328 | EMBOSS_001<br>hsa-miR-21 | 74659<br>2 | agtttatcagaatgatatt<br>\|\|.\|\|\|\|\|\|\|\|.\|\|\|\|.\|\|<br>AGCTTATCAGACTGATGTT | 74677<br>20 |
| 152 | 89.5 | 329 330 | EMBOSS_001<br>hsa-miR-924 | 22262<br>2 | gagtttcgtgatgtcttgc<br>\|\|\|\|.\|.\|\|\|\|\|\|\|\|\|\|\|\|<br>GAGTCTTGTGATGTCTTGC | 22280<br>20 |
| 153 | 84.2 | 331 332 | EMBOSS_001<br>hsa-miR-577 | 143602<br>3 | gatataata-tggttcctg<br>\|\|\|\|.\|.\|\ \|\|\|\|\|\|\|\|\|<br>GATAAAATATTGGTACCTG | 143619<br>21 |
| 154 | 81.0 | 333 334 | EMBOSS_001<br>hsa-miR-107 | 152252<br>2 | gtagcattcgacagggctgtc<br>\|.\|\|\|\|\|\|..\|\|\|\|\|\|\|\|.\|\|<br>GCAGCATTGTACAGGGCTATC | 152272<br>22 |
| 155 | 80.0 | 335 336 | EMBOSS_001<br>hsa-miR-614 | 77701<br>4 | cgccgcgtcttgccaagtgg<br>\|\|\|\|...\|\|\|\|\|\|\|\|\|.\|\|\|\|<br>CGCCTGTTCTTGCCAGGTGG | 77720<br>23 |
| 156 | 80.0 | 337 338 | EMBOSS_001<br>hsa-miR-199b- | 61000<br>1 | acagtagtcaccggattggt<br>\|\|\|\|\|\|\|\|\|..\|..\|\|\|\|\|\|<br>ACAGTAGTCTGCACATTGGT | 61019<br>20 |
| 157 | 81.8 | 339 340 | EMBOSS_001<br>hsa-miR-125b- | 112288<br>1 | acgggttagagattttggaagc<br>\|\|\|\|\|\|\|\|\| \|.\|.\|\|\|\|.\|\|\|<br>ACGGGTTAG-GCTCTTGGGAGC | 112309<br>21 |
| 158 | 80.0 | 341 342 | EMBOSS_001<br>hsa-miR-300 | 3720<br>2 | atac--gcgccgactctctc<br>\|\|\|\| \|.\|\|.\|\|\|\|\|\|\|\|\|<br>ATACAAGGGCAGACTCTCTC | 3737<br>21 |
| 159 | 81.0 | 343 344 | EMBOSS_001<br>hsa-let-7a* | 36977<br>1 | caatacaacctaccctctttc<br>\|.\|\|\|\|\|\|.\|\|\|\|..\|\|\|\|\|\|\|<br>CTATACAATCTACTGTCTTTC | 36997<br>21 |
| 160 | 83.3 | 345 346 | EMBOSS_001<br>hsa-miR-485-3 | 11057<br>1 | gtcgtgcacggcactcct<br>\|\|\|.\|.\|\|\|\|\|\|\|.\|\|\|\|\|<br>GTCATACACGGCTCTCCT | 11074<br>18 |
| 161 | 85.7 | 347 348 | EMBOSS_001<br>hsa-miR-515-3 | 94864<br>3 | gtggtttcttttggagcagtt<br>\|\|\|..\|\|\|\|\|\|\|\|\|\|\|\| \|\|\|<br>GTGCCTTCTTTTGGAGC-GTT | 94884<br>22 |
| 162 | 82.6 | 349 350 | EMBOSS_001<br>hsa-miR-219-2 | 124044<br>1 | agaattgtaggct-tccatctgt<br>\|\|\|\|\|\|\|\| \|\|\|\| ..\|\|\|\|\|\|\|<br>AGAATTGT-GGCTGGACATCTGT | 124065<br>22 |

TABLE 1A-continued

Human miRNA Showing mutual Homologies (>=80%) with HHV-6A

| No. | Homology | SEQ ID NOS: | Sequence Alignment Result | | | |
|---|---|---|---|---|---|---|
| 163 | 80.0 | 351<br>352 | EMBOSS_001<br><br>hsa-miR-455-3 | 18487<br><br>2 | cag-ccatcggcagatccac<br>\|\|\| \|\|\|\|.\|\|\|\|.\|\|.\|\|\|<br>CAGTCCATGGGCATATACAC | 18505<br><br>21 |
| 164 | 82.6 | 353<br>354 | EMBOSS_001<br><br>hsa-miR-196b | 79410<br><br>2 | aggtagtgcgtcctggtgttggg<br>\|\|\|\|\|\|\| .\|\|\|\|.\|\|\|\|\|\|\|<br>AGGTAGT--TTCCTGTTGTTGGG | 79432<br><br>22 |
| 165 | 83.3 | 355<br>356 | EMBOSS_001<br><br>hsa-miR-497 | 117069<br><br>4 | ctgcacactgttgttttt<br>\|.\|\|\|\|\|\|\|\|\|.\|\|\|\|.\|<br>CAGCACACTGTGGTTTGT | 117086<br><br>21 |
| 166 | 83.3 | 357<br>358 | EMBOSS_001<br><br>hsa-miR-372 | 151325<br><br>2 | aagtgctgcgacatttttagagtg<br>\|\|\|\|\|\|\|\|\|\|\|\|\|\|\| \|\|\|.\|<br>AAGTGCTGCGACATTT---GAGCG | 151348<br><br>22 |
| 167 | 81.0 | 359<br>360 | EMBOSS_001<br><br>hsa-miR-551b | 20411<br><br>1 | gcgtccca-acttgttttctg<br>\|\|\|.\|\|\|\| \|\|\|\|.\|\|\|\|.\|<br>GCGACCCATACTTGGTTTCAG | 20430<br><br>21 |
| 168 | 81.0 | 361<br>362 | EMBOSS_001<br><br>hsa-miR-302b* | 48153<br><br>1 | attttaacattgaagt--ttt<br>\|.\|\|\|\|\|\|\|\|.\|\|\|\| \|\|\|<br>ACTTTAACATGGAAGTGCTTT | 48171<br><br>21 |
| 169 | 81.0 | 363<br>364 | EMBOSS_001<br><br>hsa-miR-505 | 147594<br><br>3 | taaacacatggtggttctcct<br>\|.\|\|\|\|.\|\|.\|\|\|\| \|\|\|\|<br>TCAACACTTGCTGGTT-TCCT | 147614<br><br>22 |
| 170 | 80.0 | 365<br>366 | EMBOSS_001<br><br>hsa-miR-369-3 | 117295<br><br>2 | ataataactggataatcttt<br>\|\|\|\|\|\|..\|\|\|.\|.\|\|\|\|\|\|<br>ATAATACATGGTTGATCTTT | 117314<br><br>21 |
| 171 | 80.0 | 367<br>368 | EMBOSS_001<br><br>hsa-miR-16-1* | 111324<br><br>3 | agtctta--tgtgctgccga<br>\|\|\|.\|\|\| \|\|\|\|\|\|\|\|.\|\|<br>AGTATTAACTGTGCTGCTGA | 111341<br><br>22 |
| 172 | 81.8 | 369<br>370 | EMBOSS_001<br><br>hsa-miR-433 | 127772<br><br>1 | ataatgat-ggctc--cggtgt<br>\|\|.\|\|\|\| \|\|\|\|\| \|\|\|\|\|\|<br>ATCATGATGGGCTCCTCGGTGT | 127790<br><br>22 |
| 173 | 81.0 | 371<br>372 | EMBOSS_001<br><br>hsa-miR-541 | 108173<br><br>2 | ggt-ggcaccgaatccggaat<br>\|\|\| \|\|\|\|\|.\|\|\|\|\|.\|\|\|.\|<br>GGTGGGCACAGAATCTGGACT | 108192<br><br>22 |
| 174 | 84.2 | 373<br>374 | EMBOSS_001<br><br>hsa-miR-602 | 5368<br><br>2 | acacgggcg--agcggcgg<br>\|\|\|\|\|\|\|\|\|\| \|\|\|.\|\|\|\|<br>ACACGGGCGACAGCTGCGG | 5384<br><br>20 |
| 175 | 85.0 | 375<br>376 | EMBOSS_001<br><br>hsa-miR-95 | 132678<br><br>3 | cgacggg-atttagtgagca<br>\|.\|\|\|\|\| \|\|\|\|\|.\|\|\|\|\|\|<br>CAACGGGTATTTATTGAGCA | 132696<br><br>22 |
| 176 | 82.6 | 377<br>378 | EMBOSS_001<br><br>hsa-miR-340* | 15968<br><br>1 | tccgtctcagtgtcacttatata<br>\|\|\|\|\|\|\|\|\| \|\|.\|\|\|\| \|\|\|\|<br>TCCGTCTCA--GTTACTT-TATA | 15990<br><br>20 |

TABLE 1B

Human miRNA Showing mutual Homologies (>= 80%) with HHV-6B

| No. | % Homology | SEQ ID NO: | Sequence Alignment Result | | | |
|---|---|---|---|---|---|---|
| 1 | 90.5 | 379<br><br>380 | EMBOSS_001<br><br>hsa-miR-511 | 110883<br><br>1 | gtctctttctgctctgcagtc<br>\|\|.\|\|\|\|\| \|\|\|\|\|\|\|\|\|\|\|\|<br>GTGTCTTT-TGCTCTGCAGTC | 110903<br><br>20 |

TABLE 1B-continued

| | | | | | | |
|---|---|---|---|---|---|---|
| 2 | 90.5 | 381 | EMBOSS_001 | 133424 | gatatgatttgata-attagg<br>\|\|\|\|\|\| \|\|\|\|\|\|\|\| \|\|\|\|\|\|<br>GATATG-TTTGATATATTAGG | 133443 |
| | | 382 | hsa-miR-190 | 2 | | 21 |
| 3 | 90.5 | 383 | EMBOSS_001 | 81469 | ttctaaattctccgcgtcttt<br>\|\|\|\|\|\|.\|\|\|\|\|\|\|\|\|\|\|\|<br>TTCTAATTTCTCCACGTCTTT | 81489 |
| | | 384 | hsa-miR-576-5 | 2 | | 22 |
| 4 | 90.0 | 385 | EMBOSS_001 | 58982 | gatatgatttgata-attagg<br>\|\|\|\|\|\| \|\|\|\|\|\|\|\| \|\|\|\|\|\|<br>GATATG-TTTGATATATTAGG | 59000 |
| | | 386 | hsa-miR-606 | 1 | | 20 |
| 5 | 84.2 | 387 | EMBOSS_001 | 48210 | aagaagtggaaaaactgta<br>\|\|\|\|\|.\|\|\|\|\|\|\|\|.\|\|\|.\|<br>AAGATGTGGAAAAATTGGA | 48228 |
| | | 388 | hsa-miR-576-3 | 1 | | 19 |
| 6 | 81.8 | 389 | EMBOSS_001 | 146482 | tcaaagatggacaatccttgtt<br>\|\|\|.\|\|\| \|\|\|.\|\|\|\|\|.\|\|\|\|<br>TCATAGA-GGAAAATCCATGTT | 146503 |
| | | 390 | hsa-miR-376b | 2 | | 22 |
| 7 | 85.0 | 391 | EMBOSS_001 | 43448 | tcgtgcactcgatttagagt<br>\|\|\|\|\|\|\| \|\|..\|\|\|\|\|\|\|\|<br>TCGTGCA-TCCCTTTAGAGT | 43467 |
| | | 392 | hsa-miR-517a | 2 | | 20 |
| 8 | 81.0 | 393 | EMBOSS_001 | 128707 | tctaga-tgtagaactttctg<br>\|\|\|\|\|\| .\|.\|\|.\|\|\|\|\|\|\|\|<br>TCTAGAGGGAAGCACTTTCTG | 128726 |
| | | 394 | hsa-miR-518d- | 2 | | 22 |
| 8 | 81.0 | 393 | EMBOSS_001 | 128707 | tctaga-tgtagaactttctg<br>\|\|\|\|\|\| .\|.\|\|.\|\|\|\|\|\|\|\|<br>TCTAGAGGGAAGCACTTTCTG | 128726 |
| | | 394 | hsa-miR-518d- | 2 | | 22 |
| 9 | 85.0 | 395 | EMBOSS_001 | 89493 | actctgcagagtgg-aatca<br>\|\|\|\|.\|.\|\|\|\|\|\|\|\| \|\|\|\|<br>ACTCAGGAGAGTGGCAATCA | 89511 |
| | | 396 | hsa-miR-510 | 2 | | 21 |
| 10 | 89.5 | 397 | EMBOSS_001 | 89496 | ctgcaga-gtgg-aatcat<br>\|\|\|\|\|\|\| \|\|\|\| \|\|\|\|\|\|<br>CTGCAGACGTGGCAATCAT | 89512 |
| | | 398 | hsa-miR-509-3 | 3 | | 21 |
| 11 | 80.0 | 399 | EMBOSS_001 | 130704 | gaagaggagat--agcaggg<br>\|.\|\|\|\|\| \|\|\| .\|\|\|\|\|\|<br>GTAGAGGAGATGGCGCAGGG | 130721 |
| | | 400 | hsa-miR-877 | 1 | | 20 |
| 12 | 84.2 | 401 | EMBOSS_001 | 19796 | ctctccaaatctgatcctg<br>\|\|\|\|\|\|.\|\|\|.\|\| \|\|.\|\|<br>CTCTCCAAATGTG-TCTTG | 19814 |
| | | 402 | hsa-miR-642 | 5 | | 22 |
| 13 | 80.0 | 403 | EMBOSS_001 | 128530 | tctagttctgg-agtgctga<br>\|\|\|\|\| .\|\|\|\| \|.\|\|\|\|\|<br>TCTAG-GCTGGTACTGCTGA | 128548 |
| | | 404 | hsa-miR-645 | 1 | | 16 |
| 14 | 83.3 | 405 | EMBOSS_001 | 37123 | taatatagtccgtatctt<br>\|\|\|\|\|.\|\|\|\|..\|\|\|\|\|<br>TAATATGGTCCACATCTT | 37140 |
| | | 406 | hsa-miR-380 | 5 | | 22 |
| 15 | 83.3 | 407 | EMBOSS_001 | 113527 | taacggcaagtaaatatt<br>\|\|.\|.\|\|\|.\|\|\|\|\|\|\|\|\|<br>TAGCAGCACGTAAATATT | 113544 |
| | | 408 | hsa-miR-16 | 1 | | 18 |
| 16 | 84.2 | 409 | EMBOSS_001 | 116999 | agag-ttacctgatttgtg<br>\|\|\|\| \|\|\|.\|\|\|\|\|.\|\|<br>AGAGCTTAGCTGATTGGTG | 117016 |
| | | 410 | hsa-miR-27b* | 1 | | 19 |
| 17 | 84.2 | 411 | EMBOSS_001 | 110351 | ttgtgt-ttgttttgcagc<br>\|.\|\|\| \|.\|\|.\|\|\|\|\|\|\|<br>TCGTGTCTTGTGTTGCAGC | 110368 |
| | | 412 | hsa-miR-187 | 1 | | 19 |
| 18 | 82.6 | 413 | EMBOSS_001 | 16443 | agggtggaaattgtcta-agtcc<br>\|\|\|\| \|\|\|\|\|.\| \|\|\|\| \|\|\|\|\|<br>AGGG-GGAAAGT-TCTATAGTCC | 16464 |
| | | 414 | hsa-miR-625 | 1 | | 21 |
| 19 | 81.0 | 415 | EMBOSS_001 | 1179 | ctctatctcctgtcgcactcc<br>\|\|\|\|.\|\| \|\|\|\|\|.\|\|\|\|\|.\|<br>CTCTTTC-CCTGTTGCACTAC | 1199 |
| | | 416 | hsa-miR-130b* | 2 | | 21 |

TABLE 1B-continued

| | | | | | | | |
|---|---|---|---|---|---|---|---|
| 20 | 80.0 | 417 | EMBOSS_001 | 151208 | tccagccccatagtttctgc<br>\|\|\|\|\|\|\|\|\|\|.\|\|..\|\|.\|\|<br>TCCAGCCCCACAGCCTCAGC | 151227 | |
| | | 418 | hsa-miR-766 | 3 | | 22 | |
| 21 | 84.2 | 419 | EMBOSS_001 | 63245 | cttactccttccggcacgt<br>\|\|\|\|\|\|\|\|.\|\|.\|\|\|\|\|.\|<br>CTTACTCCCTCAGGCACAT | 63263 | |
| | | 420 | hsa-miR-550* | 4 | | 22 | |
| 22 | 85.0 | 421 | EMBOSS_001 | 59050 | cccttttgt-aacctatccct<br>\|\|\|\|\|\|\|\|\| \|.\|\|\|\|\|.\|\|\|<br>CCCTTTGTCATCCTATGCCT | 59068 | |
| | | 422 | hsa-miR-204 | 3 | | 22 | |
| 23 | 83.3 | 423 | EMBOSS_001 | 67320 | gattgaca-acatttccc<br>\|.\|\|\|\|\|\| \|\|.\|\|\|\|\|\|\|<br>GGTTGACATACGTTTCCC | 67336 | |
| | | 424 | hsa-miR-563 | 2 | | 19 | |
| 24* | 88.9* | 425 | EMBOSS_001 | 54899 | atcacacaaaggaaattt<br>\|\|\|\|\|\|\|\|\|\|\|\|\|.\|\|.\|\|<br>ATCACACAAAGGCAACTT | 54916 | |
| | | 426 | hsa-miR-377 | 1 | | 18 | |
| 25 | 80.0 | 427 | EMBOSS_001 | 103678 | gcactgttgggtatttggt<br>\|\|\|\|\|\|\|   \|\|\|\|\|.\|\|\|.\|<br>GCACTGT--GGGTACTTGCT | 103697 | |
| | | 428 | hsa-miR-106b* | 3 | | 20 | |
| 26 | 85.7 | 429 | EMBOSS_001 | 86008 | tcagcgagagtgaaaagagac<br>\|\|\|\|\|\| \|\|\| \|\|\|\|\|\|\|.\|\|<br>TCAGCG-GAG-GAAAAGAAAC | 86028 | |
| | | 430 | hsa-miR-923 | 2 | | 20 | |
| 27 | 80.0 | 431 | EMBOSS_001 | 91095 | agcttgcagagggtgctgat<br>\|\|\|\|   \|\|\|\|\|\|\|\|..\|\|\|\|\|<br>AGCT--CAGAGGGCTCTGAT | 91114 | |
| | | 432 | hsa-miR-127-5 | 5 | | 22 | |
| 28 | 80.0 | 433 | EMBOSS_001 | 122275 | agtcacgaagatggcatagc<br>\|\|.\|\|.\|.\|\|\|\|\|\|\|\|\|\|\|<br>AGGCAAGATGCTGGCATAGC | 122294 | |
| | | 434 | hsa-miR-31 | 1 | | 20 | |
| 29 | 81.8 | 435 | EMBOSS_001 | 66216 | aaagttgagagacactctggct<br>\|\|\|\|\|\|..\|\|\|\|\|.\|\|\|.\|.\|\|<br>AAAGTTCTGAGACACTCCGACT | 66237 | |
| | | 436 | hsa-miR-148a* | 1 | | 22 | |
| 30 | 82.6 | 437 | EMBOSS_001 | 111599 | actctgcagcttttaacaagtt<br>\|.\|\|\|\|\|\|  \|\|\|\|\|\|.\|\|\|\|\|\|<br>ATTCTGCA--TTTTTAGCAAGTT | 111621 | |
| | | 438 | hsa-miR-544 | 1 | | 21 | |
| 31 | 81.0 | 439 | EMBOSS_001 | 14018 | atgt--cgtggtccaataact<br>\|\|\|\|   \|.\|\|\|\|\|\|.\|\|\|\|\|<br>ATGTAACATGGTCCACTAACT | 14036 | |
| | | 440 | hsa-miR-379* | 2 | | 22 | |
| 32* | 80.0 | 441 | EMBOSS_001 | 14917 | gcctactgtgct-ctatctg<br>\|\|\|\|\|\|\|\|.\|\|\| .\|\|\|\|.\|<br>GCCTACTGAGCTGATATCAG | 14935 | |
| | | 442 | hsa-miR-24-1* | 2 | | 21 | |
| 33 | 88.9 | 443 | EMBOSS_001 | 76922 | ggcagagttttgttagct<br>\|\|\|\|\|.\|.\|\|\|\|\|\|\|\|\|<br>GGCAGTGTATTGTTAGCT | 76939 | |
| | | 444 | hsa-miR-449a | 2 | | 19 | |
| 34* | 80.0* | 445 | EMBOSS_001 | 1367 | tgccctgtggagactgca--tctgg<br>\|\|\|\|\|\|\|\|\|  \|\|\|\| \|\|\|\|\|<br>TGCCCTGTG--GACT-CAGTTCTGG | 1389 | |
| | | 446 | hsa-miR-146b- | 1 | | 22 | |
| 35 | 80.0 | 447 | EMBOSS_001 | 91670 | ccatcatacacgattccctgcctct<br>\|\|\|\|  \|\|\|\|\|  \|.\|\|\|\|\|\|\|\|\|\|<br>CCAT--TACAC--TACCCTGCCTCT | 91694 | |
| | | 448 | hsa-miR-885-5 | 2 | | 22 | |
| 36 | 80.0 | 449 | EMBOSS_001 | 148860 | tgctgacatagcactttcgg<br>\|\|\|\|\|\|..\|\|\|\|\|\|\|\|\|.\|.\|<br>TGCTGAGCTAGCACTTCCCG | 148879 | |
| | | 450 | hsa-miR-93* | 3 | | 22 | |
| 37 | 83.3 | 451 | EMBOSS_001 | 6526 | aggcgagggctgcagcgggacccc<br>\|\|\|\|\|  \|\|\|\|  \|\|.\|\|\|\|\|\|\|\|.\|<br>AGGCG-GGGC-GCCGCGGGACCGC | 6549 | |
| | | 452 | hsa-miR-663 | 1 | | 22 | |
| 38 | 81.0 | 453 | EMBOSS_001 | 45889 | tctccatagttgatgtactca<br>\|.\|\|\|\|\|\|\|.\|\|\|\|\| \|.\|\|\|<br>TTTCCATAGGTGATG-AGTCA | 45909 | |
| | | 454 | hsa-miR-587 | 1 | | 20 | |
| 49 | 84.2 | 455 | EMBOSS_001 | 72416 | tgatgtagaaggttgttta<br>\|\|\|.\|\|\|.\|\|\|\|\|\|.\|\|<br>TGAGGTAGGAGGTTGTATA | 72434 | |
| | | 456 | hsa-let-7e | 1 | | 19 | |

TABLE 1B-continued

| | | | | | | | |
|---|---|---|---|---|---|---|---|
| 40 | 85.0 | 457 | EMBOSS_001 | 42527 | atacgac--gct-cctttct | 42543 | |
| | | 458 | hsa-let-7d* | 3 | ATACGACCTGCTGCCTTTCT | 22 | |
| 41 | 82.6 | 459 | EMBOSS_001 | 105696 | tggttta-cgtccctcaca-aca | 105716 | |
| | | 460 | hsa-miR-299-5 | 1 | TGGTTTACCGTCC--CACATACA | 21 | |
| 42 | 81.0 | 461 | EMBOSS_001 | 59277 | atttaccgacaacagccctgc | 59297 | |
| | | 462 | hsa-miR-600 | 1 | ACTTACAGACAAGAGCCTTGC | 21 | |
| 43 | 81.0 | 463 | EMBOSS_001 | 11896 | tacagttgttaataaccagct | 11916 | |
| | | 464 | hsa-miR-582-5 | 2 | TACAGTTGTT--CAACCAGTT | 20 | |
| 44 | 87.0 | 465 | EMBOSS_001 | 106312 | caatgcaatgatattggtcaatg | 106334 | |
| | | 466 | hsa-miR-301b | 1 | CAGTGCAATGATATT-GTCAAAG | 22 | |
| 45 | 89.5 | 467 | EMBOSS_001 | 76921 | aggcagagttttgttagct | 76939 | |
| | | 468 | hsa-miR-449b | 1 | AGGCAGTGTATTGTTAGCT | 19 | |
| 46 | 83.3 | 469 | EMBOSS_001 | 47701 | tgtgaaacacttccatga | 47718 | |
| | | 470 | hsa-miR-491-5 | 3 | TGGGGAACCCTTCCATGA | 20 | |
| 47 | 81.0 | 471 | EMBOSS_001 | 150984 | acggacgcgaagcgcgtgcag | 151004 | |
| | | 472 | hsa-miR-92b* | 1 | AGGGACGGGACGCG-GTGCAG | 20 | |
| 48 | 81.8 | 473 | EMBOSS_001 | 68710 | cagaaaccaccgtttcgttttc | 68731 | |
| | | 474 | hsa-miR-548d- | 1 | CAAAAACCACAGTTTCTTTTGC | 22 | |
| 49 | 81.8 | 475 | EMBOSS_001 | 98083 | gagattttcaaaaatgtgcag | 98104 | |
| | | 476 | hsa-miR-590-5 | 1 | GAGCTTATTCATAAAGTGCAG | 22 | |
| 50 | 83.3 | 477 | EMBOSS_001 | 13663 | cgccagagcggtgcactt | 13680 | |
| | | 478 | hsa-miR-525-5 | 1 | CTCCAGAGGGATGCACTT | 18 | |
| 51 | 84.2 | 479 | EMBOSS_001 | 145189 | aataaaactgtggggccac | 145207 | |
| | | 480 | hsa-miR-371-5 | 1 | ACTCAAACTGTGGGGCAC | 19 | |
| 52 | 89.5 | 481 | EMBOSS_001 | 95153 | gaggtgcttcgattttagg | 95171 | |
| | | 482 | hsa-miR-373 | 1 | GAAGTGCTTCGATTTTGGG | 19 | |
| 53 | 80.0 | 483 | EMBOSS_001 | 17779 | cagttttccacaaaccct | 17798 | |
| | | 484 | hsa-miR-145 | 4 | CAGTTTTCCCAGGAATCCCT | 23 | |
| 54* | 80.0* | 485 | EMBOSS_001 | 72330 | aatccatgaaacttaggttt | 72349 | |
| | | 486 | hsa-miR-362-5 | 1 | AATCCTTGGAACCTAGGTGT | 20 | |
| 55 | 85.0 | 487 | EMBOSS_001 | 139247 | gaatgtta--aagtatgtat | 139264 | |
| | | 488 | hsa-miR-1 | 3 | GAATGTAAAGAAGTATGTAT | 22 | |
| 56 | 83.3 | 489 | EMBOSS_001 | 121294 | tgtgttcgctagctcatt | 121311 | |
| | | 490 | hsa-miR-581 | 4 | TGTGTTCTCTAGATCAGT | 21 | |
| 57 | 82.6 | 491 | EMBOSS_001 | 115986 | tgttgtagaagattgtataagtt | 116008 | |
| | | 492 | hsa-let-7f | 1 | TGAGGTATTAGATTGTAT-AGTT | 22 | |
| 58 | 81.8 | 493 | EMBOSS_001 | 6153 | gtgtgcgg--atgttttctgct | 6172 | |
| | | 494 | hsa-miR-147b | 1 | GTGTGCGGAAATG-CTTCTGCT | 21 | |

TABLE 1B-continued

| | | | | | | | |
|---|---|---|---|---|---|---|---|
| 59 | 84.2 | 495 | EMBOSS_001 | 132685 | atttagtgagcatgatatt<br>\|\|\|\|\|\|\|\|.\|..\|\|\|\|\|\|\|<br>ATTTAGTGTGTGTGATATT | 132703 | |
| | | 496 | hsa-miR-32* | 3 | | 21 | |
| 60 | 82.6 | 497 | EMBOSS_001 | 137846 | aattgtcttccatgttagactgt<br>\|\|.\|\|\|\|\|\|\|\|\|\|\|.\|\|.\|\|\|<br>AAGTG-CTTCCATGTTTGAGTGT | 137868 | |
| | | 498 | hsa-miR-302d | 2 | | 23 | |
| 61 | 83.3 | 499 | EMBOSS_001 | 4430 | gggcccgccctc-gtcct<br>\|\|\|\|\|\|.\|\ \|\|\|\ .\|\|\|\|<br>GGGCCCCCCCTCAATCCT | 4446 | |
| | | 500 | hsa-miR-296-5 | 2 | | 19 | |
| 62 | 88.9 | 501 | EMBOSS_001 | 73203 | tatttttatgtaaaagct<br>\|\|.\|\|\|\|\|\|\|\|.\|\|\|\|\|<br>TAATTTTATGTATAAGCT | 73220 | |
| | | 502 | hsa-miR-590-3 | 1 | | 18 | |
| 63 | 81.0 | 503 | EMBOSS_001 | 81989 | agaccaagcggttgtcatttt<br>\|\|\|\|\|\|.\|\ \|\|\|\|.\|\|\|\|\|.\|<br>AGACCATG-GGTTCTCATTGT | 82009 | |
| | | 504 | hsa-miR-591 | 1 | | 20 | |
| 64 | 85.0 | 505 | EMBOSS_001 | 46431 | atcactta-gacacggccag<br>\|\|\|\|\|\|.\|\ .\|\|\|\|\|\|\|\|\|\|\|<br>ATCACTAACCACACGGCCAG | 46449 | |
| | | 506 | hsa-miR-34c-3 | 2 | | 21 | |
| 65 | 80.0 | 507 | EMBOSS_001 | 75535 | tgatcatctcccatggttcc<br>\|\|.\|\|\|\|..\|\|\|\|\|\|\|\|\|.\|<br>TGCTCATACCCCATGGTTTC | 75554 | |
| | | 508 | hsa-miR-767-3 | 3 | | 22 | |
| 66 | 81.0 | 509 | EMBOSS_001 | 2291 | acaggagagcgagg--tcgca<br>\|\|\|\|.\|\|\|\|.\|\|\|\|\ \ \|\|\|\|\|<br>ACAGTAGAGGGAGGAATCGCA | 2309 | |
| | | 510 | hsa-miR-936 | 1 | | 21 | |
| 67 | 81.8 | 511 | EMBOSS_001 | 82706 | gcttttttattccacttatgaga<br>\|\|\|\|\|\|\|\|\|\|\|\ \ \ \ \|\|\|\|.\|\|<br>GCTTTTTATTCC---TATGTGA | 82727 | |
| | | 512 | hsa-miR-135a | 5 | | 23 | |
| 68 | 82.6 | 513 | EMBOSS_001 | 147594 | taaa-cacatggtg-gttctcct<br>\|\|\|\|\ \|.\|\|\|\|\|\|\|\ .\|\|\|\|\|\|\|<br>TAAATCCCATGGTGCCTTCTCCT | 147614 | |
| | | 514 | hsa-miR-605 | 1 | | 23 | |
| 69 | 81.0 | 515 | EMBOSS_001 | 1735 | agggcggctggcttccctttg<br>\|\|\|\ \ \ \|\|\|\|\|\|\|\|\|.\|\|\|.\|\|<br>AGG--GGCTGGCTTTCCTCTG | 1755 | |
| | | 516 | hsa-miR-185* | 1 | | 19 | |
| 70 | 85.0 | 517 | EMBOSS_001 | 104219 | ctgagaccctaatttgtta<br>\|\|\|\|\|\ \|\|\|\|\|\|\|.\|\|\|.\|<br>CTGAGA-CCCTAACTTGTGA | 104238 | |
| | | 518 | hsa-miR-125b | 4 | | 22 | |
| 71 | 81.8 | 519 | EMBOSS_001 | 77520 | tgacggtctgcactt-ctgtgc<br>\|\|.\|.\|\|\|\|\|\|\|\|\|\ \|\|\|\|\|\|<br>TGCCTGTCTACACTTGCTGTGC | 77540 | |
| | | 520 | hsa-miR-214* | 1 | | 22 | |
| 72 | 81.0 | 521 | EMBOSS_001 | 8823 | gtggtcc---gcgcgtgtcgc<br>\|\|\|\|\|\|\ \ \ \ \|\|\|\|\ \|\|\|\|<br>GTGGTCCGTGGCGCGT-TCGC | 8840 | |
| | | 522 | hsa-miR-323-5 | 3 | | 22 | |
| 73 | 80.0 | 523 | EMBOSS_001 | 3224 | ccaccaccg---ctgacagt<br>\|\|\|\|\|\|\|\|\|\ \ \ \|\|\|\|\|\|.\|<br>CCACCACCGTGTCTGACACT | 3240 | |
| | | 524 | hsa-miR-220b | 1 | | 20 | |
| 74 | 85.0 | 525 | EMBOSS_001 | 33369 | agccagagtagtcttgatgt<br>\|\|\|\|\|\|\ \|.\|\|\|.\|\|\|\|\|\|\|<br>AGCCAG-GAAGTATTGATGT | 33388 | |
| | | 526 | hsa-miR-505* | 4 | | 22 | |
| 75 | 81.0 | 527 | EMBOSS_001 | 21424 | cgtctctaccccgagtgttt<br>\|\|\|\|\|\ \|\|\|\|\|\...\|\|\|\|\|\|\|<br>CGTCT-TACCCAGCAGTGTTT | 21444 | |
| | | 528 | hsa-miR-200c* | 1 | | 20 | |
| 76 | 84.2 | 529 | EMBOSS_001 | 50705 | cagcaacaaaatttcatcc<br>\|\|\|.\|\|\|\|\|..\|\|\|\|\|\|\|\|\|<br>CAGTAACAAAGATTCATCC | 50723 | |
| | | 530 | hsa-miR-802 | 1 | | 19 | |
| 77 | 85.0 | 531 | EMBOSS_001 | 95571 | ataccagtcgatgtcgctgt<br>\|.\|\|\|\|\|\|\|\|\|\|\ .\|\|\|\|<br>ACACCAGTCGATG-GGCTGT | 95590 | |
| | | 532 | hsa-miR-21* | 3 | | 21 | |

TABLE 1B-continued

| | | | | | | | |
|---|---|---|---|---|---|---|---|
| 78 | 81.0 | 533 | EMBOSS_001 | 92213 | tggcaacgggagacagttttg<br>\|·\|\|\|·\|\|\|\|\|·\|\|\|\|\|\|·\|\| | 92233 | |
| | | 534 | hsa-miR-503 | 1 | TAGCAGCGGGA-ACAGTTCTG | 20 | |
| 79 | 85.0 | 535 | EMBOSS_001 | 33369 | agccagagtagtcttgatgt<br>\|\|\|\|\|\|·\|\|\|·\|\|\|\|\|\|\|\| | 33388 | |
| | | 536 | hsa-miR-505* | 4 | AGCCAG-GAAGTATTGATGT | 22 | |
| 80 | 80.0 | 537 | EMBOSS_001 | 66718 | cgtacagtgattgatactgc<br>\|\|\|\|\|\|·\|\|\|\|·\|·\|\|\|·\|\| | 66737 | |
| | | 538 | hsa-miR-126 | 2 | CGTACCGTGAGTAATAATGC | 21 | |
| 81 | 83.3 | 539 | EMBOSS_001 | 57607 | ctaataggtttccattaa<br>\|\|\|·\|\|\|\|·\|\|\|\·\|\|\| | 57624 | |
| | | 540 | hsa-miR-325 | 2 | CTAGTAGGTGTCCAGTAA | 19 | |
| 82 | 83.3 | 541 | EMBOSS_001 | 74504 | cccttagggtattggggt<br>\|\|\|·\|\|\|\|\|·\|\|\|\|\|·\|\| | 74521 | |
| | | 542 | hsa-miR-324-5 | 6 | CCCCTAGGGCATTGGTGT | 23 | |
| 83 | 88.9 | 543 | EMBOSS_001 | 1891 | tcctgctctcagggctcc<br>\|\|\|·\|·\|\|\|\|\|\|\|\|\|\|\| | 1908 | |
| | | 544 | hsa-miR-671-3 | 1 | TCCGGTTCTCAGGGCTCC | 18 | |
| 84 | 81.0 | 545 | EMBOSS_001 | 1725 | ctgtgcg-ggggagggcggctg<br>\|\|\|\|\|\|·\|\|·\|\|··\|\|\|\|\|\| | 1744 | |
| | | 546 | hsa-miR-210 | 1 | CTGTGCGTGTGACAGCGGCTG | 21 | |
| 85 | 85.0 | 547 | EMBOSS_001 | 139297 | aggtggaggtttctttggag<br>\|\|\|\| \|\|\|\| \|\|\|\|\|·\|\|\| | 139316 | |
| | | 548 | hsa-miR-125a- | 3 | AGGT-GAGG-TTCTTGGGAG | 20 | |
| 86 | 81.8 | 549 | EMBOSS_001 | 102320 | aaattgattcccttaggtgggt<br>\|\|\|·\|\|·\|\|\|·\|\|\|·\|\|\|\|\|\|\| | 102341 | |
| | | 550 | hsa-miR-520d- | 1 | AAAGTGCTTCTCTTTGGTGGGT | 22 | |
| 87 | 81.0 | 551 | EMBOSS_001 | 11489 | ctcgttcttgggccacctcag<br>\|\|\|·\|\|\|··\|\|\|\| \|\|\|\|\|\| | 11509 | |
| | | 552 | hsa-miR-423-3 | 3 | CTCGGTCTGAGGCC-CCTCAG | 22 | |
| 88* | 82.6* | 553 | EMBOSS_001 | 37494 | tcagaaaacgatttactgtgagc<br>\|\|\|\|·\|\|\|\| \|\|\|\|·\|\|\|\|·\|\| | 37516 | |
| | | 554 | hsa-miR-545 | 1 | TCAGCAAAC-ATTTATTGTGTGC | 22 | |
| 89 | 81.0 | 555 | EMBOSS_001 | 128707 | tctaga-tgtagaactttctg<br>\|\|\|\|\|\| ·\|·\|\|·\|\|\|\|\|\|\| | 128726 | |
| | | 556 | hsa-miR-520c- | 2 | TCTAGAGGGAAGCACTTTCTG | 22 | |
| 90 | 81.0 | 557 | EMBOSS_001 | 79448 | gttgggatcggt--cagtgtt<br>\|\|\|\|\|\|\|\|\|\|\|\| \|\|·\|\|·\| | 79466 | |
| | | 558 | hsa-miR-92a-1 | 3 | GTTGGGATCGGTTGCAATGCT | 23 | |
| 91 | 80.0 | 559 | EMBOSS_001 | 71482 | ctagtctagattcatccagt<br>\|\|\|\|\|\|··\|·\|\|·\|\|\|·\|\|\|\| | 71501 | |
| | | 560 | hsa-miR-554 | 2 | CTAGTCCTGACTCAGCCAGT | 21 | |
| 92* | 80.0* | 561 | EMBOSS_001 | 126675 | aataaccacatttggttttg<br>\|\|·\|\|\|\|·\|\|·\|\|\|·\|\|\|\|\| | 1126694 | |
| | | 562 | hsa-miR-548b- | 2 | AAGAACCTCAGTTGCTTTTG | 21 | |
| 93 | 84.2 | 563 | EMBOSS_001 | 62994 | ctccgacatctttgcatta<br>\|\|\|\|·\|\|\|\|·\|\|·\|\|·\|\|\|\| | 63012 | |
| | | 564 | hsa-miR-155* | 1 | CTCCTACATATTAGCATTA | 19 | |
| 94 | 85.0 | 565 | EMBOSS_001 | 89539 | aacatttctggtatcgatg<br>\|\|\|\|·\|·\|\|\|\|\|\|\|\|\|\|\|\| | 89558 | |
| | | 566 | hsa-miR-200a | 2 | AACACTGTCTGGTAACGATG | 21 | |
| 95 | 80.0 | 567 | EMBOSS_001 | 82436 | acaga--cgattttagagga<br>\|\|\|\|\| \|\|\|\|·\|\| ·\|\|\|\| | 82453 | |
| | | 568 | hsa-miR-10b* | 1 | ACAGATTCGATTCTAGGGGA | 20 | |
| 96 | 84.2 | 569 | EMBOSS_001 | 92268 | ggaatt-gggcagaaggc<br>\|\|\|·\|\| \|\|\|·\|\|\|\|\|\|\|\| | 92285 | |
| | | 570 | hsa-miR-422a | 4 | GGACTTAGGGTCAGAAGGC | 22 | |

TABLE 1B-continued

| | | | | | | |
|---|---|---|---|---|---|---|
| 97 | 85.0 | 571 | EMBOSS-001 | 30111 | tacagtact-cgatagctga | 30129 |
| | | | | | ||||||||| · |||| · |||| | |
| | | 572 | hsa-miR-101 | 1 | TACAGTACTGTGATAACTGA | 20 |
| 98 | 84.2 | 573 | EMBOSS_001 | 88645 | tttaatatggcggcagttg | 88663 |
| | | | | | ||||| · |||| · || | · ||| | |
| | | 574 | hsa-miR-302d* | 3 | TTTAACATGGAGGCACTTG | 21 |
| 99 | 80.0 | 575 | EMBOSS_001 | 122520 | atgaagataattatggaaat | 122539 |
| | | | | | ||| · |||| · · ||| · ||||| | |
| | | 576 | hsa-miR-620 | 1 | ATGGAGATAGATATAGAAAT | 20 |
| 100 | 84.2 | 577 | EMBOSS_001 | 72416 | tgatgtagaaggttgttta | 72434 |
| | | | | | ||| · |||| · ||||||| · || | |
| | | 578 | hsa-let-7a | 1 | TGAGGTAGTAGGTTGTATA | 19 |
| 101 | 81.8 | 579 | EMBOSS_001 | 73429 | gatggt-cttcttttagaggc | 73449 |
| | | | | | || · · || |||| · ||||||||||| | |
| | | 580 | hsa-miR-22* | 3 | GAAAGTGCTTCCTTTTAGAGGC | 22 |
| 102 | 81.0 | 581 | EMBOSS_001 | 139104 | ttcttcagtag--agacttta | 139122 |
| | | | | | |||||||| · | || ||||| | |
| | | 582 | hsa-miR-22* | 3 | TTCTTCAGTGGCAAG-CTTTA | 22 |
| 103 | 80.0 | 583 | EMBOSS_001 | 87214 | tgaattcctggacatggtga | 87233 |
| | | | | | || · · ||||||| |||| · ||| | |
| | | 584 | hsa-miR-23b* | 1 | TGGGTTCCTGG-CATGCTGA | 19 |
| 104 | 81.8 | 585 | EMBOSS_001 | 146268 | tggatgtgctcct-cagttgtc | 146288 |
| | | | | | |||||| |||||| · --|||| | |
| | | 586 | hsa-miR-432* | 2 | TGGATG-GCTCCTCCA--TGTC | 20 |
| 105 | 83.3 | 587 | EMBOSS_001 | 74620 | gctgacgtattttctgga | 74637 |
| | | | | | |||||| · ||||| · || · || | |
| | | 588 | hsa-miR-628-5 | 3 | GCTGACATATTTACTAGA | 20 |
| 106 | 89.5 | 589 | EMBOSS_001 | 142386 | ccactgacctttaactgta | 142404 |
| | | | | | ||||||||| · || · |||||| | |
| | | 590 | hsa-miR-181a- | 2 | CCACTGACCGTTGACTGTA | 20 |
| 107 | 84.2 | 591 | EMBOSS_001 | 138716 | aaaacg-taccactactga | 138733 |
| | | | | | ||| · || ||||| · ||||||| | |
| | | 592 | hsa-miR-451 | 1 | AAACCGTTACCATTACTGA | 19 |
| 108 | 81.0 | 593 | EMBOSS_001 | 7509 | aacatacttcctgtccgtgag | 7529 |
| | | | | | ||||| · | · · ||||||| ||||| | |
| | | 594 | hsa-miR-181c | 1 | AACATTCAACCTGTCGGTGAG | 21 |
| 109 | 81.0 | 595 | EMBOSS_001 | 20802 | cgagcag-tcacagtttcagt | 20821 |
| | | | | | |||| · || ||||||||| · ||| | |
| | | 596 | hsa-miR-151-5 | 2 | CGAGGAGCTCACAGTCT-AGT | 21 |
| 110 | 82.6 | 597 | EMBOSS_001 | 1427 | ggagagaacagagctggtcctga | 1449 |
| | | | | | ||||||| || || · · ||||||| | |
| | | 598 | hsa-miR-185 | 2 | GGAGAGAA-AG-GCAGTTCCTGA | 22 |
| 111 | 81.0 | 599 | EMBOSS_001 | 128707 | tctaga-tgtagaactttctg | 128726 |
| | | | | | |||||| | · | · || · ||||||| | |
| | | 600 | hsa-miR-526a | 2 | TCTAGAGGGAAGCACTTTCTG | 22 |
| 112 | 81.8 | 601 | EMBOSS_001 | 34065 | acc-ggcataaaatttagttttt | 34085 |
| | | | | | ||| ||||||| · ||| · ||| · ||| | |
| | | 602 | hsa-miR-221* | 1 | ACCTGGCATACAATGTAGATTT | 22 |
| 113 | 85.7 | 603 | EMBOSS_001 | 2700 | tcctcttcctcctcctcccccg | 2720 |
| | | | | | |||||||| · · |||||||||| · | | |
| | | 604 | hsa-miR-877* | 1 | TCCTCTTCTCCCTCCTCCCCAG | 21 |
| 114 | 80.0 | 605 | EMBOSS_001 | 123263 | tgggtgatggatgtgcactt | 123282 |
| | | | | | |||| · | · |||||||| · · |||| | |
| | | 606 | hsa-miR-30b* | 2 | TGGGAGGTGGATGTTTACTT | 21 |
| 115 | 85.0 | 607 | EMBOSS_001 | 96701 | atgagttcattg-aatatca | 96719 |
| | | | | | |||| · |||||||| ||||| · | |
| | | 608 | hsa-miR-556-5 | 2 | ATGAGCTCATTGTAATATGA | 21 |

TABLE 1B-continued

| | | | | | | |
|---|---|---|---|---|---|---|
| 116 | 81.0 | 609 | EMBOSS_001 | 149873 | ttcatatccatatatttttt | 149893 |
| | | | | | \|\|\|.\|\|\|.\|\|\|\|\|\|.\|\|.\|\|\| | |
| | | 610 | hsa-miR-202* | 1 | TTCCTATGCATATACTTCTTT | 21 |
| 117 | 81.0 | 611 | EMBOSS_001 | 2693 | ctcctcctcctcttcctcctc | 2713 |
| | | | | | \|.\|\|.\|\|\|\|\|\|\|\|\|  \|\|\|\|\|\| | |
| | | 612 | hsa-miR-1224- | 1 | CCCCACCTCCTCT--CTCCTC | 19 |
| 118 | 80.0 | 613 | EMBOSS_001 | 61000 | acagtagtcaccggattggt | 61019 |
| | | | | | \|\|\|\|\|\|\|\|..\|..\|\|\|\|\|\| | |
| | | 614 | hsa-miR-199a- | 1 | ACAGTAGTCTGCACATTGGT | 20 |
| 119 | 85.0 | 615 | EMBOSS_001 | 51041 | gacctaggcccgtacctcag | 51060 |
| | | | | | \|\|\|\|\| \|\|\|\|\|..\|\|\|\|\|\|\| | |
| | | 616 | hsa-miR-631 | 2 | GACCT-GGCCCAGACCTCAG | 20 |
| 120 | 83.3 | 617 | EMBOSS_001 | 105414 | aacacgaaactgcttgcg | 105431 |
| | | | | | \|\|\|.\|\|\|\|\|\|\|\|\|.\|\|.\| | |
| | | 618 | hsa-miR-196a* | 5 | AACAAGAAACTGCCTGAG | 22 |
| 121 | 84.2 | 619 | EMBOSS_001 | 74659 | agtttatcagaatgatatt | 74977 |
| | | | | | \|\|.\|\|\|\|\|\|\|\|.\|\|\|\|.\|\| | |
| | | 620 | hsa-miR-21 | 2 | AGCTTATCAGACTGATGTT | 20 |
| 122 | 81.8 | 621 | EMBOSS_001 | 1887 | ctg-ctcctgctctcagggctc | 1907 |
| | | | | | \|\|\| \|\|\|\|\|\|..\|\| \|\|\|\|\|\|\|\|\| | |
| | | 622 | hsa-miR-345 | 2 | CTGACTCCTAGTC-CAGGGCTC | 22 |
| 123 | 81.0 | 623 | EMBOSS_001 | 133605 | gtagactagtttgattatgtt | 133625 |
| | | | | | \|.\|\|\|\|\|\|\|\|  \|\|\|\|\|\|\|\|\| | |
| | | 624 | hsa-miR-7 | 3 | GAAGACTAG--TGATTTTGTT | 21 |
| 124 | 85.0 | 625 | EMBOSS_001 | 124054 | gcttccatctgttttagcag | 124073 |
| | | | | | \|\|\|\|\|\|\|  \|\|\|\|\|\|\|\|\|.\|\| | |
| | | 626 | hsa-miR-302b | 6 | GCTTCCA--TCTTTTAGTAG | 23 |
| 125 | 80.0 | 627 | EMBOSS_001 | 77701 | cgccgcgtcttgccaagtgg | 77720 |
| | | | | | \|\|\|\|\|...\|\|\|\|\|\|\|\|.\|\|\|\| | |
| | | 628 | hsa-miR-614 | 4 | CGCCTGTTCTTGCCAGGTGG | 23 |
| 126 | 80.0 | 629 | EMBOSS_001 | 61000 | acagtagtcaccggattggt | 61019 |
| | | | | | \|\|\|\|\|\|\|\|..\|..\|\|\|\|\|\| | |
| | | 630 | hsa-miR-199b- | 1 | ACAGTAGTCTGCACATTGGT | 20 |
| 127 | 81.8 | 631 | EMBOSS_001 | 132725 | gaagttattttcgtggttgatt | 132746 |
| | | | | | \|\|\|\|\|  \|.\|\|\|\|\|\|\|\|\|.\|\|\|\| | |
| | | 632 | hsa-miR-382 | 1 | GAAGT--TGTTCGTGGTGGATT | 20 |
| 128 | 89.5 | 633 | EMBOSS_001 | 22262 | gagtttcgtgatgtcttgc | 22280 |
| | | | | | \|\|\|\|.\|.\|\|\|\|\|\|\|\|\|\|\|\|\| | |
| | | 634 | hsa-miR-924 | 2 | GAGTCTTGTGATGTCTTGC | 20 |
| 129 | 84.2 | 635 | EMBOSS_001 | 143602 | gatataata-tggttcctg | 143619 |
| | | | | | \|\|\|\|.\|\|\|\| \|\|\|\|.\|\|\|\| | |
| | | 636 | hsa-miR-577 | 3 | GATAAAATATTGGTACCTG | 21 |
| 130 | 83.3 | 637 | EMBOSS_001 | 11057 | gtcgtgcacggcactcct | 11074 |
| | | | | | \|\|\|.\|.\|\|\|\|\|\|.\|\|\|\|\| | |
| | | 638 | hsa-miR-517a | 1 | GTCATACACGGCTCTCCT | 18 |
| 131 | 81.8 | 639 | EMBOSS_001 | 112288 | acgggttagagattttggaagc | 112309 |
| | | | | | \|\|\|\|\|\|\|\|\| \|.\|.\|\|\|\|.\|\|\| | |
| | | 640 | hsa-miR-518d- | 1 | ACGGGTTAG-GCTCTTGGGAGC | 21 |
| 132 | 80.0 | 641 | EMBOSS_001 | 18487 | cag-ccatcggcagatccac | 18505 |
| | | | | | \|\|\| \|\|\|\|.\|\|\|\|.\|\|.\|\|\| | |
| | | 642 | hsa-miR-510 | 2 | CCAGTCCATGGGCATATACAC | 21 |
| 133 | 80.0 | 643 | EMBOSS_001 | 3720 | atac--gcgccgactctctc | 3737 |
| | | | | | \|\|\|\| \|.\|\|.\|\|\|\|\|\|\|\|\| | |
| | | 644 | hsa-miR-300 | 2 | ATACAAGGGCAGACTCTCTC | 21 |
| 134 | 82.6 | 645 | EMBOSS_001 | 79410 | aggtagtgcgtcctggtgttggg | 79432 |
| | | | | | \|\|\|\|\|\|\|  .\|\|\|\|\|.\|\|\|\|\|\|\| | |
| | | 646 | hsa-miR-196b | 2 | AGGTAGT--TTCCTGTTGTTGGG | 22 |

TABLE 1B-continued

| | | | | | | |
|---|---|---|---|---|---|---|
| 135 | 81.0 | 647 | EMBOSS_001 | 152252 | gtagcattcgacagggctgtc<br>\|.\|\|\|\|\|\|.\|\|\|\|\|\|\|\|.\|\|<br>GCAGCATTGTACAGGGCTATC | 152272 |
| | | 648 | hsa-miR-107 | 2 | | 22 |
| 136 | 82.6 | 649 | EMBOSS_001 | 124044 | agaattgtaggct-tccatctgt<br>\|\|\|\|\|\|\|\|\|\|\|\|\|..\|\|\|\|\|\|\|\|<br>AGAATTGT-GGCTGGACATCTGT | 124065 |
| | | 650 | hsa-miR-219-2 | 1 | | 22 |
| 137 | 85.7 | 651 | EMBOSS_001 | 94864 | gtggtttcttttggagcagtt<br>\|\|\|..\|\|\|\|\|\|\|\|\|\|\|\|.\|\|\|<br>GTGCCTTCTTTTGGAGC-GTT | 94884 |
| | | 652 | hsa-miR-515-3 | 3 | | 22 |
| 138 | 81.0 | 653 | EMBOSS_001 | 36977 | caatacaacctaccctctttc<br>\|.\|\|\|\|\|\|.\|\|\|\|..\|\|\|\|\|\|<br>CTATACAATCTACTGTCTTTC | 36997 |
| | | 654 | hsa-let-7a* | 1 | | 21 |
| 139 | 81.0 | 655 | EMBOSS_001 | 48153 | attttaacattgaagt--ttt<br>\|.\|\|\|\|\|\|\|\|\|.\|\|\|\|\|   \|\|\|<br>ACTTTAACATGGAAGTGCTTT | 48171 |
| | | 656 | hsa-miR-302b* | 1 | | 21 |
| 140* | 80.0* | 657 | EMBOSS_001 | 117295 | ataataactggataatctttt<br>\|\|\|\|\|\|..\|\|\|.\|.\|\|\|\|\|\|\|<br>ATAATACATGGTTGATCTTT | 117314 |
| | | 658 | hsa-miR-369-3 | 2 | | 21 |
| 141 | 80.0 | 659 | EMBOSS_001 | 111324 | agtctta--tgtgctgccga<br>\|\|\|.\|\|\|  \|\|\|\|\|\|\|\|.\|\|<br>AGTATTAACTGTGCTGCTGA | 111341 |
| | | 660 | hsa-miR-16-1* | 3 | | 22 |
| 142 | 83.3 | 661 | EMBOSS_001 | 151325 | aagtgctgcgacattttagagtg<br>\|\|\|\|\|\|\|\|\|\|\|\|\|\|\|   \|\|\|.\|<br>AAGTGCTGCGACATTT---GAGCG | 151348 |
| | | 662 | hsa-miR-372 | 2 | | 22 |
| 143 | 81.8 | 663 | EMBOSS_001 | 127772 | ataatgat-ggctc--cggtgt<br>\|\|.\|\|\|\|\| \|\|\|\|\|   \|\|\|\|\|\|<br>ATCATGATGGGCTCCTCGGTGT | 127790 |
| | | 664 | hsa-miR-433 | 1 | | 22 |
| 144 | 81.0 | 665 | EMBOSS_001 | 147594 | taaacacatggtggttctcct<br>\|.\|\|\|\|\|.\|\|.\|\|\|\|\| \|\|\|\|<br>TCAACACTTGCTGGTT-TCCT | 147614 |
| | | 666 | hsa-miR-505 | 3 | | 22 |
| 145 | 83.3 | 667 | EMBOSS_001 | 117069 | ctgcacactgttgttttt<br>\|.\|\|\|\|\|\|\|\|\|\|.\|\|\|\|.\|<br>CAGCACACTGTGGTTTGT | 117086 |
| | | 668 | hsa-miR-497 | 4 | | 21 |
| 146 | 81.0 | 669 | EMBOSS_001 | 20411 | gcgtccca-acttgttttctg<br>\|\|\|.\|\|\|\| \|\|\|\|\|.\|\|\|\|.\|<br>GCGACCCATACTTGGTTTCAG | 20430 |
| | | 670 | hsa-miR-551b | 1 | | 21 |
| 147 | 84.2 | 671 | EMBOSS_001 | 5368 | acacgggcg--agcggcgg<br>\|\|\|\|\|\|\|\|\|\|   \|\|\|.\|\|\|\|<br>ACACGGGCGACAGCTGCGG | 5384 |
| | | 672 | hsa-miR-602 | 2 | | 20 |
| 148 | 85.0 | 673 | EMBOSS_001 | 132678 | cgacggg-atttagtgagca<br>\|.\|\|\|\| \|\|\|\|\| \|\|\|\|\|\|<br>CAACGGGTATTTATTGAGCA | 132696 |
| | | 674 | hsa-miR-95 | 3 | | 22 |
| 149 | 82.6 | 675 | EMBOSS_001 | 15968 | tccgtctcagtgtcacttatata<br>\|\|\|\|\|\|\|\|\|   \|\|.\|\|\|\| \|\|\|\|<br>TCCGTCTCA--GTTACTT-TATA | 15990 |
| | | 676 | hsa-miR-340* | 1 | | 20 |
| 150 | 81.0 | 677 | EMBOSS_001 | 108173 | ggt-ggcaccgaatccggaat<br>\|\|\| \|\|\|\|\|.\|\|\|\|\|\|.\|\|\|.\|<br>GGTGGGCACAGAATCTGGACT | 108192 |
| | | 678 | hsa-miR-541 | 2 | | 22 |
| 151 | 84.2 | 679 | EMBOSS_001 | 74659 | agtttatcagaatgatatt<br>\|\|.\|\|\|\|\|\|\|\|\|.\|\|\|\|.\|\|<br>AGCTTATCAGACTGATGTT | 74677 |
| | | 680 | hsa-miR-21 | 2 | | 20 |
| 152 | 89.5 | 681 | EMBOSS_001 | 22262 | gagtttcgtgatgtcttgc<br>\|\|\|\|.\|.\|\|\|\|\|\|\|\|\|\|\|\|<br>GAGTCTTGTGATGTCTTGC | 22280 |
| | | 682 | hsa-miR-924 | 2 | | 20 |
| 153 | 84.2 | 683 | EMBOSS_001 | 143602 | gatataata-tggttcctg<br>\|\|\|\|.\|\|\|\| \|\|\|\|\|.\|\|\|<br>GATAAAATATTGGTACCTG | 143619 |
| | | 684 | hsa-miR-577 | 3 | | 21 |

TABLE 1B-continued

| | | | | | | |
|---|---|---|---|---|---|---|
| 154 | 81.0 | 685 | EMBOSS_001 | 152252 | gtagcattcgacagggctgtc | 152272 |
| | | | | | \|.\|\|\|\|\|\|..\|\|\|\|\|\|\|\|.\|\| | |
| | | 686 | hsa-miR-107 | 2 | GCAGCATTGTACAGGGCTATC | 22 |
| 155 | 80.0 | 687 | EMBOSS_001 | 77701 | cgccgcgtcttgccaagtgg | 77720 |
| | | | | | \|\|\|\|...\|\|\|\|\|\|\|\|.\|\|\|\| | |
| | | 688 | hsa-miR-614 | 4 | CGCCTGTTCTTGCCAGGTGG | 23 |
| 156 | 80.0 | 689 | EMBOSS_001 | 61000 | acagtagtcaccggattggt | 61019 |
| | | | | | \|\|\|\|\|\|\|\|..\|..\|\|\|\|\|\| | |
| | | 690 | hsa-miR-199b- | 1 | ACAGTAGTCTGCACATTGGT | 20 |
| 157 | 81.8 | 691 | EMBOSS_001 | 112288 | acgggttagagattttggaagc | 112309 |
| | | | | | \|\|\|\|\|\|\|\|  \|.\|.\|\|\|\|.\|\|\| | |
| | | 692 | hsa-miR-125b- | 1 | ACGGGTTAG-GCTCTTGGGAGC | 21 |
| 158 | 80.0 | 693 | EMBOSS_001 | 3720 | atac--gcgccgactctctc | 3737 |
| | | | | | \|\|\|\|  .\|\|.\|\|\|\|\|\|\|\|\|\| | |
| | | 694 | hsa-miR-300 | 2 | ATACAAGGGCAGACTCTCTC | 21 |
| 159 | 81.0 | 695 | EMBOSS_001 | 36977 | caatacaacctaccctctttc | 36997 |
| | | | | | \|.\|\|\|\|\|\|.\|\|\|\|..\|\|\|\|\|\| | |
| | | 696 | hsa-let-7a* | 1 | CTATACAATCTACTGTCTTTC | 21 |
| 160 | 83.3 | 697 | EMBOSS_001 | 11057 | gtcgtgcacggcactcct | 11074 |
| | | | | | \|\|\|.\|.\|\|\|\|\|\|.\|\|\|\| | |
| | | 698 | hsa-miR-485-3 | 1 | GTCATACACGGCTCTCCT | 18 |
| 161 | 85.7 | 699 | EMBOSS_001 | 94864 | gtggtttcttttggagcagtt | 94884 |
| | | | | | \|\|\|..\|\|\|\|\|\|\|\|\|\|\|\|\| \|\|\| | |
| | | 700 | hsa-miR-515-3 | 3 | GTGCCTTCTTTTGGAGC-GTT | 22 |
| 162 | 82.6 | 701 | EMBOSS_001 | 124044 | agaattgtaggct-ccatctgt | 124065 |
| | | | | | \|\|\|\|\|\|\|\| \|\|\|\| ..\|\|\|\|\|\|\| | |
| | | 702 | hsa-miR-219-2 | 1 | AGAATTGT-GGCTGGACATCTGT | 22 |
| 163 | 80.0 | 703 | EMBOSS_001 | 18487 | cag-ccatcggcagatccac | 18505 |
| | | | | | \|\|\|  \|\|\|\|  \|\|\|\|.\|\|.\|\|\| | |
| | | 704 | hsa-miR-455-3 | 2 | CAGTCCATGGGCATATACAC | 21 |
| 164 | 82.6 | 705 | EMBOSS_001 | 79410 | aggtagtgcgtcctggtgttggg | 79432 |
| | | | | | \|\|\|\|\|\|\|  .\|\|\|\|.\|\|\|\|\|\|\|\| | |
| | | 706 | hsa-miR-196b | 2 | AGGTAGT--TTCCTGTTGTTGGG | 22 |
| 165 | 83.3 | 707 | EMBOSS_001 | 117069 | ctgcacactgttgttttt | 117086 |
| | | | | | \|.\|\|\|\|\|\|\|\|\|.\|\|\|\|.\| | |
| | | 708 | hsamiR-497 | 4 | CAGCACACTGTGGTTTGT | 21 |
| 166 | 83.3 | 709 | EMBOSS_001 | 151325 | aagtgctgcgacattttagagtg | 151348 |
| | | | | | \|\|\|\|\|\|\|\|\|\|\|\|\|\|\|   \|\|\|.\| | |
| | | 710 | hsa-miR-372 | 2 | AAGTGCTGCGACATTT---GAGCG | 22 |
| 167 | 81.0 | 711 | EMBOSS_001 | 20411 | gcgtccca-acttgttttctg | 20430 |
| | | | | | \|\|\|.\|\|\|\| \|\|\|\| \|\|\|\|.\| | |
| | | 712 | hsa-miR-551b | 1 | GCGACCCATACTTGGTTTCAG | 21 |
| 168 | 81.0 | 713 | EMBOSS_001 | 48153 | attttaacattgaagt--ttt | 48171 |
| | | | | | \|.\|\|\|\|\|\|\|\|\|\|.\|\|\|\|   \|\|\| | |
| | | 714 | hsa-miR-302b* | 1 | ACTTTAACATGGAAGTGCTTT | 21 |
| 169 | 81.0 | 715 | EMBOSS_001 | 147594 | taaacacatggtggttctcct | 147614 |
| | | | | | \|.\|\|\|\|\|.\|\|.\|\|\|\|\| \|\|\|\| | |
| | | 716 | hsa-miR-505 | 3 | TCAACACTTGCTGGTT-CCT | 22 |
| 170 | 80.0 | 717 | EMBOSS_001 | 117295 | ataataactggataatctttt | 117314 |
| | | | | | \|\|\|\|\|\|..\|\|\|.\|.\|\|\|\|\|\| | |
| | | 718 | hsa-miR-369-3 | 2 | ATAATACATGGTTGATCTTT | 21 |
| 171 | 80.0 | 719 | EMBOSS_001 | 111324 | agtctta--tgtgctgccga | 111341 |
| | | | | | \|\|.\|\|\|\|  \|\|\|\|\|\|\|\|\|.\|\| | |
| | | 720 | hsa-miR-16-1* | 3 | AGTATTAACTGTGCTGCTGA | 22 |
| 172 | 81.8 | 721 | EMBOSS_001 | 127772 | ataatgat-ggctc--cggtgt | 127790 |
| | | | | | \|\|.\|\|\|\|\| \|\|\|\|\|   \|\|\|\|\|\| | |
| | | 722 | hsa-miR-433 | 1 | ATCATGATGGGCTCCTCGGTGT | 22 |

TABLE 1B-continued

| 173 | 81.0 | 723 | EMBOSS_001 | 108173 | ggt-ggcaccgaatccggaat | 108192 |
|---|---|---|---|---|---|---|
| | | | | | ||| ||||| ||||| |||  | |
| | | 724 | hsa-miR-541 | 2 | GGTGGGCACAGAATCTGGACT | 22 |
| 174 | 84.2 | 725 | EMBOSS_001 | 5368 | acacgggcg--agcggcgg | 5384 |
| | | | | | ||||||||| ||| |||| | |
| | | 726 | hsa-miR-602 | 2 | ACACGGGCGACAGCTGCGG | 20 |
| 175 | 85.0 | 727 | EMBOSS_001 | 132678 | cgacggg-atttagtgagca | 132696 |
| | | | | | |.||||| ||||| ||||| | |
| | | 728 | hsa-miR-95 | 3 | CAACGGGTATTTATTGAGCA | 22 |
| 176 | 82.6 | 729 | EMBOSS_001 | 15968 | tccgtctcagtgtcacttatata | 15990 |
| | | | | | ||||||||| ||.|||| |||| | |
| | | 730 | hsa-miR-340* | 1 | TCCGTCTCA--GTTACTT-TATA | 20 |

TABLE 2

Human miRNA Showing mutual Homologies (> = 80%) with HHV-7

| No. | % Homology | SEQ ID NO: | | | Sequence Alignment Result | |
|---|---|---|---|---|---|---|
| 1 | 82.6 | 731 | EMBOSS_001 | 15472 | aaatgtggaaaaataggtaaatc | 15494 |
| | | | | | |.||||||||||||.|| |||| | |
| | | 732 | hsa-miR-576-3 | 2 | AGATGTGGAAAAATTGG--AATC | 22 |
| 2 | 83.3 | 733 | EMBOSS_001 | 5184 | ccagatggaagcacgttc | 5201 |
| | | | | | |.|||.||||||||.||| | |
| | | 734 | hsa-miR-518d- | 3 | CTAGAGGGAAGCACTTTC | 20 |
| 3 | 83.3 | 735 | EMBOSS_001 | 15100 | aagtttgaggatgtgcca | 15117 |
| | | | | | |.||||||||.|||||.| | |
| | | 736 | hsa-miR-105* | 5 | ATGTTTGAGCATGTGCTA | 22 |
| 4 | 85.0 | 737 | EMBOSS_001 | 94251 | agcatcacg-atatattggc | 94269 |
| | | | | | ||||.||| |.||||||||| | |
| | | 738 | hsa-miR-16 | 2 | AGCAGCACGTAAATATTGGC | 21 |
| 5* | 76.2* | 739 | EMBOSS_001 | 100165 | tatagactgatacgctttctg | 100185 |
| | | | | | |.||||..||..||||||||| | |
| | | 740 | hsa-miR-519a* | 2 | TCTAGAGGGAAGCGCTTTCTG | 22 |
| 6 | 81.8 | 741 | EMBOSS_001 | 33162 | tgtgccaaattcgataagtgaa | 33183 |
| | | | | | ||||.||.||| |||||.|||| | |
| | | 742 | hsa-miR-542-3 | 1 | TGTGACAGATT-GATAACTGAA | 21 |
| 7* | 76.2* | 743 | EMBOSS_001 | 100165 | tatagactgatacgctttctg | 100185 |
| | | | | | |.||||..||..||||||||| | |
| | | 744 | hsa-miR-522* | 2 | TCTAGAGGGAAGCGCTTTCTG | 22 |
| 8 | 81.8 | 745 | EMBOSS_001 | 20680 | aagat-ccagtaatgaagaact | 20700 |
| | | | | | |||.| |||||||  ||||||| | |
| | | 746 | hsa-miR-22 | 1 | AAGCTGCCAGT--TGAAGAACT | 20 |
| 9 | 80.0 | 747 | EMBOSS_001 | 122124 | ttgtacatttatggcttttcatt | 122148 |
| | | | | | |||||||||||..|||||||||| | |
| | | 748 | hsa-miR-493* | 1 | TTGTACATGGTA-GGC--TTTCATT | 22 |
| 10 | 77.3 | 749 | EMBOSS_001 | 112004 | agctaggggtgttgt-aaacag | 112024 |
| | | | | | ||||   ||||||||| ||.||| | |
| | | 750 | hsa-miR-138 | 1 | AGCT---GGTGTTGTGAATCAG | 19 |
| 11 | 80.0 | 751 | EMBOSS_001 | 7566 | tgggctgtggctgttgtgtg | 7585 |
| | | | | | |||||.|.|||.|.|||||| | |
| | | 752 | hsa-miR-1228* | 2 | TGGGCGGGGCAGGTGTGTG | 21 |
| 12 | 80.0 | 753 | EMBOSS_001 | 38009 | aaagtaactgtagtattttc | 38028 |
| | | | | | ||||||.||||.|||| ||.| | |
| | | 754 | hsa-miR-562 | 1 | AAAGTAGCTGTACCATTTGC | 20 |
| 13 | 85.7 | 755 | EMBOSS_001 | 105006 | tga-ctatgaatttgacagtc | 105025 |
| | | | | | ||| |||||||| |||||||.| | |
| | | 756 | hsa-miR-192 | 2 | TGACCTATGAA-TTGACAGCC | 21 |

TABLE 2-continued

| | | | | | | |
|---|---|---|---|---|---|---|
| 14 | 80.0 | 757 | EMBOSS_001 | 136213 | agagattacatcctgctaag | 136232 |
| | | | | | |.|.|.||||.|||||||| | |
| | | 758 | hsa-miR-374b | 1 | ATATAATACAACCTGCTAAG | 20 |
| 15 | 84.2 | 759 | EMBOSS_001 | 119859 | tctcacagtgctgaaagct | 119877 |
| | | | | | |.||||||||||| |.||| | |
| | | 760 | hsa-miR-101* | 5 | TATCACAGTGCTG-ATGCT | 22 |
| 16 | 85.0 | 761 | EMBOSS_001 | 8852 | aatcaagcgaggttgtagac | 8871 |
| | | | | | ||||||||.||.|| |||| | |
| | | 762 | hsa-miR-551b* | 3 | AATCAAGCGTGGGTG-AGAC | 21 |
| 17 | 84.2 | 763 | EMBOSS_001 | 94511 | gtcaatccttttagagatt | 94529 |
| | | | | | ||..||||||||||.|| | |
| | | 764 | hsa-miR-519b- | 4 | GTGCATCCTTTTAGAGGTT | 22 |
| 18 | 84.2 | 765 | EMBOSS_001 | 74711 | aac-acttaatacaggagt | 74728 |
| | | | | | ||| .|||.||||||||| | |
| | | 766 | hsa-miR-337-5 | 2 | AACGGCTTCATACAGGAGT | 20 |
| 19 | 88.9 | 767 | EMBOSS_001 | 127691 | gcactagcatatatttgc | 127708 |
| | | | | | |||||||||.||.|||| | |
| | | 768 | hsa-miR-96 | 5 | GCACTAGCACATTTTGC | 22 |
| 20 | 80.0 | 769 | EMBOSS_001 | 4750 | tcacaaacccaaggctcaca | 4769 |
| | | | | | ||.||.||||||||||..|| | |
| | | 770 | hsa-miR-532-3 | 3 | TCCCACACCCAAGGCTTGCA | 22 |
| 21* | 77.3* | 771 | EMBOSS_001 | 124994 | atcacttataggaaactttttt | 125015 |
| | | | | | |||||..|.|||.|||||||.| | |
| | | 772 | hsa-miR-377 | 1 | ATCACACAAAGGCAACTTTTGT | 22 |
| 22 | 81.0 | 773 | EMBOSS_001 | 122606 | cgcactgttgg-actgtcctg | 122625 |
| | | | | | ||||||||.|| ||| |.||| | |
| | | 774 | hsa-miR-106b* | 2 | CGCACTGTGGGTACT-TGCTG | 21 |
| 23* | 81.8* | 775 | EMBOSS_001 | 62445 | aaaaatatttgtgattttcgcc | 62466 |
| | | | | | ||||.||.||||.||||.||| | |
| | | 776 | hsa-miR-548b- | 1 | AAAAGTAATTGTGGTTTTGGCC | 22 |
| 24* | 73.1* | 777 | EMBOSS_001 | 93591 | ccaatattacttttgatatggattta | 93616 |
| | | | | | |||||||||| |.||.| |.|||| | |
| | | 778 | hsa-miR-16-2* | 1 | CCAATATTAC-TGTGCT---GCTTTA | 21 |
| 25 | 83.3 | 779 | EMBOSS_001 | 7170 | agccag--ggac-ggagc | 7184 |
| | | | | | ||||| ||| ||||| | |
| | | 780 | hsa-miR-575 | 2 | AGCCAGTTGGACAGGAGC | 19 |
| 26 | 80.0 | 781 | EMBOSS_001 | 61226 | tgttcgttc--cacgcttga | 61243 |
| | | | | | |||||||| |.|||.||| | |
| | | 782 | hsa-miR-378 | 3 | TGTTCGTTCGGCTCGCGTGA | 22 |
| 27 | 81.0 | 783 | EMBOSS_001 | 134732 | aagttct-acacattcccact | 134754 |
| | | | | | ||||||| |.|||.|||.||| | |
| | | 784 | hsa-miR-148a* | 2 | AAGTTCTGAGACACTCCGACT | 22 |
| 28 | 84.2 | 785 | EMBOSS_001 | 114374 | agatgaagaaatgttagct | 114392 |
| | | | | | |||||||.|.|| ||||| | |
| | | 786 | hsa-miR-143 | 3 | AGATGAAGCACTG-TAGCT | 20 |
| 29* | 80.0* | 787 | EMBOSS_001 | 65946 | attaagtagaa--caatact | 65963 |
| | | | | | ||.||||||| ||.|||| | |
| | | 788 | hsa-miR-142-5 | 2 | ATAAAGTAGAAAGCACTACT | 21 |
| 30 | 77.3 | 789 | EMBOSS_001 | 30468 | cacaccaggtgtatgacacatt | 30489 |
| | | | | | |||||| ||.||||||||.|| | |
| | | 790 | hsa-miR-220a | 2 | CACACC--GTATCTGACACTTT | 21 |
| 31* | 77.8* | 791 | EMBOSS_001 | 87949 | gactga----atatcagt | 87962 |
| | | | | | ||||| |||||||| | |
| | | 792 | hsa-miR-24-1* | 5 | TACTGAGCTGATATCAGT | 22 |

TABLE 2-continued

| | | | | | | | |
|---|---|---|---|---|---|---|---|
| 32 | 83.3 | 793 | EMBOSS_001 | 22199 | ttttgcaccttt---agt | 22213 |
| | | 794 | hsa-miR-507 | 1 | TTTTGCACCTTTTGGAGT | 18 |
| 33 | 82.6 | 795 | EMBOSS_001 | 84678 | ctgattgcatat-ttggtttaga | 84699 |
| | | 796 | hsa-miR-29b-1 | 2 | CTGGTTTCATATGGTGGTTTAGA | 24 |
| 34 | 85.7 | 797 | EMBOSS_001 | 87109 | atatgtttgaactatatcagg | 87129 |
| | | 798 | hsa-miR-190 | 3 | ATATGTTTGA--TATATTAGG | 21 |
| 35* | 85.0 | 799 | EMBOSS_001 | 14607 | gcaaatccttgtcaaaaatg | 14626 |
| | | 800 | hsa-miR-19b | 4 | GCAAATCCATG-CAAAACTG | 22 |
| 36 | 81.8 | 801 | EMBOSS_001 | 7144 | ctgaactcgttacgcgtcctcc | 7165 |
| | | 802 | hsa-miR-943 | 1 | CTG-ACT-GTTGC-CGTCCTCC | 19 |
| 37* | 72.0* | 803 | EMBOSS_001 | 61453 | cacagcatccaattttccgggtaga | 61477 |
| | | 804 | hsa-miR-892b | 1 | CACTGGCTCC---TTTCTGGGTAGA | 22 |
| 38* | 81.0* | 805 | EMBOSS_001 | 13836 | gtcctgtggactaaagtcctg | 13856 |
| | | 806 | hsa-miR-146b- | 2 | GCCCTGTGGACT-CAGTTCTG | 21 |
| 49 | 81.0 | 807 | EMBOSS_001 | 80450 | acactctg---ttactttgc | 80467 |
| | | 808 | hsa-miR-603 | 2 | ACACACTGCAATTACTTTTGC | 22 |
| 40 | 80.0 | 809 | EMBOSS_001 | 123440 | ttttgcataattg--ttaca | 123457 |
| | | 810 | hsa-miR-19a* | 3 | TTTTGCATAGTTGCACTACA | 22 |
| 41 | 84.2 | 811 | EMBOSS_001 | 20355 | tgcctgttaaaagtgaacc | 20373 |
| | | 812 | hsa-miR-938 | 1 | TGCC-CTTAAAGGTGAACC | 18 |
| 42* | 81.0* | 813 | EMBOSS_001 | 6239 | acacacatacacacacacaca | 6259 |
| | | 814 | hsa-miR-574-3 | 2 | ACGCTCATGCACACACCCACA | 22 |
| 43 | 81.0 | 815 | EMBOSS_001 | 42911 | tctcggtgaacagttctcttt | 42931 |
| | | 816 | hsa-miR-128 | 1 | TCACAGTGAACCGGTCTCTTT | 21 |
| 44 | 80.0 | 817 | EMBOSS_001 | 6967 | ttacccgattaactttttat | 6986 |
| | | 818 | hsa-miR-409-5 | 4 | TTACCCGAGCAACTTTGCAT | 23 |
| 45 | 81.8 | 819 | EMBOSS_001 | 38606 | tttgttgactttggac-acatc | 38626 |
| | | 820 | hsa-miR-455-5 | 1 | TATG-TGCCTTTGGACTACATC | 21 |
| 46 | 80.0 | 821 | EMBOSS_001 | 102437 | ccttgcagaagctgttcgtt | 102456 |
| | | 822 | hsa-miR-623 | 4 | CCTTGCAGGGGCTGTTGGGT | 23 |
| 47 | 88.9 | 823 | EMBOSS_001 | 82530 | cagcattgtacagcggta | 82547 |
| | | 824 | hsa-miR-103 | 3 | CAGCATTGTACAGGGCTA | 20 |
| 48 | 84.2 | 825 | EMBOSS_001 | 67073 | ccatttcattatcagagtt | 67091 |
| | | 826 | hsa-miR-660 | 4 | CCATTGCA-TATCGGAGTT | 21 |
| 49 | 86.4 | 827 | EMBOSS_001 | 26583 | tcaat-cactcag-actttgt | 26602 |
| | | 828 | hsa-miR-148a | 1 | TCAGTGCACTACAGAACTTTGT | 22 |
| 50 | 80.8 | 829 | EMBOSS_001 | 109590 | atgcatattgtgtattttataggtcc | 109615 |
| | | 830 | hsa-miR-586 | 2 | ATGCAT----TGTATTTT-TAGGTCC | 22 |

TABLE 2-continued

| | | | | | | |
|---|---|---|---|---|---|---|
| 51 | 86.4 | 831 | EMBOSS_001 | 51712 | ttaca-ttgttcaa--agttac | 51730 |
| | | | | | |||||| ||||||||| ||||||| | |
| | | 832 | hsa-miR-582-5 | 1 | TTACAGTTGTTCAACCAGTTAC | 22 |
| 52 | 83.3 | 833 | EMBOSS_001 | 11076 | aaacatcctccaccccgc | 11093 |
| | | | | | ||||||||.|||.|.|| | |
| | | 834 | hsa-miR-30b | 4 | AAACATCCTACACTCAGC | 21 |
| 53 | 81.0 | 835 | EMBOSS_001 | 54823 | tgagacgagcatctagcttgt | 54843 |
| | | | | | |.|||||||...||||||| | |
| | | 836 | hsa-miR-208a | 2 | TAAGACGAGCAAAAAGCTTGT | 22 |
| 54 | 81.8 | 837 | EMBOSS_001 | 133484 | taaggccagcctaaaaatactt | 133505 |
| | | | | | |||.||| ||||||||.||| | |
| | | 838 | hsa-miR-365 | 1 | TAATGCC--CCTAAAAATCCTT | 20 |
| 55 | 84.2 | 839 | EMBOSS_001 | 122847 | atgctgtgatattgttagc | 122865 |
| | | | | | |.|||||| |||||||||| | |
| | | 840 | hsa-miR-449b | 1 | AGGCAGTG-TATTGTTAGC | 18 |
| 56 | 80.0 | 841 | EMBOSS_001 | 30209 | aagtgtgttccaagttttttcagtgg | 30233 |
| | | | | | ||||| .||||  |.|||||||||| | |
| | | 842 | hsa-miR-302c | 2 | AAGTG-CTTCCA--TGTTTCAGTGG | 23 |
| 57 | 81.8 | 843 | EMBOSS_001 | 63319 | aaagttctgaaaaatcatagat | 63340 |
| | | | | | |||.|.||| |||||||.|||| | |
| | | 844 | hsa-miR-606 | 1 | AAACTACTG-AAAATCAAAGAT | 21 |
| 58 | 83.3 | 845 | EMBOSS_001 | 5184 | ccagatggaagcacgttc | 5201 |
| | | | | | |||||.|||||.||.||| | |
| | | 846 | hsa-miR-520a- | 3 | CCAGAGGGAAGTACTTTC | 20 |
| 59* | 89.5* | 847 | EMBOSS_001 | 23752 | atcaacagccatctaattg | 23770 |
| | | | | | |||||||||.||| |||||| | |
| | | 848 | hsa-miR-421 | 1 | ATCAACAGACAT-TAATTG | 18 |
| 60 | 82.6 | 849 | EMBOSS_001 | 52740 | aagacat-ggaaacag-cacctc | 52760 |
| | | | | | ||||||| |||.|.|| |||||| | |
| | | 850 | hsa-miR-641 | 2 | AAGACATAGGATAGAGTCACCTC | 24 |
| 61 | 81.8 | 851 | EMBOSS_001 | 31326 | tctgaaatttccattttttcag | 31347 |
| | | | | | |||||||||  ||.||.||||| | |
| | | 852 | hsa-miR-146a* | 3 | TCTGAAATT--CAGTTCTTCAG | 22 |
| 62 | 84.2 | 853 | EMBOSS_001 | 79168 | ttgcatagccaaacaaaag | 79186 |
| | | | | | ||||||||.|  |||||||| | |
| | | 854 | hsa-miR-153 | 1 | TTGCATAGTC--ACAAAAG | 17 |
| 63 | 83.3 | 855 | EMBOSS_001 | 5184 | ccagatggaagcacgttc | 5201 |
| | | | | | |||||.|||.||||.||| | |
| | | 856 | hsa-miR-525-5 | 3 | CCAGAGGGATGCACTTTC | 20 |
| 64 | 80.0 | 857 | EMBOSS_001 | 14382 | tagtagactgtcat--cgta | 14399 |
| | | | | | |||||||||.|| ||  |||| | |
| | | 858 | hsa-miR-411 | 1 | TAGTAGACCGT-ATAGCGTA | 19 |
| 65 | 82.6 | 859 | EMBOSS_001 | 62226 | actaatttcattttggagatcag | 62248 |
| | | | | | |||.||||| ||||.|.|||| | |
| | | 860 | hsa-miR-29a* | 1 | ACTGATTTC-TTTTGGTGTTCAG | 22 |
| 66 | 81.8 | 861 | EMBOSS_001 | 18490 | gaatgtggtaagaagtttgtat | 18511 |
| | | | | | ||||||  .||||||||.||||| | |
| | | 862 | hsa-miR-1 | 3 | GAATGT--AAAGAAGTATGTAT | 22 |
| 67 | 84.2 | 863 | EMBOSS_001 | 58325 | tgttttctatagaatcagt | 58343 |
| | | | | | |||.||||.||| |||||| | |
| | | 864 | hsa-miR-581 | 4 | TGTGTTCTCTAG-ATCAGT | 21 |
| 68 | 81.0 | 865 | EMBOSS_001 | 44627 | tcgatttttcacagaaatccc | 44647 |
| | | | | | ||.||||||||.|||.|||||| | |
| | | 866 | hsa-miR-145 | 2 | TCCAGTTTTCCCAGGAATCCC | 22 |
| 69 | 81.0 | 867 | EMBOSS_001 | 79428 | accaggtgac--gtctagaca | 79446 |
| | | | | | |.||||||||  || |||||| | |
| | | 868 | hsa-miR-552 | 1 | AACAGGTGACTGGT-TAGACA | 20 |

TABLE 2-continued

| | | | | | | |
|---|---|---|---|---|---|---|
| 70* | 84.2* | 869 | EMBOSS_001 | 56012 | gtgcgtcacacaactttt<br>\|\|\|\|.\|\|\|\|\|.\|\|\|\|\|.\|<br>GTGCATCACAGAACTTTGT | 56030 |
| | | 870 | hsa-miR-148b | 4 | | 22 |
| 71 | 73.1 | 871 | EMBOSS_001 | 37440 | ctgcacaag-tactaaatg-cttgct<br>\|\|\|\|.\|\|\|\|  \|\|\|     \|\|  \|\|\|\|\|\|<br>CTGCGCAAGCTAC----TGCCTTGCT | 37463 |
| | | 872 | hsa-let-7i* | 1 | | 22 |
| 72 | 83.3 | 873 | EMBOSS_001 | 113823 | ttca--taattcagaata<br>\|\|\|\|  \|\|\|\|\|\|\|\|.\|\|\|<br>TTCAAGTAATTCAGGATA | 113838 |
| | | 874 | hsa-miR-26b | 1 | | 18 |
| 73 | 80.0 | 875 | EMBOSS_001 | 106019 | caagat-gcttcaatggttc<br>\|\|\|\|.\| \|\|\|\|\|.\|\|\|\|.\|\|<br>CAAGCTCGCTTCTATGGGTC | 106037 |
| | | 876 | hsa-miR-99A* | 1 | | 20 |
| 74 | 81.0 | 877 | EMBOSS_001 | 143036 | caggcttattcccc-cccgtt<br>\|\|\|\|\|\|.\|.\|\|\|\|\| \|\|\|\|.\|<br>CAGGCTCAGTCCCCTCCCGAT | 143055 |
| | | 878 | hsa-miR-484 | 2 | | 22 |
| 75 | 85.7 | 879 | EMBOSS_001 | 94973 | aacaaacatgatgaacttatt<br>\|\|\|\|\|\|\|\|\|.\|\|.\|\|\|\|.\|\|<br>AACAAACATGGTGCACTTCTT | 94993 |
| | | 880 | hsa-miR-495 | 2 | | 22 |
| 76 | 80.0 | 881 | EMBOSS_001 | 116205 | agaacagccgttctcattgt<br>\|\|\|.\|\|...\|\|\|\|\|\|\|\|\|\|<br>AGACCATGGGTTCTCATTGT | 116224 |
| | | 882 | hsa-miR-591 | 1 | | 20 |
| 77 | 85.7 | 883 | EMBOSS_001 | 105006 | tga-ctatgaatttgacagtc<br>\|\|\| \|\|\|\|\|\|\|\| \|\|\|\|\|\|.\|<br>TGACCTATGAA-TTGACAGAC | 105025 |
| | | 884 | hsa-miR-215 | 2 | | 21 |
| 78 | 81.0 | 885 | EMBOSS_001 | 97069 | acttgctctgtgaaacaatgt<br>\|\|\|\|...\|..\|\|\|\|\|\|\|\|\|\|\|<br>ACTTGGGCACTGAAACAATGT | 97089 |
| | | 886 | hsa-miR-635 | 1 | | 21 |
| 79 | 81.0 | 887 | EMBOSS_001 | 4215 | cctgttctccatgccctgcct<br>\|\|\|\|\|\|\|\|\|\|\|..\|.\|\|.\|\|<br>CCTGTTCTCCATTACTTGGCT | 4235 |
| | | 888 | hsa-miR-26b* | 1 | | 21 |
| 80 | 85.0 | 889 | EMBOSS_001 | 65823 | tgatatgttt--tattcggt<br>\|\|\|\|\|\|\|\|\|\|  \|\|\|\|.\|\|\|<br>TGATATGTTTGATATTGGGT | 65840 |
| | | 890 | hsa-miR-190b | 1 | | 20 |
| 81 | 81.0 | 891 | EMBOSS_001 | 125316 | ttttcagattctacaggggga<br>\|\|.\|\|\|\|\|.\|\|\|.\|\|\|\|\|\|.\|<br>TTATCAGAATCTCCAGGGGTA | 125336 |
| | | 892 | hsa-miR-361-5 | 1 | | 21 |
| 82 | 85.4 | 893 | EMBOSS_001 | 123644 | gtggttcattttaaagggtt<br>\|\|\|.\|\|\|.\|\|\|\|\|.\|\|\|\|\|<br>GTGCTTCCTTTTAGAGGGTT | 123663 |
| | | 894 | hsa-miR-520F | 3 | | 22 |
| 83 | 81.0 | 895 | EMBOSS_001 | 37973 | tttgcagattgaattatgatt<br>\|\|.\|\|\|\|.\|\|\|.\|\|\|\|.\|\|\|<br>TTAGCAGGTTGTATTATCATT | 37993 |
| | | 896 | hsa-miR-374b* | 2 | | 22 |
| 84 | 83.3 | 897 | EMBOSS_001 | 141942 | cttacactgtagtgtttg<br>\|\|\|\|\|.\|.\|.\|\|\|\|\|\|\|\|\|<br>CTTACCCAGCAGTGTTTG | 141959 |
| | | 898 | hsa-miR-200c* | 4 | | 21 |
| 85 | 84.2 | 899 | EMBOSS_001 | 123644 | gtggttcattttaaagggt<br>\|\|\|.\|\|\|.\|\|\|\|\|.\|\|\|\|\|<br>GTGCTTCCTTTTAGAGGGT | 123662 |
| | | 900 | hsa-miR-520c- | 4 | | 22 |
| 86* | 80.0* | 901 | EMBOSS_001 | 13248 | gtccatgtagtgcagcttta<br>\|\|.\|\|\|.\|\|\|\|\|\|\|\|  \|\|\|<br>GTGCATCAGTGCAG--TTA | 13267 |
| | | 902 | hsa-miR-18b | 5 | | 22 |
| 87 | 81.0 | 903 | EMBOSS_001 | 97917 | aatagacatcttccacaaaaa<br>\|\|\|\|\|.\|\|\|\|.\|\|\|\|\|\|.\|\|<br>AATAG-TATCTACCACAATAA | 97937 |
| | | 904 | hsa-miR-633 | 3 | | 22 |
| 88 | 84.2 | 905 | EMBOSS_001 | 102558 | tacagtttagctgaagtac<br>\|\|\|\|\|\|.\|\|\|.\|\|\|.\|.\|\|\|\|<br>TACAGTATAGATGATGTAC | 102576 |
| | | 906 | hsa-miR-144 | 1 | | 19 |

TABLE 2-continued

| | | | | | | |
|---|---|---|---|---|---|---|
| 89* | 88.9* | 907 | EMBOSS_001 | 63773 | gtggaaataatctctact<br>\|\|.\|\|\|\|.\|\|\|\|\|\|\|\|\|\|\|<br>GTTGAAACAATCTCTACT | 63790 |
| | | 908 | hsa-miR-653 | 3 | | 20 |
| 90 | 80.0 | 909 | EMBOSS_001 | 30470 | cacca-ggtgtatgacacat<br>\|\|\|\|\|.\|\|\|\|.\|\|\|\|\|\|.\|<br>CACCACCGTGTCTGACACTT | 30488 |
| | | 910 | hsa-miR-220b | 2 | | 21 |
| 91 | 84.2 | 911 | EMBOSS_001 | 62561 | tttcagttagatgattaca<br>\|\|\|\|\|\|\|.\|\|.\|\|\|\|\|\|\|\|<br>TTTCAGTCGGATGTTTACA | 62579 |
| | | 912 | hsa-miR-30e* | 2 | | 20 |
| 92* | 77.3* | 913 | EMBOSS_001 | 88070 | gactgtaacttttggattata<br>\|\|.\|\|\|\|.\|.\|\|\|\|\|\|\|.\|\|.\|<br>GATTGTAGCCTTTTGGAGTAGA | 88091 |
| | | 914 | hsa-miR-508-3 | 2 | | 23 |
| 93 | 80.0 | 915 | EMBOSS_001 | 8052 | aaggccacgctgtaaatgac<br>\|\|\|\|.\|\|\|\|\|\|.\|\|.\|\|\|\|.\|<br>AAGG-CACGCGGTGAATGCC | 8071 |
| | | 916 | hsa-miR-124 | 2 | | 20 |
| 94 | 88.9 | 971 | EMBOSS_001 | 63336 | tagatggcagcactatct<br>\|\|\|\|\|\|\|\|.\|\|\|\|\|\|.\|\|\|<br>TAGATGGAAGCACTGTCT | 63353 |
| | | 918 | hsa-miR-517* | 5 | | 22 |
| 95 | 83.3 | 919 | EMBOSS_001 | 58453 | tattgcttatcttgatag<br>\|\|.\|\|\|\|.\|\|\|.\|\|\|\|\|\|<br>TAATGCTAATCGTGATAG | 58470 |
| | | 920 | hsa-miR-155 | 2 | | 19 |
| 96 | 81.8 | 921 | EMBOSS_001 | 62445 | aaaaatatttgtgattttcgcc<br>\|\|\|\|.\|\|.\|\|\|\|\|.\|\|\|\|.\|\|\|<br>AAAAGTAATTGTGGTTTTTGCC | 62466 |
| | | 922 | hsa-miR-548d- | 1 | | 22 |
| 97 | 81.0 | 923 | EMBOSS_001 | 75388 | tagtaggtgtgcaggtagagt<br>\|\|\|\|\|\|\|\|\|\|\|.\|\|\|..\|\|.\|\|<br>TAGTAGGTGTCCAGTAAGTGT | 75408 |
| | | 924 | hsa-miR-325 | 3 | | 23 |
| 98 | 81.0 | 925 | EMBOSS_001 | 102541 | aggctgtg---ttagctgatt<br>\|\|\|\|.\|\|\|   \|\|\|\|\|\|\|\|\|\|<br>AGGCAGTGTCATTAGCTGATT | 102558 |
| | | 926 | hsa-miR-34b* | 2 | | 22 |
| 99 | 80.0 | 927 | EMBOSS_001 | 89458 | atcgtttcaaaagatggtct<br>\|\|\|\|\|\|.\|\|\|\|\|.\|\|  \|\|\|\|<br>ATCGTCTCAAATGA--GTCT | 89477 |
| | | 928 | hsa-miR-136* | 5 | | 22 |
| 100* | 77.3* | 929 | EMBOSS_001 | 123160 | tttggattttctgcatctata<br>\|\|.\|\|\|\|..\|\|.\|\|\|\|\|.\|\|\|<br>TTGGGATCATTTTGCATCCATA | 123181 |
| | | 930 | hsa-miR-450b- | 1 | | 19 |
| 101 | 85.0 | 931 | EMBOSS_001 | 94251 | agcatcac-gatatattggc<br>\|\|\|\|.\|\|\| \|\|.\|\|\|\|\|\|\|\|\|<br>AGCAGCACAGAAATATTGGC | 94269 |
| | | 932 | hsa-miR-195 | 2 | | 21 |
| 102 | 84.2 | 933 | EMBOSS_001 | 82508 | tcggtctcagtctcctcag<br>\|\|\|\|\|\|\|.\|\|.\|.\|\|\|\|\|\|<br>TCGGTCTGAGGCCCCTCAG | 82526 |
| | | 934 | hsa-miR-423-3 | 4 | | 22 |
| 103 | 81.0 | 935 | EMBOSS_001 | 42931 | tcatttggaaagaggtaaatg<br>\|\|\|\|.\|.\|\|\|\|\|.\|\|\|\|.\|\|<br>TCATCTGCAAAGAAGTAAGTG | 42951 |
| | | 936 | hsa-miR-452* | 2 | | 22 |
| 104 | 84.2 | 937 | EMBOSS_001 | 68654 | ataaagctagaca--cgaa<br>\|\|\|\|\|\|\|\|\|\|.\|  \|\|\|\|<br>ATAAAGCTAGATAACCGAA | 68670 |
| | | 938 | hsa-miR-9* | 1 | | 19 |
| 105 | 80.0 | 939 | EMBOSS_001 | 4244 | cttcctcttccacgcccaga<br>\|\|\|.\|\|\|.\|\|\| \|\|\|\|\|.\|\|<br>CTTGCTCGTCC-CGCCCGCA | 4263 |
| | | 940 | hsa-miR-636 | 5 | | 23 |
| 106 | 80.0 | 941 | EMBOSS_001 | 43249 | cacattac---gtcagacct<br>\|\|\|\|\|\|\|\|   \|\|\| \|\|\|\|\|<br>CACATTACACGGTC-GACCT | 43265 |
| | | 942 | hsa-miR-323-3 | 1 | | 19 |
| 107 | 81.0 | 943 | EMBOSS_001 | 132800 | gttctaaagcaagatctgtaa<br>\|\|\|\| \|\|\|.\|.\|\|\|\|\|\|.\|\|\|<br>GTTC-AAATCCAGATCTATAA | 132820 |
| | | 944 | hsa-miR-607 | 1 | | 20 |

TABLE 2-continued

| | | | | | | |
|---|---|---|---|---|---|---|
| 108 | 88.3 | 945 | EMBOSS_001 | 5184 | ccagatggaagcacgttc<br>\|.\|\|\|.\|\|\|\|\|\|\|\|\|.\|\|\|<br>CTAGAGGGAAGCACTTTC | 5201 |
| | | 946 | hsa-miR-520c- | 3 | | 20 |
| 109 | 84.2 | 947 | EMBOSS_001 | 133868 | gtaaacaacccgga-tgga<br>\|\|\|\|\|\|\|\|.\|\|\|.\|\|\ \|\|\|\|<br>GTAAACATCCCCGACTGGA | 133885 |
| | | 948 | hsa-miR-30d | 2 | | 20 |
| 110 | 84.2 | 949 | EMBOSS_001 | 119595 | gcgagcctgtgatccccac<br>\|.\|.\|\|\|\|\|\|\|\|\|\|\|\|.\|\|<br>GGGCGCCTGTGATCCCAAC | 119613 |
| | | 950 | hsa-miR-566 | 1 | | 19 |
| 111 | 80.0 | 951 | EMBOSS_001 | 20631 | ctagtcctgattcaaaaagt<br>\|\|\|\|\|\|\|\|\|\|.\|\|\|...\|\|\|<br>CTAGTCCTGACTCAGCCAGT | 20650 |
| | | 952 | hsa-miR-554 | 2 | | 21 |
| 112 | 81.8 | 933 | EMBOSS_001 | 55412 | catcttacacgacagcattgta<br>\|\|\|\|\|\|\|\|\|..\|.\|\|\|\|\|\|\|.\|<br>CATCTTACTGGGCAGCATTGGA | 55433 |
| | | 934 | hsa-miR-200b* | 1 | | 22 |
| 113 | 88.9 | 955 | EMBOSS_001 | 73102 | tctggagggtag-acttt<br>\|\|\|\|\|\|\|\|\|\| \|\|\|\|\|<br>TCTGGAGGGAAGCACTTT | 73118 |
| | | 956 | hsa-miR-518* | 3 | | 20 |
| 114 | 84.2 | 957 | EMBOSS_001 | 137534 | ggtactagtttatcctgtt<br>\|\|\|\|.\|\|\|\|\|\|.\|.\|\|\|\|\|<br>GGTAGTAGTTTGTGCTGTT | 137552 |
| | | 958 | hsa-let-7i | 4 | | 22 |
| 115* | 78.3* | 959 | EMBOSS_001 | 87002 | tcagtggccttgaaagaactagg<br>\|\|\|\|\|\| \|.\|\|\|.\|\|\|\|\|\|.\|\|<br>TCAGTG--CATGACAGAACTTGG | 87024 |
| | | 960 | hsa-miR-152 | 1 | | 21 |
| 116 | 75.0 | 961 | EMBOSS_001 | 108371 | ggttattggaaatgagatttt<br>\|\|\|\|..\|\|\ \|\|.\|\|\ \|\|\|\|\|<br>GGTTCCTGGGGATGGGATTT | 108390 |
| | | 962 | hsa-miR-23A* | 3 | | 22 |
| 117 | 82.6 | 963 | EMBOSS_001 | 12558 | agtaagttctt-caggacaacac<br>\|\|\|\|.\|\|\|\|\| \|\|\|\|\|\|..\|\|<br>AGTATGTTCTTCCAGGACAGAAC | 12579 |
| | | 964 | hsa-miR-567 | 1 | | 23 |
| 118 | 85.0 | 965 | EMBOSS_001 | 120972 | atggagataagaaatataaa<br>\|\|\|\|\|\|\| \|\|\|.\|\|\|.\|\|\|<br>ATGGAGAT-AGATATAGAAA | 120991 |
| | | 966 | hsa-miR-620 | 1 | | 19 |
| 119 | 84.2 | 967 | EMBOSS_001 | 16140 | cttcagttc-cgtgtctcc<br>\|\|.\|\|\|\|.\| \|\|\|\|\|\|\|\|<br>CTACAGTGCACGTGTCTCC | 16157 |
| | | 968 | hsa-miR-139-5 | 2 | | 20 |
| 120 | 81.0 | 969 | EMBOSS_001 | 75940 | tccatttgttttg----tgga<br>\|\|\|\|\|\|\|\|\|\|\|\| \|\|\|<br>TCCATTTGTTTTGATGATGGA | 75956 |
| | | 970 | hsa-miR-136 | 3 | | 23 |
| 121 | 81.8 | 971 | EMBOSS_001 | 85162 | cagggcaaaaatattgacaaag<br>\|\|\|.\|\|\|\|.\|.\|\|\|\|\|.\|\|\|\|<br>CAGTGCAATAGTATTGTCAAAG | 85183 |
| | | 972 | hsa-miR-301a | 1 | | 22 |
| 122 | 85.0 | 973 | EMBOSS_001 | 78013 | gaaaatgcattgcttttaga<br>\|\|\|\|.\|\|\| \|\|.\|\|\|\|\|\|\|\|<br>GAAAGTGC-TTCCTTTTAGA | 78032 |
| | | 974 | hsa-miR-526b* | 1 | | 19 |
| 123 | 85.0 | 975 | EMBOSS_001 | 30221 | agtttttcagtggcgagttt<br>\|\|\|\|.\|\|\|\|\|\|\|\|.\|\|.\|\|<br>AGTTCTTCAGTGGCAAGCTT | 30240 |
| | | 976 | hsa-miR-22* | 1 | | 20 |
| 124 | 86.7 | 977 | EMBOSS_001 | 62313 | tgaaat-ttta-gaccaatag<br>\|\|\|\|\|\| \|\|\|\| \|\|\|\|\|.\|\|\|<br>TGAAATGTTTAGGACCACTAG | 62331 |
| | | 978 | hsa-miR-203 | 2 | | 22 |
| 125 | 81.0 | 979 | EMBOSS_001 | 48811 | ctgtcgaactttccaccgtca<br>\|\|.\|.\|\|\|\|\|\|\|\|.\|\| \|\|\|<br>CTATAGAACTTTCC-CCCTCA | 48831 |
| | | 980 | hsa-miR-625* | 3 | | 22 |
| 126 | 85.0 | 981 | EMBOSS_001 | 12893 | cttttgccac-aactctcaa<br>\|.\|\|\|\|\|\|\|\| \|\|\| \|\|\|\|\|<br>CTGTTGCCACTAAC-CTCAA | 12911 |
| | | 982 | hsa-miR-744* | 1 | | 19 |

TABLE 2-continued

| | | | | | | | |
|---|---|---|---|---|---|---|---|
| 127 | 81.0 | 983 | EMBOSS_001 | 86333 | caatcgaacgttgataagtac | 133885 | |
| | | | | | \|.\|\|\|\|\|.\|\|\|\|\|\| .\|\|\|\| | | |
| | | 984 | hsa-miR-181a* | 2 | CCATCGACCGTTGAT-TGTAC | 20 | |
| 128 | 89.5 | 985 | EMBOSS_001 | 5508 | acattc-acctggcggtga | 119613 | |
| | | | | | \|\|\|\|\|\|  \|\|\|\|\| .\|\|\|\|\| | | |
| | | 986 | hsa-miR-181c | 2 | ACATTCAACCTGTCGGTGA | 19 | |
| 129 | 83.3 | 987 | EMBOSS_001 | 5184 | ccagatggaagcacgttc | 20650 | |
| | | | | | \|.\|\|\|.\|\|\|\|\|\|\|\|.\|\|\| | | |
| | | 988 | hsa-miR-526a | 3 | CTAGAGGGAAGCACTTTC | 21 | |
| 130* | 76.2* | 989 | EMBOSS_001 | 100165 | tatagactgatacgctttctg | 100185 | |
| | | | | | \|.\|\|\|\|..\|\|..\|\|\|\|\|\|\|\|\|\|\| | | |
| | | 990 | hsa-miR-518e* | 2 | TCTAGAGGGAAGCGCTTTCTG | 22 | |
| 131* | 72.0* | 991 | EMBOSS_001 | 20425 | aggctgcatcttttcagtgaagcta | 20449 | |
| | | | | | \|\|\| \|\|\|\|\|\|\|\|    \|\|\|\|.\|\|.\|\| | | |
| | | 992 | hsa-miR-18a | 3 | AGG-TGCATCT----AGTGCAGATA | 22 | |
| 132 | 81.0 | 993 | EMBOSS_001 | 15615 | aaagtgctca-agt--aagta | 15632 | |
| | | | | | \|\|\|\|\|\|\|\|\| \|\|\| .\|\|\| | | |
| | | 994 | hsa-miR-20b | 2 | AAAGTGCTCATAGTGCAGGTA | 22 | |
| 133 | 84.2 | 995 | EMBOSS_001 | 128748 | atgagttaattgtaa-atg | 128765 | |
| | | | | | \|\|\|\|.\|.\|\|\|\|\|\|\|\| \|\|\| | | |
| | | 996 | hsa-miR-556-5 | 2 | ATGAGCTCATTGTAATATG | 20 | |
| 134 | 81.0 | 997 | EMBOSS_001 | 124253 | tgattcagaagacctgcttct | 124273 | |
| | | | | | \|\|\|\|.\|\|\|.\| \|\|\|\|\|\|.\|\|\| | | |
| | | 998 | hsa-miR-640 | 2 | TGATCCAGGA-ACCTGCCTCT | 21 | |
| 135 | 81.8 | 999 | EMBOSS_001 | 97212 | aagcttgta--tatacggaatg | 97231 | |
| | | | | | \|\|\|\|\|\|\|\|\|  \|\|\|\| \|\|.\|\|\| | | |
| | | 1000 | hsa-miR-100* | 2 | AAGCTTGTATCTATA-GGTATG | 22 | |
| 136* | 76.2* | 1001 | EMBOSS_001 | 100165 | tatagactgatacgctttctg | 100185 | |
| | | | | | \|.\|\|\|\|..\|\|..\|\|\|\|\|\|\|\|\|\|\| | | |
| | | 1002 | hsa-miR-523* | 2 | TCTAGAGGGAAGCGCTTTCTG | 22 | |
| 137 | 83.3 | 1003 | EMBOSS_001 | 85856 | caatagactgcactttgg | 85873 | |
| | | | | | \|\|.\|\|\|.\|\|\|\|\|\|.\|\|\|\| | | |
| | | 1004 | hsa-miR-199a- | 2 | CAGTAGTCTGCACATTGG | 19 | |
| 138 | 84.2 | 1005 | EMBOSS_001 | 6563 | tcctcatctcccacttccc | 6581 | |
| | | | | | \|\|\|\|.\|\|\|\|\|.\|.\|\|\|\| | | |
| | | 1006 | hsa-miR-877* | 1 | TCCTCTTCTCCCTCCTCCC | 19 | |
| 139 | 84.2 | 1007 | EMBOSS_001 | 58900 | cttgaagtaccgaatttgt | 58918 | |
| | | | | | \|.\|\|.\|\|.\|\|\|\|\|\|\|\|\|\|\| | | |
| | | 1008 | hsa-miR-10b | 4 | CCTGTAGAACCGAATTTGT | 22 | |
| 140 | 85.7 | 1009 | EMBOSS_001 | 60562 | aaaatggtt--ctttagtagt | 60580 | |
| | | | | | \|\|\|\|\|\|\|\|\|  \|\|\|\|\|\|\| \|\|\| | | |
| | | 1010 | hsa-miR-522 | 1 | AAAATGGTTCCCTTTAG-AGT | 20 | |
| 141 | 81.8 | 1011 | EMBOSS_001 | 30534 | tcctatggacatatacattttt | 30555 | |
| | | | | | \|\|\|\|\|\|\|  \|\|\|\|\|\|\|.\|.\|\|\| | | |
| | | 1012 | hsa-miR-202* | 2 | TCCTATG--CATATACTTCTTT | 21 | |
| 142* | 85.0* | 1013 | EMBOSS_001 | 120307 | ggaatggaagcacttcatta | 120326 | |
| | | | | | \|.\|\|\|.\|\|\|\|\|\|\|\|\|\|\| \|\|\| | | |
| | | 1014 | hsa-miR-106a* | 2 | GCAATGTAAGCACTTC-TTA | 21 | |
| 143 | 84.2 | 1015 | EMBOSS_001 | 75658 | tgacaactctttgagttaa | 75676 | |
| | | | | | \|\|\|\|.\|\|\|\|\|\|\|.\|\|.\|\| | | |
| | | 1016 | hsa-miR-888* | 4 | TGACACCTCTTTGGGTGAA | 22 | |
| 144 | 82.6 | 1017 | EMBOSS_001 | 37408 | tattgctctaagactacacgaag | 37430 | |
| | | | | | \|\|\|\|\|\|\|\| \|\|\|\|\|.\|\|\|.\|\|.\|\| | | |
| | | 1018 | hsa-miR-137 | 2 | TATTGCT-TAAGAATACGCGTAG | 23 | |
| 145 | 83.3 | 1019 | EMBOSS_001 | 85856 | caatagactgcactttgg | 85873 | |
| | | | | | \|\|.\|\|\|.\|\|\|\|\|\|.\|\|\|\| | | |
| | | 1020 | hsa-miR-199b- | 2 | CAGTAGTCTGCACATTGG | 19 | |

TABLE 2-continued

| | | | | | | |
|---|---|---|---|---|---|---|
| 146 | 81.8 | 1021 | EMBOSS_001 | 71303 | atagtcattgtgaatgtctttc<br>\|.\|\|\|\| \|\|\|\|\| \|\|\|\|\|\|\|\|\|.\| | 71324 |
| | | 1022 | hsa-miR-924 | 1 | AGAGTC-TTGTG-ATGTCTTGC | 20 |
| 147 | 83.3 | 1023 | EMBOSS_001 | 39508 | tctgtcc--tctgcgtag<br>\|.\|\|\|\|\| \|\|\|\|\|\|\|\|\| | 39523 |
| | | 1024 | hsa-miR-892a | 4 | TGTGTCCTTTCTGCGTAG | 21 |
| 148 | 85.7 | 1025 | EMBOSS_001 | 57900 | tagataattaat-ttggtacc<br>\|\|\|\|\|\|\|\| \|\|\| \|\|\|\|\|\|\| | 57919 |
| | | 1026 | hsa-miR-577 | 1 | TAGATAA--AATATTGGTACC | 19 |
| 149 | 88.9 | 1027 | EMBOSS_001 | 65003 | atctaaggaag-gtgtgg<br>\|\|.\|\|\|\|\|\|\|\| \|\|\|\|\|\| | 65019 |
| | | 1028 | hsa-miR-206 | 5 | ATGTAAGGAAGTGTGTGG | 22 |
| 150 | 86.4 | 1029 | EMBOSS_001 | 11271 | tggtaatgtgacaattggtgtt<br>\|\|\| .\|\|\|\|\|\|\|\| \|\|\|\|\|\|\| | 112292 |
| | | 1030 | hsa-miR-122 | 1 | TGG-AGTGTGACAA-TGGTGTT | 20 |
| 151 | 88.9 | 1031 | EMBOSS_001 | 125034 | gtgcattgtaatt-catt<br>\|\|\|\|\|\|\|\|\|\|.\|\| \|\|\|\| | 125050 |
| | | 1032 | hsa-miR-33a | 1 | GTGCATTGTAGTTGCATT | 18 |
| 152 | 81.0 | 1033 | EMBOSS_001 | 120550 | agatgttgccc---gtgaatt<br>\|\|\|.\|\|\|\|\|\| \|\|\|\|\|\|\|\| | 120567 |
| | | 1034 | hsa-miR-377* | 1 | AGAGGTTGCCCTTGGTGAATT | 21 |
| 153 | 81.8 | 1035 | EMBOSS_001 | 88253 | tcatacacgaagcccttcctct<br>\|\|\|\|\|\|\|\|\| \|\|.\| \|\|\|\|\|\| | 88274 |
| | | 1036 | hsa-miR-485-3 | 2 | TCATACACG--GCTC-TCCTCT | 20 |
| 154 | 83.3 | 1037 | EMBOSS_001 | 107329 | tatgacactgaaagaatt<br>\|\|\|\|.\|\|\|\|\|..\|\|\|\|\|\| | 107346 |
| | | 1038 | hsa-miR-183 | 1 | TATGGCACTGGTAGAATT | 18 |
| 155* | 78.3* | 1039 | EMBOSS_001 | 42169 | ggtggtttatgcaaatt--ttca<br>\|\|\|\|\|\|\|\|\| \|\|\|\|.\| \|\|\|\| | 42189 |
| | | 1040 | hsa-miR-876-3 | 2 | GGTGGTTTA--CAAAGTAATTCA | 22 |
| 156 | 84.2 | 1041 | EMBOSS_001 | 93592 | caatattactttttgatatg<br>\|\|.\|\|\|\|\|\|\|\|\|\|.\|\|.\| | 93610 |
| | | 1042 | hsa-miR-126* | 1 | CATTATTACTTTTGGTACT | 19 |
| 157 | 85.0 | 1043 | EMBOSS_001 | 67199 | ctatagaatcaact-tcttt<br>\|\|\|\|\|.\|\|\|\| \|\|\| \|\|\|\|\| | 67217 |
| | | 1044 | hsa-let-7a* | 1 | CTATACAATCTACTGTCTTT | 20 |
| 158* | 76.2* | 1045 | EMBOSS_001 | 100165 | tatagactgatacgctttctg<br>\|.\|\|\|..\|\|..\|\|\|\|\|\|\|\|\|\| | 100185 |
| | | 1046 | hsa-miR-519b- | 2 | TCTAGAGGGAAGCGCTTTCTG | 22 |
| 159 | 81.0 | 1047 | EMBOSS_001 | 112519 | agagagtgtgtgacagtgtgt<br>\|\|.\|.\|\|\|\|\|\|\|..\|\|\|\|\|\|\|\| | 112539 |
| | | 1048 | hsa-miR-574-5 | 3 | AGTGTGTGTGTGTGAGTGTGT | 23 |
| 160 | 80.0 | 1049 | EMBOSS_001 | 114087 | gggttttcagggacatatga<br>\|\|\|\|\|\|\|\|.\|\|\|\|.\|\|.\|\|\|\| | 114106 |
| | | 1050 | hsa-miR-193b* | 3 | GGGTTTTGAGGGCGAGATGA | 22 |
| 161 | 81.0 | 1051 | EMBOSS_001 | 51780 | caacattaactgt--tgctga<br>\|\|..\|\|\|\|\|\|\|\| \|\|\|\|\| | 51798 |
| | | 1052 | hsa-miR-16-1* | 2 | CAGTATTAACTGTGCTGCTGA | 22 |
| 162* | 76.2* | 1053 | EMBOSS_001 | 100165 | tatagactgatacgctttctg<br>\|.\|\|\|..\|\|..\|\|\|\|\|\|\|\|\|\| | 100185 |
| | | 1054 | hsa-miR-519c | 2 | TCTAGAGGGAAGCGCTTTCTG | 22 |
| 163 | 86.4 | 1055 | EMBOSS_001 | 22803 | actgttg-tcatatgc-actct<br>\|\|\|\|\|\|\| \|.\|\|\|\|\| \|\|\|\|\| | 22822 |
| | | 1056 | hsa-miR-367* | 1 | ACTGTTGCTAATATGCAACTCT | 22 |
| 164 | 80.0 | 1057 | EMBOSS_001 | 51212 | aacaataaagcaaatctgtg<br>\|\|\|\|..\|.\|\|\|\|\|\|.\|\|\|\|\|\| | 51231 |
| | | 1058 | hsa-miR-499-3 | 1 | AACATCACAGCAAGTCTGTG | 20 |

TABLE 2-continued

| No. | % Homology | SEQ ID NO: | | | Sequence Alignment Result | |
|---|---|---|---|---|---|---|
| 165 | 83.3 | 1059 | EMBOSS_001 | 34595 | acaaaggtaa-ccatttc | 34611 |
| | | 1060 | hsa-miR-520d- | 3 | ``|||||||.|| ||.||||``<br>ACAAAGGGAAGCCCTTTC | 20 |
| 166 | 81.8 | 1061 | EMBOSS_001 | 109067 | tgtagggtttcctaatatgtgg | 109088 |
| | | 1062 | hsa-miR-142-3 | 1 | ``|||||.||||||||.|.|||``<br>TGTAGTGTTTCCTACTTTATGG | 22 |
| 167 | 83.3 | 1063 | EMBOSS_001 | 59709 | ttaccgtacactgctgaa | 59726 |
| | | 1064 | hsa-miR-200a* | 5 | ``||||||.|||.|||||.|``<br>TTACCGGACAGTGCTGGA | 22 |
| 168 | 85.0 | 1065 | EMBOSS_001 | 74342 | ttcaaacggtatttattga | 74361 |
| | | 1066 | hsa-miR-95 | 1 | ``||||||..||||  |||||||||``<br>TTCAACGGGTA-TTTATTGA | 19 |
| 169 | 85.7 | 1067 | EMBOSS_001 | 131468 | ccgtctcattt--tttatagc | 131486 |
| | | 1068 | hsa-miR-340* | 2 | ``|||||||||.||  |||||||||``<br>CCGTCTCAGTTACTTTATAGC | 22 |
| 170* | 75.0* | 1069 | EMBOSS_001 | 17297 | tgcaaacatcattgcacacaggaa | 17320 |
| | | 1070 | hsa-miR-30e | 1 | ``||.|||||||.|||   ||.||||``<br>TGTAAACATCCTTG---ACTGGAA | 21 |

TABLE 3

Human miRNA Showing mutual Homologies (>=80%) with GBV-C

| No. | % Homology | SEQ ID NO: | | | Sequence Alignment Result | |
|---|---|---|---|---|---|---|
| 1 | 84.2 | 1071 | EMBOSS_001 | 4915 | gtgtt--cagcggaccatg | 4931 |
| | | 1072 | hsa-miR-124* | 2 | ``|||||  |||||||||.||``<br>GTGTTCACAGCGGACCTTG | 20 |
| 2 | 84.2 | 1073 | EMBOSS_001 | 8043 | gacag-tagcataactgaa | 8060 |
| | | 1074 | hsa-miR-542-3 | 4 | ``|||||.|.|||||||||``<br>GACAGATTG-ATAACTGAA | 21 |
| 3 | 84.2 | 1075 | EMBOSS_001 | 7341 | cttacctttgaatgtgaca | 7359 |
| | | 1076 | hsa-miR-192 | 1 | ``||.||||.||||| |||||``<br>CTGACCTATGAAT-TGACA | 18 |
| 4 | 84.2 | 1077 | EMBOSS_001 | 1951 | acaactgcatgctcttggg | 1969 |
| | | 1078 | hsa-miR-125b- | 3 | ``||||.| ||.||||||||||``<br>ACAAGT-CAGGCTCTTGGG | 20 |
| 5 | 82.4 | 1079 | EMBOSS_001 | 8136 | tactatgcctcaggcac | 8152 |
| | | 1080 | hsa-miR-550* | 6 | ``|||   |.|||||||||||``<br>TAC--TCCCTCAGGCAC | 20 |
| 6* | 78.9* | 1081 | EMBOSS_001 | 6723 | aatgtggcaccctct--gaggtt | 6743 |
| | | 1082 | hsa-miR-519b- | 1 | ``||.|| |||.|||.| |||||``<br>AAAGT-GCATCCTTTTAGAGGTT | 22 |
| 7* | 70.8* | 1083 | EMBOSS_001 | 956 | aaagtgggaaa--gtgagttttgg | 977 |
| | | 1084 | hsa-miR-548b- | 2 | ``|||||    || ||| |||||||``<br>AAAGT----AATTGTG-GTTTTGG | 20 |
| 8 | 84.2 | 1085 | EMBOSS_001 | 2826 | gtccttctctttggcctgt | 2844 |
| | | 1086 | hsa-miR-520a- | 4 | ``||.|||.|||||.||||``<br>GTGCTTCCCTTTGGACTGT | 22 |
| 9 | 83.3 | 1087 | EMBOSS_001 | 3196 | aggatg-tgaatcatttg | 3212 |
| | | 1088 | hsa-miR-580 | 4 | ``||.||| ||||||||||.|``<br>AGAATGATGAATCATTAG | 21 |
| 10 | 81.8 | 1089 | EMBOSS_001 | 5662 | cgcgcctggcgtctgccctcct | 5683 |
| | | 1090 | hsa-miR-615-3 | 3 | ``||.||||||  ||||  |||||.|``<br>CGAGCCTGG-GTCT-CCCTCTT | 22 |
| 11 | 85.0 | 1091 | EMBOSS_001 | 2559 | acattcgaggtggacttc | 2578 |
| | | 1092 | hsa-miR-543 | 3 | ``|||||||.||||   ||||||``<br>ACATTCGCGGTG--CACTTC | 20 |

TABLE 3-continued

Human miRNA Showing mutual Homologies (>=80%) with GBV-C

| No. | % Homology | SEQ ID NO: | Sequence Alignment Result | | | |
|---|---|---|---|---|---|---|
| 12 | 85.0 | 1093 | EMBOSS_001 | 6969 | gcacttatctcggttactga | 6988 |
| | | | | | \|\|\|\|\|\|.\|\|\|\|\|\|  \|\|\|\| | |
| | | 1094 | hsa-miR-25 | 5 | GCACTTGTCTCGGT--CTGA | 22 |
| 13 | 80.0 | 1095 | EMBOSS_001 | 8438 | ctccacttggcttgctgagt | 8457 |
| | | | | | \|\|\|.\|\|\|\|\|.\|.\|.\|\|\|\|\|\| | |
| | | 1096 | hsa-miR-618 | 4 | CTCTACTTGTCCTTCTGAGT | 23 |
| 14 | 80.0 | 1097 | EMBOSS_001 | 8037 | tgcttcgacagtagcataac | 8056 |
| | | | | | \|\|.\|\|\|.\|\|\|\|\| \|\|\|\|.\|\| | |
| | | 1098 | hsa-miR-33a* | 4 | TGTTTCCACAGT-GCATCAC | 22 |
| 15 | 83.3 | 1099 | EMBOSS_001 | 6300 | agtcgctgcctctgtggc | 6317 |
| | | | | | \|\|..\|\|\|\|\|\|\|\|\|\|.\|\|\| | |
| | | 1100 | hsa-miR-646 | 2 | AGCAGCTGCCTCTGAGGC | 19 |
| 16 | 83.3 | 1101 | EMBOSS_001 | 1327 | tgccagccttttgccaag | 1344 |
| | | | | | \|\|\|\|\|.\|\|\|\|\|\|.\|\|.\|\| | |
| | | 1102 | hsa-miR-1227 | 3 | TGCCACCCTTTTCCCCAG | 20 |
| 17 | 81.0 | 1103 | EMBOSS_001 | 1661 | ctg--ctggcccga--gaccg | 1677 |
| | | | | | \|\|\|  \|\|\|\|\|\|\|\|\|  \|\|\|\|\| | |
| | | 1104 | hsa-miR-874 | 1 | CTGCCCTGGCCCGAGGGACCG | 21 |
| 18* | 77.3* | 1105 | EMBOSS_001 | 1638 | tcctgcggcacct--gtgtgag | 1657 |
| | | | | | \|\|\|\| .\|\|.\|\|\|\|  \|\|\|\|\|\|\| | |
| | | 1106 | hsa-miR-362-5 | 3 | TCCT-TGGAACCTAGGTGTGAG | 23 |
| 19 | 80.0 | 1107 | EMBOSS_001 | 3131 | gcagtgcgtcatgggtttac | 3150 |
| | | | | | \|\|\|\|...\|.\|\|\|\| \|\|\|\|\|\|\| | |
| | | 1108 | hsa-miR-15b | 3 | GCAGCACATCAT-GGTTTAC | 21 |
| 20 | 81.0 | 1109 | EMBOSS_001 | 2406 | gtgctgtac-tttagatggtt | 2425 |
| | | | | | \|\|\|\|\| \|.\| \|\|\|\|\|\|.\|\|\|\| | |
| | | 1110 | hsa-miR-520f | 3 | GTGCT-TCCTTTTAGAGGGTT | 22 |
| 21 | 80.0 | 1111 | EMBOSS_001 | 4267 | agattc-ccttttatgggca | 4285 |
| | | | | | \|\|\|\|\|\| \|\|\|\|.\|\|\|\|.\|.\| | |
| | | 1112 | hsa-miR-376a* | 3 | AGATTCTCCTTCTATGAGTA | 22 |
| 22* | 77.8* | 1113 | EMBOSS_001 | 5504 | tgttg--acaagctcttc | 5519 |
| | | | | | \|\|\|\|\|  \|\|\|\|.\|\|\|\|.\| | |
| | | 1114 | hsa-miR-653 | 2 | TGTTGAAACAATCTCTAC | 19 |
| 23 | 80.0 | 1115 | EMBOSS_001 | 6481 | gga--cgtctg-gctgggct | 6497 |
| | | | | | \|\|\|  \|\|\|\|\|\|\| \|\|\|.\|\|\|\| | |
| | | 1116 | hsa-miR-127-3 | 3 | GGATCCGTCTGAGCTTGGCT | 22 |
| 24* | 77.3* | 1117 | EMBOSS_001 | 2856 | gattg-ggcc--ttggaggaga | 2874 |
| | | | | | \|\|\|\|\| .\|\|\|  \|\|\|\|\|.\|\|\| | |
| | | 1118 | hsa-miR-508-3 | 2 | GATTGTAGCCTTTTGGAGTAGA | 23 |
| 25 | 80.0 | 1119 | EMBOSS_001 | 3668 | agggcacgcagtaggaatgc | 3687 |
| | | | | | \|.\|\|\|\|\|\|\|.\|\|  \|\|\|\|\|\| | |
| | | 1120 | hsa-miR-124 | 2 | AAGGCACGCGGT--GAATGC | 19 |
| 26 | 85.0 | 1121 | EMBOSS_001 | 4522 | tggaggaggtcgttgaggtg | 4541 |
| | | | | | \|\|\|\|\|.\|\|\|\|\|.\|\|\| \|\|\|\| | |
| | | 1122 | hsa-miR-432 | 4 | TGGAGTAGGTCATTG-GGTG | 22 |
| 27 | 81.0 | 1123 | EMBOSS_001 | 2921 | gtgctgtgtgatggcgggtga | 2941 |
| | | | | | \|\|\|\| \|\|\|\|\|\|\|...\|\|\|\|.\|\| | |
| | | 1124 | hsa-miR-210 | 3 | GTGC-GTGTGACAGCGGCTGA | 22 |
| 28* | 72.7* | 1125 | EMBOSS_001 | 3299 | tcgggatcctgacttacatcca | 3320 |
| | | | | | \|.\|\|\|\|\|\|.\|  .\|\|.\|\|\|\|\|\|\| | |
| | | 1126 | hsa-miR-450b- | 1 | TTGGGATCAT--TTTGCATCCA | 20 |
| 29 | 75.0 | 1127 | EMBOSS_001 | 1302 | tgccctaacggcccctgggtgtgg | 1325 |
| | | | | | \|\|\|\|\|\|\|\|..\|\|\|\|\|\|   \|.\|\|\| | |
| | | 1128 | hsa-miR-18b* | 1 | TGCCCTAAATGCCCCT---TCTGG | 21 |

TABLE 3-continued

Human miRNA Showing mutual Homologies (>=80%) with GBV-C

| No. | % Homology | SEQ ID NO: | | | Sequence Alignment Result | | |
|---|---|---|---|---|---|---|---|
| 30 | 81.0 | 1129 | EMBOSS_001 | 554 | ggcagtccttct--gctcctt | 572 | |
|  |  |  |  |  | \|\|\|\|\|..\|\|\|\|\|  \|\|\|\|\|\|\| |  |  |
|  |  | 1130 | hsa-miR-612 | 5 | GGCAGGGCTTCTGAGCTCCTT | 25 | |
| 31 | 81.8 | 1131 | EMBOSS_001 | 3981 | tgtgggcatgatacaactgctt | 4002 | |
|  |  |  |  |  | \|\|\|\|\|\| \|\|\|.\|\| \|\|\|.\|\|\|\| |  |  |
|  |  | 1132 | hsa-miR-299-3 | 3 | TGTGGG-ATGGTA-AACCGCTT | 22 | |
| 32 | 80.0 | 1133 | EMBOSS_001 | 1203 | gggttgac-ttggcagacct | 1221 | |
|  |  |  |  |  | \|\|\|\|\|.\|\| \|\|\|\|.\|\|\|.\|\| |  |  |
|  |  | 1134 | hsa-miR-629 | 2 | GGGTTTACGTTGGGAGAACT | 21 | |
| 33 | 76.2 | 1135 | EMBOSS_001 | 2190 | gactttgta-tttgtcctgtt | 2209 | |
|  |  |  |  |  | \|\|...\|.\|\|\| \|\|\|\|\|.\|\|\|\|\| |  |  |
|  |  | 1136 | hsa-let-7i | 2 | GAGGTAGTAGTTTGTGCTGTT | 22 | |
| 34 | 80.0 | 1137 | EMBOSS_001 | 2829 | cttctc---tttggcc-tgt | 2844 | |
|  |  |  |  |  | \|\|\|\|\|\|   \|\|\|\|\|\|\| \|\|\| |  |  |
|  |  | 1138 | hsa-miR-942 | 2 | CTTCTCTGTTTTGGCCATGT | 21 | |
| 35 | 81.8 | 1139 | EMBOSS_001 | 9328 | acagtgcactgtgat--ctgaa | 9347 | |
|  |  |  |  |  | \|\|\|\|\|  \|\|\|\|\|\|\|\|  \|\|\|\|\| |  |  |
|  |  | 1140 | hsa-miR-101 | 2 | ACAGT--ACTGTGATAACTGAA | 21 | |
| 36 | 83.3 | 1141 | EMBOSS_001 | 8958 | gggggtttccctc-tctc | 8974 | |
|  |  |  |  |  | \|\|\|.\|\|\|\|\|.\|\|\| \|\|\|\| |  |  |
|  |  | 1142 | hsa-miR-609 | 2 | GGGTGTTTCTCTCATCTC | 19 | |
| 37 | 83.3 | 1143 | EMBOSS_001 | 5523 | ggagggtgggcggctgtg | 5540 | |
|  |  |  |  |  | \|\|\|\|\|\|..\|\|.\|\|\|\|\|\|\| |  |  |
|  |  | 1144 | hsa-miR-149* | 3 | GGAGGGACGGGGGCTGTG | 20 | |
| 38 | 81.0 | 1145 | EMBOSS_001 | 9328 | acagtgcactgtgatctgaag | 9348 | |
|  |  |  |  |  | \|\|\|\|\|\|\|\|\|\| \|\|\| \|\|\|..\|\| |  |  |
|  |  | 1146 | hsa-miR-139-5 | 4 | ACAGTGCAC-GTG-TCTCCAG | 22 | |
| 49 | 80.0 | 1147 | EMBOSS_001 | 2845 | tcgacgcgttggattgggcc | 2864 | |
|  |  |  |  |  | \|\|\|\|\| \|\|\|\|  \|\|\|\|\|..\|\| |  |  |
|  |  | 1148 | hsa-miR-181a* | 5 | TCGAC-CGTT-GATTGTACC | 22 | |
| 40 | 83.3 | 1149 | EMBOSS_001 | 2753 | acccctgacctttgcctg | 2770 | |
|  |  |  |  |  | \|\|\|.\|\|\|\|\|\|\|.\|\|\|.\|\|\| |  |  |
|  |  | 1150 | hsa-miR-181a- | 1 | ACCACTGACCGTTGACTG | 18 | |
| 41 | 81.0 | 1151 | EMBOSS_001 | 5243 | agaccagg-ccacgcctcagc | 5262 | |
|  |  |  |  |  | \|\|\|\|\|.\|\| \|\|\|..\|\|\|\|\|\|\|\| |  |  |
|  |  | 1152 | hsa-miR-631 | 1 | AGACCTGGCCCAGACCTCAGC | 21 | |
| 42 | 81.0 | 1153 | EMBOSS_001 | 9188 | tgggaggcatgg-tggttact | 9207 | |
|  |  |  |  |  | \|\|\|\|\|\|\| \|\|\| \|\|.\|\|\|\|\|\| |  |  |
|  |  | 1154 | hsa-miR-30b* | 2 | TGGGAGG--TGGATGTTTACT | 20 | |
| 43* | 76.2* | 1155 | EMBOSS_001 | 7819 | aagaccggaaggaggagaagg | 7839 | |
|  |  |  |  |  | \|\|\|\|\|.\|\|\|.\|.\|  \|\|\|\|\|\| |  |  |
|  |  | 1156 | hsa-miR-483-5 | 1 | AAGACGGGAGGAA--AGAAGG | 19 | |
| 44 | 85.0 | 1157 | EMBOSS_001 | 3512 | aacaccttgtacttgccagg | 3531 | |
|  |  |  |  |  | \|\|\|.\|\| \|\|\|.\|\|\|\|\|\|\|\|\|\| |  |  |
|  |  | 1158 | hsa-miR-614 | 2 | AACGCC-TGTTCTTGCCAGG | 20 | |
| 45 | 81.0 | 1159 | EMBOSS_001 | 4897 | actggccctcttggtgggtg | 4917 | |
|  |  |  |  |  | \|\|\|\|.\|.\|\|\|\|\|\|  \|\|\|\|\|\| |  |  |
|  |  | 1160 | hsa-miR-888* | 2 | ACTGACACCTCTT--TGGGTG | 20 | |
| 46 | 82.4 | 1161 | EMBOSS_001 | 8412 | gcatcattggacacggc | 8428 | |
|  |  |  |  |  | \|\|\|.\|\|\|\|\|.\|\|\|.\|\|\| |  |  |
|  |  | 1162 | hsa-miR-107 | 2 | GCAGCATTGTACAGGGC | 18 | |
| 47 | 83.3 | 1163 | EMBOSS_001 | 6155 | tgtctgggacctgtggga | 6172 | |
|  |  |  |  |  | \|\|\|\|\|\|\|\|...\|\|\|\|\|\|\|\|\| |  |  |
|  |  | 1164 | hsa-miR-632 | 2 | TGTCTGCTTCCTGTGGGA | 19 | |

TABLE 3-continued

Human miRNA Showing mutual Homologies (>=80%) with GBV-C

| No. | % Homology | SEQ ID NO: | Sequence Alignment Result | | | |
|---|---|---|---|---|---|---|
| 48 | 83.3 | 1165 | EMBOSS_001 | 3725 | ggcacggt-tcactaggc | 3741 |
|  |  |  |  |  | \|\|\|\|\|\|\|\| \|\|\|..\|\|\|\| |  |
|  |  | 1166 | hsa-miR-564 | 2 | GGCACGGTGTCAGCAGGC | 19 |
| 49 | 83.3 | 1167 | EMBOSS_001 | 175 | gtgggtct-taagagaag | 191 |
|  |  |  |  |  | \|\|\|.\|\|\|\| \|\|\|\|\|.\|\|\| |  |
|  |  | 1168 | hsa-miR-627 | 1 | GTGAGTCTCTAAGAAAAG | 18 |
| 50 | 80.0 | 1169 | EMBOSS_001 | 4562 | catctccctgcggacagtgc | 4581 |
|  |  |  |  |  | \|\|\|\|\|..\|  \|\|\|\|\|\|\|\|\|\|\| |  |
|  |  | 1170 | hsa-miR-200a* | 1 | CATCTTAC--CGGACAGTGC | 18 |
| 51 | 80.0 | 1171 | EMBOSS_001 | 3680 | aggaatgctcgtgtctgtgc | 3699 |
|  |  |  |  |  | \|\|\|\|\|\|\|.\|\|.\| \|\|\|.\|\|\| |  |
|  |  | 1172 | hsa-miR-613 | 1 | AGGAATGTTCCT-TCTTTGC | 19 |

TABLE 4

Human miRNA Showing mutual Homologies (>=80%) with HIV-1 and with one or more co-infecting viruses (i.e., GBV-C (>=70%), HHV-6 (>=80%) and HHV-7 (>=70%))

| No. | % Homology | SEQ ID NO: | Sequence Alignment Result | | | | Common With | Target |
|---|---|---|---|---|---|---|---|---|
| 1 | 80.0 | 1173 | AF033819.3 | 811 | TAGAAGAGAAG-GCTTTCAG | 829 | HHV-7 (76.2) | HIV (gag, gag-pol) HHV (U60) |
|  |  | 1174 | hsa-miR-519a* | 4 | TAG-AGGGAAGCGCTTTCTG | 22 |  |  |
| 2 | 80.0 | 1175 | AF033819.3 | 811 | TAGAAGAGAAG-GCTTTCAG | 829 | HHV-7 (76.2) | HIV (gag, gag-pol) HHV (U60) |
|  |  | 1176 | hsa-miR-522* | 4 | TAG-AGGGAAGCGCTTTCTG | 22 |  |  |
| 3 | 80.0 | 1177 | AF033819.3 | 394 | GGTTAAGGCCAGGGGGAAAG | 413 |  | HIV (gag, gag-pol) |
|  |  | 1178 | hsa-miR-150* | 3 | GGTACAGGCCTGGGGGACAG | 22 |  |  |
| 4 | 84.2 | 1179 | AF033819.3 | 8686 | ACCACACACAAGGCTACTT | 8704 | HHV-6A (94.0) HHV-6B (88.9) HHV-7 (77.3) | HIV (nef) HHV-6A (U34) HHV-6B (U34) HHV-7 (U86) |
|  |  | 1180 | hsa-miR-377 | 1 | ATCACACA-AAGGCAACTT | 18 |  |  |
| 5 | 80.0 | 1181 | AF033819.3 | 7339 | GGGAGCAGCAGGAAGCACTA | 7358 |  | HIV (gp160, env) |
|  |  | 1182 | hsa-miR-920 | 2 | GGGAGCTG-TGGAAGCAGTA | 20 |  |  |
| 6 | 82.6 | 1183 | AF033819.3 | 7110 | CAAATATTACAGGGCTGCTATTA | 7132 | HHV-7 (73.1) | HIV (gp160, env) HHV-7 (U58) |
|  |  | 1184 | hsa-miR-16-2* | 1 | CCAATATTACTGTGCTGCT-TTA | 22 |  |  |
| 7 | 81.8 | 1185 | AF033819.3 | 2281 | CATAAAGAAAAAGACAGTACT | 2302 | HHV-7 (80.0) | HIV (gag-pol) HHV-7 (U41) |
|  |  | 1186 | hsa-miR-142-5 | 1 | CATAAAGTAGAAAG-CACTACT | 21 |  |  |
| 8 | 81.0 | 1187 | AF033819.3 | 2105 | CCTATTGAGACTG-TACCAGT | 2124 | HHV-6A (88.9) HHV-6B (80.0) HHV-7 (77.8) | HIV (gag-pol) HHV-6A (Unknown) HHV-6B (U7) HHV-7 (U57) |
|  |  | 1188 | hsa-miR-24-1* | 3 | CCTACTGAG-CTGATATCAGT | 22 |  |  |

TABLE 4-continued

Human miRNA Showing mutual Homologies (>=80%) with HIV-1 and with one or more co-infecting viruses (i.e., GBV-C (>=70%), HHV-6 (>=80%) and HHV-7 (>=70%))

| No. | % Homology | SEQ ID NO: | Sequence Alignment Result | | | | Common With | Target |
|---|---|---|---|---|---|---|---|---|
| 9* | 80.0* | 1189 | | 6575 | GAGGTAGTAATTAGATCTGT | 6594 | HHV-7 (84.2) | HHV-7 (U95) |
| | | 1190 | hsa-let-7i | 2 | \|\|\|\|\|\|\|\|\|\|.\|\|.\|...\|\|\|\|<br>GAGGTAGTAGTTTGTGCTGT | 22 | HHV-6A (62.1)<br>HHV-6B (62.1)<br>GBV-C (70.8) | HHV-6A (U42)<br>HHV-6B (U42)<br>GBV-C (HGV1gp1) |
| 10 | 84.2 | 1191 | AF033819.3 | 2251 | TGAAAATCCATACAATACT | 2269 | HHV-7 (85.0) | HIV (gag-pol) |
| | | 1192 | hsa-miR-19b | 3 | \|\|.\|\|\|\|\|\|\|\|.\|\|\|.\|\|\|<br>TGCAAATCCATGCAAAACT | 21 | | HHV-7 (Unknown) |
| 11 | 81.0 | 1193 | AF033819.3 | 9082 | ACTGGGT-CTCTCTGGTTAGA | 9101 | HHV-6A (83.3) | HHV-6A (U50) |
| | | 1194 | hsa-miR-892b | 2 | \|\|\|\|\|.\|  \|\|.\|\|\|\|\|.\|\|\|\|<br>ACTGGCTCCTTTCTGGGTAGA | 22 | HHV-7 (72.0) | HHV-7 (U40) |
| 12 | 83.3 | 1195 | AF033819.3 | 2063 | CTGTTGACTCAGAT-TGG | 2079 | HHV-6B (80.0) | HIV (gag-pol) |
| | | 1196 | hsa-miR-146b- | 5 | \|\|\|\|.\|\|\|\|\|\|\|\|.\|\|\|\|<br>CTGTGGACTCAGTTCTGG | 22 | HHV-7 (81.0) | HHV-6B (DR1)<br>HHV-7 (U4) |
| 13 | 80.0 | 1197 | AF033819.3 | 8212 | GCTCAATGC-CACAGCCATA | 8230 | HHV-7 (81.0) | HIV (gp160, env) |
| | | 1198 | hsa-miR-574-3 | 4 | \|\|\|\|  \|\|\|\|  \|\|\|\|.\|\|\|.\|<br>GCTC-ATGCACACACCCACA | 22 | | HHV-7 (Unknown) |
| 14 | 80.0 | 1199 | AF033819.3 | 2053 | TGGAAGAAATCTGTTGACTC | 2072 | | HIV (gag-pol) |
| | | 1200 | hsa-miR-30c-2 | 2 | \|\|\|.\|\|\|\|..\|\|\|\|\|.\|\|\|\|<br>TGGGAGAAGGCTGTTTACTC | 21 | | |
| 15 | 83.3 | 1201 | AF033819.3 | 3058 | ATCAAAAGAC-TTAATAG | 3074 | HHV-7 (89.5) | HIV (gag-pol) |
| | | 1202 | hsa-miR-421 | 1 | \|\|\|\|\|.\|\|\|\|  \|\|\|\|\|.\|<br>ATCAACAGACATTAATTG | 18 | | HHV-7 (U13) |
| 16 | 81.0 | 1203 | AF033819.3 | 5175 | AGGAGCTTAAGAATGAAGCTG | 5195 | | HIV (vpr) |
| | | 1204 | hsa-miR-708 | 2 | \|\|\|\|\|\|\|\| \|.\|\|\|..\|\|\|\|\|<br>AGGAGCTT-ACAATCTAGCTG | 21 | | |
| 17 | 81.8 | 1205 | AF033819.3 | 7414 | AGTGCAGCAGCAGAACAATTTG | 7435 | HHV-7 (84.2) | HIV (gp160, env) |
| | | 1206 | hsa-miR-148b | 3 | \|\|\|\|\|\|.\|\| \|\|\|\|\|\|  \|\|\|\|<br>AGTGCATCA-CAGAAC--TTTG | 21 | | HHV-7 (U38) |
| 18 | 81.8 | 1207 | AF033819.3 | 7595 | CCTTGGAATGCTAGTTG-GAGT | 7615 | GBV-C (77.3) | HIV (gp160, env) |
| | | 1208 | hsa-miR-362-5 | 4 | \|\|\|\|\|\|\|\| .\|\|\|\|.\|\| \|\|\|\|<br>CCTTGGAA-CCTAGGTGTGAGT | 24 | HHV-6A (85.0)<br>HHV-6B (80.0) | GBV-C (HGV1 gp1)<br>HHV-6A (U39)<br>HHV-6B (U43) |
| 19* | 80.0* | 1209 | | 7417 | GCAGCAGCAGAACAATTTGC | 7436 | HHV-7 (85.0) | HHV-7 (U59) |
| | | 1210 | hsa-miR-195 | 3 | \|\|\|\|\|\|  \|\|\|\|\|..\|\|\|.\|\|<br>GCAGCA-CAGAAATATTGGC | 21 | HHV-6A (66.7)<br>HHV-6B (69.6)<br>GBV-C (53.1) | HHV-6A (U27)<br>HHV-6B (U28)<br>GBV-C (HGV1 gp1) |

TABLE 4-continued

Human miRNA Showing mutual Homologies (>=80%) with HIV-1 and with one or more co-infecting viruses (i.e., GBV-C (>=70%), HHV-6 (>=80%) and HHV-7 (>=70%))

| No. | % Homology | SEQ ID NO: | Sequence Alignment Result | | | | Common With | Target |
|---|---|---|---|---|---|---|---|---|
| 20 | 83.3 | 1211 | AF033819.3 | 974 | TAGAGTGCATCCAGTGCA | 991 | HHV-7 (80.0) | HIV (gag, gag-pol) HHV-7 (U4) |
| | | 1212 | hsa-miR-18b | 1 | \|\|..\|\|\|\|\|\|\|.\|\|\|\|\|\|<br>TAAGGTGCATCTAGTGCA | 18 | | |
| 21 | 80.0 | 1213 | AF033819.3 | 7469 | CAACTCACAGTCTGGGGCAT | 7488 | | HIV (gp160, env) |
| | | 1214 | hsa-miR-7-1* | 4 | \|\|\|.\|\|\|\|\|\|\|\|\|\|  \|.\|\|\|<br>CAAATCACAGTCT--GCCAT | 21 | | |
| 22 | 83.3 | 1215 | AF033819.3 | 162 | GTGTGGAA--AATCTCTA | 177 | GBV-C (77.8) HHV-7 (88.9) | HIV (Unknown) GBV-C (HGV1 gp1) HHV-7 (U41) |
| | | 1216 | hsa-miR-653 | 1 | \|\|\|\|.\|\|\|  \|\|\|\|\|\|\|\|<br>GTGTTGAAACAATCTCTA | 18 | | |
| 23 | 80.0 | 1217 | AF033819.3 | 7241 | ATTG-AACCATTAGGAGTAG | 7259 | GBV-C (77.3) HHV-7 (77.3) | HIV (gp160, env) GBV-C (HGV1 gp1) HHV-7 (U57) |
| | | 1218 | hsa-miR-508-3 | 3 | \|\|\|\| \|.\|\|.\|\|.\|\|\|\|\|\|<br>ATTGTAGCCTTTTGGAGTAG | 22 | | |
| 24 | 80.0 | 1219 | AF033819.3 | 3458 | GCAGGATATGTTACT-AATA | 3476 | GBV-C (72.7) HHV-7 (77.3) | HIV (gag-pol) GBV-C (HGV1 gp1) HHV-7 (U86) |
| | | 1220 | hsa-miR-450b- | 5 | \|\|\|   \|\|\|\|\|\|\|\|.\|\| \|\|\|\|<br>GCA--ATATGTTCCTGAATA | 22 | | |
| 25 | 85.0 | 1221 | AF033819.3 | 581 | AGCAACCCTCTATTGTGTGC | 600 | HHV-6B (82.6) | HIV (gag, gag-pol) HHV-6B (U25) |
| | | 1222 | hsa-miR-545 | 3 | \|\|\|\|\|.\|.\|.\|\|\|\|\|\|\|\|\|\|\|<br>AGCAAACATTTATTGTGTGC | 22 | | |
| 26 | 80.0 | 1223 | AF033819.3 | 2763 | AAGAACCTCCATTCCTTTGG | 2782 | GBV-C (77.8) HHV-6B (80.0) HHV-7 (81.8) | HIV (gag-pol) GBV-C (HGV1 gp1) HHV-6B (U85) HHV-7 (U40) |
| | | 1224 | hsa-miR-548b- | 2 | \|\|\|\|\|\|\|\|\|..\|\|.\|\|\|\|.\|<br>AAGAACCTCAGTTGCTTTTG | 21 | | |
| 27 | 80.0 | 1225 | AF033819.3 | 1279 | ATTGGATGACAGAAACCTTG | 1298 | HHV-7 (78.3) | HIV (gag, gag-pol) HHV-7 (U56) |
| | | 1226 | hsa-miR-152 | 3 | \|.\|\|.\|\|\|\|\|\|\|\|\|  \|\|\|\|<br>AGTGCATGACAGAA--CTTG | 20 | | |
| 28 | 80.0 | 1227 | AF033819.3 | 2899 | TCAGATTTACCCAGGGATTA | 2918 | | HIV (gag-pol) |
| | | 1228 | hsa-miR-23b | 2 | \|\|\|.\|\|\|  .\|\|\|\|\|\|\|\|\|<br>TCACATT--GCCAGGGATTA | 19 | | |
| 29 | 80.0 | 1229 | AF033819.3 | 7543 | GCTCCTGGGGATTTGGGGTT | 7562 | HHV-7 (75.0) | HIV (gp160, env) HHV-7 (U74) |
| | | 1230 | hsa-miR-23a* | 4 | \|.\|\|\|\|\|\|\|\|  \|\|\|\|.\|\|<br>GTTCCTGGGGA--TGGGATT | 21 | | |
| 30 | 81.0 | 1231 | AF033819.3 | 3335 | TGGGAGTTTGT-TAATACCCC | 3354 | | HIV (gag-pol) |
| | | 1232 | hsa-miR-223 | 1 | \|\|..\|\|\|\|\|\|\| .\|\|\|\|\|\|\|\|<br>TGTCAGTTTGTCAAATACCCC | 21 | | |
| 31 | 83.3 | 1233 | AF033819.3 | 974 | TAGAGTGCATCCAGTGCA | 991 | HHV-7 (72.0) | HIV (gag, gag-pol) HHV-7 (U11) |
| | | 1234 | hsa-miR-18a | 1 | \|\|..\|\|\|\|\|\|\|.\|\|\|\|\|\|<br>TAAGGTGCATCTAGTGCA | 18 | | |

TABLE 4-continued

Human miRNA Showing mutual Homologies (>=80%) with HIV-1 and with one or more co-infecting viruses (i.e., GBV-C (>=70%), HHV-6 (>=80%) and HHV-7 (>=70%))

| No. | % Homology | SEQ ID NO: | Sequence Alignment Result | | | | Common With | Target |
|---|---|---|---|---|---|---|---|---|
| 32 | 80.0 | 1235 | AF033819.3 | 811 | TAGAAGAGAAG-GCTTTCAG  ||| ||.|||| ||||||.| | 829 | HHV-7 (76.2) | HIV (gag, gag-pol) HHV-7 (U60) |
|  |  | 1236 | hsa-miR-518e* | 4 | TAG-AGGGAAGCGCTTTCTG | 22 |  |  |
| 33 | 81.0 | 1237 | AF033819.3 | 4827 | TTGGGTCAGGGA--GTCTCCA  ||||.||||||| |||.||| | 4845 |  | HIV (vif) |
|  |  | 1238 | hsa-miR-659 | 2 | TTGGTTCAGGGAGGGTCCCCA | 22 |  |  |
| 34 | 80.0 | 1239 | AF033819.3 | 811 | TAGAAGAGAAG-GCTTTCAG  ||| ||.|||| ||||||.| | 829 | HHV-7 (76.2) | HIV (gag, gag-pol) HHV-7 (U60) |
|  |  | 1240 | hsa-miR-523* | 4 | TAG-AGGGAAGCGCTTTCTG | 22 |  |  |
| 35 | 85.0 | 1241 | AF033819.3 | 1531 | GGCACACAGCCAGAAATTGC  ||||| |||||||..||||| | 1550 |  | HIV (gag, gag-pol) |
|  |  | 1242 | hsa-miR-593* | 2 | GGCAC-CAGCCAGGCATTGC | 20 |  |  |
| 36 | 80.0 | 1243 | AF033819.3 | 4847 | AGAATGGAGGAAA-AAGAGA  |||..|||||||| |||.|| | 4865 | GBV-C (76.2) | GBV-C (HGV1 gp1) |
|  |  | 1244 | hsa-miR-483-5 | 2 | AGACGGGAGGAAAGAAGGGA | 21 |  |  |
| 37 | 81.0 | 1245 | AF033819.3 | 9053 | CTGC-ATATAAGCAGCTGCTT  |||| ||.|||||| ||.||| | 9072 | HHV-7 (85.0) | HIV (Unknown) HHV-7 (U82) |
|  |  | 1246 | hsa-miR-106a* | 1 | CTGCAATGTAAGCA-CTTCTT | 20 |  |  |
| 38 | 82.6 | 1247 | AF033819.3 | 569 | ATATAATACAGTAGCAACCCTCT  ||||.||||||| ||| ||||| | 591 |  | HIV (gag, gag-pol) |
|  |  | 1248 | hsa-miR-656 | 2 | ATATTATACAGT--CAA-CCTCT | 21 |  |  |
| 39 | 81.8 | 1249 | AF033819.3 | 1445 | AACAAAT-TCAG-CTACCATAA  ||||||| .||| ||||| ||| | 1464 |  | HIV (gag, gag-pol) |
|  |  | 1250 | hsa-miR-7-2* | 2 | AACAAATCCCAGTCTACC-TAA | 22 |  |  |
| 40 | 84.2 | 1251 | AF033819.3 | 8878 | AAGTG-TTAGAGTGGAGGT  ||||| |||.||||.|||| | 8895 |  | HIV (nef) |
|  |  | 1252 | hsa-miR-20a | 3 | AAGTGCTTATAGTGCAGGT | 21 |  |  |
| 41 | 80.0 | 1253 | AF033819.3 | 7807 | GTGGTATATAAAATTATTCA  |||||.||.|||.|.||||| | 7826 | HHV-7 (78.3) | HIV (gp160, env) HHV-7 (U30) |
|  |  | 1254 | hsa-miR-876-3 | 3 | GTGGTTTACAAAGTAATTCA | 22 |  |  |
| 42 | 80.0 | 1255 | AF033819.3 | 811 | TAGAAGAGAAG-GCTTTCAG  ||| ||.|||| ||||||.| | 829 | GBV-C (78.9) HHV-7 (76.2) | HIV (gag, gag-pol) GBV-C (HGV1 gp1) HHV-7 (U60) |
|  |  | 1256 | hsa-miR-519b- | 4 | TAG-AGGGAAGCGCTTTCTG | 22 |  |  |
| 43 | 84.2 | 1257 | AF033819.3 | 5756 | CAGAAGACAGTGGCAATGA  |.|.|||||||||||||.| | 5774 |  | HIV (gp160, env) |
|  |  | 1258 | hsa-miR-509-5 | 3 | CTGCAGACAGTGGCAATCA | 21 |  |  |
| 44 | 83.3 | 1259 | AF033819.3 | 5926 | ATT-TTGTGCATCAGATG  ||| ||||.||||.|||| | 5942 |  | HIV (gp160, env) |
|  |  | 1260 | hsa-miR-944 | 3 | ATTATTGTACATCGGATG | 20 |  |  |
| 45 | 83.3 | 1261 | AF033819.3 | 2640 | AATACATGGATGATTTGT  |||||||||.||||.|.| | 2657 | HHV-6B (80.0) | HIV (gag-pol) HHV-6B (U77) |
|  |  | 1262 | hsa-miR-369-3 | 4 | AATACATGGTTGATCTTT | 21 |  |  |
| 46 | 84.2 | 1263 | AF033819.3 | 6136 | AACCCCACTCT-GTGTTAG  ||||.||||.| |||||||  | 6153 |  | HIV (gp160, env) |
|  |  | 1264 | hsa-miR-497* | 3 | AACCACACTGTGGTGTTAG | 21 |  |  |
| 47 | 80.0 | 1265 | AF033819.3 | 6356 | TGTAAC--ACCTCAGTCATT  ||.||| |||.|||||||| | 6373 |  | HIV (gp160, env) |
|  |  | 1266 | hsa-miR-891b | 1 | TGCAACTTACCTGAGTCATT | 20 |  |  |

TABLE 4-continued

Human miRNA Showing mutual Homologies (>=80%) with HIV-1 and with one
or more co-infecting viruses (i.e., GBV-C (>=70%), HHV-6 (>=80%) and HHV-7 (>=70%))

| No. | % Homology | SEQ ID NO: | Sequence Alignment Result | | | Common With | Target |
|---|---|---|---|---|---|---|---|
| 48 | 81.8 | 1267 | AF033819.32951 | 2933 | TGTAAAC-TCCTTAGA--GGAA | HHV-7 (75.0) | HIV (gag-pol) HHV-7 (Unknown) |
|  |  | 1268 | hsa-miR-30e21 | 1 | TGTAAACATCCTT-GACTGGAA |  |  |
| 49 | 83.3 | 1269 | AF033819.3 | 1563 | AAAAAGGGCTGTTG-GAA | 1579 | HIV (gag, gag-pol) |
|  |  | 1270 | hsa-miR-220c | 1 | ACACAGGGCTGTTGTGAA | 18 |  |
| 50 | 80.0 | 1271 | AF033819.3 | 811 | TAGAAGAGAAG-GCTTTCAG | 829 HHV-7 (76.2) | HIV (gag, gag-pol) HHV-7 (U60) |
|  |  | 1272 | hsa-miR-519c- | 4 | TAG-AGGGAAGCGCTTTCTG | 22 |  |

% Homology with asterisk (*) shows the alignment between miRNA and HIV-1 (pNL 4-3)

TABLE 5

Human miRNA Showing mutual Homologies (>=80%) with HIV-1 and with one or more co-infecting viruses
(i.e., GBV-C (>=70%), HHV-6 (>=80%) and HHV-7 (>=70%) and Triplex Stability Index

| No. | % Homology | SEQ ID NO: | Sequence Alignment Result | | | Number and triplex stability index or TSI@ | |
|---|---|---|---|---|---|---|---|
| 1 | 80.0 | 1273 | AF033819.3 | 811 | TAGAAGAGAAG-GCTTTCAG | 829 | 6/20 30% |
|  |  | 1274 | hsa-miR-519a* | 4 | TAG-AGGGAAGCGCTTTCTG | 22 |  |
| 2 | 80.0 | 1275 | AF033819.3 | 811 | TAGAAGAGAAG-GCTTTCAG | 829 | 6/20 30% |
|  |  | 1276 | hsa-miR-522* | 4 | TAG-AGGGAAGCGCTTTCTG | 22 |  |
| 3 | 80.0 | 1277 | AF033819.3 | 394 | GGTTAAGGCCAGGGGAAAG | 413 | 3/20 15% |
|  |  | 1278 | hsa-miR-150* | 3 | GGTACAGGCCTGGGGACAG | 22 |  |
| 4 | 84.2 | 1279 | AF033819.3 | 8686 | ACCACACACAAGGCTACTT | 8704 | 8/19 42% |
|  |  | 1280 | hsa-miR-377 | 1 | ATCACACA-AAGGCAACTT | 18 |  |
| 5 | 80.0 | 1281 | AF033819.3 | 7339 | GGGAGCAGCAGGAAGCACTA | 7358 | 4/20 20% |
|  |  | 1282 | hsa-miR-920 | 2 | GGGAGCTG-TGGAAGCAGTA | 20 |  |
| 6 | 82.6 | 1283 | AF033819.3 | 7110 | CAAATATTACAGGGCTGCTATTA | 7132 | 11/23 47% |
|  |  | 1284 | hsa-miR-16-2* | 1 | CCAATATTACTGTGCTGCT-TTA | 22 |  |
| 7 | 81.8 | 1285 | AF033819.3 | 2281 | CATAAAGAAAAAGACAGTACT | 2302 | 6/22 27% |
|  |  | 1286 | hsa-miR-142-5 | 1 | CATAAAGTAGAAAG-CACTACT | 21 |  |
| 8 | 81.0 | 1287 | AF033819.3 | 2105 | CCTATTGAGACTG-TACCAGT | 2124 | 9/21 42 |
|  |  | 1288 | hsa-miR-24-1* | 3 | CCTACTGAG-CTGATATCAGT | 22 |  |
| 9* | 80.0* | 1289 |  | 6575 | GAGGTAGTAATTAGATCTGT | 6594 | 8/20 40% |
|  |  | 1290 | hsa-let-7i | 2 | GAGGTAGTAATTAGATCTGT | 21 |  |
| 10 | 84.2 | 1291 | AF033819.3 | 2251 | TGAAAATCCATACAATACT | 2269 | 8/19 42% |
|  |  | 1292 | hsa-miR-19b | 3 | TGCAAATCCATGCAAAACT | 21 |  |
| 11 | 81.0 | 1293 | AF033819.3 | 9082 | ACTGGGT-CTCTCTGGTTAGA | 9101 | 9/21 42% |
|  |  | 1294 | hsa-miR-892b | 2 | ACTGGCTCCTTTCTGGGTAGA | 22 |  |
| 12 | 83.3 | 1295 | AF033819.3 | 2063 | CTGTTGACTCAGAT-TGG | 2079 | 8/18 44% |
|  |  | 1296 | hsa-miR-146b- | 5 | CTGTGGACTCAGTTCTGG | 22 |  |

TABLE 5-continued

Human miRNA Showing mutual Homologies (>=80%) with HIV-1 and with one or more co-infecting viruses (i.e., GBV-C (>=70%), HHV-6 (>=80%) and HHV-7 (>=70%)) and Triplex Stability Index

| No. | % Homology | SEQ ID NO: | Sequence Alignment Result | | | | Number and triplex stability index or TSI@ | |
|---|---|---|---|---|---|---|---|---|
| 13 | 80.0 | 1297 | AF033819.3 | 8212 | GCTCAATGC-CACAGCCATA | 8230 | 9/20 | 45% |
|  |  | 1298 | hsa-miR-574-3 | 4 | GCTC-ATGCACACACCCACA | 22 |  |  |
| 14 | 80.0 | 1299 | AF033819.3 | 2053 | TGGAAGAAATCTGTTGACTC | 2072 | 8/20 | 40% |
|  |  | 1300 | hsa-miR-30c-2 | 2 | TGGGAGAAGGCTGTTTACTC | 22 |  |  |
| 15 | 83.3 | 1301 | AF033819.3 | 3058 | ATCAAAAGAC-TTAATAG | 3074 | 6/18 | 33% |
|  |  | 1302 | hsa-miR-421 | 1 | ATCAACAGACATTAATTG | 18 |  |  |
| 16 | 81.0 | 1303 | AF033819.3 | 5175 | AGGAGCTTAAGAATGAAGCTG | 5195 | 6/21 | 28% |
|  |  | 1304 | hsa-miR-708 | 2 | AGGAGCTT-ACAATCTAGCTG | 21 |  |  |
| 17 | 81.8 | 1305 | AF033819.3 | 7414 | AGTGCAGCAGCAGAACAATTTG | 7435 | 8/22 | 36% |
|  |  | 1306 | hsa-miR-148b | 3 | AGTGCATCA-CAGAAC--TTTG | 21 |  |  |
| 18 | 81.8 | 1307 | AF033819.3 | 7595 | CCTTGGAATGCTAGTTG-GAGT | 7615 | 9/22 | 40% |
|  |  | 1308 | hsa-miR-362-5 | 4 | CCTTGGAA-CCTAGGTGTGAGT | 24 |  |  |
| 19* | 80.0* | 1309 |  | 7417 | GCAGCAGCAGAACAATTTGC | 7436 | 8/20 | 40% |
|  |  | 1310 | hsa-miR-195 | 3 | GCAGCAGCAGAACAATTTGC | 21 |  |  |
| 20 | 83.3 | 1311 | AF033819.3 | 974 | TAGAGTGCATCCAGTGCA | 991 | 7/18 | 38% |
|  |  | 1312 | hsa-miR-18b | 1 | TAAGGTGCATCTAGTGCA | 18 |  |  |
| 21 | 80.0 | 1313 | AF033819.3 | 7469 | CAACTCACAGTCTGGGGCAT | 7488 | 9/20 | 45% |
|  |  | 1314 | hsa-miR-7-1* | 4 | CAAATCACAGTCT--GCCAT | 21 |  |  |
| 22 | 83.3 | 1315 | AF033819.3 | 162 | GTGTGGAA--AATCTCTA | 177 | 7/18 | 38% |
|  |  | 1316 | hsa-miR-653 | 1 | GTGTTGAAACAATCTCTA | 18 |  |  |
| 23 | 80.0 | 1317 | AF033819.3 | 7241 | ATTG-AACCATTAGGAGTAG | 7259 | 8/20 | 40% |
|  |  | 1318 | hsa-miR-508-3 | 3 | ATTGTAACCATTAGGAGTAG | 22 |  |  |
| 24 | 80.0 | 1319 | AF033819.3 | 3458 | GCAGGATATGTTACT-AATA | 3476 | 8/20 | 40% |
|  |  | 1320 | hsa-miR-450b- | 5 | GCA--ATATGTTCCTGAATA | 22 |  |  |
| 25 | 85.0 | 1321 | AF033819.3 | 581 | AGCAACCCTCTATTGTGTGC | 600 | 8/20 | 40% |
|  |  | 1322 | hsa-miR-545 | 3 | AGCAAACATTTATTGTGTGC | 22 |  |  |
| 26 | 80.0 | 1323 | AF033819.3 | 2763 | AAGAACCTCCATTCCTTTGG | 2782 | 10/20 | 50% |
|  |  | 1324 | hsa-miR-548b- | 2 | AAGAACCTCAGTTGCTTTTG | 21 |  |  |
| 27 | 80.0 | 1325 | AF033819.3 | 1279 | ATTGGATGACAGAAACCTTG | 1298 | 7/20 | 35% |
|  |  | 1326 | hsa-miR-152 | 3 | AGTGCATGACAGAA--CTTG | 20 |  |  |
| 28 | 80.0 | 1327 | AF033819.3 | 2899 | TCAGATTTACCCAGGGATTA | 2918 | 9/20 | 45% |
|  |  | 1328 | hsa-miR-23b | 2 | TCACATT--GCCAGGGATTA | 19 |  |  |
| 29 | 80.0 | 1329 | AF033819.3 | 7543 | GCTCCTGGGGATTTGGGGTT | 7562 | 9/20 | 45% |
|  |  | 1330 | hsa-miR-23a* | 4 | GTTCCTGGGA--TGGGATT | 21 |  |  |

TABLE 5-continued

Human miRNA Showing mutual Homologies (>=80%) with HIV-1 and with one or more co-infecting viruses (i.e., GBV-C (>=70%), HHV-6 (>=80%) and HHV-7 (>=70%) and Triplex Stability Index

| No. | % Homology | SEQ ID NO: | Sequence Alignment Result | | | Number and triplex stability index or TSI@ | |
|---|---|---|---|---|---|---|---|
| 30 | 81.0 | 1331 | AF033819.3 | 3335 TGGGAGTTTGT-TAATACCCC<br>    ||..||||||| .|||||||| | 3354 | 10/21 | 47% |
|  |  | 1332 | hsa-miR-223 | 1 TGTCAGTTTGTCAAATACCCC | 21 |  |  |
| 31 | 83.3 | 1333 | AF033819.3 | 974 TAGAGTGCATCCAGTGCA<br>    ||..|||||||.|||||| | 991 | 7/18 | 38% |
|  |  | 1334 | hsa-miR-18a | 1 TAAGGTGCATCTAGTGCA | 18 |  |  |
| 32 | 80.0 | 1335 | AF033819.3 | 811 TAGAAGAGAAG-GCTTTCAG<br>    ||| ||.|||| ||||||.| | 829 | 6/20 | 30% |
|  |  | 1336 | hsa-miR-518e* | 4 TAG-AGGGAAGCGCTTTCTG | 22 |  |  |
| 33 | 81.0 | 1337 | AF033819.3 | 4827 TTGGGTCAGGGA--GTCTCCA<br>    |||||||||||  ||||||| | 4845 | 9/21 | 42% |
|  |  | 1338 | hsa-miR-659 | 2 TTGGGTCAGGGAGGGTCTCCA | 22 |  |  |
| 34 | 80.0 | 1339 | AF033819.3 | 811 TAGAAGAGAAG-GCTTTCAG<br>    ||| ||.|||| ||||||.| | 829 | 6/20 | 30% |
|  |  | 1340 | hsa-miR-523* | 4 TAG-AGGGAAGCGCTTTCTG | 22 |  |  |
| 35 | 85.0 | 1341 | AF033819.3 | 1531 GGCACACAGCCAGAAATTGC<br>    ||||| |||||||..|||| | 1550 | 8/20 | 40% |
|  |  | 1342 | hsa-miR-593* | 2 GGCAC-CAGCCAGGCATTGC | 20 |  |  |
| 36 | 80.0 | 1343 | AF033819.3 | 4847 AGAATGGAGGAAA-AAGAGA<br>    |||..||||||| |||.|| | 4865 | — | — |
|  |  | 1344 | hsa-miR-483-5 | 2 AGACGGGAGGAAAGAAGGGA | 21 |  |  |
| 37 | 81.0 | 1345 | AF033819.3 | 9053 CTGC-ATATAAGCAGCTGCTT<br>    |||| ||.||||| ||.||| | 9072 | 11/21 | 52% |
|  |  | 1346 | hsa-miR-106a* | 1 CTGCAATGTAAGCA-CTTCTT | 20 |  |  |
| 38 | 82.6 | 1347 | AF033819.3 | 569 ATATAATACAGTAGCAACCCTCT<br>    |||||.||||||  |||  ||||| | 591 | 12/23 | 52% |
|  |  | 1348 | hsa-miR-656 | 2 ATATTATACAGT--CAA-CCTCT | 21 |  |  |
| 39 | 81.8 | 1349 | AF033819.3 | 1445 AACAAAT-TCAG-CTACCATAA<br>    ||||||| .||| ||||| ||| | 1464 | 8/22 | 36% |
|  |  | 1350 | hsa-miR-7-2* | 2 AACAAATCCCAGTCTACC-TAA | 22 |  |  |
| 40 | 84.2 | 1351 | AF033819.3 | 8878 AAGTG-TTAGAGTGGAGGT<br>    ||||| |||.||||.|||| | 8895 | 5/19 | 26% |
|  |  | 1352 | hsa-miR-20a | 3 AAGTGCTTATAGTGCAGGT | 21 |  |  |
| 41 | 80.0 | 1353 | AF033819.3 | 7807 GTGGTATATAAAATTATTCA<br>    |||||.||.|||.|.||||| | 7826 | 7/20 | 35% |
|  |  | 1354 | hsa-miR-876-3 | 3 GTGGTTTACAAAGTAATTCA | 22 |  |  |
| 42 | 80.0 | 1355 | AF033819.3 | 811 TAGAAGAGAAG-GCTTTCAG<br>    ||| ||.|||| ||||||.| | 829 | 6/20 | 30% |
|  |  | 1356 | hsa-miR-519b- | 4 TAG-AGGGAAGCGCTTTCTG | 22 |  |  |
| 43 | 84.2 | 1357 | AF033819.3 | 5756 CAGAAGACAGTGGCAATGA<br>    |.|.|||||||||||||.| | 5774 | 5/19 | 26% |
|  |  | 1358 | hsa-miR-509-5 | 3 CTGCAGACAGTGGCAATCA | 21 |  |  |
| 44 | 83.3 | 1359 | AF033819.3 | 5926 ATT-TTGTGCATCAGATG<br>    ||| ||||.||||.|||| | 5942 | 9/18 | 50% |
|  |  | 1360 | hsa-miR-944 | 3 ATTATTGTACATCGGATG | 20 |  |  |
| 45 | 83.3 | 1361 | AF033819.3 | 2640 AATACATGGATGATTTGT<br>    |||||||||.||||.|.| | 2657 | 7/18 | 38% |
|  |  | 1362 | hsa-miR-369-3 | 4 AATACATGGTTGATCTTT | 21 |  |  |
| 46 | 84.2 | 1363 | AF033819.3 | 6136 AACCCCACTCT-GTGTTAG<br>    ||||.||||.| ||||||| | 6153 | 9/19 | 47% |
|  |  | 1364 | hsa-miR-497* | 3 AACCACACTGTGGTGTTAG | 21 |  |  |
| 47 | 80.0 | 1365 | AF033819.3 | 6356 TGTAAC--ACCTCAGTCATT<br>    ||.||| ||||.||||||| | 6373 | 9/20 | 45% |
|  |  | 1366 | hsa-miR-891b | 1 TGCAACTTACCTGAGTCATT | 20 |  |  |

TABLE 5-continued

Human miRNA Showing mutual Homologies (>=80%) with HIV-1 and with one or more co-infecting viruses (i.e., GBV-C (>=70%), HHV-6 (>=80%) and HHV-7 (>=70%) and Triplex Stability Index

| No. | % Homology | SEQ ID NO: | Sequence Alignment Result | | | | Number and triplex stability index or TSI@ | |
|---|---|---|---|---|---|---|---|---|
| 48 | 81.8 | 1367 | AF033819.3 | 2933 | TGTAAAC-TCCTTAGA--GGAA<br>\|\|\|\|\|\|\| \|\|\|\|\| \|\|   \|\|\|\| | 2951 | 8/22 | 36% |
|  |  | 1368 | hsa-miR-30e | 1 | TGTAAACATCCTT-GACTGGAA | 21 |  |  |
| 49 | 83.3 | 1369 | AF033819.3 | 1563 | AAAAAGGGCTGTTG-GAA<br>\|.\|.\|\|\|\|\|\|\|\|\|\| \|\|\| | 1579 | 4/18 | 22% |
|  |  | 1370 | hsa-miR-220c | 1 | ACACAGGGCTGTTGTGAA | 18 |  |  |
| 50 | 80.0 | 1371 | AF033819.3 | 811 | TAGAAGAGAAG-GCTTTCAG<br>\|\|\| \|\|.\|\|\|\| \|\|\|\|\|\|.\| | 829 | 6/21 | 28% |
|  |  | 1372 | hsa-miR-519c- | 4 | TAG-AGGGAAGCGCTTTCTG | 22 |  |  |

% Homology with asterisk (*) shows the alignment between miRNA and HIV-1 (pNL 4-3). The nucleotides highlighted above indicate the modified or replaced nucleotides. These replacements were carried out to increase the triplex forming ability and stability of the miRNAs.

---

What is claimed is:

1. A method of inhibiting replication of a virus in a target cell in vitro, said method comprising the steps of: (a) introducing into a target cell in a cell culture infected with the virus a microRNA (miRNA) selected from the group consisting of: (i) a nucleotide sequence selected from among SEQ ID NOs: 1290, 1310, 1318, and 1338; (ii) a nucleotide sequence consisting of a full-length complement of SEQ ID NOs: 1290, 1310, 1318, or 1338; and (iii) a 15-25 sequence length oligonucleotide having at least 90% sequence identity to a nucleotide sequence of (i) or (ii), and (b) allowing the miRNA to hybridize with the viral genome.

2. The method of claim 1, wherein the hybridization of step (b) results in the formation of a stable triplex molecule.

3. The method of claim 1, wherein said miRNA is encoded by a recombinant vector.

4. The method of claim 1, wherein said virus is a retrovirus.

5. The method of claim 1, wherein said virus is a lentivirus.

6. The method of claim 1, wherein said virus is HIV.

7. The method of claim 1, wherein said virus is HIV-1.

8. The method of claim 1, wherein said viral genome comprises a proviral or preintegration version of the virus.

9. A method of reducing the level of HIV-1 replication in a target cell in vitro, said method comprising the steps of: (a) introducing into a target cell in a cell culture infected with the virus a microRNA (miRNA) selected from the group consisting of: (i) a nucleotide sequence selected from among SEQ ID NOs: 1290, 1310, 1318, and 1338; (ii) a nucleotide sequence consisting of a full-length complement of SEQ ID NOs: 1290, 1310, 1318, or 1338; and (iii) a 15-25 sequence length oligonucleotide having at least 90% sequence identity with a nucleotide sequence of (i) or (ii), wherein said miRNA additionally is at least 80% complementary to a portion of the HIV-1 genome; and (b) allowing the miRNA to hybridize with the HIV-1 genome or a proviral or preintegration version thereof.

10. The method of claim 9, wherein said hybridization of step (b) results in the formation of a stable triplex molecule.

11. The method according to claim 9, wherein said miRNA is encoded by a recombinant vector.

* * * * *